US012790373B2

(12) United States Patent
Sivasubramanian et al.

(10) Patent No.: US 12,790,373 B2
(45) Date of Patent: Nov. 10, 2026

(54) CH1 DOMAIN VARIANTS ENGINEERED FOR PREFERENTIAL KAPPA LIGHT CHAIN PAIRING AND MULTISPECIFIC ANTIBODIES COMPRISING THE SAME

(71) Applicant: ADIMAB, LLC, Lebanon, NH (US)

(72) Inventors: Arvind Sivasubramanian, Lebanon, NH (US); Kevin Schutz, Lebanon, NH (US); Michaela Helble, Lebanon, NH (US); Eric Krauland, Lebanon, NH (US); Paul Widboom, Lebanon, NH (US)

(73) Assignee: ADIMAB, LLC, Lebanon, NH (US)

( * ) Notice: Subject to any disclaimer, the term of this patent is extended or adjusted under 35 U.S.C. 154(b) by 1184 days.

(21) Appl. No.: 17/765,009

(22) PCT Filed: Sep. 30, 2020

(86) PCT No.: PCT/US2020/053482

§ 371 (c)(1),
(2) Date: Mar. 30, 2022

(87) PCT Pub. No.: WO2021/067404

PCT Pub. Date: Apr. 8, 2021

(65) Prior Publication Data

US 2023/0265134 A1 Aug. 24, 2023

Related U.S. Application Data

(60) Provisional application No. 62/908,367, filed on Sep. 30, 2019.

(51) Int. Cl.

| | |
|---|---|
| ***C07K 14/47*** | (2006.01) |
| ***C07K 16/24*** | (2006.01) |
| ***C07K 16/28*** | (2006.01) |
| ***C12N 15/10*** | (2006.01) |

(52) U.S. Cl.

CPC ............ *C07K 14/47* (2013.01); *C07K 16/244* (2013.01); *C07K 16/2863* (2013.01); *C12N 15/1093* (2013.01); *C07K 2317/14* (2013.01); *C07K 2317/31* (2013.01); *C07K 2317/522* (2013.01)

(58) Field of Classification Search

CPC .. C07K 14/47; C07K 16/244; C07K 16/2863; C07K 16/40; C07K 16/00; C07K 2317/14; C07K 2317/31; C07K 2317/522; C07K 2317/21; C07K 2317/526; C07K 2317/76; C07K 2317/55; C07K 2317/92; C07K 2317/94; C07K 2317/51; C07K 2317/515; C12N 15/1093; C12N 15/81; H04N 19/10; A61P 43/00; A61K 2039/505

See application file for complete search history.

(56) References Cited

U.S. PATENT DOCUMENTS

| | | | |
|---|---|---|---|
| 2005/0244403 A1 | 11/2005 | Lazar et al. | |
| 2011/0064727 A9 | 3/2011 | Lazar et al. | |
| 2017/0081421 A1 | 3/2017 | Harms et al. | |
| 2018/0177873 A1 | 6/2018 | Carter et al. | |

FOREIGN PATENT DOCUMENTS

| | | | |
|---|---|---|---|
| CN | 107787332 | 3/2018 | |
| CN | 109475627 | 3/2019 | |
| EP | 2966085 A1 * | 1/2016 | ......... C07K 16/2887 |
| EP | 2970469 | 1/2016 | |
| EP | 3489262 | 5/2019 | |
| RU | 2745648 | 3/2021 | |
| WO | 2005092925 | 10/2005 | |
| WO | 2006116260 | 11/2006 | |
| WO | WO2011118739 | 7/2013 | |
| WO | 2014138449 | 9/2014 | |
| WO | 2015173756 | 11/2015 | |
| WO | 2016172485 | 10/2016 | |
| WO | 2017205014 | 11/2017 | |
| WO | 2018141894 | 8/2018 | |

OTHER PUBLICATIONS

Brinkmann U and Kontermann RE. (2017) MABS. 9(2):182-212. (http://dx.doi.org/10.1080/19420862.2016.1268307).*

Chen et al. "Improving the CH1-CK heterodimerization and pharmacokinetics of 4Dm2m, a novel potent CD4-antibody fusion protein against HIV-1." InMAbs May 18, 2016 (vol. 8, No. 4, pp. 761-774). Taylor & Francis.

Froning et al. "Fitchett Jr. Computational design of a specific heavy chain/κ light chain interface for expressing fully IgG bispecific antibodies." Protein Science. Oct. 2017;26(10):2021-38.

Dillon et al. "Efficient production of bispecific IgG of different isotypes and species of origin in single mammalian cells." InMAbs Feb. 17, 2017 (vol. 9, No. 2, pp. 213-230). Taylor & Francis.

* cited by examiner

*Primary Examiner* — Robert S Landsman

(74) *Attorney, Agent, or Firm* — Robin L. Teskin; Baker, Donelson, Bearman, Caldwell & Berkowitz PC

(57) ABSTRACT

CH1 domain variants engineered for preferential binding to either a kappa CL domain or a lambda CL domain, as well as polypeptides, e.g., antibody heavy chains or antibodies, comprising such engineered CH1 domain variants, and pharmaceutical compositions comprising such CH1 domain variants and/or such polypeptides, and methods for making and using such CH1 domain variants are provided. The CH1 domain variants minimize heavy chain-light chain mispairing and promote cognate heavy chain-light chain pairing, thereby improving the generation of multispecific, e.g., bispecific, antibodies. Also provided are methods of making CH1 domain variant libraries and methods of identifying one or more CH1 domain variants.

14 Claims, 55 Drawing Sheets

Specification includes a Sequence Listing.

| Clone | Substitutions | IL12B | EGFR |
| --- | --- | --- | --- |
| Pani-κ Uste-λ BsAb1 | None |  |  |
| Pani-κ Uste-λ BsAb2 | 141D |  |  |
| Pani-κ Uste-λ BsAb3 | 183R |  |  |

| Clone | Substitutions | IL12B | EGFR |
|---|---|---|---|
| Pani-κ Uste-λ BsAb5 | 183K |  |  |
| Pani-κ Uste-λ BsAb7 | 183Y |  |  |
| Pani-κ Uste-λ BsAb4 | 141D, 183R |  |  |

| Clone | Substitutions | IL12B | EGFR |
|---|---|---|---|
| Pani-κ Uste-λ BsAb9 | 147F, 183R |  |  |
| Pani-κ Uste-λ BsAb10 | 141D, 147F, 183R |  |  |
| Pani-κ Uste-λ BsAb6 | 141D, 183K |  |  |

| Clone | Substitutions | IL12B | EGFR |
|---|---|---|---|
| Pani-κ Uste-λ BsAb11 | 147F, 183K |  |  |
| Pani-κ Uste-λ BsAb12 | 141D, 147F, 183K |  |  |
| Pani-κ Uste-λ BsAb8 | 141D, 183Y |  |  |

| Clone | Substitutions | IL12B | EGFR |
| --- | --- | --- | --- |
| Pani-κ Uste-λ<br>BsAb13 | 147F, 183Y |  |  |
| Pani-κ Uste-λ<br>BsAb14 | 141D, 147F, 183Y |  |  |
| Pani-λ Uste-κ<br>BsAb15 | None |  |  |

SEQUENCE LISTING

```
<160> NUMBER OF SEQ ID NOS: 189

<210> SEQ ID NO 1
<211> LENGTH: 112
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

<210> SEQ ID NO 2
<211> LENGTH: 107
<212> TYPE: PRT
<213> ORGANISM: Homo sapiens

<400> SEQUENCE: 2

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 3
<211> LENGTH: 106
<212> TYPE: PRT
<213> ORGANISM: Homo sapiens

<400> SEQUENCE: 3

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 4
<211> LENGTH: 101
<212> TYPE: PRT
<213> ORGANISM: Artificial Sequence
<220> FEATURE:
<223> OTHER INFORMATION: SAD9611_P01_B08

<400> SEQUENCE: 4

```
Gly Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Phe Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 5
<211> LENGTH: 101
<212> TYPE: PRT
<213> ORGANISM: Artificial Sequence
<220> FEATURE:
<223> OTHER INFORMATION: SAD9611_P01_D09

<400> SEQUENCE: 5

Ala Ser Thr Lys Gly Pro His Val Phe Pro Leu Ala Pro Ser Ser Lys
1               5                   10                  15

Ser Thr Ser Gly Gly Thr Ala Ala Leu Gly Cys Leu Val Ile Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 6
<211> LENGTH: 101
<212> TYPE: PRT
<213> ORGANISM: Artificial Sequence
<220> FEATURE:
<223> OTHER INFORMATION: SAD9611_P01_H09

<400> SEQUENCE: 6

Ala Ser Thr Lys Gly Pro Arg Val Phe Pro Leu Ala Pro Ser Ser Lys
1               5                   10                  15

Ser Thr Ser Gly Gly Thr Ala Ala Leu Gly Cys Leu Val Leu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 7
<211> LENGTH: 101
<212> TYPE: PRT
<213> ORGANISM: Artificial Sequence
<220> FEATURE:
<223> OTHER INFORMATION: SAD9611_P01_B09
```

```
<400> SEQUENCE: 7

Ala Ser Thr Lys Gly Pro Ser Val Ala Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ile Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 8
<211> LENGTH: 101
<212> TYPE: PRT
<213> ORGANISM: Artificial Sequence
<220> FEATURE:
<223> OTHER INFORMATION: SAD9611_P01_E08

<400> SEQUENCE: 8

Ala Ser Thr Lys Gly Pro Ser Val Phe Val Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys
            100


<210> SEQ ID NO 9
<211> LENGTH: 101
<212> TYPE: PRT
<213> ORGANISM: Artificial Sequence
<220> FEATURE:
<223> OTHER INFORMATION: SAD9611_P01_H07

<400> SEQUENCE: 9

Ala Ser Thr Lys Gly Pro Ser Val Phe Pro His Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Trp Ser Val Val Thr Val Pro Ser Ser Ser Leu Gly Thr Gln Thr
65                  70                  75                  80
```

Tyr Ile Cys Asn Val Asn His Lys Pro Ser Asn Thr Lys Val Asp Lys
85 90 95

Lys Val Glu Pro Lys
100

<210> SEQ ID NO 10
<211> LENGTH: 101
<212> TYPE: PRT
<213> ORGANISM: Artificial Sequence
<220> FEATURE:
<223> OTHER INFORMATION: SAD9611_P01_F08

<400> SEQUENCE: 10

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Phe Val Ile Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 11
<211> LENGTH: 101
<212> TYPE: PRT
<213> ORGANISM: Artificial Sequence
<220> FEATURE:
<223> OTHER INFORMATION: SAD9611_P01_D07

<400> SEQUENCE: 11

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Ile Val Thr Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Gln
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 12
<211> LENGTH: 101
<212> TYPE: PRT
<213> ORGANISM: Artificial Sequence
<220> FEATURE:
<223> OTHER INFORMATION: SAD9611_P01_C07

<400> SEQUENCE: 12

Ala Ser Thr Lys Gly Pro Ser Val Phe Pro Leu Ala Pro Ser Ser Lys

```
1               5                   10                  15

Ser Thr Ser Gly Gly Thr Ala Ala Leu Gly Cys Leu Val Leu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 13
<211> LENGTH: 101
<212> TYPE: PRT
<213> ORGANISM: Artificial Sequence
<220> FEATURE:
<223> OTHER INFORMATION: SAD9611_P01_E09

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Ser Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 14
<211> LENGTH: 101
<212> TYPE: PRT
<213> ORGANISM: Artificial Sequence
<220> FEATURE:
<223> OTHER INFORMATION: SAD9611_P01_F09

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Leu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Tyr
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys
100

<210> SEQ ID NO 15
<211> LENGTH: 101
<212> TYPE: PRT
<213> ORGANISM: Artificial Sequence
<220> FEATURE:
<223> OTHER INFORMATION: SAD9611_P01_A07

<400> SEQUENCE: 15

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Met Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Gln
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 16
<211> LENGTH: 101
<212> TYPE: PRT
<213> ORGANISM: Artificial Sequence
<220> FEATURE:
<223> OTHER INFORMATION: SAD9611_P01_C09

<400> SEQUENCE: 16

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Val Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gly Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 17
<211> LENGTH: 101
<212> TYPE: PRT
<213> ORGANISM: Artificial Sequence
<220> FEATURE:
<223> OTHER INFORMATION: SAD9611_P01_B07

<400> SEQUENCE: 17

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Glu Ile Tyr

```
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gly Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 18
<211> LENGTH: 101
<212> TYPE: PRT
<213> ORGANISM: Artificial Sequence
<220> FEATURE:
<223> OTHER INFORMATION: SAD9611_P01_G09

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Gly Pro Ala Val Leu Gln Ser Ser Gly Leu Tyr Ser
    50                  55                  60

Leu Phe Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 19
<211> LENGTH: 101
<212> TYPE: PRT
<213> ORGANISM: Artificial Sequence
<220> FEATURE:
<223> OTHER INFORMATION: SAD9611_P01_C08

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Glu Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 20
<211> LENGTH: 101
<212> TYPE: PRT
<213> ORGANISM: Artificial Sequence
<220> FEATURE:
<223> OTHER INFORMATION: SAD9611_P01_G08

<400> SEQUENCE: 20

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Tyr Ser Val Val Thr Val Pro Ser Ile Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 21
<211> LENGTH: 101
<212> TYPE: PRT
<213> ORGANISM: Artificial Sequence
<220> FEATURE:
<223> OTHER INFORMATION: SAD9611_P01_G07

<400> SEQUENCE: 21

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Trp Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 22
<211> LENGTH: 101
<212> TYPE: PRT
<213> ORGANISM: Artificial Sequence
<220> FEATURE:
<223> OTHER INFORMATION: SAD9613_P02_D10

<400> SEQUENCE: 22

Ala Ser Thr Lys Gly Pro Glu Val Phe Pro Leu Ala Pro Ser Ser Lys
1 5 10 15

Ser Thr Ser Gly Gly Thr Ala Ala Leu Gly Cys Leu Val Val Asp Tyr
20 25 30

Phe Pro Glu Pro Val Thr Val Ser Trp Asn Ser Gly Ala Leu Thr Ser

```
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 23
<211> LENGTH: 101
<212> TYPE: PRT
<213> ORGANISM: Artificial Sequence
<220> FEATURE:
<223> OTHER INFORMATION: SAD9613_P02_D12

<400> SEQUENCE: 23

Ala Ser Thr Lys Gly Pro Leu Val Phe Pro Leu Ala Pro Ser Ser Lys
1               5                   10                  15

Ser Thr Ser Gly Gly Thr Ala Ala Leu Gly Cys Leu Val Phe Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 24
<211> LENGTH: 101
<212> TYPE: PRT
<213> ORGANISM: Artificial Sequence
<220> FEATURE:
<223> OTHER INFORMATION: SAD9613_P02_B10

<400> SEQUENCE: 24

Ala Ser Thr Lys Gly Pro Val Val Phe Pro Leu Ala Pro Ser Ser Lys
1               5                   10                  15

Ser Thr Ser Gly Gly Thr Ala Ala Leu Gly Cys Leu Val Tyr Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 25
<211> LENGTH: 101
```

<212> TYPE: PRT
<213> ORGANISM: Artificial Sequence
<220> FEATURE:
<223> OTHER INFORMATION: SAD9613_P02_A11

<400> SEQUENCE: 25

```
Ala Ser Thr Lys Gly Pro Ser Val Thr Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 26
<211> LENGTH: 101
<212> TYPE: PRT
<213> ORGANISM: Artificial Sequence
<220> FEATURE:
<223> OTHER INFORMATION: SAD9613_P02_E12

<400> SEQUENCE: 26

```
Ala Ser Thr Lys Gly Pro Ser Val Phe Leu Leu Ala Pro Ser Ser Lys
1               5                   10                  15

Ser Thr Glu Gly Gly Thr Ala Ala Leu Ser Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 27
<211> LENGTH: 101
<212> TYPE: PRT
<213> ORGANISM: Artificial Sequence
<220> FEATURE:
<223> OTHER INFORMATION: SAD9613_P02_F10

<400> SEQUENCE: 27

```
Ala Ser Thr Lys Gly Pro Ser Val Phe Pro Leu Pro Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
    50                  55                  60

Leu Glu Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 28
<211> LENGTH: 101
<212> TYPE: PRT
<213> ORGANISM: Artificial Sequence
<220> FEATURE:
<223> OTHER INFORMATION: SAD9613_P02_A10

<400> SEQUENCE: 28

Ala Ser Thr Lys Gly Pro Ser Val Phe Pro Leu Ala Pro Ala Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Leu Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 29
<211> LENGTH: 101
<212> TYPE: PRT
<213> ORGANISM: Artificial Sequence
<220> FEATURE:
<223> OTHER INFORMATION: SAD9613_P02_C12

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Ile Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Tyr Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 30
<211> LENGTH: 101
<212> TYPE: PRT
<213> ORGANISM: Artificial Sequence
<220> FEATURE:
```

<223> OTHER INFORMATION: SAD9613_P02_H10

<400> SEQUENCE: 30

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Asn Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Leu Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 31
<211> LENGTH: 101
<212> TYPE: PRT
<213> ORGANISM: Artificial Sequence
<220> FEATURE:
<223> OTHER INFORMATION: SAD9613_P02_G11

<400> SEQUENCE: 31

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Thr Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Phe Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 32
<211> LENGTH: 101
<212> TYPE: PRT
<213> ORGANISM: Artificial Sequence
<220> FEATURE:
<223> OTHER INFORMATION: SAD9613_P02_D11

<400> SEQUENCE: 32

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Val Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

65 70 75 80

Tyr Ile Cys Asn Val Asn His Lys Pro Ser Asn Thr Lys Val Asp Lys
85 90 95

Lys Val Glu Pro Lys
100

<210> SEQ ID NO 33
<211> LENGTH: 101
<212> TYPE: PRT
<213> ORGANISM: Artificial Sequence
<220> FEATURE:
<223> OTHER INFORMATION: SAD9613_P02_E10

<400> SEQUENCE: 33

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Glu Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Glu Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 34
<211> LENGTH: 101
<212> TYPE: PRT
<213> ORGANISM: Artificial Sequence
<220> FEATURE:
<223> OTHER INFORMATION: SAD9613_P02_B12

<400> SEQUENCE: 34

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Leu Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gly Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 35
<211> LENGTH: 101
<212> TYPE: PRT
<213> ORGANISM: Artificial Sequence
<220> FEATURE:
<223> OTHER INFORMATION: SAD9613_P02_F11

<400> SEQUENCE: 35

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Gln Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Glu Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 36
<211> LENGTH: 101
<212> TYPE: PRT
<213> ORGANISM: Artificial Sequence
<220> FEATURE:
<223> OTHER INFORMATION: SAD9613_P02_G10

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Val Asp Tyr
            20                  25                  30

Phe Ala Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 37
<211> LENGTH: 101
<212> TYPE: PRT
<213> ORGANISM: Artificial Sequence
<220> FEATURE:
<223> OTHER INFORMATION: SAD9613_P02_A12

<400> SEQUENCE: 37

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Tyr Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Gly
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
                85                  90                  95

Lys Val Glu Pro Lys
            100


<210> SEQ ID NO 38
<211> LENGTH: 101
<212> TYPE: PRT
<213> ORGANISM: Artificial Sequence
<220> FEATURE:
<223> OTHER INFORMATION: SAD9613_P02_F12

<400> SEQUENCE: 38

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Met Gln Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gly Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 39
<211> LENGTH: 101
<212> TYPE: PRT
<213> ORGANISM: Artificial Sequence
<220> FEATURE:
<223> OTHER INFORMATION: SAD9613_P02_G12

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Tyr Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Ala Ser Ser Gly Leu Tyr Ser
    50                  55                  60

Leu Ser Ser Val Val Thr Val Pro Tyr Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 40
<211> LENGTH: 101
<212> TYPE: PRT
<213> ORGANISM: Artificial Sequence
<220> FEATURE:
<223> OTHER INFORMATION: SAD9613_P02_B11

<400> SEQUENCE: 40

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Tyr Tyr Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Ala Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 41
<211> LENGTH: 101
<212> TYPE: PRT
<213> ORGANISM: Artificial Sequence
<220> FEATURE:
<223> OTHER INFORMATION: SAD9613_P02_H11

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Lys Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 42
<211> LENGTH: 101
<212> TYPE: PRT
<213> ORGANISM: Artificial Sequence
<220> FEATURE:
<223> OTHER INFORMATION: SAD9613_P02_C10

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Gln Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
```

100

<210> SEQ ID NO 43
<211> LENGTH: 101
<212> TYPE: PRT
<213> ORGANISM: Artificial Sequence
<220> FEATURE:
<223> OTHER INFORMATION: SAD9613_P02_E11

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Gln Ser Val Val Thr Val Pro Ser Ser Ser Leu Gly Thr Gln Thr
65                  70                  75                  80

Tyr Ile Cys Asn Val Asn His Lys Pro Ser Asn Thr Arg Val Asp Lys
                85                  90                  95

Lys Val Glu Pro Lys
            100

<210> SEQ ID NO 44
<211> LENGTH: 101
<212> TYPE: PRT
<213> ORGANISM: Artificial Sequence
<220> FEATURE:
<223> OTHER INFORMATION: SAD9610_P01_C03

<400> SEQUENCE: 44

Ala Ser Thr Lys Gly Pro Ser Val Phe Pro Leu Ala Pro Ser Ser Lys
1               5                   10                  15

Ser Thr Ser Gly Gly Ile Ala Ala Leu Gly Cys Leu Val Lys Asp Tyr
            20                  25                  30

Leu Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100

<210> SEQ ID NO 45
<211> LENGTH: 101
<212> TYPE: PRT
<213> ORGANISM: Artificial Sequence
<220> FEATURE:
<223> OTHER INFORMATION: SAD9610_P01_G03

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Val Cys Leu Val Lys Asp Tyr
            20                  25                  30

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 46
<211> LENGTH: 101
<212> TYPE: PRT
<213> ORGANISM: Artificial Sequence
<220> FEATURE:
<223> OTHER INFORMATION: SAD9610_P01_F03

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 47
<211> LENGTH: 101
<212> TYPE: PRT
<213> ORGANISM: Artificial Sequence
<220> FEATURE:
<223> OTHER INFORMATION: SAD9610_P01_H01

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Ala
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 48
<211> LENGTH: 101
<212> TYPE: PRT
<213> ORGANISM: Artificial Sequence
<220> FEATURE:
<223> OTHER INFORMATION: SAD9610_P01_C01

<400> SEQUENCE: 48

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Ser Ser Asn Thr Lys Val Asp Lys
                85                  90                  95

Lys Val Glu Pro Lys
            100
```

<210> SEQ ID NO 49
<211> LENGTH: 101
<212> TYPE: PRT
<213> ORGANISM: Artificial Sequence
<220> FEATURE:
<223> OTHER INFORMATION: SAD9610_P01_A01

<400> SEQUENCE: 49

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Gln Pro Ser Asn Thr Lys Val Asp Lys
                85                  90                  95

Lys Val Glu Pro Lys
            100
```

<210> SEQ ID NO 50
<211> LENGTH: 101
<212> TYPE: PRT
<213> ORGANISM: Artificial Sequence
<220> FEATURE:
<223> OTHER INFORMATION: SAD9610_P01_D02

<400> SEQUENCE: 50

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Cys
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 51
<211> LENGTH: 101
<212> TYPE: PRT
<213> ORGANISM: Artificial Sequence
<220> FEATURE:
<223> OTHER INFORMATION: SAD9610_P01_H03

<400> SEQUENCE: 51

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Ser
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 52
<211> LENGTH: 101
<212> TYPE: PRT
<213> ORGANISM: Artificial Sequence
<220> FEATURE:
<223> OTHER INFORMATION: SAD9610_P01_B03

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Cys
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Gln
            100


<210> SEQ ID NO 53
<211> LENGTH: 101
<212> TYPE: PRT
```

<213> ORGANISM: Artificial Sequence
<220> FEATURE:
<223> OTHER INFORMATION: SAD9610_P01_H02

<400> SEQUENCE: 53

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp His
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys
            100
```

<210> SEQ ID NO 54
<211> LENGTH: 101
<212> TYPE: PRT
<213> ORGANISM: Artificial Sequence
<220> FEATURE:
<223> OTHER INFORMATION: SAD9610_P01_E02

<400> SEQUENCE: 54

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp His
            20                  25                  30

Leu Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 55
<211> LENGTH: 101
<212> TYPE: PRT
<213> ORGANISM: Artificial Sequence
<220> FEATURE:
<223> OTHER INFORMATION: SAD9610_P01_B02

<400> SEQUENCE: 55

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Leu Pro Glu Pro Met Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 56
<211> LENGTH: 101
<212> TYPE: PRT
<213> ORGANISM: Artificial Sequence
<220> FEATURE:
<223> OTHER INFORMATION: SAD9610_P01_A03

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Leu Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 57
<211> LENGTH: 101
<212> TYPE: PRT
<213> ORGANISM: Artificial Sequence
<220> FEATURE:
<223> OTHER INFORMATION: SAD9610_P01_E03

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Ser Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Gly Lys
                85                  90                  95

Lys Val Glu Pro Lys
            100


<210> SEQ ID NO 58
<211> LENGTH: 101
<212> TYPE: PRT
<213> ORGANISM: Artificial Sequence
<220> FEATURE:
<223> OTHER INFORMATION: SAD9610_P01_D01
```

<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Gly Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100

<210> SEQ ID NO 59
<211> LENGTH: 101
<212> TYPE: PRT
<213> ORGANISM: Artificial Sequence
<220> FEATURE:
<223> OTHER INFORMATION: SAD9610_P01_C02

<400> SEQUENCE: 59

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Asn Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100

<210> SEQ ID NO 60
<211> LENGTH: 101
<212> TYPE: PRT
<213> ORGANISM: Artificial Sequence
<220> FEATURE:
<223> OTHER INFORMATION: SAD9610_P01_B01

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Arg Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Lys Val Glu Pro Lys
            100


<210> SEQ ID NO 61
<211> LENGTH: 101
<212> TYPE: PRT
<213> ORGANISM: Artificial Sequence
<220> FEATURE:
<223> OTHER INFORMATION: SAD9610_P01_G01

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Ser Tyr Lys Pro Ser Asn Thr Arg Val Asp Lys
                85                  90                  95

Lys Val Glu Pro Lys
            100


<210> SEQ ID NO 62
<211> LENGTH: 101
<212> TYPE: PRT
<213> ORGANISM: Artificial Sequence
<220> FEATURE:
<223> OTHER INFORMATION: SAD9612_P02_E05

<400> SEQUENCE: 62

Ala Ser Thr Lys Gly Pro Ser Val Leu Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 63
<211> LENGTH: 101
<212> TYPE: PRT
<213> ORGANISM: Artificial Sequence
<220> FEATURE:
<223> OTHER INFORMATION: SAD9612_P02_C04

<400> SEQUENCE: 63
```

```
Ala Ser Thr Lys Gly Pro Ser Val Leu Pro Leu Ala Pro Ser Ser Lys
1               5                   10                  15

Gly Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys
            100


<210> SEQ ID NO 64
<211> LENGTH: 101
<212> TYPE: PRT
<213> ORGANISM: Artificial Sequence
<220> FEATURE:
<223> OTHER INFORMATION: SAD9612_P02_B06

<400> SEQUENCE: 64

Ala Ser Thr Lys Gly Pro Ser Val Phe Pro Leu Ala Pro Ala Ser Lys
1               5                   10                  15

Ser Thr Ser Gly Gly Thr Ala Ala Leu Gly Cys Leu Val Lys Asp Cys
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 65
<211> LENGTH: 101
<212> TYPE: PRT
<213> ORGANISM: Artificial Sequence
<220> FEATURE:
<223> OTHER INFORMATION: SAD9612_P02_F05

<400> SEQUENCE: 65

Ala Ser Thr Lys Gly Pro Ser Val Phe Pro Leu Ala Pro Ser Pro Lys
1               5                   10                  15

Ser Thr Ser Gly Gly Thr Ala Ala Leu Ser Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys
100

<210> SEQ ID NO 66
<211> LENGTH: 101
<212> TYPE: PRT
<213> ORGANISM: Artificial Sequence
<220> FEATURE:
<223> OTHER INFORMATION: SAD9612_P02_D05

<400> SEQUENCE: 66

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Glu Asp Tyr
20 25 30

Phe Pro Glu Pro Val Thr Val Ser Trp Asn Ser Gly Ala Leu Thr Ser
35 40 45

Gly Val His Thr Phe Pro Val Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 67
<211> LENGTH: 101
<212> TYPE: PRT
<213> ORGANISM: Artificial Sequence
<220> FEATURE:
<223> OTHER INFORMATION: SAD9612_P02_C06

<400> SEQUENCE: 67

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Gly Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 68
<211> LENGTH: 101
<212> TYPE: PRT
<213> ORGANISM: Artificial Sequence
<220> FEATURE:
<223> OTHER INFORMATION: SAD9612_P02_C05

<400> SEQUENCE: 68

Ala Ser Thr Lys Gly Pro Ser Val Phe Pro Leu Ala Pro Ser Ser Lys
1 5 10 15

```
Ser Thr Ser Gly Gly Thr Ala Ala Leu Gly Cys Leu Val Lys Asp Tyr
            20                  25                  30

Leu Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 69
<211> LENGTH: 101
<212> TYPE: PRT
<213> ORGANISM: Artificial Sequence
<220> FEATURE:
<223> OTHER INFORMATION: SAD9612_P02_H06

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Leu Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Arg
                85                  90                  95

Lys Val Glu Pro Lys
            100


<210> SEQ ID NO 70
<211> LENGTH: 101
<212> TYPE: PRT
<213> ORGANISM: Artificial Sequence
<220> FEATURE:
<223> OTHER INFORMATION: SAD9612_P02_A06

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Leu Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Ser Val Asn His Lys Pro Ser Asn Thr Lys Val Asp Lys
                85                  90                  95

Lys Val Glu Pro Lys
            100
```

<210> SEQ ID NO 71
<211> LENGTH: 101
<212> TYPE: PRT
<213> ORGANISM: Artificial Sequence
<220> FEATURE:
<223> OTHER INFORMATION: SAD9612_P02_F06

<400> SEQUENCE: 71

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Ser Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 72
<211> LENGTH: 101
<212> TYPE: PRT
<213> ORGANISM: Artificial Sequence
<220> FEATURE:
<223> OTHER INFORMATION: SAD9612_P02_E04

<400> SEQUENCE: 72

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Leu Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 73
<211> LENGTH: 101
<212> TYPE: PRT
<213> ORGANISM: Artificial Sequence
<220> FEATURE:
<223> OTHER INFORMATION: SAD9612_P02_B05

<400> SEQUENCE: 73

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
35 40 45

Gly Val His Thr Phe Pro Ala Val Leu Gln Pro Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 74
<211> LENGTH: 101
<212> TYPE: PRT
<213> ORGANISM: Artificial Sequence
<220> FEATURE:
<223> OTHER INFORMATION: SAD9611_P02_F12

<400> SEQUENCE: 74

Ala Ser Thr Lys Gly Pro Val Val Val Pro Leu Ala Pro Ser Ser Lys
1 5 10 15

Ser Thr Ser Gly Gly Thr Ala Asp Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Ser
65 70 75 80

Tyr Ile Cys Asn Val Asn His Lys Pro Ser Ile Thr Lys Val Asp Lys
85 90 95

Lys Val Glu Pro Lys
100

<210> SEQ ID NO 75
<211> LENGTH: 101
<212> TYPE: PRT
<213> ORGANISM: Artificial Sequence
<220> FEATURE:
<223> OTHER INFORMATION: SAD9611_P02_D12

<400> SEQUENCE: 75

Ala Ser Thr Lys Gly Pro Ser Val Phe Gly Leu Ala Pro Ser Ser Lys
1 5 10 15

Ser Thr Ser Gly Gly Thr Ala Thr Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 76

<211> LENGTH: 101
<212> TYPE: PRT
<213> ORGANISM: Artificial Sequence
<220> FEATURE:
<223> OTHER INFORMATION: SAD9611_P02_D11

<400> SEQUENCE: 76

```
Ala Ser Thr Lys Gly Pro Ser Val Phe Pro Leu Ala His Ser Ser Lys
1               5                   10                  15

Ser Thr Ser Gly Gly Thr Ala Arg Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 77
<211> LENGTH: 101
<212> TYPE: PRT
<213> ORGANISM: Artificial Sequence
<220> FEATURE:
<223> OTHER INFORMATION: SAD9611_P02_C12

<400> SEQUENCE: 77

```
Ala Ser Thr Lys Gly Pro Ser Val Phe Pro Leu Ala Pro Gln Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 78
<211> LENGTH: 101
<212> TYPE: PRT
<213> ORGANISM: Artificial Sequence
<220> FEATURE:
<223> OTHER INFORMATION: SAD9611_P02_H12

<400> SEQUENCE: 78

```
Ala Ser Thr Lys Gly Pro Ser Val Phe Pro Leu Ala Pro Thr Ser Lys
1               5                   10                  15

Ser Thr Ser Gly Gly Thr Ala Arg Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 79
<211> LENGTH: 101
<212> TYPE: PRT
<213> ORGANISM: Artificial Sequence
<220> FEATURE:
<223> OTHER INFORMATION: SAD9611_P02_C10

<400> SEQUENCE: 79

Ala Ser Thr Lys Gly Pro Ser Val Phe Pro Leu Ala Pro Asn Ser Lys
1               5                   10                  15

Ser Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val Phe Thr Asn Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 80
<211> LENGTH: 101
<212> TYPE: PRT
<213> ORGANISM: Artificial Sequence
<220> FEATURE:
<223> OTHER INFORMATION: SAD9611_P02_A11

<400> SEQUENCE: 80

Ala Ser Thr Lys Gly Pro Ser Val Phe Pro Leu Ala Pro Ser Ser Asp
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 81
<211> LENGTH: 101
<212> TYPE: PRT
<213> ORGANISM: Artificial Sequence
```

<220> FEATURE:
<223> OTHER INFORMATION: SAD9611_P02_A10

<400> SEQUENCE: 81

Ala Ser Thr Lys Gly Pro Ser Val Phe Pro Leu Ala Pro Ser Ser Thr
1 5 10 15

Ser Thr Ser Gly Gly Thr Ala Thr Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Pro
100

<210> SEQ ID NO 82
<211> LENGTH: 101
<212> TYPE: PRT
<213> ORGANISM: Artificial Sequence
<220> FEATURE:
<223> OTHER INFORMATION: SAD9611_P02_B11

<400> SEQUENCE: 82

Ala Ser Thr Lys Gly Pro Ser Val Phe Pro Leu Ala Pro Ser Ser Lys
1 5 10 15

Ala Thr Ser Gly Gly Thr Ala Lys Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 83
<211> LENGTH: 101
<212> TYPE: PRT
<213> ORGANISM: Artificial Sequence
<220> FEATURE:
<223> OTHER INFORMATION: SAD9611_P02_G12

<400> SEQUENCE: 83

Ala Ser Thr Lys Gly Pro Ser Val Phe Pro Leu Ala Pro Ser Ser Lys
1 5 10 15

His Thr Ser Gly Gly Thr Ala Arg Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 84
<211> LENGTH: 101
<212> TYPE: PRT
<213> ORGANISM: Artificial Sequence
<220> FEATURE:
<223> OTHER INFORMATION: SAD9611_P02_F11

<400> SEQUENCE: 84

Ala Ser Thr Lys Gly Pro Ser Val Phe Pro Leu Ala Pro Ser Ser Lys
1               5                   10                  15

Ile Thr Ser Gly Gly Thr Ala Arg Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 85
<211> LENGTH: 101
<212> TYPE: PRT
<213> ORGANISM: Artificial Sequence
<220> FEATURE:
<223> OTHER INFORMATION: SAD9611_P02_E10

<400> SEQUENCE: 85

Ala Ser Thr Lys Gly Pro Ser Val Phe Pro Leu Ala Pro Ser Ser Lys
1               5                   10                  15

Pro Thr Ser Gly Gly Thr Ala Arg Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 86
<211> LENGTH: 101
<212> TYPE: PRT
<213> ORGANISM: Artificial Sequence
<220> FEATURE:
<223> OTHER INFORMATION: SAD9611_P02_A12
```

<400> SEQUENCE: 86

```
Ala Ser Thr Lys Gly Pro Ser Val Phe Pro Leu Ala Pro Ser Ser Lys
1               5                   10                  15

Val Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 87
<211> LENGTH: 101
<212> TYPE: PRT
<213> ORGANISM: Artificial Sequence
<220> FEATURE:
<223> OTHER INFORMATION: SAD9611_P02_B10

<400> SEQUENCE: 87

```
Ala Ser Thr Lys Gly Pro Ser Val Phe Pro Leu Ala Pro Ser Ser Lys
1               5                   10                  15

Val Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 88
<211> LENGTH: 101
<212> TYPE: PRT
<213> ORGANISM: Artificial Sequence
<220> FEATURE:
<223> OTHER INFORMATION: SAD9611_P02_C11

<400> SEQUENCE: 88

```
Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys
            100


<210> SEQ ID NO 89
<211> LENGTH: 101
<212> TYPE: PRT
<213> ORGANISM: Artificial Sequence
<220> FEATURE:
<223> OTHER INFORMATION: SAD9611_P02_H10

<400> SEQUENCE: 89

Ala Ser Thr Lys Gly Pro Ser Val Phe Pro Leu Ala Pro Ser Ser Lys
1               5                   10                  15

Ser Thr Ser Gly Gly Thr Ala Arg Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 90
<211> LENGTH: 101
<212> TYPE: PRT
<213> ORGANISM: Artificial Sequence
<220> FEATURE:
<223> OTHER INFORMATION: SAD9611_P02_B12

<400> SEQUENCE: 90

Ala Ser Thr Lys Gly Pro Ser Val Phe Pro Leu Ala Pro Ser Ser Lys
1               5                   10                  15

Ser Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Arg Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 91
<211> LENGTH: 101
<212> TYPE: PRT
<213> ORGANISM: Artificial Sequence
<220> FEATURE:
<223> OTHER INFORMATION: SAD9611_P02_G10

<400> SEQUENCE: 91

Ala Ser Thr Lys Gly Pro Ser Val Phe Pro Leu Ala Pro Ser Ser Lys
```

```
1               5                   10                  15

Ser Thr Ser Gly Gly Thr Ala Arg Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Leu Val Asp Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 92
<211> LENGTH: 101
<212> TYPE: PRT
<213> ORGANISM: Artificial Sequence
<220> FEATURE:
<223> OTHER INFORMATION: SAD9611_P02_E11

<400> SEQUENCE: 92

Ala Ser Thr Lys Gly Pro Ser Val Phe Pro Leu Ala Pro Ser Ser Lys
1               5                   10                  15

Ser Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Ser Val Glu Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 93
<211> LENGTH: 101
<212> TYPE: PRT
<213> ORGANISM: Artificial Sequence
<220> FEATURE:
<223> OTHER INFORMATION: SAD9611_P02_D10

<400> SEQUENCE: 93

Ala Ser Thr Lys Gly Pro Ser Val Phe Pro Leu Ala Pro Ser Ser Lys
1               5                   10                  15

Ser Thr Ser Gly Gly Thr Ala Val Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Ser Val Tyr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys
100

<210> SEQ ID NO 94
<211> LENGTH: 101
<212> TYPE: PRT
<213> ORGANISM: Artificial Sequence
<220> FEATURE:
<223> OTHER INFORMATION: SAD9613_P01_F07

<400> SEQUENCE: 94

Ala Arg Thr Lys Gly Pro Ser Val Phe Pro Leu Ala Pro Ser Ser Lys
1 5 10 15

Ser Thr Ser Gly Gly Thr Ala Lys Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 95
<211> LENGTH: 101
<212> TYPE: PRT
<213> ORGANISM: Artificial Sequence
<220> FEATURE:
<223> OTHER INFORMATION: SAD9613_P01_B07

<400> SEQUENCE: 95

Ala Ser Thr Lys Gly Pro Ser Val Phe Pro Leu Ala Ser Ser Ser Lys
1 5 10 15

Ser Thr Ser Gly Gly Thr Ala Thr Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Thr Val Ser Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 96
<211> LENGTH: 101
<212> TYPE: PRT
<213> ORGANISM: Artificial Sequence
<220> FEATURE:
<223> OTHER INFORMATION: SAD9613_P01_A09

<400> SEQUENCE: 96

Ala Ser Thr Lys Gly Pro Ser Val Phe Pro Leu Ala Pro Asn Ser Lys
1 5 10 15

Ser Thr Ser Gly Gly Thr Ala Asp Leu Gly Cys Leu Val Lys Asp Tyr 20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 97
<211> LENGTH: 101
<212> TYPE: PRT
<213> ORGANISM: Artificial Sequence
<220> FEATURE:
<223> OTHER INFORMATION: SAD9613_P01_G08

<400> SEQUENCE: 97

Ala Ser Thr Lys Gly Pro Ser Val Phe Pro Leu Ala Pro Arg Ser Lys
1 5 10 15

Ser Thr Ser Gly Gly Thr Ala Met Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 98
<211> LENGTH: 101
<212> TYPE: PRT
<213> ORGANISM: Artificial Sequence
<220> FEATURE:
<223> OTHER INFORMATION: SAD9613_P01_G07

<400> SEQUENCE: 98

Ala Ser Thr Lys Gly Pro Ser Val Phe Pro Leu Ala Pro Thr Ser Lys
1 5 10 15

Ser Thr Ser Gly Gly Thr Ala Glu Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 99
<211> LENGTH: 101
<212> TYPE: PRT
<213> ORGANISM: Artificial Sequence
<220> FEATURE:
<223> OTHER INFORMATION: SAD9613_P01_B09

<400> SEQUENCE: 99

```
Ala Ser Thr Lys Gly Pro Ser Val Phe Pro Leu Ala Pro Asp Ser Leu
1               5                   10                  15

Asn Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 100
<211> LENGTH: 101
<212> TYPE: PRT
<213> ORGANISM: Artificial Sequence
<220> FEATURE:
<223> OTHER INFORMATION: SAD9613_P01_E07

<400> SEQUENCE: 100

```
Ala Ser Thr Lys Gly Pro Ser Val Phe Pro Leu Ala Pro Asp Ser Lys
1               5                   10                  15

Ser Thr Ser Gly Gly Thr Ala Arg Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Asp Ser Ser Gly Leu Tyr Val
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 101
<211> LENGTH: 101
<212> TYPE: PRT
<213> ORGANISM: Artificial Sequence
<220> FEATURE:
<223> OTHER INFORMATION: SAD9613_P01_A08

<400> SEQUENCE: 101

```
Ala Ser Thr Lys Gly Pro Ser Val Phe Pro Leu Ala Pro Ser Ser Glu
1               5                   10                  15

Ser Thr Ser Gly Gly Thr Ala Arg Leu Gly Cys Leu Val Lys Asp Tyr
            20                  25                  30

Phe Pro Glu Pro Val Thr Val Ser Trp Asn Ser Gly Ala Leu Thr Ser
```

```
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 102
<211> LENGTH: 101
<212> TYPE: PRT
<213> ORGANISM: Artificial Sequence
<220> FEATURE:
<223> OTHER INFORMATION: SAD9613_P01_H09

<400> SEQUENCE: 102

Ala Ser Thr Lys Gly Pro Ser Val Phe Pro Leu Ala Pro Ser Ser Pro
1               5                   10                  15

Ser Thr Ser Gly Gly Ala Ala Lys Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 103
<211> LENGTH: 101
<212> TYPE: PRT
<213> ORGANISM: Artificial Sequence
<220> FEATURE:
<223> OTHER INFORMATION: SAD9613_P01_D07

<400> SEQUENCE: 103

Ala Ser Thr Lys Gly Pro Ser Val Phe Pro Leu Ala Pro Ser Ser Lys
1               5                   10                  15

Leu Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 104
<211> LENGTH: 101
```

<212> TYPE: PRT
<213> ORGANISM: Artificial Sequence
<220> FEATURE:
<223> OTHER INFORMATION: SAD9613_P01_A07

<400> SEQUENCE: 104

```
Ala Ser Thr Lys Gly Pro Ser Val Phe Pro Leu Ala Pro Ser Ser Lys
1               5                   10                  15

Asn Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 105
<211> LENGTH: 101
<212> TYPE: PRT
<213> ORGANISM: Artificial Sequence
<220> FEATURE:
<223> OTHER INFORMATION: SAD9613_P01_H08

<400> SEQUENCE: 105

```
Ala Ser Thr Lys Gly Pro Ser Val Phe Pro Leu Ala Pro Ser Ser Lys
1               5                   10                  15

Pro Thr Ser Gly Gly Thr Ala Lys Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 106
<211> LENGTH: 101
<212> TYPE: PRT
<213> ORGANISM: Artificial Sequence
<220> FEATURE:
<223> OTHER INFORMATION: SAD9613_P01_F08

<400> SEQUENCE: 106

```
Ala Ser Thr Lys Gly Pro Ser Val Phe Pro Leu Ala Pro Ser Ser Lys
1               5                   10                  15

Val Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 107
<211> LENGTH: 101
<212> TYPE: PRT
<213> ORGANISM: Artificial Sequence
<220> FEATURE:
<223> OTHER INFORMATION: SAD9613_P01_D08

<400> SEQUENCE: 107

Ala Ser Thr Lys Gly Pro Ser Val Phe Pro Leu Ala Pro Ser Ser Lys
1               5                   10                  15

Ser Thr Ser Gly Gly Thr Ala Lys Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 108
<211> LENGTH: 101
<212> TYPE: PRT
<213> ORGANISM: Artificial Sequence
<220> FEATURE:
<223> OTHER INFORMATION: SAD9613_P01_E09

<400> SEQUENCE: 108

Ala Ser Thr Lys Gly Pro Ser Val Phe Pro Leu Ala Pro Ser Ser Lys
1               5                   10                  15

Ser Thr Ser Gly Gly Thr Ala Lys Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Thr Val Glu Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 109
<211> LENGTH: 101
<212> TYPE: PRT
<213> ORGANISM: Artificial Sequence
<220> FEATURE:
```

<223> OTHER INFORMATION: SAD9613_P01_C09

<400> SEQUENCE: 109

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val Val Thr Thr Asn Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 110
<211> LENGTH: 101
<212> TYPE: PRT
<213> ORGANISM: Artificial Sequence
<220> FEATURE:
<223> OTHER INFORMATION: SAD9613_P01_H07

<400> SEQUENCE: 110

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Leu Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 111
<211> LENGTH: 101
<212> TYPE: PRT
<213> ORGANISM: Artificial Sequence
<220> FEATURE:
<223> OTHER INFORMATION: SAD9610_P02_F04

<400> SEQUENCE: 111

Ala Ser Thr Lys Gly Pro Ser Val Phe Pro Leu Ala Pro Ser Ser Lys
1 5 10 15

Ser Thr Ser Gly Gly Thr Val Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr

```
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 112
<211> LENGTH: 101
<212> TYPE: PRT
<213> ORGANISM: Artificial Sequence
<220> FEATURE:
<223> OTHER INFORMATION: SAD9610_P02_B04

<400> SEQUENCE: 112

Ala Ser Thr Lys Gly Pro Ser Val Phe Pro Leu Ala Pro Ser Ser Lys
1               5                   10                  15

Ser Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 113
<211> LENGTH: 101
<212> TYPE: PRT
<213> ORGANISM: Artificial Sequence
<220> FEATURE:
<223> OTHER INFORMATION: SAD9610_P02_G06

<400> SEQUENCE: 113

Ala Ser Thr Lys Gly Pro Ser Val Phe Pro Leu Ala Pro Ser Ser Lys
1               5                   10                  15

Ser Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asp His Lys Pro Ser Asn Thr Lys Val Asp Lys
                85                  90                  95

Lys Val Glu Pro Lys
            100


<210> SEQ ID NO 114
<211> LENGTH: 101
<212> TYPE: PRT
<213> ORGANISM: Artificial Sequence
<220> FEATURE:
<223> OTHER INFORMATION: SAD9610_P02_G04

<400> SEQUENCE: 114
```

```
Ala Ser Thr Lys Gly Pro Ser Val Phe Pro Leu Ala Pro Ser Ser Lys
1               5                   10                  15

Ser Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Ala Asp Lys
                85                  90                  95

Lys Val Glu Pro Lys
            100


<210> SEQ ID NO 115
<211> LENGTH: 101
<212> TYPE: PRT
<213> ORGANISM: Artificial Sequence
<220> FEATURE:
<223> OTHER INFORMATION: SAD9610_P02_C06

<400> SEQUENCE: 115

Ala Ser Thr Lys Gly Pro Ser Val Phe Pro Leu Ala Pro Ser Ser Lys
1               5                   10                  15

Ser Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Gly Pro Lys
            100


<210> SEQ ID NO 116
<211> LENGTH: 101
<212> TYPE: PRT
<213> ORGANISM: Artificial Sequence
<220> FEATURE:
<223> OTHER INFORMATION: SAD9610_P02_G05

<400> SEQUENCE: 116

Ala Ser Thr Lys Gly Pro Ser Val Phe Pro Leu Ala Pro Ser Ser Lys
1               5                   10                  15

Ser Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Met Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

85 90 95

Lys Val Glu Pro Lys
100

<210> SEQ ID NO 117
<211> LENGTH: 101
<212> TYPE: PRT
<213> ORGANISM: Artificial Sequence
<220> FEATURE:
<223> OTHER INFORMATION: SAD9610_P02_C04

<400> SEQUENCE: 117

Ala Ser Thr Lys Gly Pro Ser Val Phe Pro Leu Ala Pro Ser Ser Lys
1 5 10 15

Ser Thr Ser Gly Gly Thr Ala Val Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asn Lys
85 90 95

Lys Val Glu Pro Lys
100

<210> SEQ ID NO 118
<211> LENGTH: 101
<212> TYPE: PRT
<213> ORGANISM: Artificial Sequence
<220> FEATURE:
<223> OTHER INFORMATION: SAD9610_P02_E05

<400> SEQUENCE: 118

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Thr
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 119
<211> LENGTH: 101
<212> TYPE: PRT
<213> ORGANISM: Artificial Sequence
<220> FEATURE:
<223> OTHER INFORMATION: SAD9612_P01_A01

<400> SEQUENCE: 119

Ala Ser Thr Lys Gly Pro Ser Val Phe Pro Leu Ala Pro Ser Ser Lys
1 5 10 15

```
Ser Thr Ser Gly Gly Thr Pro Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 120
<211> LENGTH: 101
<212> TYPE: PRT
<213> ORGANISM: Artificial Sequence
<220> FEATURE:
<223> OTHER INFORMATION: SAD9612_P01_G01

<400> SEQUENCE: 120

Ala Ser Thr Lys Gly Pro Ser Val Phe Pro Leu Ala Pro Ser Ser Lys
1               5                   10                  15

Ser Thr Ser Gly Gly Thr Val Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Gly Pro Lys
            100


<210> SEQ ID NO 121
<211> LENGTH: 101
<212> TYPE: PRT
<213> ORGANISM: Artificial Sequence
<220> FEATURE:
<223> OTHER INFORMATION: SAD9612_P01_H02

<400> SEQUENCE: 121

Ala Ser Thr Lys Gly Pro Ser Val Phe Pro Leu Ala Pro Ser Ser Lys
1               5                   10                  15

Ser Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys
```

100

<210> SEQ ID NO 122
<211> LENGTH: 101
<212> TYPE: PRT
<213> ORGANISM: Artificial Sequence
<220> FEATURE:
<223> OTHER INFORMATION: SAD9612_P01_D03

<400> SEQUENCE: 122

Ala Ser Thr Lys Gly Pro Ser Val Phe Pro Leu Ala Pro Ser Ser Lys
1 5 10 15

Ser Thr Ser Gly Gly Thr Ala Thr Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys
100

<210> SEQ ID NO 123
<211> LENGTH: 101
<212> TYPE: PRT
<213> ORGANISM: Artificial Sequence
<220> FEATURE:
<223> OTHER INFORMATION: SAD9612_P01_E01

<400> SEQUENCE: 123

Ala Ser Thr Lys Gly Pro Ser Val Phe Pro Leu Ala Pro Ser Ser Lys
1 5 10 15

Ser Thr Ser Gly Gly Thr Ala Thr Leu Gly Cys Leu Val Lys Asp Tyr
20 25 30

Phe Pro Gly Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 124
<211> LENGTH: 101
<212> TYPE: PRT
<213> ORGANISM: Artificial Sequence
<220> FEATURE:
<223> OTHER INFORMATION: SAD9612_P01_H03

<400> SEQUENCE: 124

Ala Ser Thr Lys Gly Pro Ser Val Phe Pro Leu Ala Pro Ser Ser Lys
1 5 10 15

Ser Thr Ser Gly Gly Thr Ala Val Leu Gly Cys Leu Val Lys Asp Tyr
20 25 30

```
Phe Pro Gly Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 125
<211> LENGTH: 101
<212> TYPE: PRT
<213> ORGANISM: Artificial Sequence
<220> FEATURE:
<223> OTHER INFORMATION: SAD9612_P01_F02

<400> SEQUENCE: 125

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Gly Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 126
<211> LENGTH: 101
<212> TYPE: PRT
<213> ORGANISM: Artificial Sequence
<220> FEATURE:
<223> OTHER INFORMATION: S 4 AD9612_P01_A02

<400> SEQUENCE: 126

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Val Ser Thr Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 127
<211> LENGTH: 101
<212> TYPE: PRT
<213> ORGANISM: Artificial Sequence
<220> FEATURE:
<223> OTHER INFORMATION: SAD9612_P01_C01

<400> SEQUENCE: 127

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Thr Val Asp Lys
85 90 95

Lys Val Glu Pro Lys
100

<210> SEQ ID NO 128
<211> LENGTH: 101
<212> TYPE: PRT
<213> ORGANISM: Artificial Sequence
<220> FEATURE:
<223> OTHER INFORMATION: SAD10791_P01_F07

<400> SEQUENCE: 128

Ala Ser Thr Lys Gly Pro Ser Val Phe Pro Leu Ala Pro Ser Ser Lys
1 5 10 15

Ser Thr Ser Gly Gly Thr Tyr Asp Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 129
<211> LENGTH: 101
<212> TYPE: PRT
<213> ORGANISM: Artificial Sequence
<220> FEATURE:
<223> OTHER INFORMATION: SAD10791_P01_C07

<400> SEQUENCE: 129

Ala Ser Thr Lys Gly Pro Ser Val Phe Pro Leu Ala Pro Ser Ser Lys
1 5 10 15

Ser Thr Ser Gly Gly Thr Lys Asp Leu Gly Cys Leu Val Lys Asp Tyr
20 25 30

Phe Pro Glu Pro Val Thr Val Ser Trp Asn Ser Gly Ala Leu Thr Ser
35 40 45

```
Asp Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 130
<211> LENGTH: 101
<212> TYPE: PRT
<213> ORGANISM: Artificial Sequence
<220> FEATURE:
<223> OTHER INFORMATION: SAD10791_P01_A07

<400> SEQUENCE: 130

Ala Ser Thr Lys Gly Pro Ser Val Phe Pro Leu Ala Pro Ser Ser Lys
1               5                   10                  15

Ser Thr Ser Gly Gly Thr Ser Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Ser Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 131
<211> LENGTH: 101
<212> TYPE: PRT
<213> ORGANISM: Artificial Sequence
<220> FEATURE:
<223> OTHER INFORMATION: SAD10791_P02_G08

<400> SEQUENCE: 131

Ala Ser Thr Lys Gly Pro Ser Val Phe Pro Leu Ala Pro Ser Ser Lys
1               5                   10                  15

Ser Thr Ser Gly Gly Thr Trp Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 132
<211> LENGTH: 100
<212> TYPE: PRT
```

<213> ORGANISM: Artificial Sequence
<220> FEATURE:
<223> OTHER INFORMATION: SAD10791_P02_D08

<400> SEQUENCE: 132

Ala Ser Thr Lys Gly Pro Ser Val Phe Pro Leu Ala Pro Ser Ser Lys
1 5 10 15

Thr Ser Gly Gly Thr Arg Asp Leu Gly Cys Leu Val Lys Asp Tyr Phe
20 25 30

Pro Glu Pro Val Thr Val Ser Trp Asn Ser Gly Ala Leu Thr Ser Gly
35 40 45

Val His Thr Phe Pro Ala Val Leu Gln Ser Ser Gly Leu Tyr Ser Leu
50 55 60

Ser Ser Val Val Thr Val Pro Ser Ser Ser Leu Gly Thr Gln Thr Tyr
65 70 75 80

Ile Cys Asn Val Asn His Lys Pro Ser Asn Thr Lys Val Asp Lys Lys
85 90 95

Val Glu Pro Asn
100

<210> SEQ ID NO 133
<211> LENGTH: 101
<212> TYPE: PRT
<213> ORGANISM: Artificial Sequence
<220> FEATURE:
<223> OTHER INFORMATION: SAD10791_P02_F07

<400> SEQUENCE: 133

Ala Ser Thr Lys Gly Pro Ser Val Phe Pro Leu Ala Pro Ser Ser Lys
1 5 10 15

Ser Thr Ser Gly Gly Thr Leu Asp Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 134
<211> LENGTH: 101
<212> TYPE: PRT
<213> ORGANISM: Artificial Sequence
<220> FEATURE:
<223> OTHER INFORMATION: A140I; A141D

<400> SEQUENCE: 134

Ala Ser Thr Lys Gly Pro Ser Val Phe Pro Leu Ala Pro Ser Ser Lys
1 5 10 15

Ser Thr Ser Gly Gly Thr Ile Asp Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 135
<211> LENGTH: 101
<212> TYPE: PRT
<213> ORGANISM: Artificial Sequence
<220> FEATURE:
<223> OTHER INFORMATION: A140V; A141D

<400> SEQUENCE: 135

Ala Ser Thr Lys Gly Pro Ser Val Phe Pro Leu Ala Pro Ser Ser Lys
1               5                   10                  15

Ser Thr Ser Gly Gly Thr Val Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 136
<211> LENGTH: 101
<212> TYPE: PRT
<213> ORGANISM: Artificial Sequence
<220> FEATURE:
<223> OTHER INFORMATION: S183Y

<400> SEQUENCE: 136

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Tyr Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 137
<211> LENGTH: 101
<212> TYPE: PRT
<213> ORGANISM: Artificial Sequence
<220> FEATURE:
<223> OTHER INFORMATION: K147F; S183R
```

<400> SEQUENCE: 137

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Phe Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Arg Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 138
<211> LENGTH: 101
<212> TYPE: PRT
<213> ORGANISM: Artificial Sequence
<220> FEATURE:
<223> OTHER INFORMATION: K147F; S183K

<400> SEQUENCE: 138

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Phe Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Lys Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 139
<211> LENGTH: 101
<212> TYPE: PRT
<213> ORGANISM: Artificial Sequence
<220> FEATURE:
<223> OTHER INFORMATION: K147F S183Y

<400> SEQUENCE: 139

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Phe Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Tyr Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys
            100


<210> SEQ ID NO 140
<211> LENGTH: 101
<212> TYPE: PRT
<213> ORGANISM: Artificial Sequence
<220> FEATURE:
<223> OTHER INFORMATION: A141D

<400> SEQUENCE: 140

Ala Ser Thr Lys Gly Pro Ser Val Phe Pro Leu Ala Pro Ser Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 141
<211> LENGTH: 101
<212> TYPE: PRT
<213> ORGANISM: Artificial Sequence
<220> FEATURE:
<223> OTHER INFORMATION: A141D; S181K

<400> SEQUENCE: 141

Ala Ser Thr Lys Gly Pro Ser Val Phe Pro Leu Ala Pro Ser Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Lys
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 142
<211> LENGTH: 101
<212> TYPE: PRT
<213> ORGANISM: Artificial Sequence
<220> FEATURE:
<223> OTHER INFORMATION: A141D; S181K; K218A

<400> SEQUENCE: 142
```

```
Ala Ser Thr Lys Gly Pro Ser Val Phe Pro Leu Ala Pro Ser Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Lys
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Ala
            100


<210> SEQ ID NO 143
<211> LENGTH: 101
<212> TYPE: PRT
<213> ORGANISM: Artificial Sequence
<220> FEATURE:
<223> OTHER INFORMATION: A141D; S181K; K218P

<400> SEQUENCE: 143

Ala Ser Thr Lys Gly Pro Ser Val Phe Pro Leu Ala Pro Ser Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Lys
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Pro
            100


<210> SEQ ID NO 144
<211> LENGTH: 101
<212> TYPE: PRT
<213> ORGANISM: Artificial Sequence
<220> FEATURE:
<223> OTHER INFORMATION: A141E

<400> SEQUENCE: 144

Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys
            100


<210> SEQ ID NO 145
<211> LENGTH: 101
<212> TYPE: PRT
<213> ORGANISM: Artificial Sequence
<220> FEATURE:
<223> OTHER INFORMATION: A141E; S181K

<400> SEQUENCE: 145

Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Lys
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 146
<211> LENGTH: 101
<212> TYPE: PRT
<213> ORGANISM: Artificial Sequence
<220> FEATURE:
<223> OTHER INFORMATION: A141K

<400> SEQUENCE: 146

Ala Ser Thr Lys Gly Pro Ser Val Phe Pro Leu Ala Pro Ser Ser Lys
1               5                   10                  15

Ser Thr Ser Gly Gly Thr Ala Lys Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 147
<211> LENGTH: 101
<212> TYPE: PRT
<213> ORGANISM: Artificial Sequence
<220> FEATURE:
<223> OTHER INFORMATION: A141K; S181K

<400> SEQUENCE: 147

Ala Ser Thr Lys Gly Pro Ser Val Phe Pro Leu Ala Pro Ser Ser Lys
1               5                   10                  15
```

```
Ser Thr Ser Gly Gly Thr Ala Lys Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Lys
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 148
<211> LENGTH: 101
<212> TYPE: PRT
<213> ORGANISM: Artificial Sequence
<220> FEATURE:
<223> OTHER INFORMATION: A141K; S181K; K218E

<400> SEQUENCE: 148

Ala Ser Thr Lys Gly Pro Ser Val Phe Pro Leu Ala Pro Ser Ser Lys
1               5                   10                  15

Ser Thr Ser Gly Gly Thr Ala Lys Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Lys
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Glu
            100


<210> SEQ ID NO 149
<211> LENGTH: 101
<212> TYPE: PRT
<213> ORGANISM: Artificial Sequence
<220> FEATURE:
<223> OTHER INFORMATION: A141K; S181K; K218P

<400> SEQUENCE: 149

Ala Ser Thr Lys Gly Pro Ser Val Phe Pro Leu Ala Pro Ser Ser Lys
1               5                   10                  15

Ser Thr Ser Gly Gly Thr Ala Lys Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Lys
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Pro
            100
```

<210> SEQ ID NO 150
<211> LENGTH: 101
<212> TYPE: PRT
<213> ORGANISM: Artificial Sequence
<220> FEATURE:
<223> OTHER INFORMATION: P127G; G138R; A141T; F170G; S176R; S181L

<400> SEQUENCE: 150

```
Ala Ser Thr Lys Gly Pro Ser Val Phe Gly Leu Ala Pro Ser Ser Lys
1               5                   10                  15

Ser Thr Ser Gly Arg Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Gly Pro Ala Val Leu Gln Arg Ser Gly Leu Tyr Leu
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 151
<211> LENGTH: 101
<212> TYPE: PRT
<213> ORGANISM: Artificial Sequence
<220> FEATURE:
<223> OTHER INFORMATION: S131R; A141E; S181K

<400> SEQUENCE: 151

```
Ala Ser Thr Lys Gly Pro Ser Val Phe Pro Leu Ala Pro Arg Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Lys
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 152
<211> LENGTH: 101
<212> TYPE: PRT
<213> ORGANISM: Artificial Sequence
<220> FEATURE:
<223> OTHER INFORMATION: S134R; A141E; P171D; S181V; V185R

<400> SEQUENCE: 152

```
Ala Ser Thr Lys Gly Pro Ser Val Phe Pro Leu Ala Pro Ser Ser Lys
1               5                   10                  15

Arg Thr Ser Gly Gly Thr Ala Glu Leu Gly Cys Leu Val Lys Asp Tyr
            20                  25                  30
```

```
Phe Pro Glu Pro Val Thr Val Ser Trp Asn Ser Gly Ala Leu Thr Ser
        35                  40                  45

Gly Val His Thr Phe Asp Ala Val Leu Gln Ser Ser Gly Leu Tyr Val
    50                  55                  60

Leu Ser Ser Arg Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 153
<211> LENGTH: 101
<212> TYPE: PRT
<213> ORGANISM: Artificial Sequence
<220> FEATURE:
<223> OTHER INFORMATION: A141D; H168I; F170G; T187R

<400> SEQUENCE: 153

Ala Ser Thr Lys Gly Pro Ser Val Phe Pro Leu Ala Pro Ser Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val Ile Thr Gly Pro Ala Val Leu Gln Ser Ser Gly Leu Tyr Ser
    50                  55                  60

Leu Ser Ser Val Val Arg Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 154
<211> LENGTH: 101
<212> TYPE: PRT
<213> ORGANISM: Artificial Sequence
<220> FEATURE:
<223> OTHER INFORMATION: A141E; F170E; S181L; T187R

<400> SEQUENCE: 154

Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Glu Pro Ala Val Leu Gln Ser Ser Gly Leu Tyr Leu
    50                  55                  60

Leu Ser Ser Val Val Arg Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 155
```

```
<211> LENGTH: 101
<212> TYPE: PRT
<213> ORGANISM: Artificial Sequence
<220> FEATURE:
<223> OTHER INFORMATION: A141E; F170E; S181V; T187R

<400> SEQUENCE: 155

Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Glu Pro Ala Val Leu Gln Ser Ser Gly Leu Tyr Val
    50                  55                  60

Leu Ser Ser Val Val Arg Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 156
<211> LENGTH: 101
<212> TYPE: PRT
<213> ORGANISM: Artificial Sequence
<220> FEATURE:
<223> OTHER INFORMATION: A141E; P171D; V185R; K218F

<400> SEQUENCE: 156

Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Asp Ala Val Leu Gln Ser Ser Gly Leu Tyr Ser
    50                  55                  60

Leu Ser Ser Arg Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Phe
            100


<210> SEQ ID NO 157
<211> LENGTH: 101
<212> TYPE: PRT
<213> ORGANISM: Artificial Sequence
<220> FEATURE:
<223> OTHER INFORMATION: A141E; P171D; V185R

<400> SEQUENCE: 157

Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Asp Ala Val Leu Gln Ser Ser Gly Leu Tyr Ser
50 55 60

Leu Ser Ser Arg Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 158
<211> LENGTH: 101
<212> TYPE: PRT
<213> ORGANISM: Artificial Sequence
<220> FEATURE:
<223> OTHER INFORMATION: A141E; P171E; S181A

<400> SEQUENCE: 158

Ala Ser Thr Lys Gly Pro Ser Val Phe Pro Leu Ala Pro Ser Ser Lys
1 5 10 15

Ser Thr Ser Gly Gly Thr Ala Glu Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Glu Ala Val Leu Gln Ser Ser Gly Leu Tyr Ala
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 159
<211> LENGTH: 101
<212> TYPE: PRT
<213> ORGANISM: Artificial Sequence
<220> FEATURE:
<223> OTHER INFORMATION: A141E; P171E; V185R

<400> SEQUENCE: 159

Ala Ser Thr Lys Gly Pro Ser Val Phe Pro Leu Ala Pro Ser Ser Lys
1 5 10 15

Ser Thr Ser Gly Gly Thr Ala Glu Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Glu Ala Val Leu Gln Ser Ser Gly Leu Tyr Ser
50 55 60

Leu Ser Ser Arg Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 160
<211> LENGTH: 101
<212> TYPE: PRT
<213> ORGANISM: Artificial Sequence

<220> FEATURE:
<223> OTHER INFORMATION: A141E; P171E; S181T; V185R

<400> SEQUENCE: 160

```
Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Glu Ala Val Leu Gln Ser Ser Gly Leu Tyr Thr
    50                  55                  60

Leu Ser Ser Arg Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 161
<211> LENGTH: 101
<212> TYPE: PRT
<213> ORGANISM: Artificial Sequence
<220> FEATURE:
<223> OTHER INFORMATION: A141E; P171E; S181V

<400> SEQUENCE: 161

```
Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Glu Ala Val Leu Gln Ser Ser Gly Leu Tyr Val
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 162
<211> LENGTH: 101
<212> TYPE: PRT
<213> ORGANISM: Artificial Sequence
<220> FEATURE:
<223> OTHER INFORMATION: A141E; P171G; V185R; T187R

<400> SEQUENCE: 162

```
Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Gly Ala Val Leu Gln Ser Ser Gly Leu Tyr Ser
    50                  55                  60
```

Leu Ser Ser Arg Val Arg Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 163
<211> LENGTH: 101
<212> TYPE: PRT
<213> ORGANISM: Artificial Sequence
<220> FEATURE:
<223> OTHER INFORMATION: A141E; V185R; T187R

<400> SEQUENCE: 163

Ala Ser Thr Lys Gly Pro Ser Val Phe Pro Leu Ala Pro Ser Ser Lys
1 5 10 15

Ser Thr Ser Gly Gly Thr Ala Glu Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Arg Val Arg Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 164
<211> LENGTH: 101
<212> TYPE: PRT
<213> ORGANISM: Artificial Sequence
<220> FEATURE:
<223> OTHER INFORMATION: A141E; P171S; S181K

<400> SEQUENCE: 164

Ala Ser Thr Lys Gly Pro Ser Val Phe Pro Leu Ala Pro Ser Ser Lys
1 5 10 15

Ser Thr Ser Gly Gly Thr Ala Glu Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Ser Ala Val Leu Gln Ser Ser Gly Leu Tyr Lys
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 165
<211> LENGTH: 101
<212> TYPE: PRT
<213> ORGANISM: Artificial Sequence
<220> FEATURE:
<223> OTHER INFORMATION: A141E; F170G; Q175M; S181V; S184R; T187R

<400> SEQUENCE: 165

Ala Ser Thr Lys Gly Pro Ser Val Phe Pro Leu Ala Pro Ser Ser Lys
1 5 10 15

Ser Thr Ser Gly Gly Thr Ala Glu Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Gly Pro Ala Val Leu Met Ser Ser Gly Leu Tyr Val
50 55 60

Leu Ser Arg Val Val Arg Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 166
<211> LENGTH: 101
<212> TYPE: PRT
<213> ORGANISM: Artificial Sequence
<220> FEATURE:
<223> OTHER INFORMATION: A141E; F170R; V173H; S181V

<400> SEQUENCE: 166

Ala Ser Thr Lys Gly Pro Ser Val Phe Pro Leu Ala Pro Ser Ser Lys
1 5 10 15

Ser Thr Ser Gly Gly Thr Ala Glu Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Arg Pro Ala His Leu Gln Ser Ser Gly Leu Tyr Val
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 167
<211> LENGTH: 101
<212> TYPE: PRT
<213> ORGANISM: Artificial Sequence
<220> FEATURE:
<223> OTHER INFORMATION: A141E; F170S; P171A; S181V

<400> SEQUENCE: 167

Ala Ser Thr Lys Gly Pro Ser Val Phe Pro Leu Ala Pro Ser Ser Lys
1 5 10 15

Ser Thr Ser Gly Gly Thr Ala Glu Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Ser Ala Ala Val Leu Gln Ser Ser Gly Leu Tyr Val
50 55 60

Leu Ser Ser Val Val Thr Val Pro Ser Ser Ser Leu Gly Thr Gln Thr
65 70 75 80

```
Tyr Ile Cys Asn Val Asn His Lys Pro Ser Asn Thr Lys Val Asp Lys
                85                  90                  95

Lys Val Glu Pro Lys
            100


<210> SEQ ID NO 168
<211> LENGTH: 101
<212> TYPE: PRT
<213> ORGANISM: Artificial Sequence
<220> FEATURE:
<223> OTHER INFORMATION: A141E; L142M; F170S; P171A; S181V

<400> SEQUENCE: 168

Ala Ser Thr Lys Gly Pro Ser Val Phe Pro Leu Ala Pro Ser Ser Lys
1               5                   10                  15

Ser Thr Ser Gly Gly Thr Ala Glu Met Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Ser Ala Ala Val Leu Gln Ser Ser Gly Leu Tyr Val
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 169
<211> LENGTH: 101
<212> TYPE: PRT
<213> ORGANISM: Artificial Sequence
<220> FEATURE:
<223> OTHER INFORMATION: A141K; S181K; V185E

<400> SEQUENCE: 169

Ala Ser Thr Lys Gly Pro Ser Val Phe Pro Leu Ala Pro Ser Ser Lys
1               5                   10                  15

Ser Thr Ser Gly Gly Thr Ala Lys Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Lys
    50                  55                  60

Leu Ser Ser Glu Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 170
<211> LENGTH: 101
<212> TYPE: PRT
<213> ORGANISM: Artificial Sequence
<220> FEATURE:
<223> OTHER INFORMATION: A141K; S181K; K218D

<400> SEQUENCE: 170

Ala Ser Thr Lys Gly Pro Ser Val Phe Pro Leu Ala Pro Ser Ser Lys
```

```
1               5                   10                  15

Ser Thr Ser Gly Gly Thr Ala Lys Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Lys
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Asp
            100


<210> SEQ ID NO 171
<211> LENGTH: 101
<212> TYPE: PRT
<213> ORGANISM: Artificial Sequence
<220> FEATURE:
<223> OTHER INFORMATION: A141T; F170V; P171A; S181V

<400> SEQUENCE: 171

Ala Ser Thr Lys Gly Pro Ser Val Phe Pro Leu Ala Pro Ser Ser Lys
1               5                   10                  15

Ser Thr Ser Gly Gly Thr Ala Thr Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Val Ala Ala Val Leu Gln Ser Ser Gly Leu Tyr Val
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 172
<211> LENGTH: 101
<212> TYPE: PRT
<213> ORGANISM: Artificial Sequence
<220> FEATURE:
<223> OTHER INFORMATION: G137R; A141E; P171E; S181V

<400> SEQUENCE: 172

Ala Ser Thr Lys Gly Pro Ser Val Phe Pro Leu Ala Pro Ser Ser Lys
1               5                   10                  15

Ser Thr Ser Arg Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Glu Ala Val Leu Gln Ser Ser Gly Leu Tyr Val
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys
100

<210> SEQ ID NO 173
<211> LENGTH: 101
<212> TYPE: PRT
<213> ORGANISM: Artificial Sequence
<220> FEATURE:
<223> OTHER INFORMATION: F126R; S131V; T139V; A141E; K218E

<400> SEQUENCE: 173

Ala Ser Thr Lys Gly Pro Ser Val Arg Pro Leu Ala Pro Val Ser Lys
1 5 10 15

Ser Thr Ser Gly Gly Val Ala Glu Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Glu
100

<210> SEQ ID NO 174
<211> LENGTH: 101
<212> TYPE: PRT
<213> ORGANISM: Artificial Sequence
<220> FEATURE:
<223> OTHER INFORMATION: F126V; S131V; S136P; A141D

<400> SEQUENCE: 174

Ala Ser Thr Lys Gly Pro Ser Val Val Pro Leu Ala Pro Val Ser Lys
1 5 10 15

Ser Thr Pro Gly Gly Thr Ala Asp Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys
100

<210> SEQ ID NO 175
<211> LENGTH: 101
<212> TYPE: PRT
<213> ORGANISM: Artificial Sequence
<220> FEATURE:
<223> OTHER INFORMATION: F126V; S131V; S136P; G137R; A141D

<400> SEQUENCE: 175

Ala Ser Thr Lys Gly Pro Ser Val Val Pro Leu Ala Pro Val Ser Lys
1 5 10 15

Ser Thr Pro Arg Gly Thr Ala Asp Leu Gly Cys Leu Val Lys Asp Tyr

```
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 176
<211> LENGTH: 102
<212> TYPE: PRT
<213> ORGANISM: Artificial Sequence
<220> FEATURE:
<223> OTHER INFORMATION: F126V; S131V; A141D; K218S

<400> SEQUENCE: 176

Ala Ser Thr Lys Gly Pro Ser Val Val Pro Leu Ala Pro Val Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Ser Ser
            100


<210> SEQ ID NO 177
<211> LENGTH: 101
<212> TYPE: PRT
<213> ORGANISM: Artificial Sequence
<220> FEATURE:
<223> OTHER INFORMATION: F126V; S131V; K133S; A141K; K218A

<400> SEQUENCE: 177

Ala Ser Thr Lys Gly Pro Ser Val Val Pro Leu Ala Pro Val Ser Ser
1               5                   10                  15

Ser Thr Ser Gly Gly Thr Ala Lys Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Ala
            100
```

<210> SEQ ID NO 178
<211> LENGTH: 101
<212> TYPE: PRT
<213> ORGANISM: Artificial Sequence
<220> FEATURE:
<223> OTHER INFORMATION: A141E; V185R

<400> SEQUENCE: 178

```
Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Arg Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 179
<211> LENGTH: 101
<212> TYPE: PRT
<213> ORGANISM: Artificial Sequence
<220> FEATURE:
<223> OTHER INFORMATION: A141E; T187R

<400> SEQUENCE: 179

```
Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Arg Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 180
<211> LENGTH: 101
<212> TYPE: PRT
<213> ORGANISM: Artificial Sequence
<220> FEATURE:
<223> OTHER INFORMATION: A141E; F170E; V185R

<400> SEQUENCE: 180

```
Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
```

```
        35                  40                  45

Gly Val His Thr Glu Pro Ala Val Leu Gln Ser Ser Gly Leu Tyr Ser
    50                  55                  60

Leu Ser Ser Arg Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 181
<211> LENGTH: 101
<212> TYPE: PRT
<213> ORGANISM: Artificial Sequence
<220> FEATURE:
<223> OTHER INFORMATION: A141E; F170E; T187R

<400> SEQUENCE: 181

Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Glu Pro Ala Val Leu Gln Ser Ser Gly Leu Tyr Ser
    50                  55                  60

Leu Ser Ser Val Val Arg Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 182
<211> LENGTH: 101
<212> TYPE: PRT
<213> ORGANISM: Artificial Sequence
<220> FEATURE:
<223> OTHER INFORMATION: A141D; V185R

<400> SEQUENCE: 182

Ala Ser Thr Lys Gly Pro Ser Val Phe Pro Leu Ala Pro Ser Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Arg Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 183
<211> LENGTH: 101
```

<212> TYPE: PRT
<213> ORGANISM: Artificial Sequence
<220> FEATURE:
<223> OTHER INFORMATION: A141D; T187R

<400> SEQUENCE: 183

```
Ala Ser Thr Lys Gly Pro Ser Val Phe Pro Leu Ala Pro Ser Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Arg Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 184
<211> LENGTH: 101
<212> TYPE: PRT
<213> ORGANISM: Artificial Sequence
<220> FEATURE:
<223> OTHER INFORMATION: A141D; V185R; T187R

<400> SEQUENCE: 184

```
Ala Ser Thr Lys Gly Pro Ser Val Phe Pro Leu Ala Pro Ser Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Arg Val Arg Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

<210> SEQ ID NO 185
<211> LENGTH: 101
<212> TYPE: PRT
<213> ORGANISM: Artificial Sequence
<220> FEATURE:
<223> OTHER INFORMATION: A141D; F170E; V185R

<400> SEQUENCE: 185

```
Ala Ser Thr Lys Gly Pro Ser Val Phe Pro Leu Ala Pro Ser Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Glu Pro Ala Val Leu Gln Ser Ser Gly Leu Tyr Ser
```

```
    50                  55                  60

Leu Ser Ser Arg Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 186
<211> LENGTH: 101
<212> TYPE: PRT
<213> ORGANISM: Artificial Sequence
<220> FEATURE:
<223> OTHER INFORMATION: A141D; F170E; T187R

<400> SEQUENCE: 186

Ala Ser Thr Lys Gly Pro Ser Val Phe Pro Leu Ala Pro Ser Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Glu Pro Ala Val Leu Gln Ser Ser Gly Leu Tyr Ser
    50                  55                  60

Leu Ser Ser Val Val Arg Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 187
<211> LENGTH: 101
<212> TYPE: PRT
<213> ORGANISM: Artificial Sequence
<220> FEATURE:
<223> OTHER INFORMATION: A141E; P171E; T187R

<400> SEQUENCE: 187

Ala Ser Thr Lys Gly Pro Ser Val Phe Pro Leu Ala Pro Ser Ser Lys
1               5                   10                  15

Ser Thr Ser Gly Gly Thr Ala Glu Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Glu Ala Val Leu Gln Ser Ser Gly Leu Tyr Ser
    50                  55                  60

Leu Ser Ser Val Val Arg Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 188
<211> LENGTH: 101
<212> TYPE: PRT
<213> ORGANISM: Artificial Sequence
<220> FEATURE:
```

-continued

```
<223> OTHER INFORMATION: A141D; P171E; V185R

<400> SEQUENCE: 188

Ala Ser Thr Lys Gly Pro Ser Val Phe Pro Leu Ala Pro Ser Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Glu Ala Val Leu Gln Ser Ser Gly Leu Tyr Ser
    50                  55                  60

Leu Ser Ser Arg Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100


<210> SEQ ID NO 189
<211> LENGTH: 101
<212> TYPE: PRT
<213> ORGANISM: Artificial Sequence
<220> FEATURE:
<223> OTHER INFORMATION: A141D; P171E; T187R

<400> SEQUENCE: 189

Ala Ser Thr Lys Gly Pro Ser Val Phe Pro Leu Ala Pro Ser Ser Lys
1               5                   10                  15

Ser Thr Ser Gly Gly Thr Ala Asp Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Glu Ala Val Leu Gln Ser Ser Gly Leu Tyr Ser
    50                  55                  60

Leu Ser Ser Val Val Arg Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100
```

CH1 DOMAIN VARIANTS ENGINEERED FOR PREFERENTIAL KAPPA LIGHT CHAIN PAIRING AND MULTISPECIFIC ANTIBODIES COMPRISING THE SAME

CROSS-REFERENCE TO RELATED APPLICATIONS

This application is a U.S. National Phase application of Int'l Appl. No. PCT/US2020/053482, filed Sep. 30, 2020, which claims priority to U.S. Provisional Appl. No. 62/908,367, filed Sep. 30, 2019, each of which are incorporated herein by reference in their entireties.

SEQUENCE DISCLOSURE

This application includes a sequence listing which has been submitted via EFS-Web in a file named "11604300002401.txt" created Sep. 1, 2022, and having a size of 185,166185,189 bytes, which is hereby incorporated by reference in its entirety.

FIELD OF THE INVENTION

The present invention relates to CH1 domain variants that contain at least one amino acid substitution that promotes proper heavy chain-light chain pairing and antibody heavy chains and antibodies, particularly multispecific antibodies, comprising the same. The present invention further relates to compositions comprising such antibodies and the use thereof, e.g., as therapeutics or diagnostics. The present invention further relates to methods of making a CH1 domain variant library and methods of identifying one or more CH1 domain variants.

BACKGROUND OF THE INVENTION

There are ongoing efforts to develop antibody therapeutics that have more than one antigen binding specificity, e.g., bispecific antibodies. Bispecific antibodies can be used to interfere with multiple surface receptors associated with cancer, inflammatory processes, or other disease states. Bispecific antibodies can also be used to place targets into close proximity and modulate protein complex formation or drive contact between cells. Production of bispecific antibodies was first reported in the early 1960s (Nisonoff et al., *Arch Biochem Biophys* 1961 93(2): 460-462) and the first monoclonal bispecific antibodies were generated using hybridoma technology in the 1980s (Milstein et al., *Nature* 1983 305(5934): 537-540). Interest in bispecific antibodies has increased significantly in the last decade due to their therapeutic potential and bispecific antibodies are now used in the clinic, e.g., blinatumomab and emicizumab have been approved for treatment of particular cancers (see Sedykh et al., *Drug Des Devel Ther* 12:195-208 (2018) and Labrijn et al. *Nature Reviews Drug Discovery* 18:585-608 (2019), for recent reviews of bispecific antibody production methods and features of bispecific antibodies approved for medical use).

While bispecific antibodies have shown considerable benefits over monospecific antibodies, broad commercial application of bispecific antibodies has been hampered by the lack of efficient/low-cost production methods, the lack of stability of bispecific antibodies, and the lack of long half-lives in humans. A large variety of methods have been developed over the last few decades to improve production of bispecific antibodies. These include recombinant co-expression of two immunoglobulin heavy chain-light chain pairs having different specificities (see Milstein and Cuello, *Nature* 305: 537 (1983)), WO 93/08829, and Traunecker et al., *EMBO J* 10: 3655 (1991)); "knob-in-hole" engineering (see, e.g., U.S. Pat. No. 5,731,168); immunoglobulin cross-over technology (also known as Fab domain exchange or CrossMab format) (see e.g., WO2009/080253; Schaefer et al., *Proc. Natl. Acad. Sci. USA,* 108:11187-11192 (2011)); engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); leucine zippers (see, e.g., Kostelny et al., *J. Immunol,* 148(5):1547-1553 (1992)); "diabody" technology (see, e.g., Hollinger et al., *Proc. Natl. Acad. Sci. USA,* 90:6444-6448 (1993)); single-chain Fv (scFv) dimers (see, e.g. Gruber et al., *J. Immunol,* 152:5368 (1994)); and trispecific antibodies as described, e.g., in Tutt et al. *J. Immunol* 147: 60 (1991).

Despite these improvements, generating bispecific antibodies with correct heavy chain-light chain pairing remains a challenge. A bispecific antibody can be formed by co-expression of two different heavy chains and two different light chains. Properly forming bispecific antibodies in a desired format remains a challenge, because heavy chains have evolved to bind light chains in a relatively promiscuous manner. Consequently, co-expression of two heavy chains and two light chains can lead to a scrambling of heavy chain-light chain pairings—a complex mixture of sixteen possible combinations, representing ten different antibodies only one of which corresponds with the desired bispecific antibody (maximal yield 12.5% in the mixture if there is perfect promiscuity). This mispairing (also referred to as the chain-association issue) remains a major challenge for generating bispecifics, since homogeneous pairing is essential for manufacturability and efficacy.

One strategy used to alleviate mispairing is to generate bispecific antibodies having a common light chain (see e.g., Merchant et al., *Nat. Biotech.* 16:677-681 (1998)). Alternatively, a single common heavy chain and two different light chains (one kappa and one lambda) can be used (see e.g., Fischer et al., *Nature Commun.* 6:6113 (2015)). However, this strategy requires identifying an antibody with a common chain, which is difficult and tends to compromise the specificity of each binding arm and substantially reduces diversity (see, e.g., Wang et al., *MABS* 10(8):1226-1235 (2018)).

Other approaches to improve correct heavy chain-light chain pairing include CrossMab technology (Roche), in which the light chain or one of the sub-domains therein of one fragment antigen-binding (Fab) arm is exchanged with the corresponding regions of the heavy chain Fd region, and DuetMab technology (MedImmune), in which the native disulfide bond in one Fab arm is replaced with an engineered disulfide bond. However, these approaches require significant changes to the native IgG format that may result in compounds not adequately resembling natural antibodies.

Another strategy is to utilize amino acid substitutions in the constant and/or variable regions of the heavy and light chains in an IgG format to reduce or eliminate heavy chain-light chain mispairing. To the best of the inventors' knowledge, modification of only the CH1 domain has not previously been demonstrated to solve the chain-association or mispairing issue often observed during expression of multispecific antibodies. Rather, multispecific antibodies engineered to comprise CH1 domain variants have further required modifications also outside the CH1 domain in order to address the problem of chain-association, such as the CL domain, and in certain instances VH, CH2, CH3, and/or VL domains. Examples thereof include Lewis et al., *Nature Biotech.* 32(2):191-198 (2014) who generated mutant CH1 and CL domains, CRD1 (with heavy chain substitutions with D148K, F170T, V185F and light chain substitutions K129D, L135F; EU numbering) and CRD2 (with heavy chain substitutions H168A and F170T and light chain substitutions L135Y, S176W), in an attempt to drive preferential pairing of the altered heavy and light chains and to disfavor pairing of heavy and light chain domains with wild-type constant domains. However, they reported that any pairing specificity obtained with the mutant CH1 and CL domains in the absence of the variable domains did not translate to a full-length IgG format without additional engineering within the VH-VL interface, i.e., substitutions within the VH-VL interface were required along with the CL and CH1 domain substitutions in order to achieve preferential heavy chain-light chain pairing. Engineering CH1 and CL domains to contain charged amino acid residues has also been purported to promote preferential heavy chain-light chain pairing (see, e.g., U.S. Pat. No. 10,047,163). Bispecific antibodies having at least two Fab fragments with different CH1 and CL domains, in which one Fab fragment has substitutions within the CH1 domain and the Cκ domain to drive preferential pairing are also known (see US20180022829 and U.S. Pat. No. 9,631,031 disclosing CH1: T187E and Cκ: N137K+S114A; CH1: L145Q+S183V and Cκ: V133T+S176V; CH1: L128A+L145E and Cκ: V133W; CH1: V185A and Cκ: L135W+N137A). Additional examples of specific CH1 domain substitutions alleged to promote preferential heavy chain-light chain pairing when the light chain, or in some instances the CH2, CH3, and/or VH, is also appropriately substituted to promote the preferential pairing include: A141C/L, K147D, G166D, G166K, or substitution with cysteine at position 128, 129, 162, or 171 (WO2019183406 (Invenra Inc.)); substitution of cysteine at position 126 or 220 is substituted with valine or alanine, or substitution of non-cysteine at position 128, 141, or 168 with cysteine, L145F, K147A, F170V, S183F, or V185W/F (U.S. Pat. No. 9,527,927 (MedImmune)); 172A and 174G (WO2020060924 (Dualogics)); A172R and 174G, or substitution of residue 190 to M or I (U.S. Pat. No. 10,047,167 (University of North Carolina Chapel Hill and Eli Lilly)); L128F, A141I/M/T/L, F170S/A/Y/M, S181M/I/T, S183A/E/K/V and V185A/L (US20180177873 (Genentech)); 131C/S, 133R/K, 137E/G, 138S/G 178S/Y, 192N/S, and/or 193F/L (U.S. Pat. No. 10,487,156 (Argenx BVBA)); 145D/E/R/H/K (IMGT position 26) (WO2018141894 (Merck)); 124K/E/R/D (U.S. Pat. No. 10,392,438 (Pfizer)); 133V, 150A, 150D, 152D, 173D, or 188W (US20190023810 (MIT)); 133S/W/A, 139W/V/G/I, 143K/E/A, 145E/T/L/Y, 146G, 147T/E, 174V, 175D/R/S, 179K/D/R, 181R, 186R, 188F/L, and/or 190S/A/G/Y (US20180179296 and U.S. Pat. No. 9,914,785 (Zymeworks)); 143A/E/R/K/D and 145T/L (U.S. Pat. No. 10,077,298 (Zymeworks)); 124A/R/E/W, 145M/T, 143E/R/D/F, 172R/T, 139W/G/C, 179E, or 186R (US20170204199 (Zymeworks)); substitution with cysteine at position 126, 127, 128, 134, 141, 171, or 173 (Zenyaku Kogyo); L145Q, H168A, F170G, S183V, and T187E (WO2020127354 (Alligator Bioscience)); 143D/E, 145T, 190E/D and 124R (WO2017/059551 (Zymeworks)). Also, U.S. Pat. No. 9,150,639, Kyowa Hakko Kirin reportedly generated heavy chains comprising A140C, K147C, or S183C for the purpose of introducing a cysteine to allow chemical modulation. Kirin suggests that antibody variants containing these heavy chain mutations may comprise wild-type light chains, however, there is no indication that this would facilitate preferential heavy chain-light chain pairing.

Yet another strategy used to minimize heavy chain-light chain mispairing is to utilize different light chains, e.g., light chains with different constant domains. For example, Loew et al. generated multispecific antibodies having a kappa light chain and a lambda light chain and observed minimal mispairing because certain naturally occurring kappa light chains have high fidelity and do not pair with heavy chains from a lambda antibody, and vice versa (WO2018057955). Unfortunately, applicability of this methodology is limited to those light chains having high fidelity. Others have generated multispecific antibodies using kappa and lambda light chains in which amino acid substitutions are utilized in both the heavy chains and light chains to electrostatically or sterically drive preferential pairing (see e.g., WO2017059551 (Zymeworks), US20140154254 (Amgen), and U.S. Pat. No. 10,047,163 (AbbVie Stemcentrx)). However, introducing numerous amino acid substitutions into both heavy and light chains presents additional technical hurdles and moreover may have deleterious effects on antibody function and/or immunogenicity.

SUMMARY OF THE INVENTION

An object of the present invention is to provide engineered bispecific antibodies with proper heavy chain-light chain pairing. In one aspect, provided herein are CH1 domain variant polypeptides (also referred to herein as CH1 domain variants) that promote preferential pairing of the heavy chain with particular light chains and polypeptides, such as antibodies, comprising the same. The CH1 domain variants contain at least one amino acid substitution (relative to a parent, e.g., wild-type, sequence).

In some embodiments, the CH1 domain variants contain at least one amino acid substitution at a CH1 domain position that forms an interface with the CL domain of a light chain, including but not limited to position 140 and/or 141 or 147 and/or 183 (EU numbering). The substitution promotes preferential pairing of the CH1 domain variant-containing heavy chain with specific light chains, e.g., CH1 domain variant 141 preferentially pairs with a lambda CL domain as opposed to a kappa CL domain, whereas CH1 domain variant 147F and/or 183R, 183K, or 183Y preferentially pairs with a kappa CL domain as opposed to a lambda CL domain.

In some embodiments, the CH1 domain variants contain at least one amino acid substitution at a CH1 domain position that forms an interface between the CH1 domain and VH, such as CH1 position 151 (EU numbering).

This preferential pairing of the constant domains is expected to drive the pairing of the full-length light and heavy chain, including the variable domains, thus generating a solution to the chain pairing issue for bispecifics. In particular, the CH1 domain variant polypeptide comprises an amino acid substitution at one or more of the following positions: 118, 119, 124, 126-134, 136, 138-143, 145, 147-154, 163, 168, 170-172, 175, 176, 181, 183-185, 187, 190, 191, 197, 201, 203-206, 208, 210-214, 216, and 218, according to EU numbering. Optionally, such a CH1 domain variant polypeptide preferentially pairs: (i) with a kappa light chain constant region ("CL") domain as compared to a lambda CL domain and/or with a kappa light chain polypeptide as compared to a lambda light chain polypeptide; (ii) with a lambda CL domain as compared to a kappa CL domain and/or with a lambda light chain polypeptide as compared to a kappa light chain polypeptide.

Optionally, in some embodiments, certain CH1 domain variants may be excluded and the CH1 domain variants according to the present invention may meet the following:

(a) if residue 141 on CH1 is substituted to C or L, residue 166 is substituted with D or K, residue 128, 129, 162, or 171 on CH1 is substituted to C, and/or residue 147 is substituted to D, the CL domain with which the CH1 domain variant preferentially pairs does not comprise amino acid substitution;

(b) if position 126 or 220 on CH1 is substituted with valine or alanine, non-cysteine at position 128, 141, or 168 is substituted with cysteine, or CH1 substitutions is L145F, K147A, F170V, S183F, or V185W/F, the CL domain with which the CH1 domain variant preferentially pairs does not comprise an amino acid substitution;

(c) if residue 172 on CH1 is substituted to 172R, residue 174 is mutated to 174G, or residue 190 is substituted to 190M or 190I, these are not the only substitution(s) the CH1 comprises;

(d) if the CH1 substitutions consist of L128F, A141I/M/T/L, F170S/A/Y/M, S181M/I/T, S183A/E/K/V and/or V185A/L, the CL domain with which the CH1 domain variant preferentially pairs is not modified;

(e) if the CH1 substitutions consist of 131C/S, 133R/K, 137E/G, 138S/G, 178S/Y, 192N/S, and/or 193F/L, these are not the only CH1 substitutions and/or, in a bispecific antibody, the CH1 domains are of the same human immunoglobulin subtype or allotype;

(f) if the CH1 substitutions consist of 145D/E/R/H/K (IMGT position 26), there is not a corresponding LC substitution, 129D/E/R/H/K (IMGT position 18);

(g) if the CH1 substitutions consist of 124K/E/R/D, there is not a corresponding substitution at position 176 of LC with which the CH1 domain variant preferentially pairs;

(h) if the CH1 substitutions consist of 133V, 150A, 150D, 152D, 173D, and/or 188W, there are not corresponding substitutions in the LC with which the CH1 domain variant preferentially pairs;

(i) if the CH1 substitutions consist of 133S/W/A, 139W/V/G/I, 143K/E/A, 145E/T/L/Y, 146G, 147T/E, 174V, 175D/R/S, 179K/D/R, 181R, 186R, 188F/L, and/or 190S/A/G/Y, there are not corresponding substitutions in the LC with which the CH1 domain variant preferentially pairs;

(j) if the CH1 substitutions consist of 143A/E/R/K/D and 145T/L there are not corresponding substitutions in the LC with which the CH1 domain variant preferentially pairs;

(k) if the CH1 substitutions consist of 124A/R/E/W, 145M/T, 143E/R/D/F, 172R/T and 139W/G/C, 179E, and/or 186R, there are not corresponding substitutions in the LC with which the CH1 domain variant preferentially pairs;

(l) if the CH1 substitutions consist of substituting with cysteine at position 126 127, 128, 134, 141, 171, or 173, then the corresponding LC positions are not modified to form a disulfide bond;

(m) if the CH1 substitutions consist of L145Q, H168A, F170G, S183V, and/or T187E, there are not corresponding substitutions in the kappa or lambda LC with which the CH1 domain variant preferentially pairs;

(n) if the CH1 substitutions consist of 143D/E, 145T, 190E/D, and/or 124R, are no corresponding substitutions in the LC with which the CH1 domain variant preferentially pairs; or (o) if the CH1 substitutions consist of A140C, K147C, and/or S183C, there are substitutions in the LC with which the CH1 domain variant preferentially pairs.

In some embodiments, the CH1 domain variant polypeptide comprises an amino acid substitution at one or more of the following positions: 118, 124, 126-129, 131, 132, 134, 136, 139, 143, 145, 147-151, 153, 154, 170, 172, 175, 176, 181, 183, 185, 190, 191, 197, 201, 203-206, 210, 212-214, and 218, according to EU numbering. Optionally such that the CH1 domain variant polypeptide preferentially pairs with: (i) a kappa CL domain (or a kappa CL-containing polypeptide) as compared to a lambda CL domain (or a lambda CL-containing polypeptide); and/or (ii) a kappa light chain polypeptide as compared to a lambda light chain polypeptide.

In certain embodiments, such a CH1 domain variant comprises an amino acid substitution at position 147, position 183, or positions 147 and 183.

In certain embodiments, such a CH1 domain variant comprises one or more of the following amino acid substitutions; position 118 is substituted with G; position 124 is substituted with H, R, E, L, or V; position 126 is substituted with A, T, or L; position 127 is substituted with V or L; position 128 is substituted with H; position 129 is substituted with P; position 131 is substituted with A; position 132 is substituted with P; position 134 is substituted with G; position 136 is substituted with E; position 139 is substituted with I; position 143 is substituted with V or S; position 145 is substituted with F, I, N, or T; position 147 is substituted with F, I, L, R, T, S, M, V, N, E, H, Y, Q, A, or G; position 148 is substituted with I, Q, Y, or G; position 149 is substituted with C, S, or H; position 150 is substituted with L or S; position 151 is substituted with A or L; position 153 is substituted with S; position 154 is substituted with M or G; position 170 is substituted with G or L; position 172 is substituted with V; position 175 is substituted with G, L, E, A; position 176 is substituted with P; position 181 is substituted with Y, Q, or G; position 183 is substituted with I, W, F, E, Y, L, K, Q, N, R, or H; position 185 is substituted with W; position 190 is substituted with P; position 191 is substituted with I; position 197 is substituted with A; position 201 is substituted with S; position 203 is substituted with S; position 204 is substituted with Y; position 205 is substituted with Q; position 206 is substituted with S; position 210 is substituted with R; position 212 is substituted with G; position 213 is substituted with E or R; position 214 is substituted with R; and position 218 is substituted with Q.

In certain embodiments, the kappa-preferring CH1 domain variant polypeptide may comprise: (i) amino acid residue F, I, L, R, T, S, M, V, N, E, H, Y, or Q at position 147; and/or (ii) amino acid residue I, W, F, E, Y, L, K, Q, N, or R at position 183.

In some preferred embodiments of a kappa-preferring CH1 domain variant, the CH1 domain variant polypeptide may comprise: (i) amino acid residue R, K, or Y at position 183; and/or (ii) amino acid residue F at position 147.

In further embodiments, the CH1 domain variant polypeptide comprises: (i) amino acid residue F at position 147 and amino acid residue R at position 183; (ii) amino acid residue F at position 147 and amino acid residue K at position 183; (iii) amino acid residue F at position 147 and amino acid residue Y at position 183; (iv) amino acid residue R at position 183; (v) amino acid residue K at position 183; or (vi) amino acid residue Y at position 183. Optionally, such an CH1 domain variant may comprise the amino acid sequence of: (i) SEQ ID NO: 137; (ii) SEQ ID NO: 138; (iii) SEQ ID NO: 139; (iv) SEQ ID NO: 60; (v) SEQ ID NO: 41; or (vi) SEQ ID NO: 136.

In some embodiments, the CH1 domain variant polypeptide comprises an amino acid substitution at a CH1 amino acid position within the interface between a CH1 and a VH. Optionally, the CH1 amino acid position within such an interface is position 151. Further optionally, such a CH1 domain variant may comprise amino acid residue A or L at position 151.

In some embodiments, the CH1 domain variant polypeptide further comprises one or more amino acid substitutions that increase pairing of a CH1 domain with: (i) a kappa CL domain as compared to a lambda CL domain; and/or (ii) a kappa light chain polypeptide as compared to a lambda light chain polypeptide.

In some embodiments, the CH1 domain variant polypeptide of any one of claims 2-10, which results in increased pairing with: (i) a kappa CL domain as compared to a lambda CL domain; and/or (ii) a kappa light chain polypeptide as compared to a lambda light chain polypeptide, by at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. Increases in kappa pairing may optionally be measured by liquid chromatography-mass spectrometry (LCMS).

In some embodiments, the CH1 domain variant polypeptide of any one of claims 2-10, which results in increased pairing with: (i) a kappa CL domain as compared to a lambda CL domain; and/or (ii) a kappa light chain polypeptide as compared to a lambda light chain polypeptide, by at least 1.2-fold, at least 1.5-fold, at least 2-fold, by 2.5-fold, by at least 3-fold, by at least 3.5-fold, by at least 4-fold, by at least 4.5-fold, by at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, or at least 25-fold. Increases in kappa pairing may optionally be quantified by flow cytometry, for example by comparing the mean fluorescence intensity (MFI) ration of kappa CL staining to lambda CL staining.

In some embodiments, the CH1 domain variant polypeptide according to the present invention comprises an amino acid substitution at one or more of the following positions: 119, 124, 126, 127, 130, 131, 133, 134, 138-142, 152, 163, 168, 170, 171, 175, 176, 181, 183-185, 187, 197, 203, 208, 210-214, 216, and 218, according to EU numbering. Optionally, the CH1 domain variant preferentially pairs with: (i) a lambda CL domain as compared to a kappa CL domain; and/or (ii) a lambda light chain polypeptide as compared to a kappa light chain polypeptide.

In certain embodiments, the lambda-preferring CH1 domain variant polypeptide comprises an amino acid substitution at one or more of positions 141, 170, 171, 175, 181, 184, 185, 187, and 218.

In certain embodiments, the lambda-preferring CH1 domain variant polypeptide comprises one or more of the following amino acid substitutions: position 119 is substituted with R; position 124 is substituted with V; position 126 is substituted with V; position 127 is substituted with G; position 130 is substituted with H or S; position 131 is substituted with Q, T, N, R, V, or D; position 133 is substituted with D, T, L, E, S, or P; position 134 is substituted with A, H, I, P, V, N, or L; position 138 is substituted with R; position 139 is substituted with A; position 140 is substituted with I, V, D, Y, K, S, W, R, L or P; position 141 is substituted with D, K, E, T, R, Q, V, or M; position 142 is substituted with M; position 152 is substituted with G; position 163 is substituted with M; position 168 is substituted with F, I, or V; position 170 is substituted with N, G, E, S, or T; position 171 is substituted with N, E, G, S, A, or D; position 175 is substituted with D or M; position 176 is substituted with R or M; position 181 is substituted with V, L, A, K, or T; position 183 is substituted with L or V; position 184 is substituted with R; position 185 is substituted with M, L, S, R, or T; position 187 is substituted with R, D, E, Y, or S; position 197 is substituted with S; position 203 is substituted with D; position 208 is substituted with I; position 210 is substituted with T; position 211 is substituted with A; position 212 is substituted with N; position 213 is substituted with E; position 214 is substituted with R; position 216 is substituted with G; and position 218 is substituted with L, E, D, P, A, H, S, Q, N, T, I, M, G, C, K, or W.

In yet certain embodiments, the lambda-preferring CH1 domain variant polypeptide comprises any one or more of (i)-(xvii): (i) amino acid residue V at position 126; (ii) amino acid residue G at position 127; (iii) amino acid residue V at position 131; (iv) amino acid residue S at position 133; (v) amino acid residue R at position 138; (vi) amino acid residue I or V at position 140; (vii) amino acid residue D, K, E, or T at position 141; (viii) amino acid residue M at position 142; (ix) amino acid residue I at position 168; (x) amino acid residue E, G, or S at position 170; (xi) amino acid residue E, D, G, S, or A at position 171; (xii) amino acid residue M at position 175; (xiii) amino acid residue R at position 176; (xiv) amino acid residue K, V, A, or L at position 181; (xv) amino acid residue R at position 184; (xvi) amino acid residue R at position 185; (xvii) amino acid residue R at position 187; and (xviii) amino acid residue L, E, D, P, A, H, S, Q, N, T, I, M, G, C, or W at position 218.

In certain preferred embodiments, the lambda-preferring CH1 domain variant polypeptide according to the present invention comprises or consists of one or more of the following substitutions: 141D, 141E, 171E, 170E, 185R and 187R.

In certain preferred embodiments, the lambda-preferring CH1 domain variant polypeptide according to the present invention comprises or consists of two or more of the following substitutions: 141D, 141E, 171E, 170E, 185R and 187R.

In certain preferred embodiments, the lambda-preferring CH1 domain variant polypeptide according to the present invention comprises or consists of three or more of the following substitutions: 141D, 141E, 171E, 170E, 185R and 187R.

In certain preferred embodiments, the lambda-preferring CH1 domain variant polypeptide according to the present invention comprises or consists of the following substitutions: (i) 141E and 185R; (ii) 141E and 187R; (iii) 141E, 170E or 171E, and 185R; (iv) 141E, 170E or 171E, and 187R; (v) 141D and 185R; (vi) 141D and 187R; (vii) 141D, 170E or 171E, and 185R; (viii) 141D, 170E or 171E, and 187R; (ix) 141E, 185R, and 187R; or (x) 141D, 185R, and 187R.

In yet some embodiments, the lambda-preferring CH1 domain variant polypeptide according to the present invention comprises a substitution at one or more position 141 to D, K, or E optionally paired with a substitution at position 181 to K and further optionally paired with a substitution at position 218 to L, E, D, P, A, H, S, Q, N, T, I, M, G, C, or W.

In yet some embodiments, the lambda-preferring CH1 domain variant polypeptide according to the present invention comprises a substitution at position 141 to D, K, or E paired with a substitution at position 181 to K and/or r a substitution at position 218 to L, E, D, P, A, H, S, Q, N, T, I, M, G, C, or W.

In further embodiments, the lambda-preferring CH1 domain variant polypeptide according to the present invention comprises any one or more of (i)-(xvii): (i) amino acid residue D, E, or K at position 141; (ii) amino acid residue E at position 170; (iii) amino acid residue E at position 171; (iv) amino acid residue M at position 175; (v) amino acid residue K at position 181; (vi) amino acid residue R at position 184; (vii) amino acid residue R at position 185; (viii) amino acid residue R at position 187; (ix) amino acid residue P, A, or E at position 218.

In further embodiments, the lambda-preferring CH1 domain variant polypeptide according to the present invention comprises: (i) amino acid residue D at position 141; (ii) amino acid residue D at position 141 and amino acid residue K at position 181; (iii) amino acid residue D at position 141, amino acid residue K at position 181, and amino acid residue A at position 218; (iv) amino acid residue D at position 141, amino acid residue K at position 181, and amino acid residue P at position 218; (v) amino acid residue E at position 141; (vi) amino acid residue E at position 141 and amino acid residue K at position 181; (vii) amino acid residue K at position 141; (viii) amino acid residue K at position 141 and amino acid residue K at position 181; (ix) amino acid residue K at position 141, amino acid residue K at position 181, and amino acid residue E at position 218; (x) amino acid residue K at position 141, amino acid residue K at position 181, and amino acid residue P at position 218; (xi) amino acid residue E at position 141, amino acid residue E at position 170, amino acid residue V at position 181, and amino acid residue R at position 187; (xii) amino acid residue E at position 141, amino acid residue D at position 171, and amino acid residue R at position 185; (xiii) amino acid residue E at position 141, amino acid residue E at position 171, and amino acid residue R at position 185; (xiv) amino acid residue E at position 141, amino acid residue G at position 171, amino acid residue R at position 185, and amino acid residue R at position 187; (xv) amino acid residue E at position 141, amino acid residue R at position 185, and amino acid residue R at position 187; (xvi) amino acid residue E at position 141, amino acid residue S at position 171, and amino acid residue K at position 181; (xvii) amino acid residue E at position 141, amino acid residue G at position 170, amino acid residue M at position 175, amino acid residue V at position 181, amino acid residue R at position 184, and amino acid residue R at position 187; (xviii) amino acid residue E at position 141 and amino acid residue R at position 185; (xix) amino acid residue E at position 141 and amino acid residue R at position 187; (xx) amino acid residue E at position 141, amino acid residue E at position 170, and amino acid residue R at position 185; (xxi) amino acid residue E at position 141, amino acid residue E at position 170, and amino acid residue R at position 187; (xxii) amino acid residue D at position 141 and amino acid residue R at position 185; (xxiii) amino acid residue D at position 141 and amino acid residue R at position 187; (xxiv) amino acid residue D at position 141, amino acid residue R at position 185, and amino acid residue R at position 187; (xxv) amino acid residue D at position 141, amino acid residue E at position 170, and amino acid residue R at position 185; (xxvi) amino acid residue D at position 141, amino acid residue E at position 170, and amino acid residue R at position 187; (xxvii) amino acid residue E at position 141, amino acid residue E at position 171, and amino acid residue R at position 187; (xxiii) amino acid residue D at position 141, amino acid residue E at position 171, and amino acid residue R at position 185; or (xxix) amino acid residue D at position 141, amino acid residue E at position 171, and amino acid residue R at position 187.

Optionally, such a CH1 domain variant comprises the amino acid sequence of: (i) SEQ ID NO: 140; (ii) SEQ ID NO: 141; (iii) SEQ ID NO: 142; (iv) SEQ ID NO: 143; (v) SEQ ID NO: 144; (vi) SEQ ID NO: 145; (vii) SEQ ID NO: 146; (viii) SEQ ID NO: 147; (ix) SEQ ID NO: 148; (x) SEQ ID NO: 149; (xi) SEQ ID NO: 155; (xii) SEQ ID NO: 157; (xiii) SEQ ID NO: 159; (xiv) SEQ ID NO: 162; (xv) SEQ ID NO: 163; (xvi) SEQ ID NO: 164; (xvii) SEQ ID NO: 165; (xviii) SEQ ID NO: 178; (xix) SEQ ID NO: 179; (xx) SEQ ID NO: 180; (xxi) SEQ ID NO: 181; (xxii) SEQ ID NO: 182; (xxiii) SEQ ID NO: 183; (xxiv) SEQ ID NO: 184; (xxv) SEQ ID NO: 185; (xxvi) SEQ ID NO: 186; (xxvii) SEQ ID NO: 187; (xxviii) SEQ ID NO: 188; or (xxix) SEQ ID NO: 189.

In some preferred embodiments, the lambda-preferring CH1 domain variant comprises: (i) amino acid residue D at position 141, amino acid residue E at position 171, and amino acid residue R at position 185; or (ii) amino acid residue D at position 141, amino acid residue E at position 170, and amino acid residue R at position 187.

In further preferred embodiments, the lambda-preferring CH1 domain variant comprises amino acid substitutions consisting of: (i) amino acid residue D at position 141, amino acid residue E at position 171, and amino acid residue R at position 185; or (ii) amino acid residue D at position 141, amino acid residue E at position 170, and amino acid residue R at position 187.

In certain preferred embodiments, the lambda-preferring CH1 domain variant comprises amino acid substitutions consisting of: (i) SEQ ID NO: 188; or (ii) SEQ ID NO: 186.

In some embodiments, the lambda-preferring CH1 domain variant polypeptide may further comprise one or more amino acid substitutions that increase pairing of a CH1 domain with: (i) a lambda CL domain as compared to a kappa CL domain; and/or (ii) a lambda light chain polypeptide as compared to a kappa light chain polypeptide.

In some embodiments, the CH1 domain variant polypeptide may result in increased pairing with: (i) a lambda CL domain as compared to a kappa CL domain; and/or (ii) a lambda light chain polypeptide as compared to a kappa light chain polypeptide, by at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. Increases in lambda pairing may be optionally measured by liquid chromatography-mass spectrometry (LCMS).

In some embodiments, the CH1 domain variant polypeptide may result in increased pairing with: (i) a lambda CL domain as compared to a kappa CL domain; and/or (ii) a lambda light chain polypeptide as compared to a kappa light chain polypeptide, by at least 1.2-fold, at least 1.5-fold, at least 2-fold, by at least 2.5-fold, by at least 3-fold, by at least 3.5-fold, by at least 4-fold, by at least 4.5-fold, by at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, or at least 25-fold. Increases in lambda pairing may be optionally measured by flow cytometry, optionally by comparing the MFI value ration of lambda CL staining to kappa CL staining.

In another aspect, further provided herein are antibody heavy chain polypeptides comprising a variable region and a constant region, wherein the constant region comprises the CH1 domain variant according to any of those described above.

In some embodiments, the CH1 domain variant of such an antibody heavy chain polypeptide is according to comprises amino acid substitutions consisting of:

(I) (i) amino acid residue F at position 147 and amino acid residue R at position 183; (ii) amino acid residue F at position 147 and amino acid residue K at position 183; (iii) amino acid residue F at position 147 and amino acid residue Y at position 183; (iv) amino acid residue R at position 183; (v) amino acid residue K at position 183; or (vi) amino acid residue Y at position 183; or (II) (i) amino acid residue D at position 141, amino acid residue E at position 171, and amino acid residue R at position 185; or (ii) amino acid residue D at position 141, amino acid residue E at position 170, and amino acid residue R at position 187.

In another aspect, further provided herein are antibodies or antibody fragments comprising a first heavy chain polypeptide and a first light chain polypeptide, wherein (a) the first heavy chain polypeptide and the first light chain polypeptide form a first cognate pair; and (b) the first heavy chain polypeptide comprises a first CH1 domain variant comprising an amino acid substitution at one or more of the following positions: 118, 119, 124, 126-134, 136, 138-143, 145, 147-154, 163, 168, 170-172, 175, 176, 181, 183-185, 187, 190, 191, 197, 201, 203-206, 208, 210-214, 216, and 218, according to EU numbering, such that the first CH1 domain variant preferentially binds to the first light chain. Optionally, the first light chain polypeptide comprises a first CL domain which is a wild-type CL domain. Further optionally, certain CH1 domain variants may be excluded as described above and the CH1 domain variants according to the present invention may meet one or more of the items (a)-(o) as described above. Also provided herein are such antibodies or antibody fragments, further comprising a second heavy chain polypeptide and a second light chain polypeptide, wherein: (a) the second heavy chain polypeptide and the second light chain polypeptide form a second cognate pair; and (b) the second heavy chain polypeptide comprises a second CH1 domain variant comprising an amino acid substitution at one or more of the following positions: 118, 119, 124, 126-134, 136, 138-143, 145, 147-154, 163, 168, 170-172, 175, 176, 181, 183-185, 187, 190, 191, 197, 201, 203-206, 208, 210-214, 216, and 218, according to EU numbering, such that the second CH1 domain variant preferentially binds to the second light chain polypeptide comprising a second CL domain. Again, optionally, certain CH1 domain variants may be excluded as described above and the CH1 domain variants according to the present invention may meet one or more of the items (a)-(o) as described above. Further optionally, such an antibody or antibody fragment comprises one or more of features (i)-(vii): (i) the first CL domain is a wild-type CL domain; (ii) the second CL Domain is a wild-type CL domain; (iii) the first CL domain is a kappa CL domain; (iv) the first CL domain is a lambda CL domain; (v) the second CL domain is a kappa CL domain; (vi) the second CL domain is a lambda CL domain; (vii) the first CH1 domain variant is the CH1 domain variant according to the claims below; (viii) the second CH1 domain variant is the CH1 domain variant according to the claims below; and/or (ix) the amino acid substitution(s) in the first CH1 domain variant are different from the amino acid substitution(s) in the second CH1 domain variant.

Further provided herein are antibodies or antibody fragments, comprising a first heavy chain polypeptide and a first light chain polypeptide, wherein: (a) the first heavy chain polypeptide and the first light chain polypeptide form a first cognate pair; (b) the first heavy chain polypeptide comprises a first CH1 domain variant according to any one of the kappa-preferring CH1 domain variant described above; and (c) the first light chain polypeptide comprises a kappa CL domain and optionally is a kappa light chain polypeptide. Optionally, (i) the kappa CL domain is a wild-type CL domain; and/or (ii) the first light chain polypeptide is a wild-type light chain polypeptide. In certain embodiments, the first heavy chain polypeptide optionally comprises one or more amino acid substitutions outside the CH1 domain which further promotes preferential pairing of the heavy chain with: (i) a kappa CL domain as compared to a lambda CL domain, and/or (ii) a kappa light chain polypeptide as compared to a lambda light chain polypeptide. The one or more amino acid substitutions outside the CH1 domain may be, for example, in the VH.

Also provided herein are antibodies or antibody fragments, comprising a second heavy chain polypeptide and a second light chain polypeptide, wherein: (a) the second heavy chain polypeptide and the second light chain polypeptide form a first cognate pair; (b) the second heavy chain polypeptide comprises a second CH1 domain variant according to any one of the lambda-preferring CH1 domain variant described above; and (c) the second light chain polypeptide comprises a lambda CL domain and optionally is a lambda light chain polypeptide. Optionally, (i) the lambda CL domain is a wild-type CL domain; and/or (ii) the second light chain polypeptide is a wild-type light chain polypeptide. In certain embodiments, the second heavy chain polypeptide optionally comprises one or more amino acid substitutions outside the CH1 domain which further promotes preferential pairing of the heavy chain with: (i) a lambda CL domain as compared to a kappa CL domain, and/or (ii) a lambda light chain polypeptide as compared to a kappa light chain polypeptide.

Also provided herein are antibodies or antibody fragments, comprising a first heavy chain polypeptide, a first light chain polypeptide, a second heavy chain polypeptide, and a second light chain polypeptide, wherein: (a) the first heavy chain polypeptide and the first light chain polypeptide form a first cognate pair; (b) the first heavy chain polypeptide comprises a first CH1 domain comprising the CH1 domain variant according to any one of the kappa-preferring CH1 domain variant described above; (c) the first light chain polypeptide comprises a kappa CL domain and optionally is a kappa light chain polypeptide; (d) the second heavy chain polypeptide and the second light chain polypeptide form a second cognate pair; (e) the second heavy chain polypeptide comprises a second CH1 domain comprising the CH1 domain variant according to any one of the lambda-preferring CH1 domain variant described above; and (f) the second light chain polypeptide comprises a lambda CL domain and optionally is a lambda light chain polypeptide. In certain embodiments, the first heavy chain polypeptide optionally comprises one or more amino acid substitutions outside the CH1 domain which further promote preferential pairing of the heavy chain with: (i) a kappa CL domain as compared to a lambda CL domain, and/or (ii) a kappa light chain polypeptide as compared to a lambda light chain polypeptide. The one or more amino acid substitutions outside the CH1 domain may be, for example, in the VH. In certain embodiments, the second heavy chain polypeptide optionally comprises one or more amino acid substitutions outside the CH1 domain which further promotes preferential pairing of the heavy chain with: (i) a lambda CL domain as compared to a kappa CL domain, and/or (ii) a lambda light chain polypeptide as compared to a kappa light chain polypeptide.

Any of the antibodies or antibody fragments may be multispecific, optionally bispecific. Optionally, the structure of such an antibody or antibody fragment is as depicted in any one of FIGS. 24-29.

In some embodiments, in a multispecific antibody or antibody fragment as described above, first and second CH1 domain variants reduce formation of non-cognate heavy chain-light chain pairs by at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. In some embodiments, in a multispecific antibody or antibody fragment as described above, first and second CH1 domain variants increase formation of cognate heavy chain-light chain pairs by at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

In some embodiments, the reduction of non-cognate heavy-light pairing and/or increase of cognate heavy-light pairing may be quantified by transfecting cells with HC (or VH plus CH1) comprising the CH1 of interest, kappa LC, and lambda LC with a pre-determined ratio such as HC:kappa LC:lambda LC=2:1:1 and measuring the light chain species by LCMS, as in Example 7 and FIG. 23, 30, or 31. In certain embodiments using such a or a similar quantification method, an exemplary WT CH1 may result in HC-LC pairs, 60% of which are cognate pairs and 40% of which are non-cognate pairs, and with a CH1 variant according to the present disclosure, the percentage of the cognate pairs may be increased to at least 65%, at least 70%, at least 75%, at least 80%, at least 85%, at least 90%, at least 95%, or 100%, and the percentage of the non-cognate pairs may be decreased to at least 35%, at least 30%, at least 25%, at least 20%, at least 15%, at least 10%, at least 5%, or 0%. In particular embodiments using such a or a similar quantification method, the percentage of the cognate pair may be increased to at least 85%, at least 90%, at least 95%, or 100%, while the percentage of the non-cognate pair may be reduced to at least 15%, at least 10%, at least 5%, or 0%.

In some embodiments, in a multispecific antibody or antibody fragment as described above, first and second CH1 domain variants reduce formation of non-cognate heavy chain-light chain pairs by at least 1.2-fold, at least 1.5-fold, at least 2-fold, by at least 2.5-fold, by at least 3-fold, by at least 3.5-fold, by at least 4-fold, by at least 4.5-fold, by at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, or at least 25-fold. In some embodiments, in a multispecific antibody or antibody fragment as described above, first and second CH1 domain variants increase formation of cognate heavy chain-light chain pairs by at least 1.2-fold, at least 1.5-fold, at least 2-fold, by at least 2.5-fold, by at least 3-fold, by at least 3.5-fold, by at least 4-fold, by at least 4.5-fold, by at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, or at least 25-fold.

In In some embodiments, the reduction of non-cognate heavy-light pair and/or increase of cognate heavy-light pair may be quantified by simultaneously expressing HC (or VH plus CH1) comprising the CH1 of interest, kappa LC, and lambda LC with a pre-determined ratio to allow for presentation of the heavy-light pairs on a cell (e.g., yeast cell), staining the cells with anti-kappa and anti-lambda antibodies, and quantifying the kappa and lambda presence by FACS, e.g., by comparing the MFI values, as in FIGS. 2-5, 8-13, and 19-22. For comparing kappa preference of a certain CH1, the ratio of MFI of cells stained with anti-kappa:MFI of cells stained with anti-lambda may be calculated and divided by such a ratio for the WT CH1 to obtain the fold-over-parent (FOP) value. For comparing lambda preference of a certain CH1, the ratio of MFI of cells stained with anti-lambda:MFI of cells stained with anti-kappa may be calculated and divided by such a ratio for the WT CH1.

In certain embodiments using such a or a similar quantification method, with a kappa-preferring CH1 variant according to the present disclosure, the FOP value (calculated for kappa preference, i.e., MFI of kappa:lambda) may be increased by at least 1.2-fold, at least 1.5-fold, at least 2-fold, by 2.5-fold, by at least 3-fold, by at least 3.5-fold, by at least 4-fold, by at least 4.5-fold, by at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, or at least 25-fold. In certain embodiments using such a or a similar quantification method, with a lambda-preferring CH1 variant according to the present disclosure, the FOP value (calculated for lambda preference, i.e., MFI of lambda:kappa) may be increased by at least 1.2-fold, at least 1.5-fold, at least 2-fold, by 2.5-fold, by at least 3-fold, by at least 3.5-fold, by at least 4-fold, by at least 4.5-fold, by at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, or at least 25-fold.

In some embodiments, a second CH1 domain variant comprises a substitution at position 141 and reduces formation of non-cognate heavy chain-light chain pairs by at least 50%. In some embodiments, a second CH1 domain variant comprises a substitution at position 141 and the first CH1 domain variant comprises a substitution at position 183 and optionally at position 147, or vice versa, and reduces formation of non-cognate heavy chain-light chain pairs by at least 50% to at least 75%. In some embodiments, a second CH1 domain variant comprises 141D or 141E and the second CH1 domain variant comprises 183R, 183K, or 183Y and optionally 147F, or vice versa, and reduces formation of non-cognate heavy chain-light chain pairs by at least 50% to at least 75%. In some embodiments, a second CH1 domain variant comprises one or more of 141D or 141E, 170E, 171E, 181K, 185R, 187R, and 218P and the first CH1 domain variant comprises 183R, 183K, or 183Y and optionally 147F, or vice versa, and reduces formation of non-cognate heavy chain-light chain pairs by at least 50% to at least 75%. In some embodiments, a second CH1 domain variant comprises a combination of 141D, 171E, and 185R, a combination of 141D, 171E, and 187R, or a combination of 141D, 181K, and 218P, and the second CH1 domain variant comprises 183R, 183K, or 183Y and optionally 147F, or vice versa, and reduces formation of non-cognate heavy chain-light chain pairs by at least 50% to at least 75%.

In some embodiments, first and second CH1 domain variants provide at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% formation of the desired first and second cognate pairs. In some embodiments, first and second CH1 domain variants provide about 85% to about 95% formation of the desired first and second cognate pairs. In some embodiments, a second CH1 domain variant comprises a substitution at position 141 and the first CH1 domain variant comprises a substitution at position 183 and optionally at position 147, and provide about 85% to at least about 95% formation of the desired first and second cognate pairs. In some embodiments, a second CH1 domain variant comprises 141D or 141E and the first CH1 domain variant comprises 183R, 183K, or 183Y and optionally 147F, or vice versa, and provides about 85% to at least about 95% formation of the desired first and second cognate pairs. In some embodiments, first and second CH1 domain variants provide decreased formation of non-cognate heavy chain-light chain pairs of less than 25%, less than 20%, less than 15%, less than 14%, less than 13%, less than 12%, less than 11I % less than 10%, less than 9%, less than 8%, less than 7%, less than 6%, less than 5%, less than 4%, less than 3%, less than 2%, or less than 1%. In some embodiments, a second CH1 domain variant comprises a substitution at position 141, 170, 171, 181, 185, 187, and/or 218 and the first CH1 domain variant comprises a substitution at position 183 and optionally at position 147, or vice versa, and provides decreased formation of non-cognate heavy chain-light chain pairs of less than about 15%, less than about 10%, or less than about 5%. In some embodiments, a second CH1 domain variant comprises one or more of 141D or 141E, 170E, 171E, 181K, 185R, 187R, and 218P and the first CH1 domain variant comprises 183R, 183K, or 183Y and optionally 147F, or vice versa, and provides decreased formation of non-cognate heavy chain-light chain pairs of less than about 15%, less than about 10%, or less than about 5%.

In yet another aspect, further provided herein are pharmaceutical and diagnostic compositions comprising: (i) a CH1 domain variant polypeptide as described above; (ii) an antibody heavy chain polypeptide as described; and/or (iii) an antibody or antibody fragment of as described above.

In another aspect, further provided herein are therapeutic and diagnostic uses of antibodies and pharmaceutical compositions comprising: (i) a CH1 domain variant polypeptide as described above; (ii) an antibody heavy chain polypeptide as described; and/or (iii) an antibody or antibody fragment of as described above.

In still another aspect, further provided herein nucleic acids encoding: (i) a CH1 domain variant polypeptide as described above; (ii) an antibody heavy chain polypeptide as described; and/or (iii) an antibody or antibody fragment of as described above.

In yet another aspect, further provided herein are vectors comprising or cells transfected with nucleic acids encoding: (i) a CH1 domain variant polypeptide as described above; (ii) an antibody heavy chain polypeptide as described; and/or (iii) an antibody or antibody fragment of as described above and the use thereof to produce the foregoing.

In another aspect, the present disclosure provides methods of generating a CH1 variant domain library, the method comprising steps (a)-(c): (a) providing (i) one or more sets of a polypeptide comprising a CH1 domain paired with a polypeptide comprising a kappa CL domain ("Cκ set"); (ii) one or more sets of a polypeptide comprising a CH1 domain paired with a polypeptide comprising a lambda CL domain ("Cλ set"); and/or (iii) in the VH in the $C_\kappa$ set and/or in the $C_\lambda$ set; (b) selecting one or more amino acid positions of the CH1 domain that are in contact with one or more amino acid positions in the kappa CL domain in the Cκ set and/or in the lambda CL domain in the Cλ set; and (c) producing a library of CH1 domain variant polypeptides or a library of CH1 domain variant-encoding constructs, wherein one or more of the one or more amino acid positions selected in step (b) are substituted with any non-wild-type amino acid. Optionally, the polypeptide comprising a CH1 domain further comprises a heavy chain variable region (VH), further optionally wherein the polypeptide comprising a kappa or a lambda CL domain further comprises a light chain variable region (VL).

Optionally: (I) in step (a), said CH1 domain, said kappa CL domain, and said lambda CL domain are wild-type and/or human; (II) in step (a), both (i) said polypeptide comprising a CH1 domain paired with a polypeptide comprising a kappa CL domain and (ii) said polypeptide comprising a CH1 domain paired with a polypeptide comprising a lambda CL domain are an intact antibody or are an fragment antigen-binding ("Fab"); (III) in step (b), one or more amino acid positions of the CH1 domain is selected if the amino acid residue at said one or more amino acid positions of the CH1 domain have a side-chain atom within a distance of 5 Å of (i) a side-chain atom of the amino acid residue at said one or more amino acid positions in the kappa CL domain, (ii) a side-chain atom of the amino acid residue at said one or more amino acid positions in the lambda CL domain, and/or (iii) a side-chain atom of the amino acid residue at said one or more amino acid positions in the VH; and/or (IV) said producing in step (c) is via a degenerate codon, optionally a degenerate RMW codon representing six naturally occurring amino acids (D, T, A, E, K, and N) or a degenerate NNK codon representing all 20 naturally occurring amino acid residues.

In some embodiments, one or more CH1 amino acid positions selected in step (b) are: (i) at an interface with the kappa CL domain in at least 10% of a representative set of the Cκ set and has a fractional solvent accessible surface area greater than 10% in at least 90% of a representative set of the Cκ set, (ii) at an interface with the lambda CL domain in at least 10% of a representative set of the Cλ set and has a fractional solvent accessible surface area greater than 10% in at least 90% of a representative set of the Cλ set, and/or (iii) at an interface with the VH in at least 10% of a representative set of the $C_\kappa$ and/or $C_\lambda$ set and has a fractional solvent accessible surface area greater than 10% in at least 90% of a representative set of the $C_\kappa$ and/or $C_\lambda$ set.

In some embodiments, the amino acid positions selected in step (b) comprise one or more of positions 118, 119, 124, 126-134, 136, 138-143, 145, 147-154, 163, 168, 170-172, 175, 176, 181, 183-185, 187, 190, 191, 197, 201, 203-206, 208, 210-214, 216, and 218 according to EU numbering. Optionally, certain CH1 domain variants may be excluded as described above and the CH1 domain variants according to the present invention may meet the criteria (a)-(o) as described above.

In some embodiments, synthesized polypeptides that encode the CH1 variant domains or the library of CH1 domain variants in step (c) are expressed in a yeast strain. In some embodiments, a yeast strain is *Saccharomyces cerevisiae*. In some embodiments, a cell system, such as a yeast strain, co-expresses (i) one or more polypeptides comprising a kappa CL domain, such as a kappa light chain, and (ii) one or more polypeptides comprising a lambda CL domain, such as a lambda light chain. Optionally wherein the kappa and/or lambda CL domains are wild-type. Further optionally, the kappa and/or lambda CL domains are human.

In some embodiments, a method of the present disclosure further comprises validating that the one or more substituted CH1 amino acid residues drives preferential pairing for a kappa light chain or a lambda light chain. In some embodiments, fluorescence-activated cell sorting is used to validate that the one or more substituted CH1 amino acid residues drives preferential pairing for a kappa light chain or a lambda light chain.

In some embodiments, one or more kappa constant (Cκ) domains, one or more lambda constant (Cλ) domains, and one or more CH1 domains are wild-type. In some embodiments, one or more kappa constant (Cκ) domains, one or more lambda constant (Cλ) domains, and one or more CH1 domains are human.

In some embodiments, the method of generating a CH1 domain library comprises steps (a)-(c): (a) selecting one or more of the following CH1 amino acid positions: 118, 119, 124, 126-134, 136, 138-143, 145, 147-154, 163, 168, 170-172, 175, 176, 181, 183-185, 187, 190, 191, 197, 201, 203-206, 208, 210-214, 216, and 218, according to EU numbering, (b) selecting one or more CH1 amino acid positions of interest different from the position(s) selected in step (a); and (c) producing a library of CH1 domain variant polypeptides or a library of CH1 domain variant-encoding constructs, wherein one or more of the one or more amino acid positions selected in step (a) and (b) are substituted with any non-wild-type amino acid. In certain embodiments, the amino acid position(s) selected in (a) may comprise position 141, 147, 151, 170, 171, 181, 183, 185, 187, or 218, or any combination thereof. In certain embodiments, said producing in step (c) is via a degenerate codon, optionally a degenerate RMW codon representing six naturally occurring amino acids (D, T, A, E, K, and N) or a degenerate NNK codon representing all 20 naturally occurring amino acid residues. In certain embodiments, in step (c), the amino acid positions(s) selected in step (a) may substituted to a pre-determined amino acid and the amino acid position(s) selected in (b) is substituted via a degenerate codon. Optionally, the substitution to a pre-determined amino acid may comprise A141D, A141E, K147F, P151A, P151L, F170E, P171E, S181K, S183R, V185R, T187R, or K218P, or any combination thereof.

In yet another aspect, the present disclosure provides methods of identifying one or more CH1 domain variant polypeptides that preferentially pair with: (A) a polypeptide comprising a kappa CL domain as compared to a polypeptide comprising a lambda CL domain; or (B) a polypeptide comprising a lambda CL domain as compared to a polypeptide comprising a kappa CL domain. Such a method comprises steps (a)-(c): (a) co-expressing one or more candidate CH1 domain variant polypeptides with (i) one or more polypeptides comprising a kappa CL domain and (ii) one or more polypeptides comprising a lambda CL domain; (b) comparing (i) the amount of a candidate CH1 domain variant polypeptide paired with a polypeptide comprising a kappa CL domain and (ii) the amount of a candidate CH1 domain variant polypeptide paired with a polypeptide comprising a lambda CL domain; (c) based on the comparison in step (b), selecting one or more CH1 domain variants that provide preferential pairing with (A) a polypeptide comprising a kappa CL domain as compared to a polypeptide comprising a lambda CL domain; or (B) a polypeptide comprising a lambda CL domain as compared to a polypeptide comprising a kappa CL domain. In step (a), generally the total amount of the candidate CH1 domain variant polypeptides expressed and the total amount of the polypeptides comprising a (kappa and lambda) CL domain expressed may be approximately the same. Optionally wherein in step (a), the candidate CH1 domain variant polypeptides, the polypeptides comprising a kappa CL domain, and the polypeptides comprising a lambda CL domain are expressed approximately at the ratio of 2:1:1.

In some embodiments, in step (a), said (i) one or more polypeptides comprising a kappa CL domain and (ii) one or more polypeptides comprising a lambda CL domain are wild-type and/or human.

In some embodiments, in step (b), the amount is determined via fluorescence-activated cell sorting or via liquid chromatography-mass spectrometry.

In some embodiments, the method further comprises step (d): (d) co-expressing one or more control CH1 domain variants with (i) one or more polypeptides comprising a kappa CL domain and (ii) one or more polypeptides comprising a lambda CL domain, optionally wherein one or more of said one or more control CH1 domain variants is according to the CH1 domain variant of any of those described above.

BRIEF DESCRIPTION OF THE DRAWING

FIG. 1A shows heterodimerization of a wild-type CH1 domain with Cλ and Cκ (the wild-type or unmodified CH1 domain is referred to a $CHT_{WT}$). FIG. 1B shows a CH1 domain variant having preferential pairing with Cκ (such CH1 domain variants with preferential pairing to Cκ are referred to as CH1κ). FIG. 1C shows a CH1 domain variant having preferential pairing with Cλ (such CH1 domain variants with preferential pairing to Cλ are referred to as CH1λ).

FIG. 6A shows IL12B and EGFR binding data for BsAbs1-3. FIG. 6B shows IL12B and EGFR binding data for BsAbs 5, 7, and 4. FIG. 6C shows IL12B and EGFR binding data for BsAbs 9, 10, and 6. FIG. 6D shows IL12B and EGFR binding data for BsAbs 11, 12, and 8. FIG. 6E shows IL12B and EGFR binding data for BsAbs13-15. Pani=Panitumumab; Uste=Ustekinumab.

Figure 1A:
FIG. 1A-C are a schematic of binding of a CH1 domain variant to a Cλ domain or a Cκ domain.

(filled arrow) showed higher % lambda and lower % kappa chains compared to the positive control, "DKP".

FIGS. 24-29 provide exemplary and non-limiting embodiments of various multispecific antibody structures with which the CH1 domain variants disclosed herein may be used. In FIGS. 24-29, the following applies unless otherwise indicated; (1) Each domain is presented as a rectangle with the text therein showing the domain name (e.g., CH1, VH1, etc); (2) filled rectangles and dotted rectangles are CH1 domain variants with kappa or lambda preference, which may be a CH1 domain variant disclosed herein; (3) "CH1κ" is a CH1 domain variant with kappa CL preference, "CH1λ" is a CH1 domain variant with lambda preference, and "CH1" without an indication of "κ" or "λ" is any CH1 domain, wildtype or a variant, with or without light chain isotype preference; (4) "Cκ" is a kappa CL domain, "Cλ" is a lambda CL domain, and "CL" without an indication of "κ" or "λ", when shown to be paired with a filled or dotted CH1 domain, represents a CL domain of the isotype (kappa or lambda) that the paired filled or dotted CH1 domain has preference for; (5) when more than one filled and/or dotted CH1 domains are present in a multispecific structure, at least one is a CH1 domain variant disclosed herein and the rest may or may not be a CH1 domain variant disclosed herein; (6) when both filled and dotted CH1 domains are present in a multispecific structure, filled and dotted represent CH1 domains with different light chain isotype preference (i.e., when the filled represents a CH1 domain with kappa preference, the dotted represents a CH1 domain with lambda preference, and vice versa); (7) VH1 and VL1 form an antigen-binding site for a first epitope, VH2 and VL2 form an antigen-binding site for a second epitope, VH3 and VL3 form an antigen-binding site for a third epitope, VH4 and VL4 form an antigen-binding site for a fourth epitope, VH5 and VL5 form an antigen-binding site for a fifth epitope, and VH6 and VL6 form an antigen-binding site for a sixth epitope; (8) all of the first through sixth epitopes may be different from each other, or not all of the first through sixth epitopes may be different from each other, as long as the specificity combination overall renders the presented structure multispecific; (9) a set of multiple domains connected with each other represents a polypeptide (e.g., a heavy chain polypeptide, a light chain polypeptide, etc); (10) the direction of domains within a polypeptide is according to the direction of the text showing domain names, from the N-terminus to the C-terminus; (11) a linker or a hinge may be used between domains as necessary and a disulfide bond(s) may exist between polypeptides (and/or within a domain), perhaps to allow correct formation of the antigen-binding site(s), even when the FIGS. do not explicitly show a linker, a hinge, or a disulfide bond; (12) a CH2 and/or CH3 domain(s) shown in figures may be omitted whenever possible and, when appropriate, may be replaced with a hinge; (13) CH1, CH2, and CH3 domains may individually be a wildtype or a variant and may individually be of any (heavy chain) isotype; and (14) when more than one CH1 domains are present in a structure, the CH1 domains may or may not be of the same isotype, when more than one CH2 domains are present in a structure, the CH2 domains may or may not be of the same isotype, and when more than one CH3 domains are present in a structure, the CH3 domains may or may not be of the same isotype.

Figure 24A:
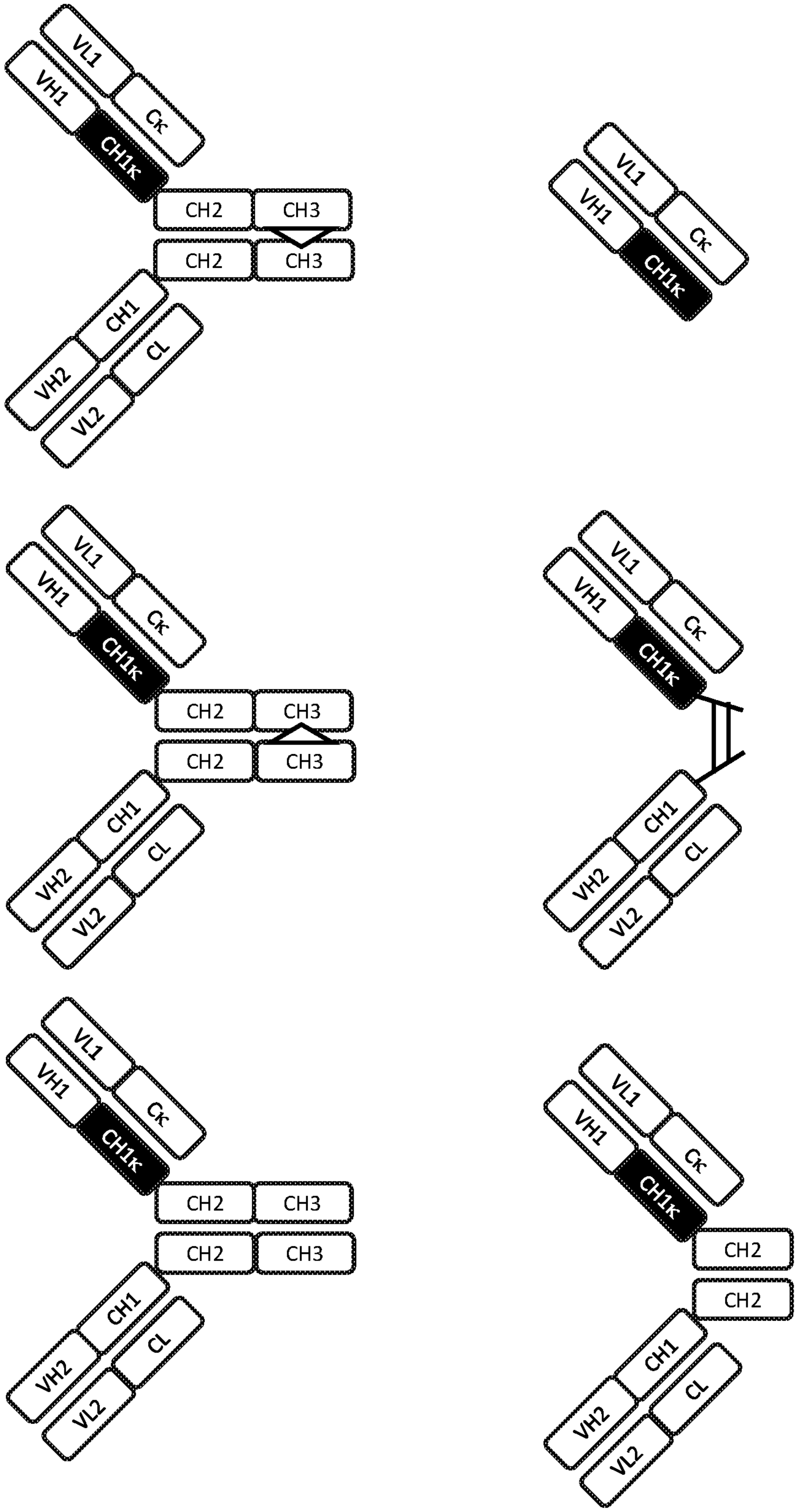
Figure 24B:
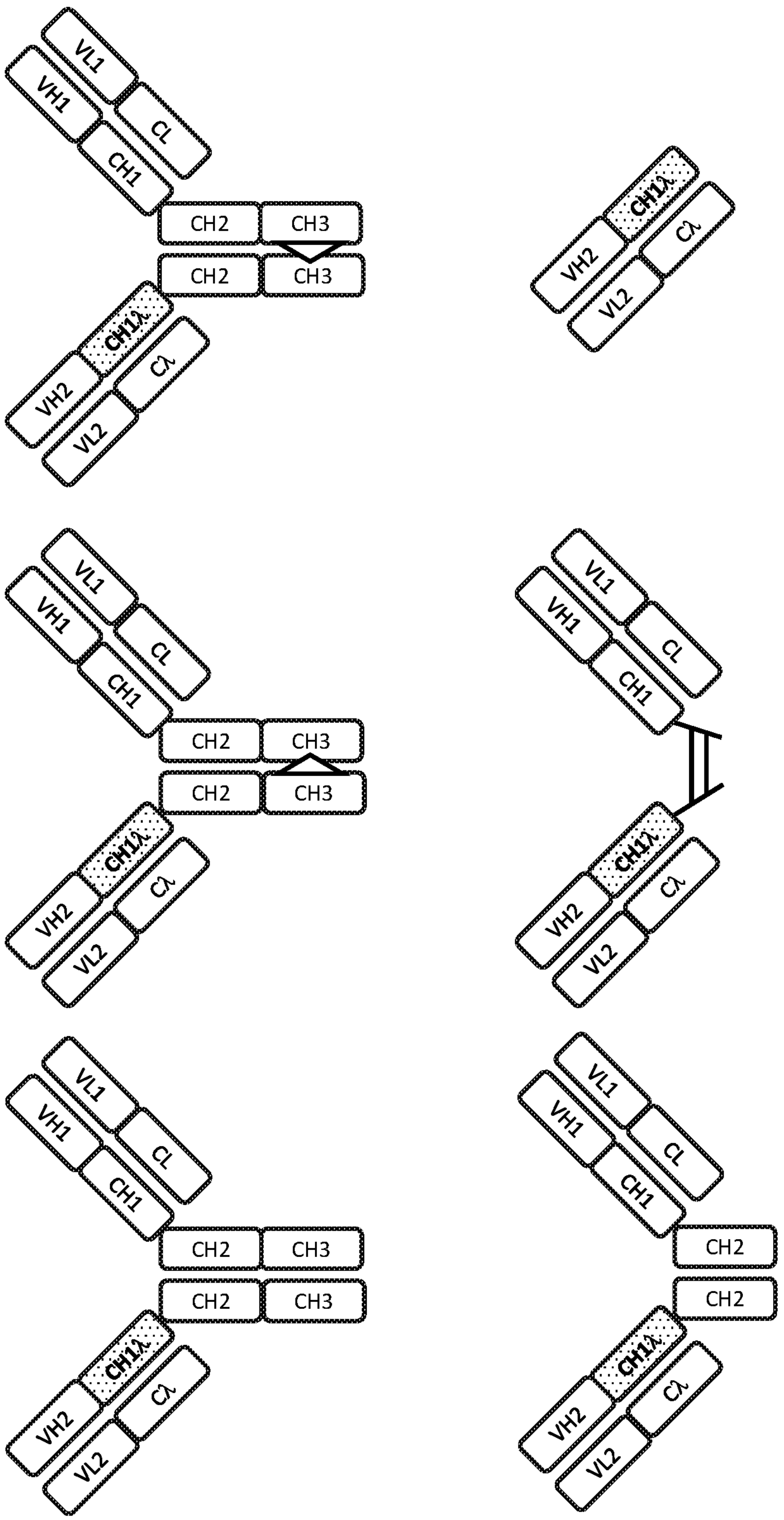
Figure 24C:
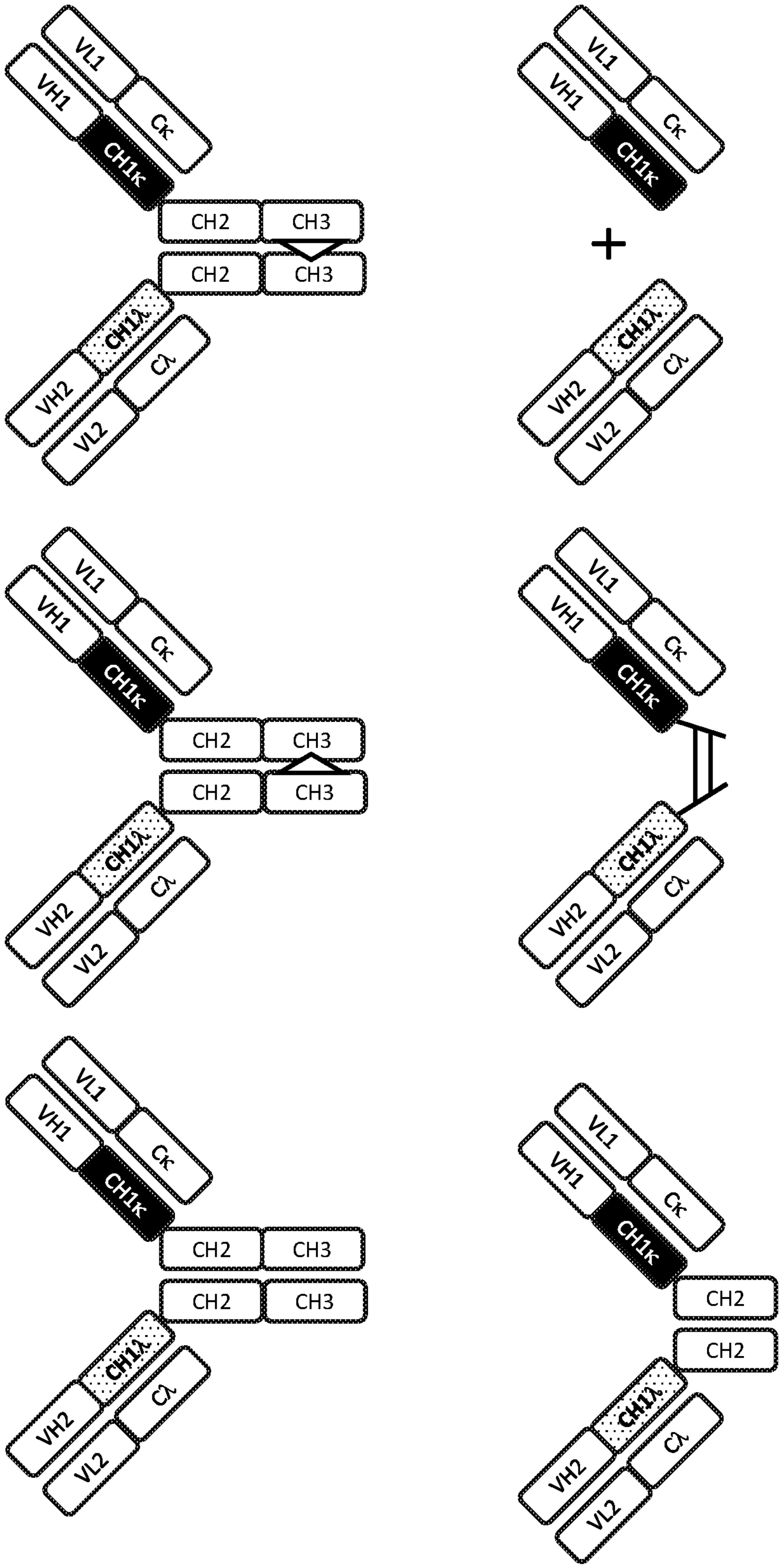

FIGS. 24A-24C provide some exemplary and non-limiting embodiments of various multispecific antibody structures with which the CH1 domain variants disclosed herein may be used. In FIG. 24A, a kappa-preferring CH1 domain ("CH1κ") is used in one polypeptide. The other CH1 domain may or may not have preference for a lambda CL domain and may or may not be a CH1 domain variant disclosed herein. In FIG. 24B, a lambda-preferring CH1 domain ("CH1λ") is used in one polypeptide. The other CH1 domain may or may not have preference for a kappa CL domain and may or may not be a CH1 domain variant disclosed herein. In FIG. 24C, a CH1κ is used in one polypeptide and a CH1λ is used in one polypeptide. This generic structure allows for manufacturing of a bispecific compound without or with minimal or less effort for removing mis-paired compounds. At least one of the CH1κ and CH1λ domains is a CH1 domain variant disclosed herein. As described above in (10), the direction of domains within a polypeptide is according to the direction of the text showing domain names, from the N-terminus to the C-terminus. Therefore, in case of the top left compound of FIG. 24A, a first polypeptide comprises VH1-CHTk-CH2-CH3, a second polypeptide comprises VL1-Cλ, a third polypeptide comprises VH2-CH1-CH2-CH3, and a fourth polypeptide comprises VL2-CL, in the direction from the N-terminus to the C-terminus. The triangle in the top center and top right compounds in FIGS. 24A-24C (and all other applicable FIGS.) represents a mechanism that promotes heterodimerization of two non-identical polypeptides, such as the "knobs-in-holes" engineering. The bottom center compound of FIGS. 24A-24C (and all other applicable FIGS.) shows the hinge structure that connects the CH1κ-containing polypeptide and the CH1λ-containing polypeptide. Although two bonds (e.g., disulfide bonds) are explicitly shown to connect the two polypeptide, the number of bonds and the exact location/position of the bonds may be vary and be selected appropriately. In the bottom right of FIG. 24C, "+" indicates a mixture of two different Fab fragments.

Figure 25A:
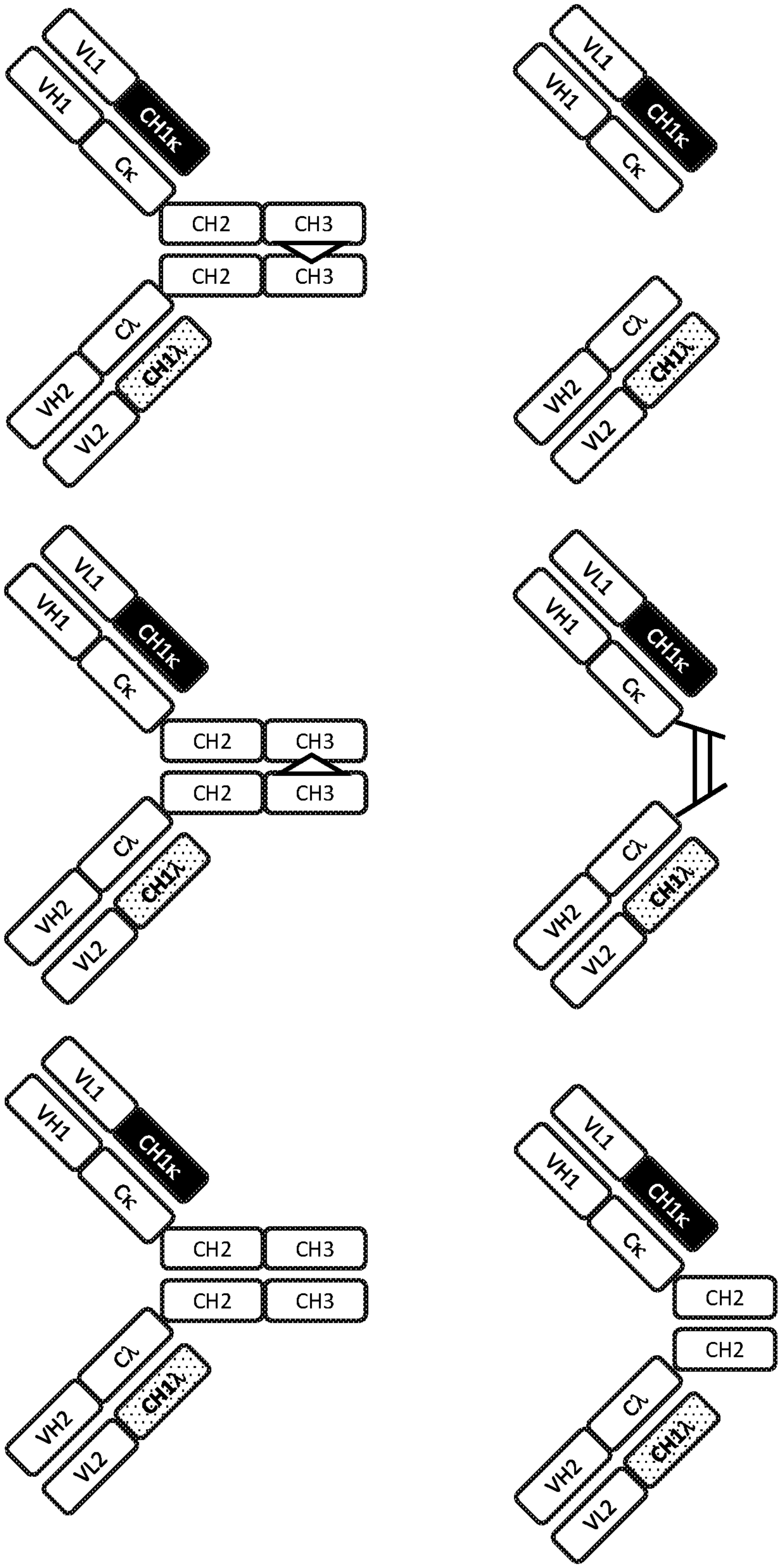
Figure 25B:
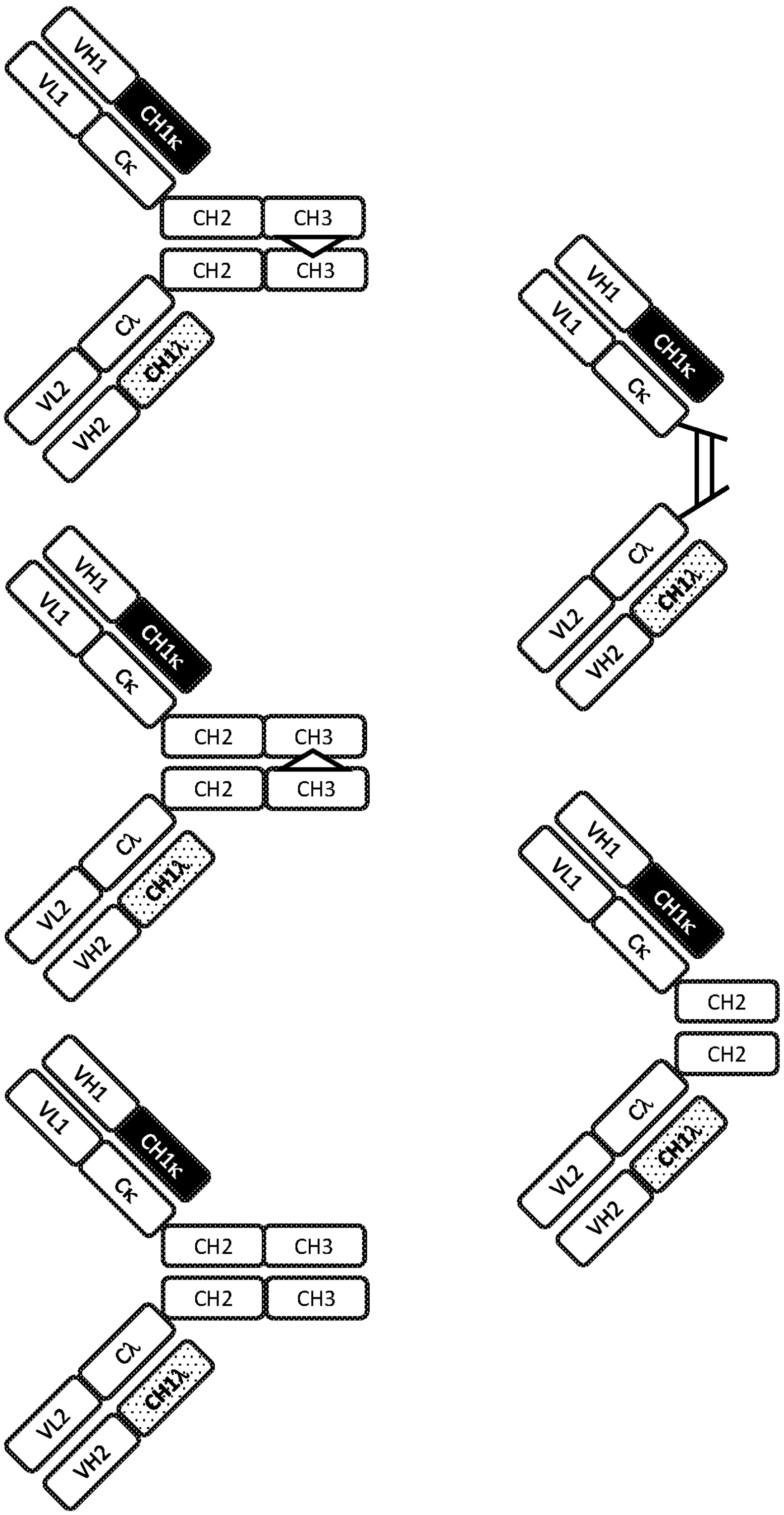

FIGS. 25A-25B provide further exemplary and non-limiting embodiments of various multispecific antibody structures with which the CH1 domain variants disclosed herein may be used. The structures are similar to those in FIGS. 24A-23C, but the domain orders differ. In FIG. 25A, the CH1κ is in the same polypeptide with a VL and CH1λ is in the same polypeptide with a VL. In FIG. 25B, the Cλ is in the same polypeptide with a CH2 (top three and bottom left) and the Cλ is in the heavy chain-like polypeptide (hinge-containing polypeptide) (bottom right).

Figure 26A:
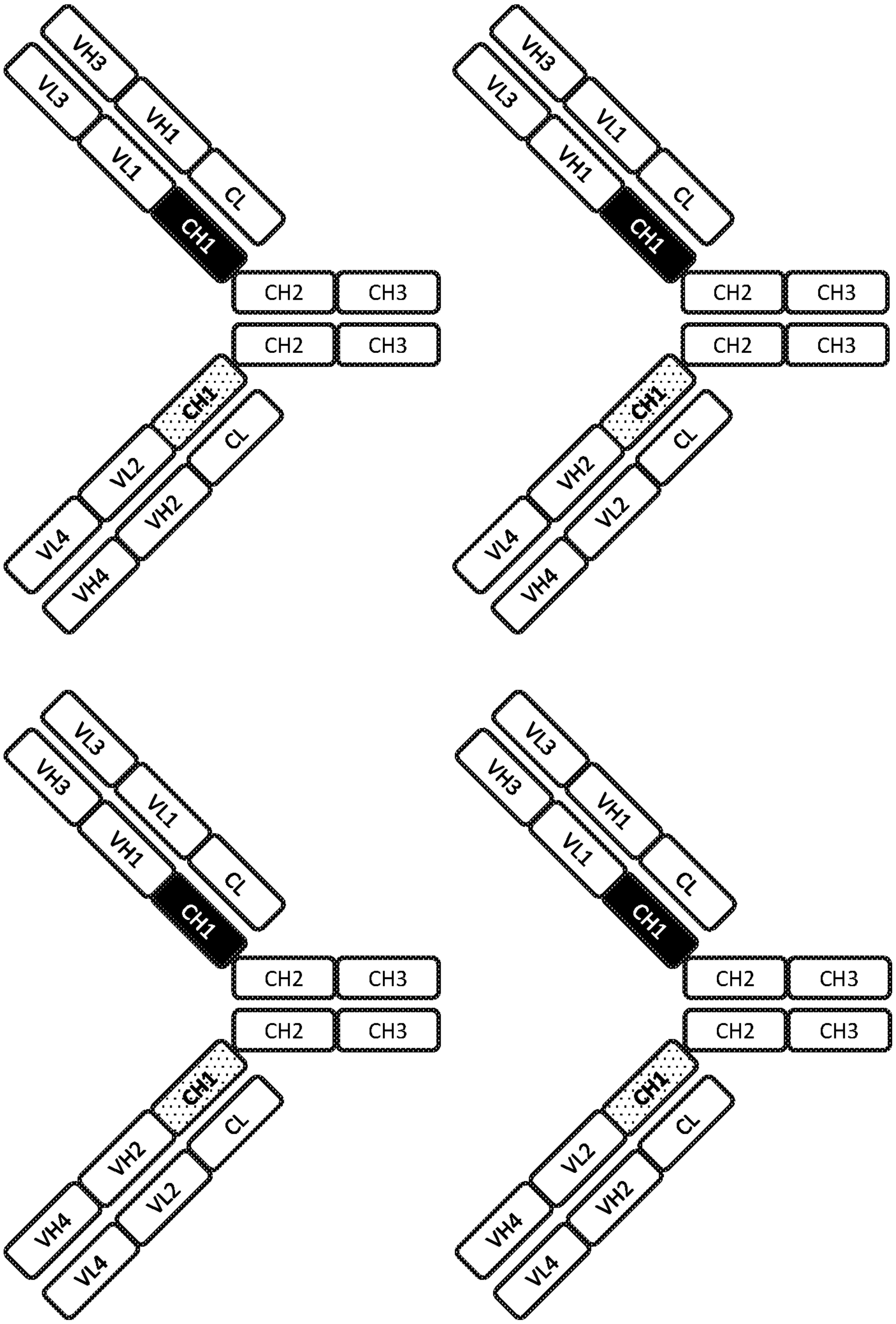
Figure 26B:
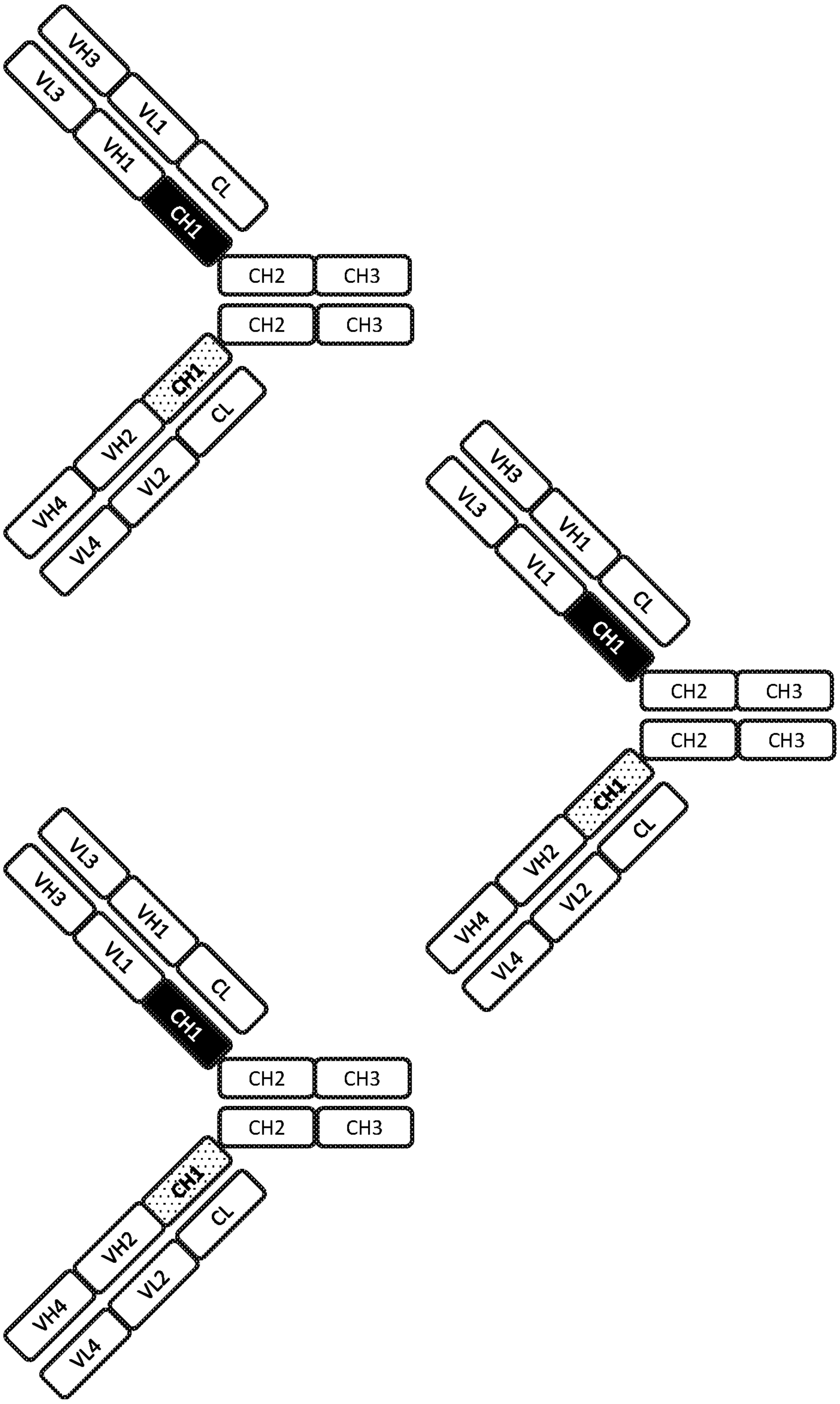
Figure 26C:
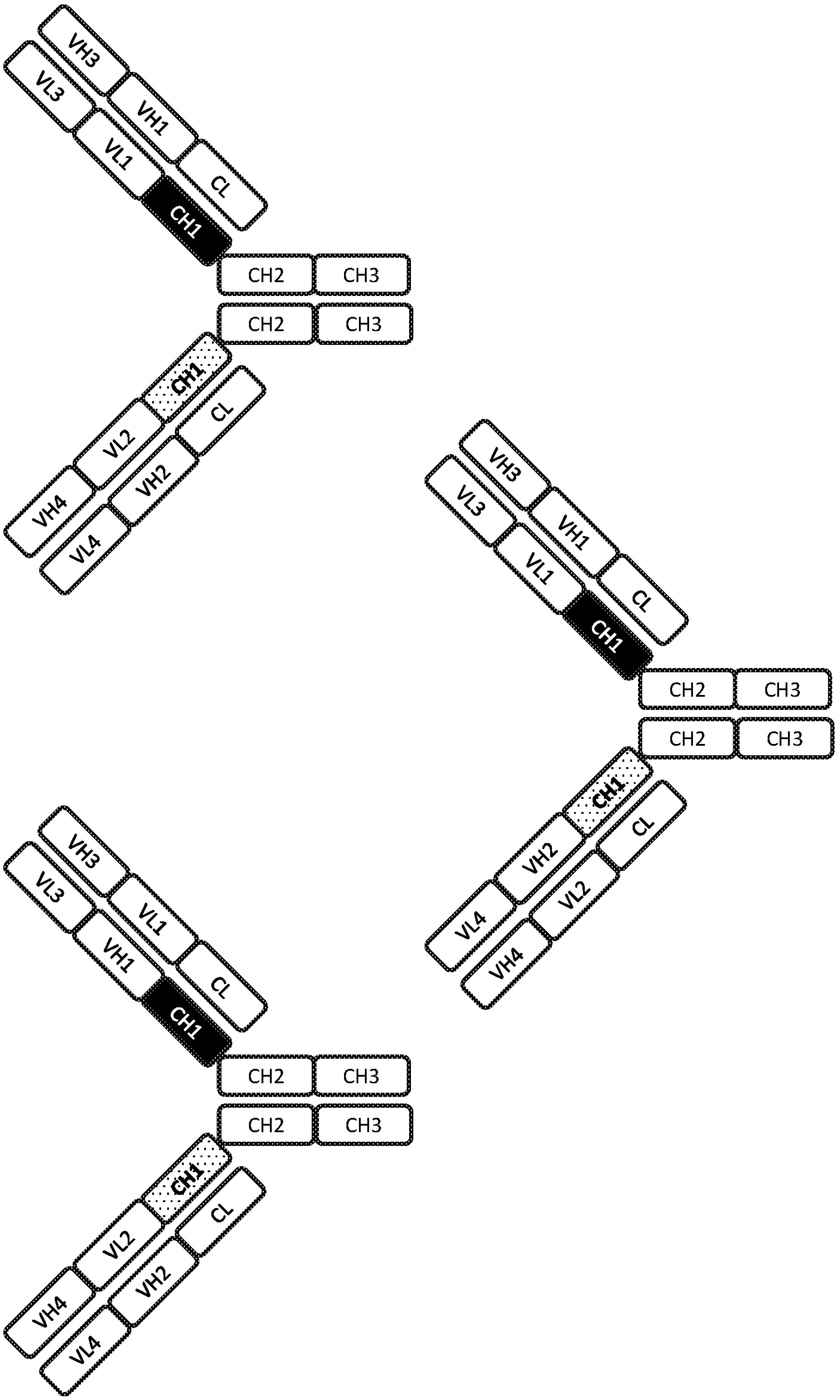

FIGS. 26A-26C provide further exemplary and non-limiting embodiments of various multispecific antibody structures, which comprise two sets of two antigen-binding sites in tandem and therefore are tetravalent. The structure may be bispecific, trispecific, or tetraspecific, depending on what the first, second, third, and fourth epitopes are. For example, if the first, second, and epitopes are different from each other, and if fourth epitope is same as the first, second, or third epitope, the structure would be a tetravalent trispecific structure.

Figure 27A:
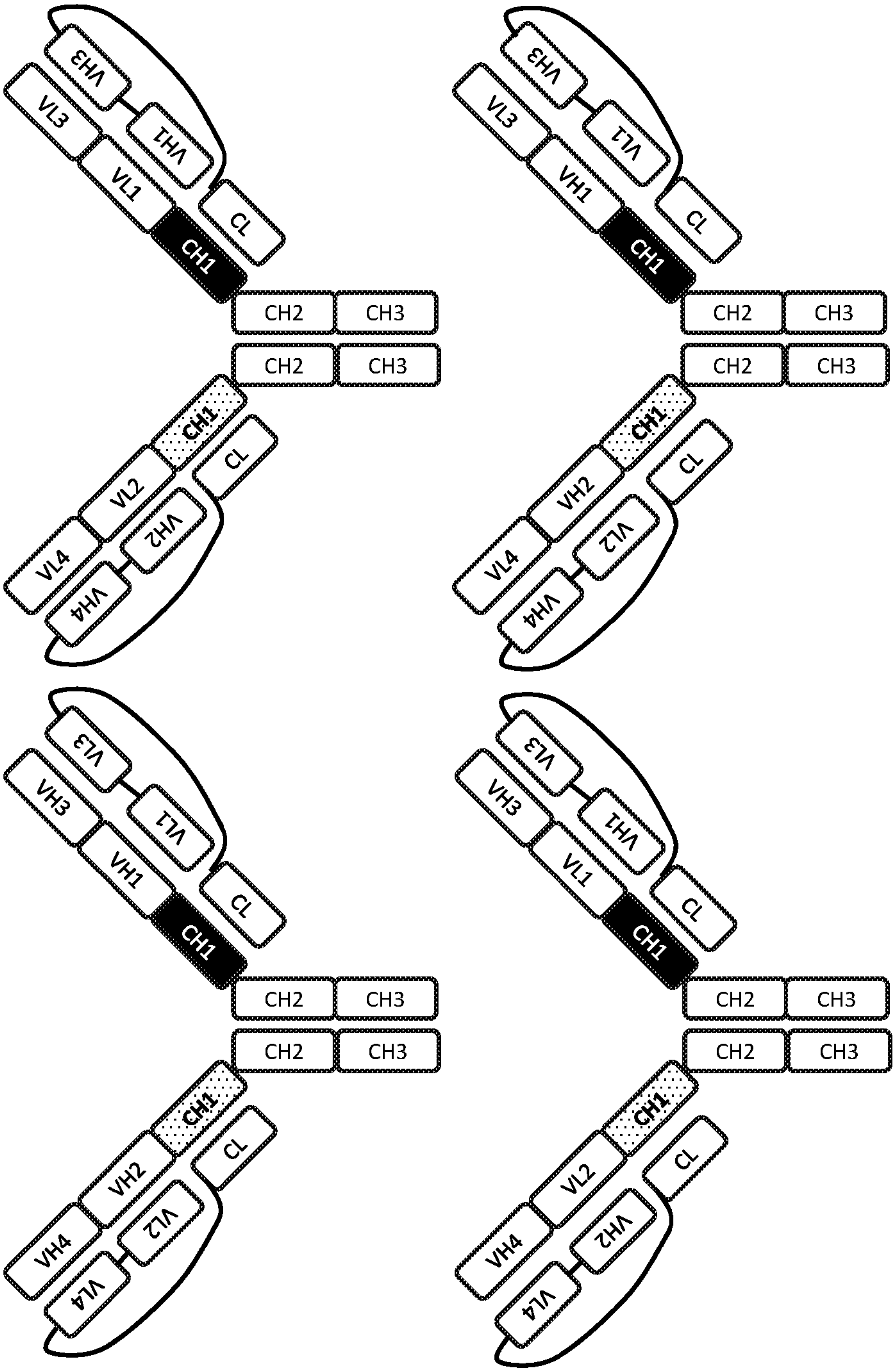
Figure 27B:
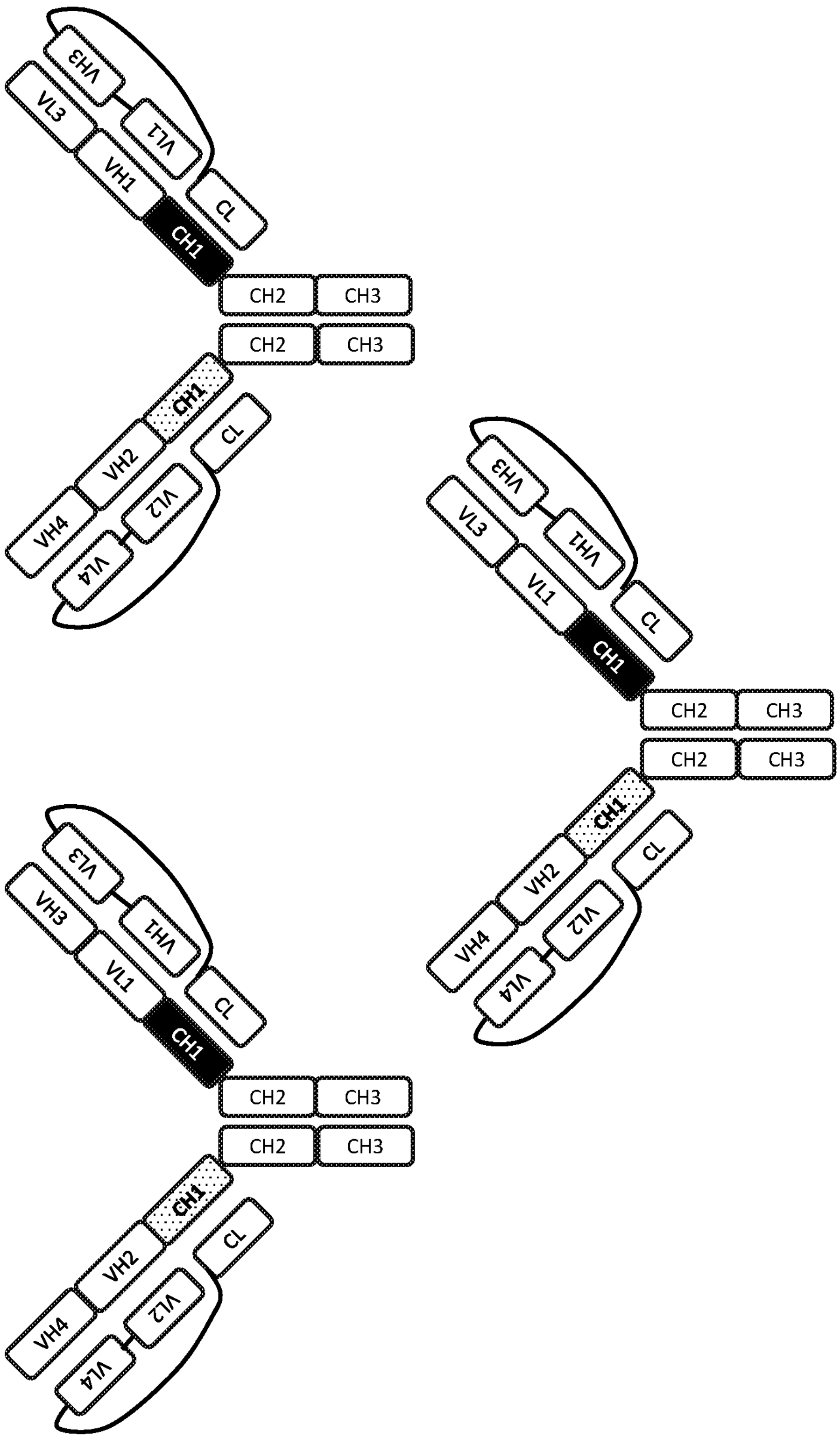
Figure 27C:
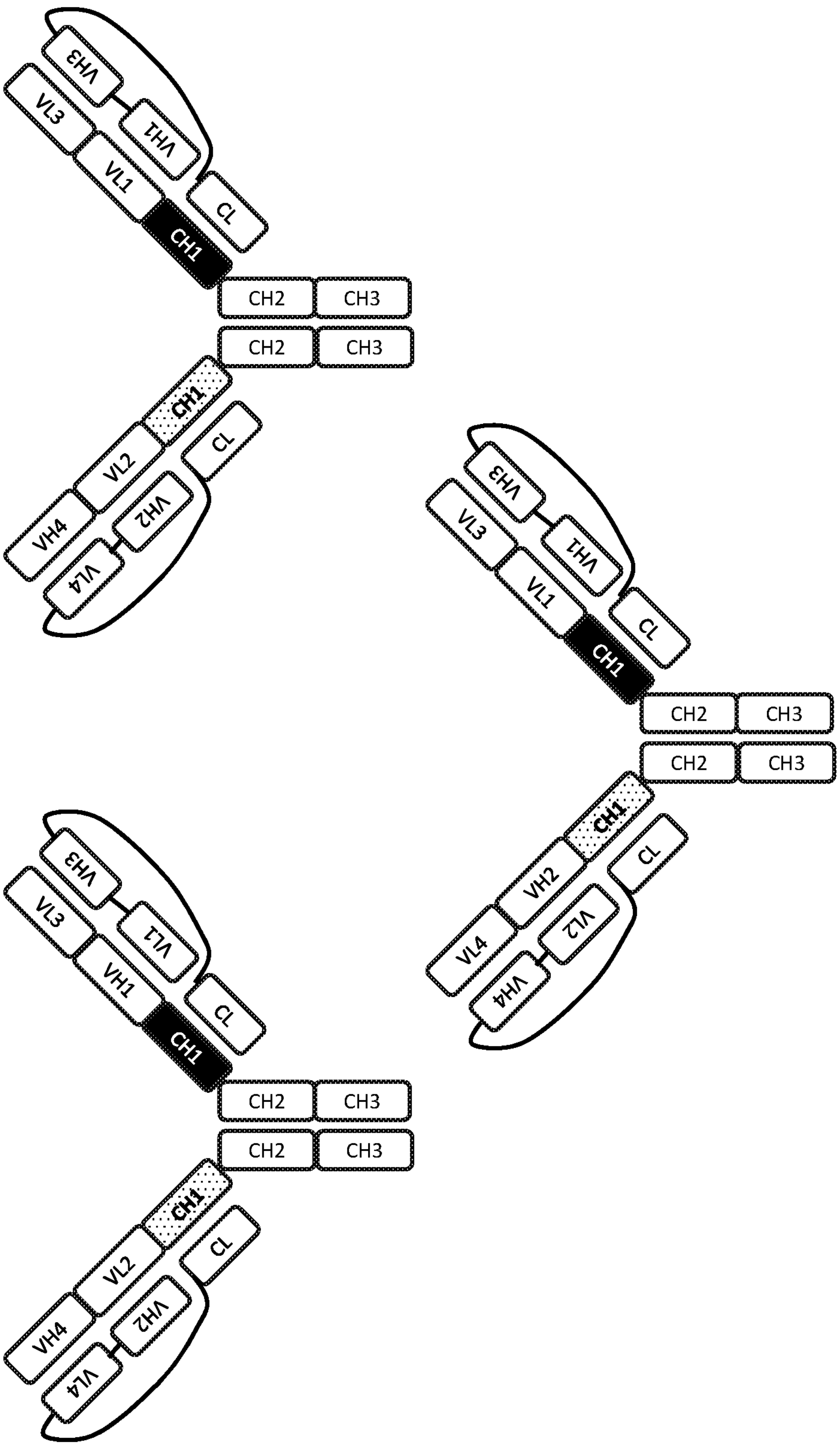

FIGS. 27A-27C provide further exemplary and non-limiting embodiments of various multispecific antibody structures, which are similar to those in FIGS. 26A-26C but differ in the domain orders. As described above in (10), the direction of domains within a polypeptide is according to the direction of the text showing domain names, from the N-terminus to the C-terminus. Therefore, in case of the top left structure of FIG. 27A, a first polypeptide comprises VH3-VH1-CH1(filled)-CH2-CH3, a second polypeptide comprises VL1-VL3-CL, a third polypeptide comprises VH4-VH2-CH1(dotted)-CH2-CH3, and a fourth polypeptide comprises VL2-VL4-CL, in the direction from the N-terminus to the C-terminus. In any structures in FIGS.

27A-27C, an appropriate may be used between domains to allow for appropriate formation of antigen-binding sites.

Figure 28A:
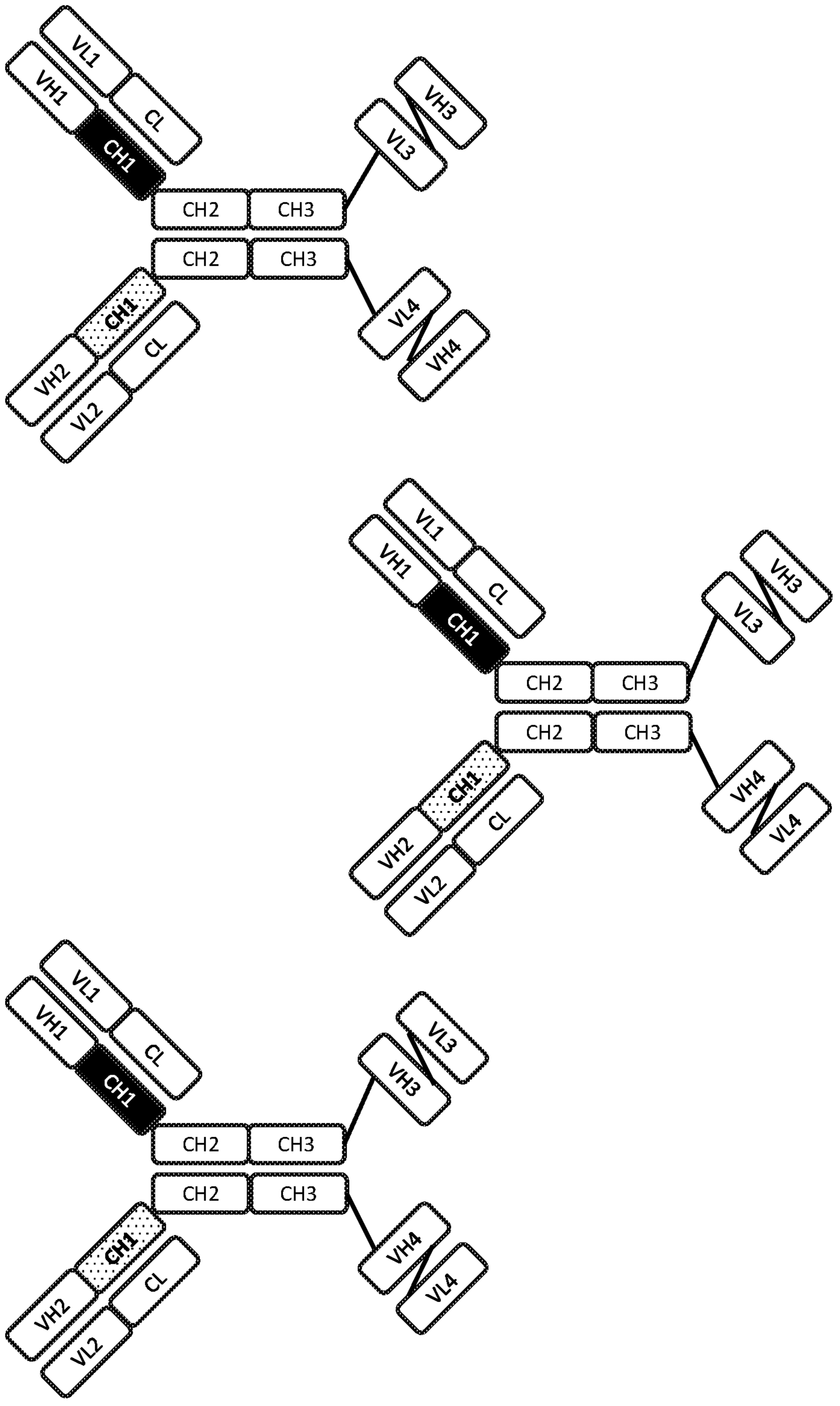
Figure 28B:
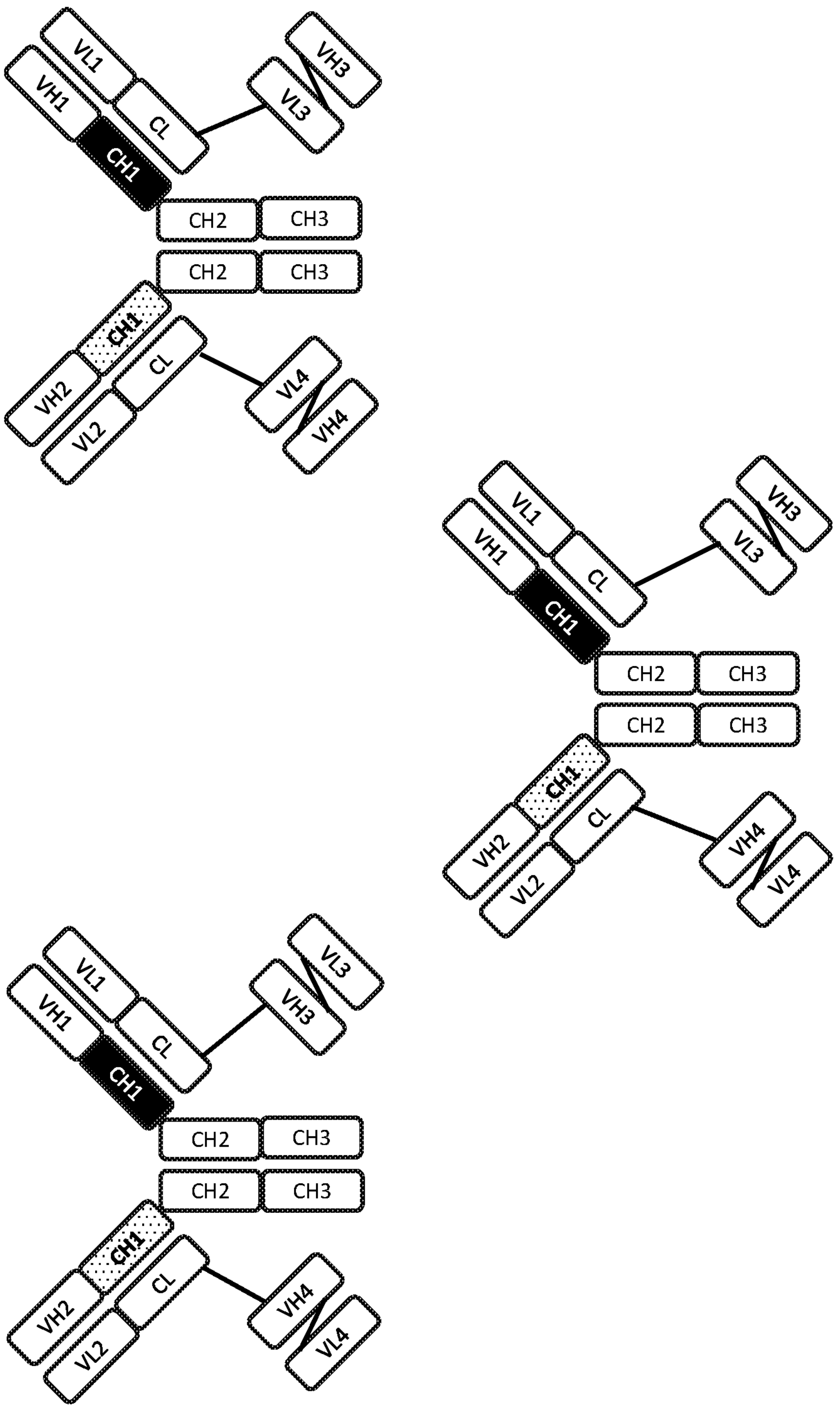
Figure 28C:
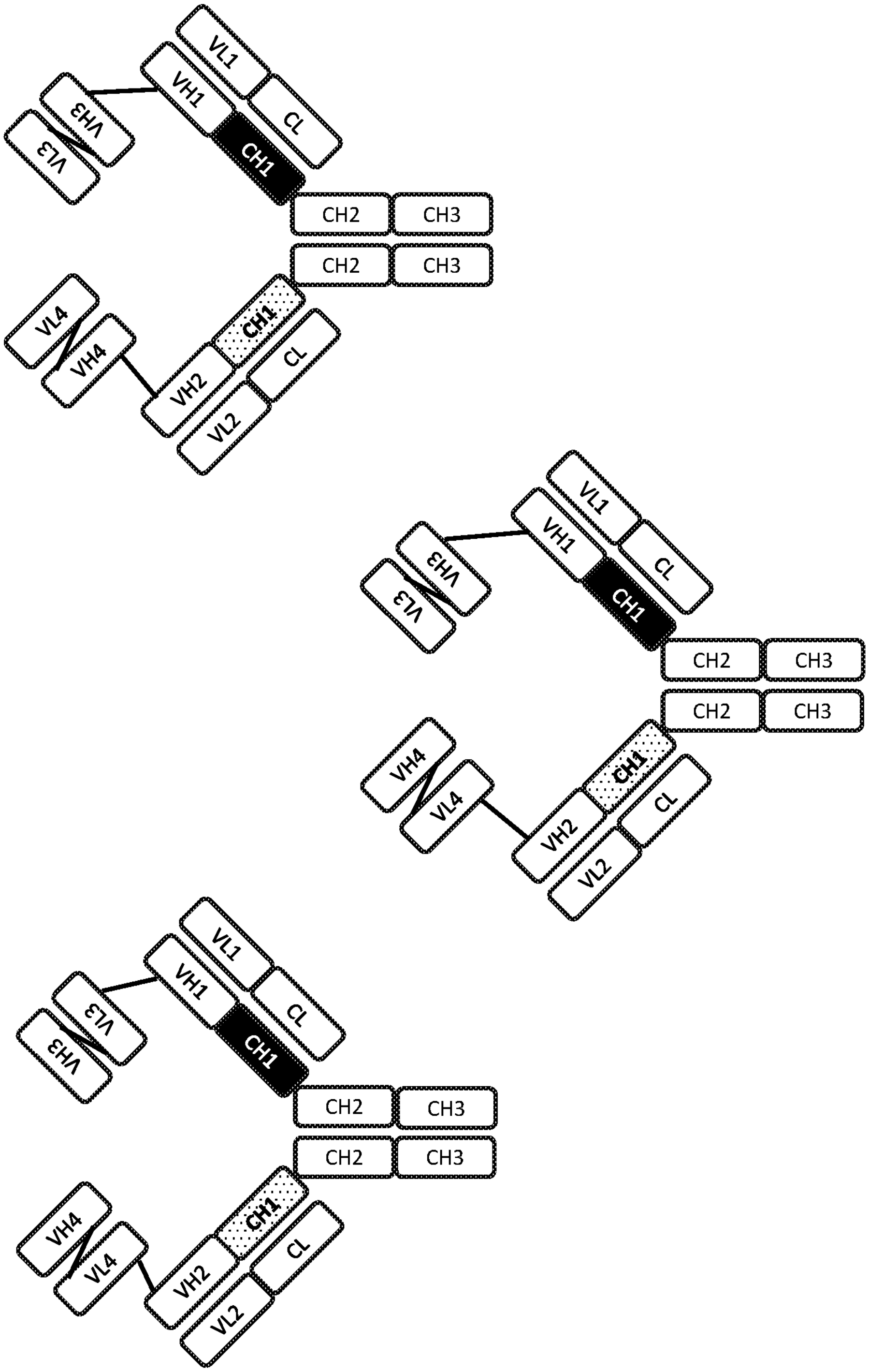
Figure 28D:
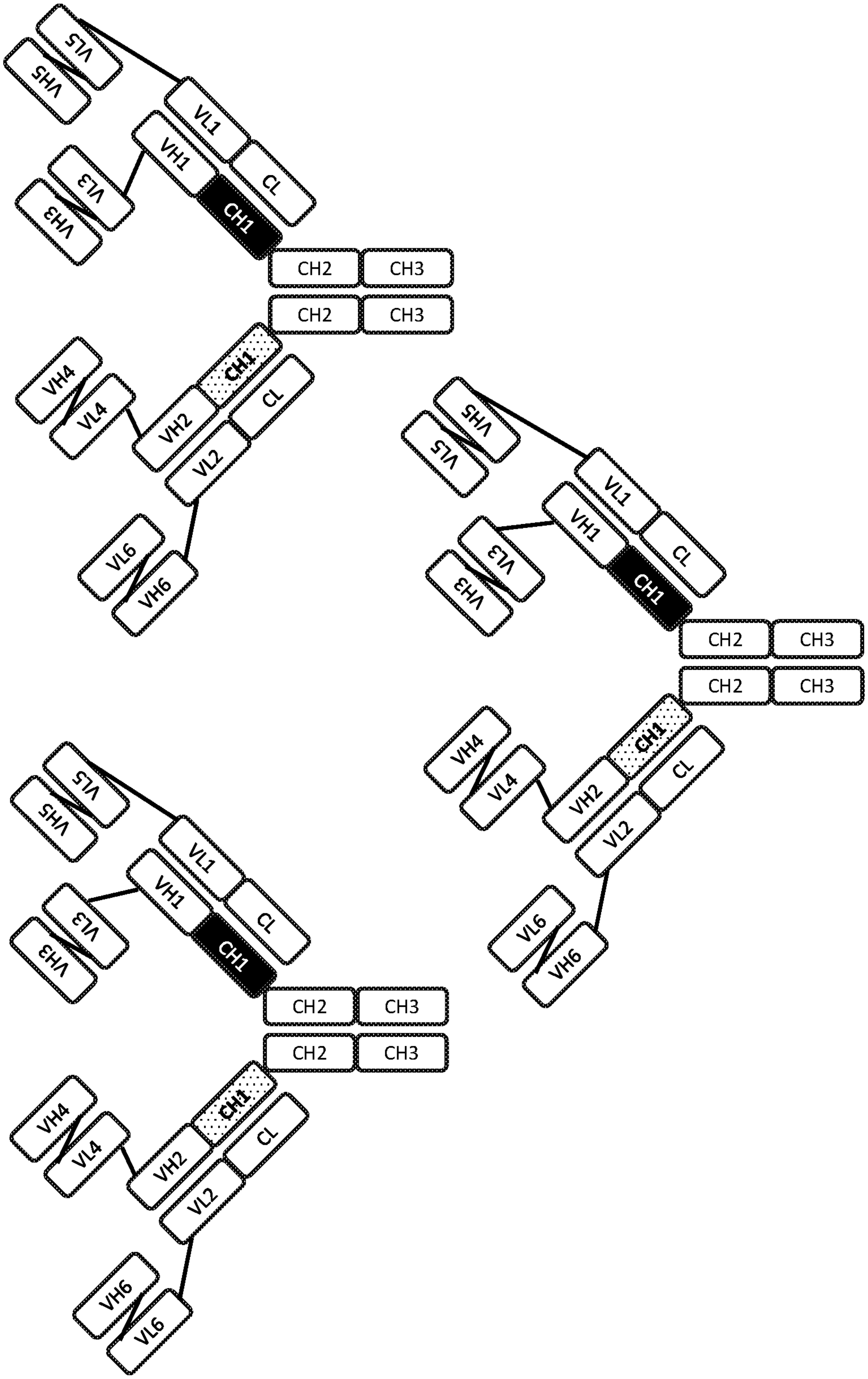

FIGS. 28A-28D provide further exemplary and non-limiting embodiments of various multispecific antibody structures, which contain at least one scFv. Any of the structures provided in FIGS. 24-29 may additionally comprise or be modified to comprise one or more scFv-containing moieties, for example, conjugated to any of the heavy chain constant domains, light chain constant domains, and/or the antigen-binding domains. By way of example, FIGS. 28A-28C provide structures in which the top left structure in FIG. 24A is conjugated with two scFvs, allowing for specificity for up to four epitopes. In FIG. 28A, scFvs are conjugated to the CH3 domains. In FIG. 28B, scFvs are conjugated to the CL domains. In FIG. 28C, scFvs are conjugated to the VH domains. In certain instances, more than two scFvs may be conjugated. By way of example, FIGS. 28A-28C provide structures in which the top left structure in FIG. 24A is conjugated with four scFvs, allowing for specificity for up to six epitopes.

Figure 29A:
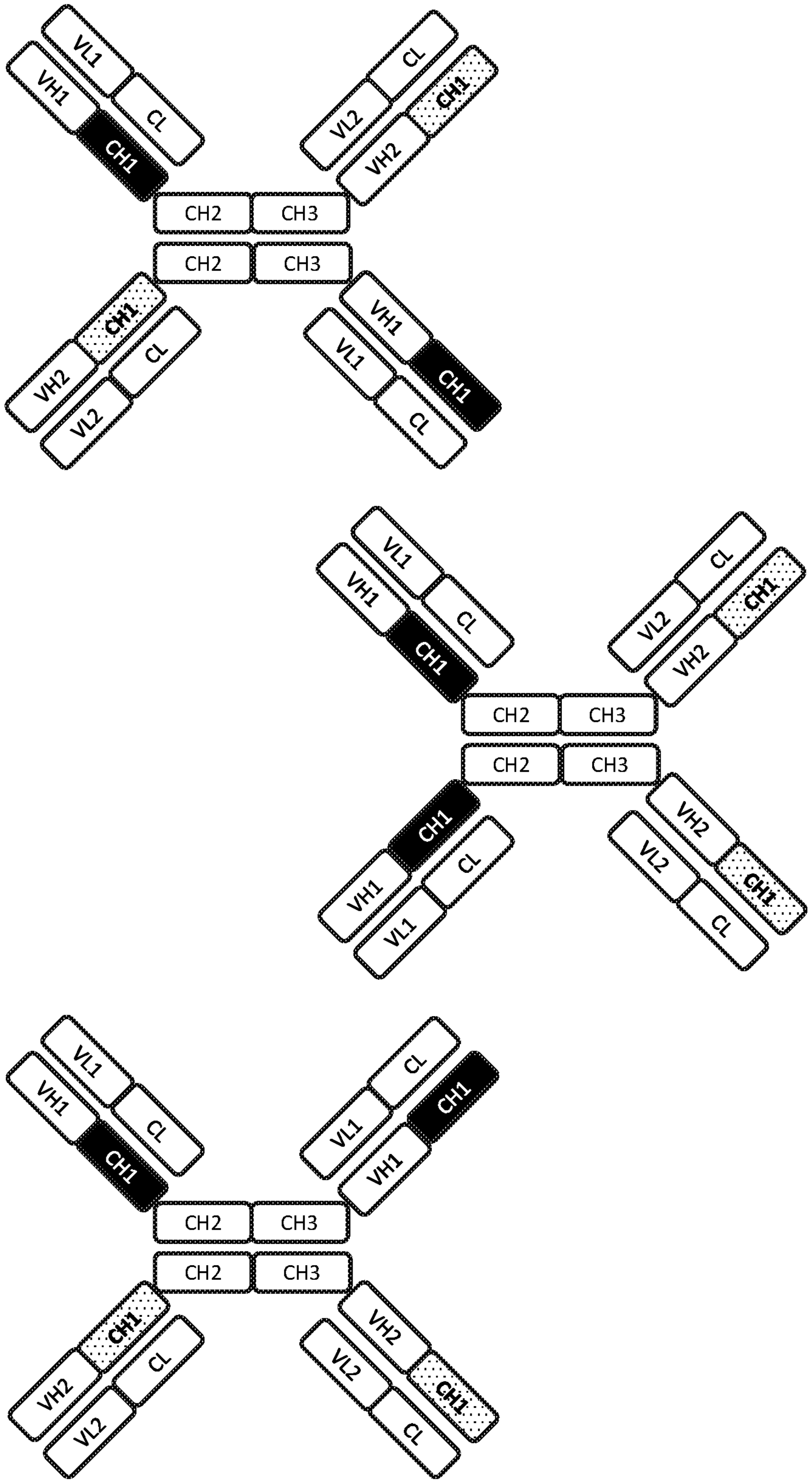
Figure 29B:
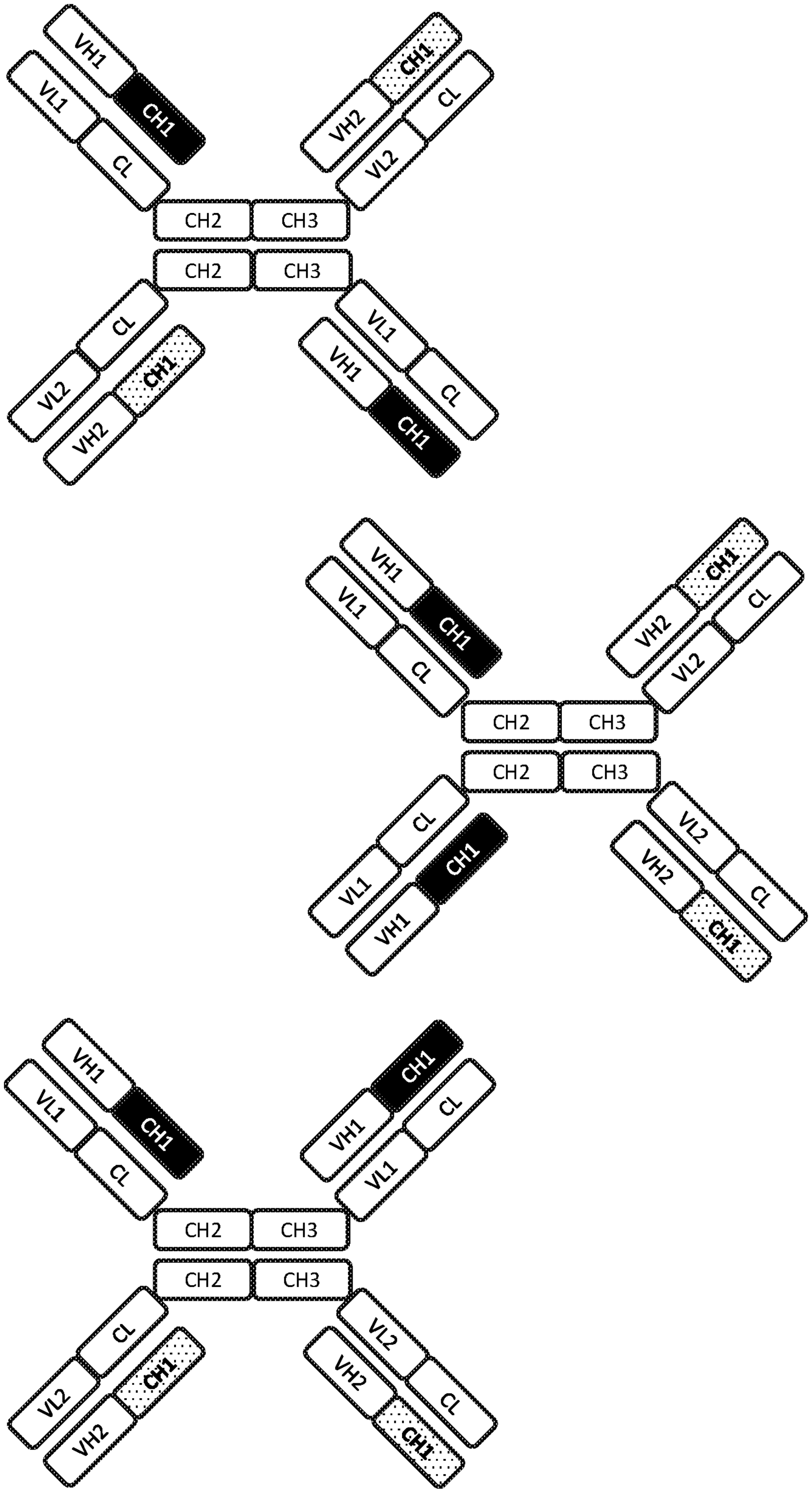
Figure 29C:
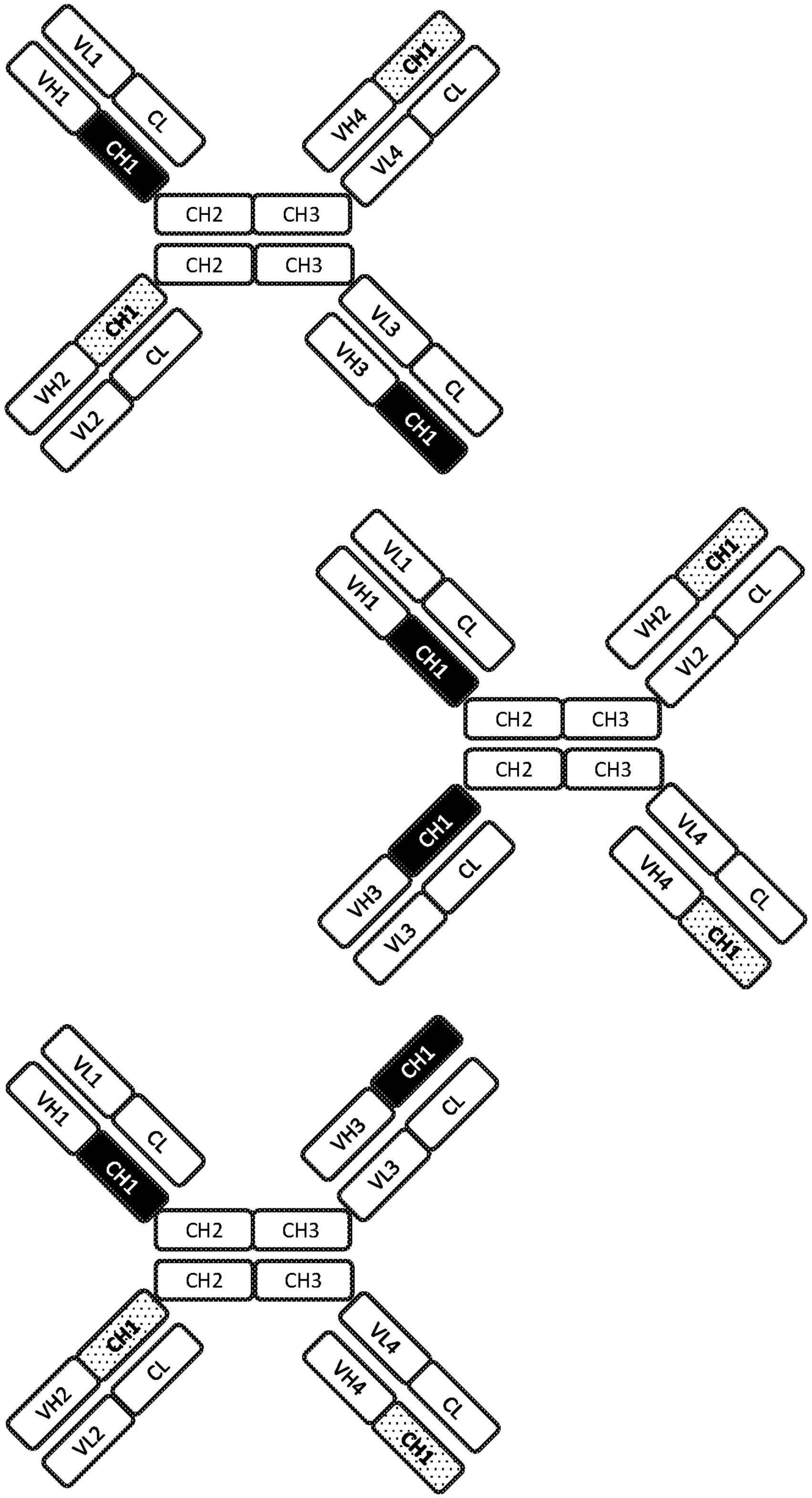
Figure 29D:
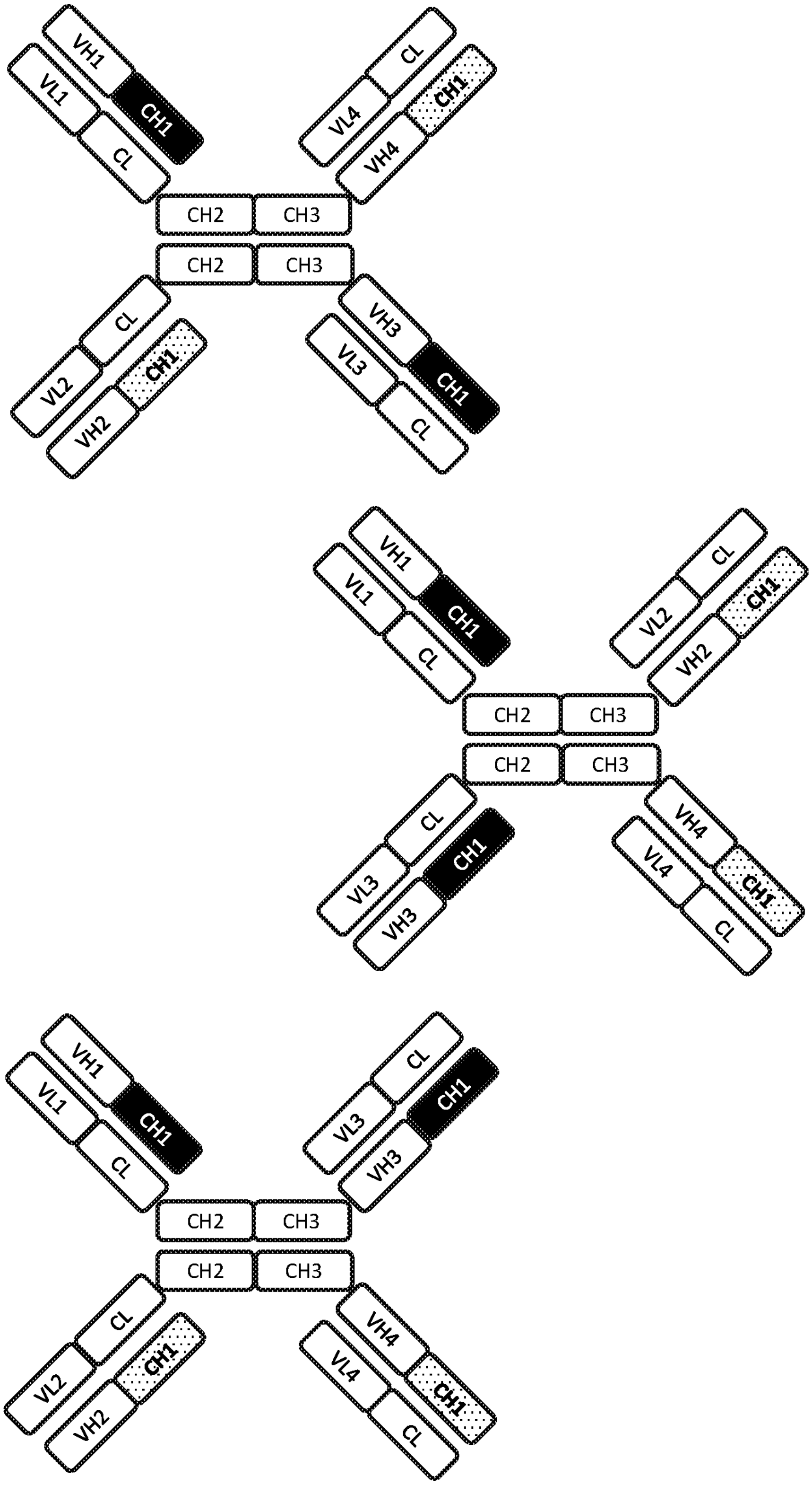

FIGS. 29A-29D provide yet further exemplary and non-limiting embodiments of various multispecific antibody structures, which contain two additional Fab fragments. Although two Fab fragments are conjugated to the CH3 domains, it is noted that Fab fragments may be conjugated to any other part of the structure and also that one (or three or more), instead of two, Fab fragment(s) may be conjugated. In FIG. 29A, two CH1 domains are in the same polypeptide with CH2 and CH3 domains. In the middle structure, a kappa-preferring CH1 domain and a lambda-preferring CH1 domain are present within the same polypeptide (for both of the two CH1-containing polypeptides). When the two CH1-containing polypeptides are the same, this structure facilitates production of tetravalent bispecific compounds without the need for a mechanism that promotes heterodimerization of two non-identical polypeptides (such as the "knobs-in-holes" engineering), for example by simply using the 3-chain transfection system utilized in Examples. In FIG. 29B, two polypeptides do not contain any CH1 domains. In the middle structure, when the two CH1-uncontaining polypeptides are the same, this structure facilitates production of tetravalent bispecific compounds without the need for a mechanism that promotes heterodimerization of two non-identical polypeptides (such as the "knobs-in-holes" engineering), for example by simply using the 3-chain transfection system utilized in Examples. In FIGS. 29C and 29D, each polypeptide contains a CH1 domain. In the middle structures of FIGS. 29C and 29D, if the first and third epitopes are the same epitope and the second and fourth epitopes are the same epitope but differ from the first and third epitopes, the structure is bispecific. In such a structure, if the two CH2/CH3-containing polypeptides are the same, this structure facilitates production of tetravalent bispecific compounds without the need for a mechanism that promotes heterodimerization of two non-identical polypeptides (such as the "knobs-in-holes" engineering), for example by simply using the 3-chain transfection system utilized in Examples.

Figure 30:
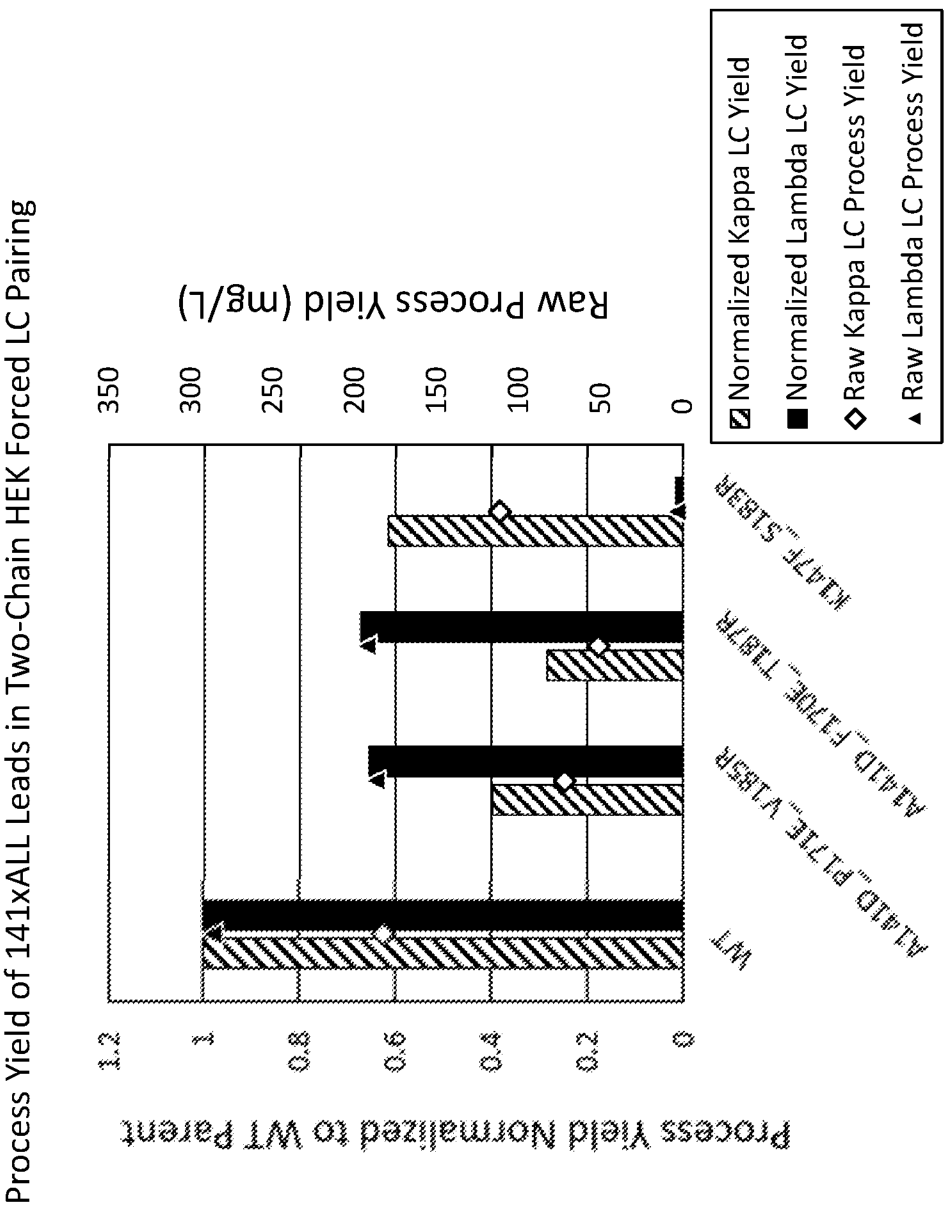

FIG. 30 shows exemplary process yields of full IgGs containing one of the top two lambda-preferring CH1 variants identified in Example 7 ("A141D_P171E V185R" or "A141D F170E T187R") or a kappa-preferring CH1 variant identified in Example 4 ("K147F S183R"), or WT CH1. normalized to the process yield of WT. Striped bars (paired with kappa) and filled bars (paired with lambda) represent process yields normalized to the WT counterpart yield. Open diamonds (paired with kappa) and filled triangles (paired with lambda) represent raw process yields (mg/L).

Figure 31:
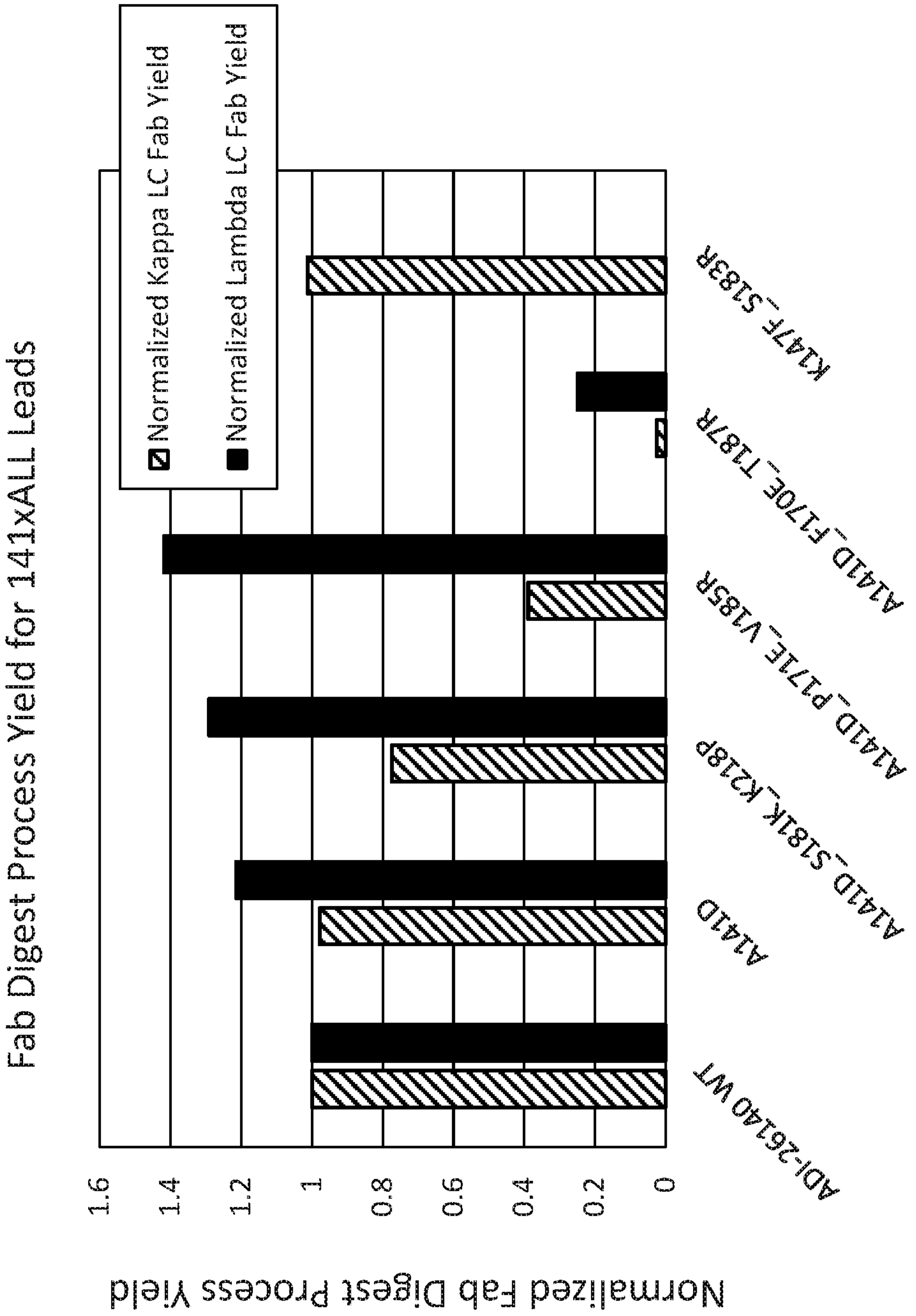

FIG. 31 shows exemplary process yields of Fabs containing one of the top two lambda-preferring CH1 variants identified in Example 7 ("A141D_P171E V185R" or "A141D F170E T187R") or lambda-preferring CH1 variants identified in Examples 4 and 5 ("A141D" or "A141D S181K K218P"), or a kappa-preferring CH1 variant identified in Example 4 ("K147F S183R"), or WT CH1. normalized to the process yield of WT. Yields are normalized to the WT counterpart yield. Striped bars represent Fabs containing kappa LC, and filled bars represent Fabs containing lambda LC.

Figure 32:
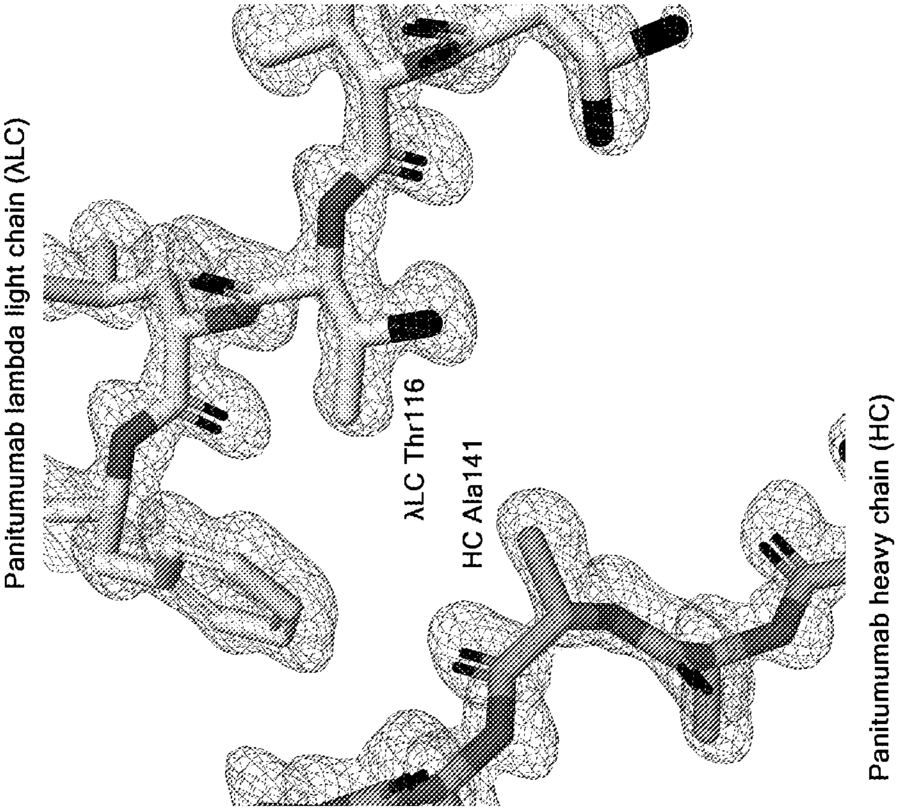

FIG. 32 shows wildtype CH1-Cλ interface in its electron density. Representative electron density in the region of interest for the Fab crystal structure of the panitumumab variable fragment (Fv) and wildtype IgG1-CH1 paired to the wildtype lambda constant domain (Cλ). Heavy chain (HC) carbon atoms are colored light grey, lambda light chain (λLC) carbon atoms are colored white, nitrogen atoms are colored dark grey, and oxygen atoms are colored black. Protein is shown in stick representation. The 2Fo-Fc electron density map is shown as a grey mesh contoured at 1σ with a 1.6 Å carve. Data for this crystal structure extend to 1.09 Å atomic resolution.

Figure 33:
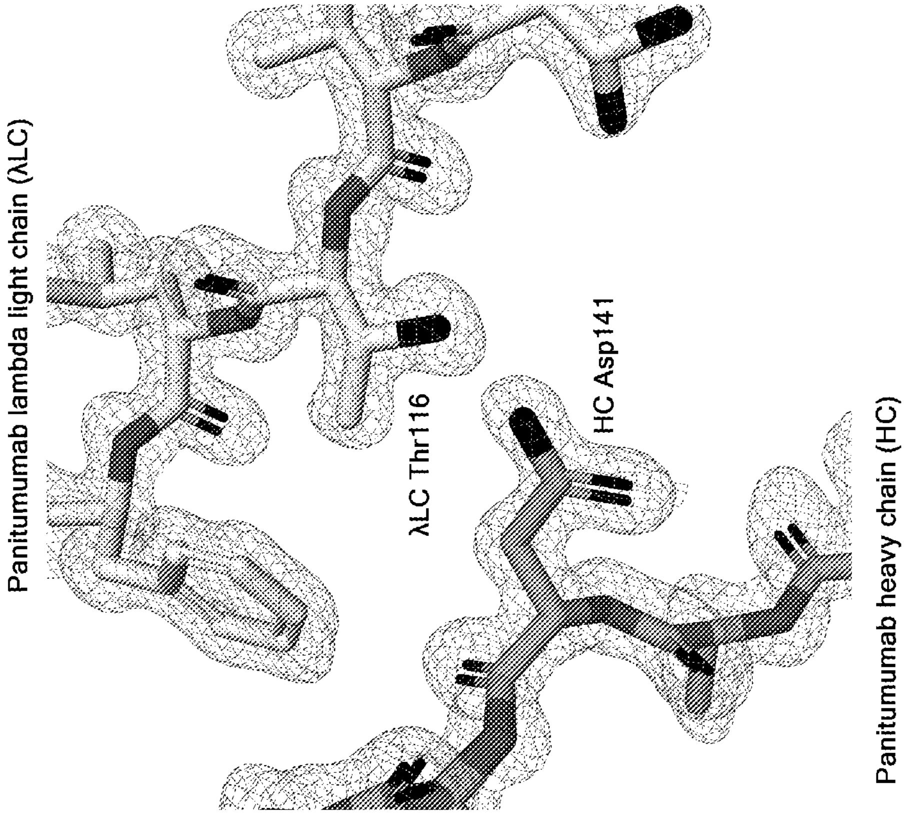

FIG. 33 shows A141D CH1-Cλ interface in its electron density. Representative electron density in the region of interest for the Fab crystal structure of the panitumumab variable fragment (Fv) and A141D-substituted IgG1-CH1 paired to the wildtype lambda constant domain (Cλ). Heavy chain (HC) carbon atoms are colored light grey, lambda light chain (λLC) carbon atoms are colored white, nitrogen atoms are colored dark grey, and oxygen atoms are colored black. Protein is shown in stick representation. The 2Fo-Fc electron density map is shown as a grey mesh contoured at 1a with a 2.0 Å carve. Data for this crystal structure extend to 1.2 Å atomic resolution.

Figure 34:
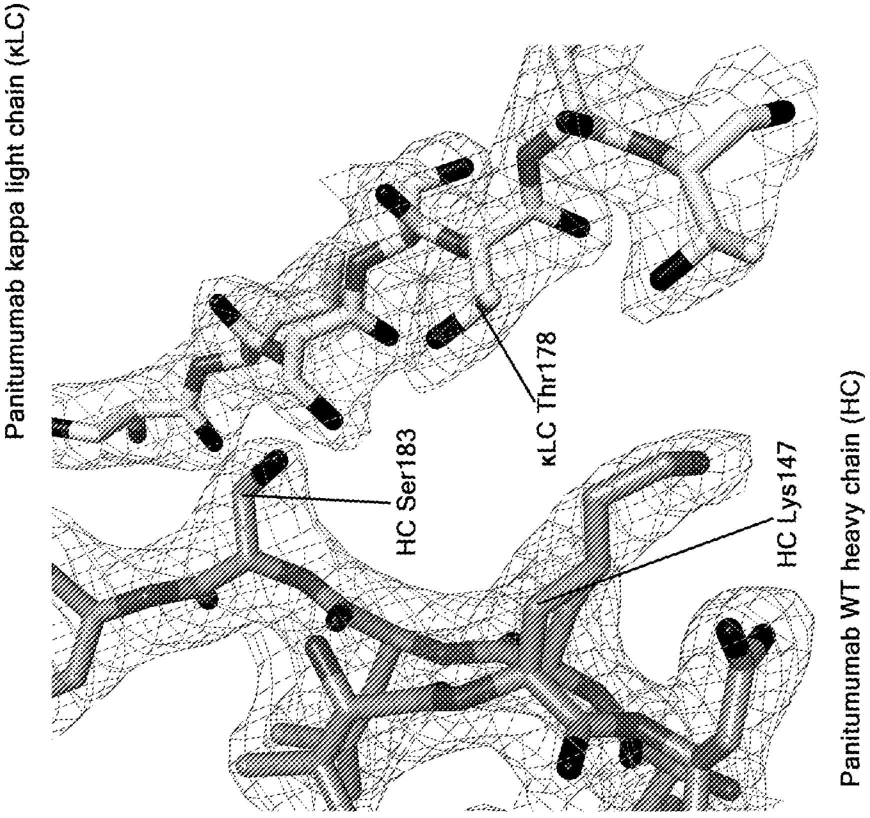

FIG. 34 shows wildtype CH1-Cκ interface in its electron density. Representative electron density in the region of interest for the Fab crystal structure of the panitumumab variable fragment (Fv) and wildtype IgG1-CH1 paired to the wildtype kappa constant domain (Cκ). Heavy chain (HC) carbon atoms are colored light grey, kappa light chain (κLC) carbon atoms are colored white, nitrogen atoms are colored dark grey, and oxygen atoms are colored black. Protein is shown in stick representation. The 2Fo-Fc electron density map is shown as a grey mesh contoured at 0.9a with a 1.6 Å carve. Data for this crystal structure extend to 2.6 Å near-atomic resolution.

Figure 35:
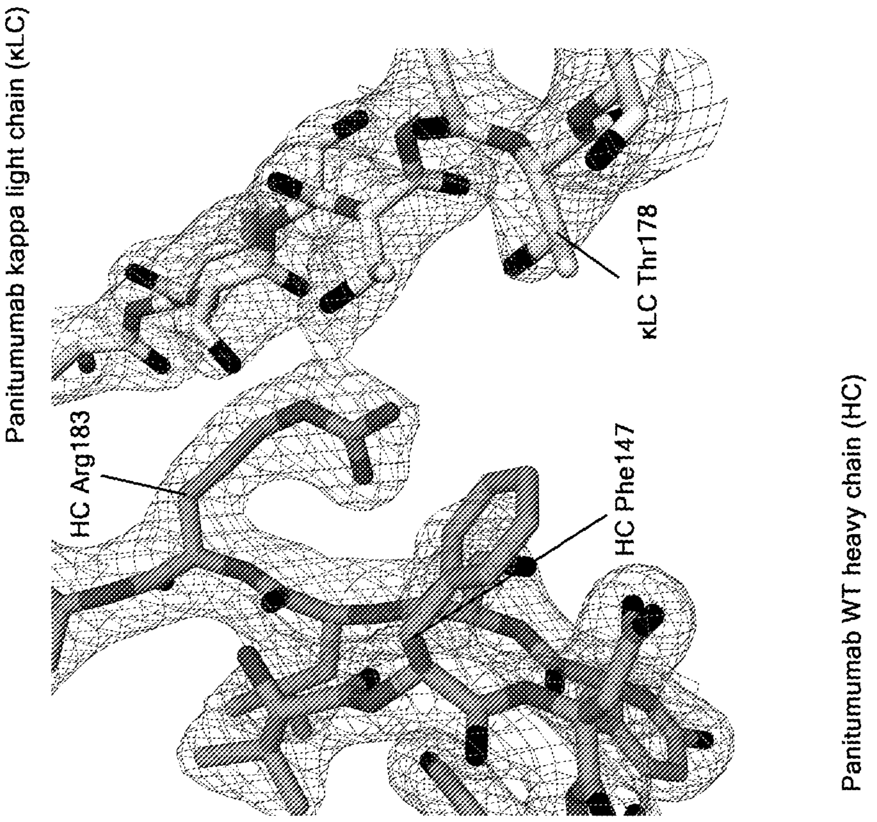

FIG. 35 shows K147F-S183R CH1-Cκ interface in its electron density. Representative electron density in the region of interest for the crystal structure of the panitumumab variable fragment (Fv) and K147F-S183R-substituted IgG1-CH1 paired to the wildtype kappa constant domain (Cκ). Heavy chain (HC) carbon atoms are colored light grey, kappa light chain (κLC) carbon atoms are colored white, nitrogen atoms are colored dark grey, and oxygen atoms are colored black. Protein is shown in stick representation. The 2Fo-Fc electron density map is shown as a grey mesh contoured at 0.9a with a 1.6 Å carve. Data for this crystal structure extend to 2.1 Å near-atomic resolution.

Figure 36:
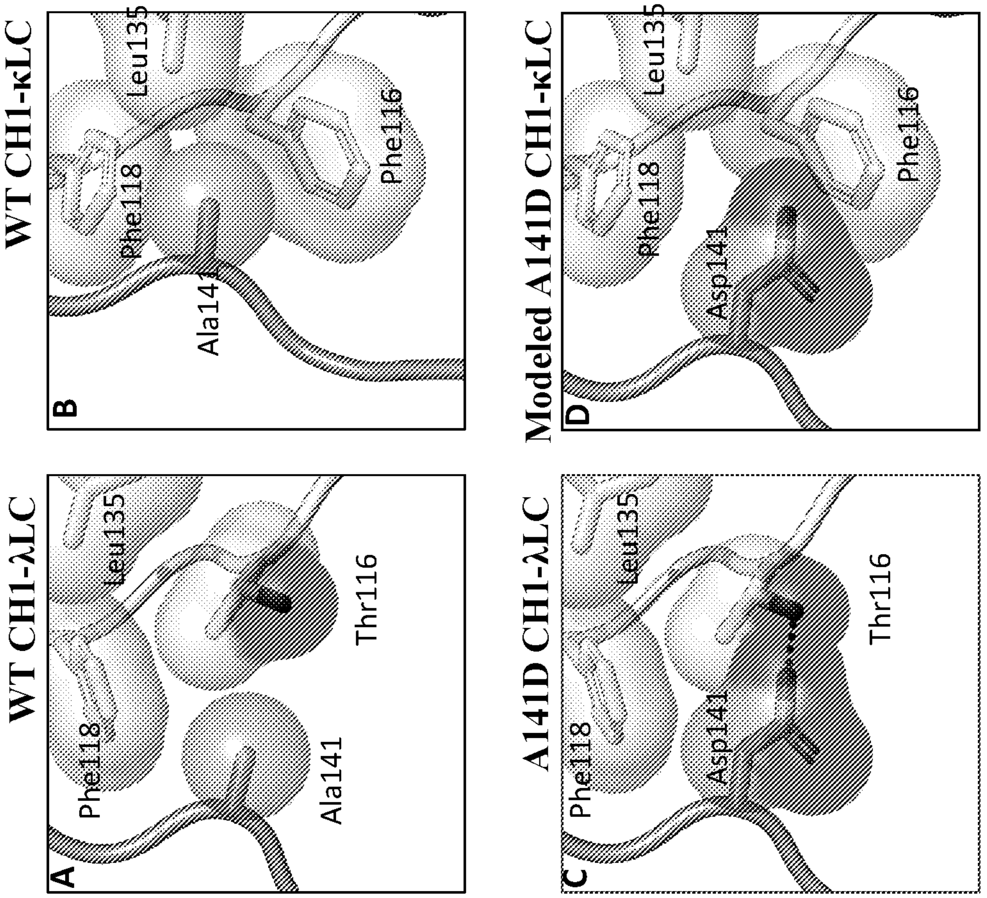

FIGS. 36A-36D show HC-A141D substitution allows for hydrogen bonding to λLC while simultaneously de-stabilizing kappa pairing via steric clash with κLC. FIGS. 36A-36D provide views of the pairing interface surrounding the HC-Ala141 position between WT CH1 and λLC (FIG. 36A), between WT CH1 and κLC (FIG. 36B), between A141D CH1 and λLC (FIG. 36C), or between A141D CH1 and κLC (FIG. 36D). The kappa light chain constant domain (κLC)

interface contains three hydrophobic residues Phe116, Phe118, and Leu135, exemplified in FIG. 36B. Presence of Thr116 in λLC at the structurally equivalent κLC-Phe116 position enables hydrogen bonding to the carboxyl group of HC-Asp141, shown as a black dotted line (FIG. 36C). In FIG. 36D, HC alignment of A141D CH1-constant lambda (Cλ) and WT CH1-Cκ shows steric clash of the HC-Asp141 side chain with that of κLC-Phe116. Heavy chain (HC) carbon atoms are colored light grey, light chain (LC) carbon atoms are colored white, nitrogen atoms are colored dark grey, and oxygen atoms are colored black. Side chains are shown in stick representation with a transparent molecular surface and main chain atoms are shown in cartoon representation.

Figure 37:
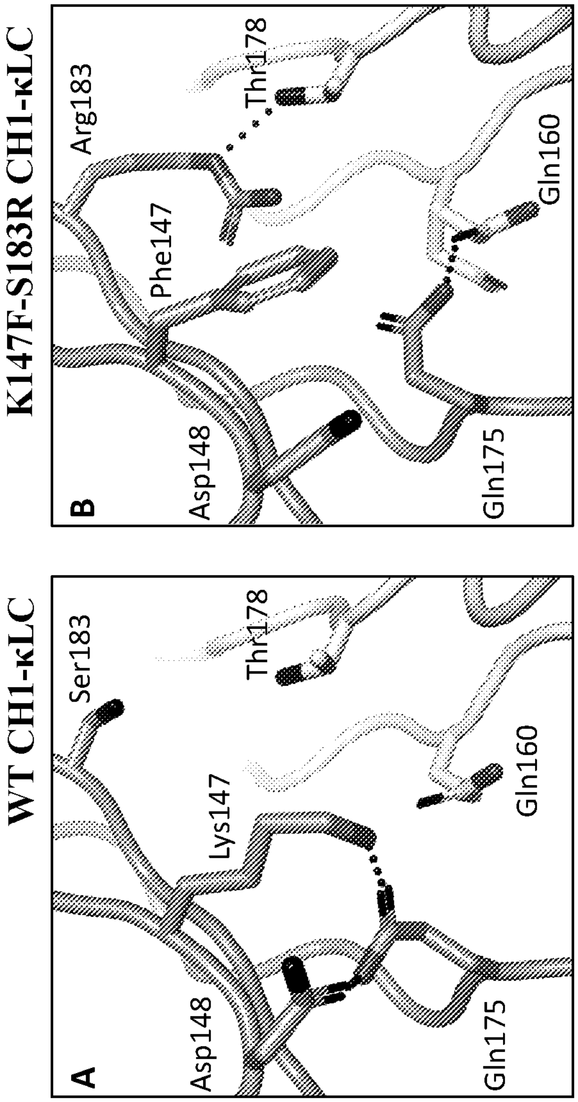

FIGS. 37A and 37B show wildtype CH1 sequence sequesters HC-Gln175 in an intrachain hydrogen bond network, which may be broken by substitution of K147F, allowing HC-Gln175 freedom to interact with κLC-Gln160. FIGS. 37A and 37B provide views of the triadic hydrogen bond network in the HC involving Lys147, Asp148, and Gln175 in the panitumumab wildtype CH1-constant kappa (Cκ) structure (FIG. 37A) and the panitumumab K147F-S183R-CH1-Cκ structure (FIG. 37B). Heavy chain (HC) carbon atoms are colored light grey, kappa light chain (κLC) carbon atoms are colored white, nitrogen atoms are colored dark grey, and oxygen atoms are colored black. Side chains are shown in stick representation and main chain atoms are shown in cartoon representation. Hydrogen bonds are shown as a dotted line.

Figure 38:
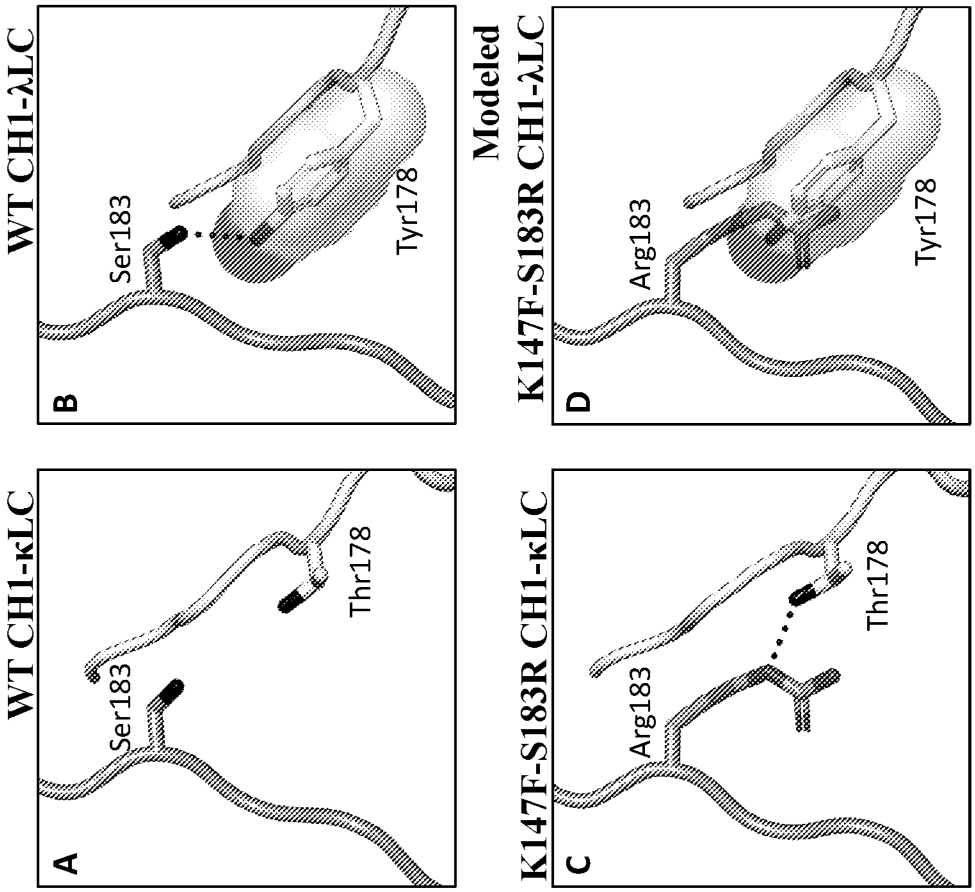

FIGS. 38A-38D show hydrogen bonding between HC-Arg183 and κLC-Thr178 may drive kappa pairing while steric clashing of HC-Arg183 with λLC-Tyr178 reduces preference for lambda pairing. FIGS. 38A-38D provide views of the region surrounding the S183R substitution in the IgG1-CH1, with hydrogen bonds between HC-Ser183 and λLC-Thr178 in the panitumumab wildtype CH1-constant lambda (Cλ) structure (FIG. 38B) and between HC-Arg183 and κLC-Thr178 in the panitumumab K147F-S183R-CH1-constant kappa (Cκ) structure (FIG. 38C). FIG. 38A shows that HC-Ser183 and κLC-Thr178 are too distant for hydrogen bonding to occur. Heavy chain (HC) carbon atoms are colored light grey, light chain (LC) carbon atoms are colored white, nitrogen atoms are colored dark grey, and oxygen atoms are colored black. Side chains are shown in stick representation. The side chain of λLC-Tyr178 is also shown as a transparent molecular surface. Hydrogen bonds are shown as black dotted lines. FIG. 38D provides a model in which the HC of the panitumumab K147F-S183R-CH1-Cκ structure was superimposed with the HC of the panitumumab wildtype CH1-Cλ structure. The resulting model shows apparent steric clashes between HC-Arg183 and λLC-Tyr178.

DETAILED DESCRIPTION OF THE INVENTION

Unless defined otherwise, all technical and scientific terms used herein have the same meaning as commonly understood by one of ordinary skill in the art to which this disclosure belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

It is understood that aspects and embodiments of the disclosure described herein include "comprising," "consisting," and "consisting essentially of" aspects and embodiments.

Provided herein are engineered CH1 domains containing at least one amino acid substitution that prevents heavy chain-light chain mispairing by promoting preferential pairing of the CH1 domain-containing heavy chain with either a kappa CL domain (or a kappa light chain) or a lambda CL domain (or a lambda light chain). The term "preferential pairing" refers to the pairing of a heavy chain (or CH1 domain) with a light chain (or CL domain) in a polypeptide, e.g., antibody, e.g., bispecific antibody. When a heavy chain (H1) is co-expressed with two different light chains (L1 and L2), H1 will pair with each of L1 and L2 resulting in a mixture of H1:L1 and H1:L2. In some instances, H1 may pair equally well with both L1 and L2 resulting in a mixture of approximately 50:50 H1:L1 to H1:L2. By way of example, "preferential pairing" would occur between H1 and L1 if the amount of H1:L1 heterodimer formed was greater than the amount of H1:L2 heterodimer formed when H1 is co-expressed with L1 and L2. In this example, H1 preferentially pairs with L1 relative to L2. Should H1 have an inherent bias to pair with L1 over L2 (such that the ratio of H1:L1 to H1:L2 is not 50:50 but, e.g., 60:40 or 70:30, in which case formation of H1:L2 is still undesirable), then preferential pairing between the desired pair, i.e., H1:L1, would occur when there is an improvement (increase) in the amount of pairing between H1:L1 as compared to H1:L2. As used herein, the term "preferential pairing" encompasses pairing of the heavy chain and the light chain (as described above) as well as pairing of a CH1 domain and a CL domain. By way of example, "preferential pairing" would occur between a CH1 domain and a kappa CL domain if the amount of CH1:Cκ formed was greater than the amount of CH1:Cλ formed when CH1 is co-expressed with Cκ and Cλ. Likewise, "preferential pairing" would occur between a CH1 domain and a lambda CL domain if the amount of CH1:Cλ formed is greater than the amount of CH1:Cκ formed when CH1 is co-expressed with Cλ and Cκ.

Certain positions within the CH1 domain, identified as part of the CH1-CL interface (for both Cκ and Cλ), were found to influence binding of the heavy chain to the light chain. Additionally, positions within the CH1 domain at the CH1:VH interface were also shown to influence binding of the heavy chain to the light chain. A heavy chain pairs with a light chain via two sets of domain interfaces: one between the VH and VL domains, and the other between the CH1 and CL domains, and where the chains pair or meet or make contact is referred to as an "interface." Furthermore, within a heavy chain, the CH1 domain also come in contact with part of the VH, and such a space in which the CH1 domain and VH are in the close proximity is also encompassed by the term "interface" An interface comprises the amino acid residues in the heavy chain and the amino acid residues in the light chain, or alternatively the amino acid residues in the CH1 domain and the amino acid residues in the VH, that contact each other in three-dimensional space. In some embodiments, an interface comprises the CH1 domain of the heavy chain and the CL domain of the light chain. In other embodiments, an interface comprises the CH1 domain and the VH domain of the heavy chain. The "interface" is preferably derived from an IgG antibody or a Fab thereof.

The CH1 variant domains described herein contain an amino acid substitution at one or more CH1:CL interface (CH1:kappa CL, or CH1:lambda CL) positions, e.g., positions 141, 147, 170, 171, 175, 181, 183, 184, 185, 187 and/or 218, or one or more CH1:VH interface position, e.g., position 151, as compared to parent. The term "parent" refers to a polypeptide (and the amino acid sequence that encodes it) that is subsequently modified to generate a variant. The parent polypeptide may be a wild-type or naturally occurring polypeptide or a variant or engineered version thereof. Accordingly, a "parent CH1 domain" refers to a CH1 domain polypeptide (and the amino acid sequence encoding the CH1 domain polypeptide) that is subsequently modified to generate a CH1 domain variant. Such a parent CH1 domain may be a wildtype or naturally occurring CH1 domain or a variant or engineered version thereof, e.g., a wild-type CH1 domain modified to conjugate a toxin or small molecule drug. Such a parent CH1 domain may be isolated or part of a larger construct, e.g., Fab, $F(ab')_2$, or IgG, which may optionally contain additional modifications, e.g., CH3 modifications to promote heterodimerization, CH2 and/or CH3 modifications to alter Fc receptor binding, extend half-life and/or link additional binding domains.

The resultant CH1 variant domains have preferential pairing with either a kappa CL (Cκ) domain or a lambda CL (Cλ) domain, which Cκ and Cλ domains may be part of a light chain. Amino acid variation at one or both of CH1 domain positions 147 and 183 (EU numbering) promote binding to Cκ (and simultaneously discourage pairing with Cλ) whereas amino acid variation at CH1 domain position 141 promote binding to Cλ (and simultaneously discourage pairing to Cκ). The kappa and lambda CL domains may exist in any number of formats, including but not limited to Fab or IgG, wild-type or chimeric, e.g., a Fab or IgG containing Vκ and Cκ, Vκ and Cλ, Vλ and Cκ, or Vλ and Cλ. Such CH1 variant domains may be useful in engineering multispecific antibodies by improving the fidelity of heavy chain-light chain pairing while maintaining the native IgG structure of a bispecific antibody, which is favorable due to its well-established properties as a therapeutic molecule, including a long in vivo half-life and the ability to elicit effector functions.

The term "CH1 domain" refers to the first constant domain of the heavy chain of an antibody, C-terminal of the variable domain of the heavy chain and N-terminal of the hinge region. According to IMGT, the CH1 domain is the amino acid sequence from positions 118-215 (EU numbering) and the hinge region is the amino acid sequence from positions 216-230 (EU numbering). As used herein, the term "CH1 domain variant" refers to an amino acid sequence including the entire CH1 domain (positions 118-215 according to EU numbering) or fragments thereof comprising at least 7 of CH1 residues 118-215 (according to EU numbering) wherein such fragments include 1 or more of the modifications disclosed herein, as well as a portion of the hinge region (positions 216-218). The libraries screened to identify the described CH1 domain variants included variegation in the hinge region, e.g., positions 216 and 218.

The CH1 domain pairs with the CL domain of the light chain. In some embodiments, a light chain is a kappa chain. In some embodiments, a light chain is a lambda chain. The term "kappa constant domain", "kappa CL domain", or "Cκ" refers to the constant domain of a kappa light chain. The term "lambda constant domain", "lambda CL domain", or "Cλ" refers to the constant domain of a lambda light chain. A single disulfide bond covalently connects a CH1 with a CL domain. The CH1 domain, as used herein, refers to all antibody isotypes, e.g., IgG1, IgG2, IgG3, IgG4, IgA1, IgA2, IgD, IgM, and IgE.

The term "antibody" is used herein in the broadest sense and encompasses various antibody structures, including but not limited to monoclonal antibodies, polyclonal antibodies, multispecific antibodies (e.g., bispecific antibodies), and/or antibody fragments (preferably those fragments that exhibit the desired antigen-binding activity, which is also referred to as "antigen-binding antibody fragments").

A "monoclonal antibody" or "mAb" refers to an antibody obtained from a population of substantially homogeneous antibodies, i.e., the individual antibodies comprising the population are identical and/or bind the same epitope, except for possible variant antibodies (e.g., containing a naturally occurring mutation(s) and/or substitution(s) or arising during production of a monoclonal antibody preparation), such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

A "multispecific antibody", which may also be referred to as "multispecific compound" herein, refers to an antibody comprising at least two different antigen binding domains that recognize and specifically bind to at least two different antigens or at least two different epitopes. In some embodiments, a multispecific antibody contains (1) a first heavy chain and a first light chain, which form a cognate pair and bind to a first antigen, and (2) a second heavy chain and a second light chain, which form a cognate pair and bind to a second antigen.

A "bispecific antibody", which may also be referred to as "bispecific compound" herein, is a type of multispecific antibody and refers to an antibody comprising two different antigen binding domains which recognize and specifically bind to at least two different antigens or at least two epitopes. The at least two epitopes may or may not be within the same antigen. A bispecific antibody may target, for example, two different surface receptors on the same or different (e.g., an immune cell and a cancer cell) cells, two different cytokines/chemokines, a receptor and a ligand. Combinations of antigens that may be targeted by a bispecific antibody may include but are not limited to: CD3 and Her2; CD3 and Her3; CD3 and EGFR; CD3 and CD19; CD3 and CD20; CD3 and EpCAM; CD3 and CD33; CD3 and PSMA; CD3 and CEA; CD3 and gp100; CD3 and gpA33; CD3 and B7-H3; CD64 and EGFR; CEA and HSG; TRAIL-R2 and LTbetaR; EGFR and IGFR; VEGFR2 and VEGFR3; VEGFR2 and PDGFR alpha; PDGFRalpha and PDGFR beta; EGFR and MET; EGFR and EDV-miR16; EGFR and CD64; EGFR and Her2; EGFR and Her3; Her2 domain ECD2 and Her2 domain ECD4; Her2 and Her3; IGF-1R and HER3; CD19 and CD22; CD20 and CD22; CD30 and CD16A; FceRI and CD32B; CD32B and CD79B; MP65 and SAP-2; IL-17A and IL-23; IL-1alpha and IL-1beta; IL-12 and IL-18; VEGF and osteopontin; VEGF and Ang-2; VEGF and PDGFRbeta; VEGF and Her2; VEGF and DLL4; FAP and DR5; FcgRII and IgE; CEA and DTPA; CEA and IMP288; and LukS-PV and LukF-PV.

A "different antigen" may refer to different and/or distinct proteins, polypeptides, or molecules; as well as different and/or distinct epitopes, which epitopes may be contained within one protein, polypeptide, or other molecule. Consequently, a bispecific antibody may bind to two epitopes on the same polypeptide.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

In some instances, an antibody comprises four polypeptide chains: two heavy (H) chains and two light (L) chains interconnected by disulfide bonds. Each heavy chain comprises a variable region, such as a heavy chain variable region ("VH"), and a heavy chain constant region ("CH"). In case of an intact antibody, a CH comprises domains CH1, CH2 and CH3. In case of an antibody fragment, a CH may comprise CH1, CH2, and/or CH3 domains, and in some preferred embodiments, the CH comprises at least a CH1 domain. The CH1 domain variants disclosed herein may be used in combination with wild-type CH2 and/or CH3 domains or CH2 and/or CH3 domains comprising one or more amino acid substitutions, e.g., those that alter or improve antibodies' stability and/or effector functions. Each light chain comprises a variable region, such as a light chain variable region ("VL"), and a light chain constant region ("CL"). The VH and VL regions, can be further subdivided into regions of hypervariability, termed complementarity determining regions (CDRs), interspersed with regions that are more conserved, termed framework regions (FRs). Each VH and VL comprises three CDRs and four FRs, arranged from amino-terminus to carboxy-terminus in the following order: FR1, CDR1, FR2, CDR2, FR3, CDR3, FR4. In certain embodiments of the disclosure, the FRs of the antibody (or antigen-binding fragment thereof) may be identical to the human germline sequences or may be naturally or artificially modified. An amino acid consensus sequence may be defined based on a side-by-side analysis of two or more CDRs. Accordingly, the CDRs in a heavy chain are designated "CDRH1", "CDRH2", and "CDRH3", respectively, and the CDRs in a light chain are designated "CDRL1", "CDRL2", and "CDRL3". In other instances, an antibody may comprise multimers thereof (e.g., IgM) or antigen-binding fragments thereof.

In certain instances, a VH and a CL may exist in one polypeptide. In certain instances, a VL and a CH1, CH2, and/or CH3 domain(s) may exist in one polypeptide. For example, in a certain antibody or antibody fragment, while a first polypeptide comprises a VH1 and a CH1 and a second polypeptide comprises a VL1 and CL (VH1 and VL form an antigen-binding site for a first epitope), a third polypeptide comprises a VH2 and a CL, and a fourth polypeptide comprises a VL2 and a CH1 (VH2 and VL2 forms an antigen-binding site for a second epitope). In another certain antibody or antibody fragment, while a first polypeptide comprises a VH1 and a CH1 and a second polypeptide comprises a VL1 and CL (VH1 and VL form an antigen-binding site for a first epitope), a third polypeptide comprises a VL2, a CL, and one or more of CH2 and/or CH3 domains, and a fourth polypeptide comprises a VH and a CH1. Any antibodies or antibody fragments that comprises any of the CH1 variants disclosed herein that provide preferential pairing with a kappa CL or preferential pairing with a lambda CL, regardless of whether the CH1 domain is in the heavy chain or in the light chain, are encompassed by the present invention.

The term "cognate pair" or "cognate pairing" used herein refers to a pair or pairing of two antibody chains (e.g., a heavy chain and a light chain), each containing a variable region (e.g., a VH and a VL, respectively), in which the combination of the variable regions provides intended binding specificity to an epitope or to an antigen. The term "non-cognate pair" or "non-cognate pairing" used herein refers to a pair or pairing of two antibody chains (e.g., a heavy chain and a light chain) each containing a variable region (e.g., a VH and a VL, respectively), in which the combination of the variable regions does not provide intended binding specificity to an epitope or to an antigen.

There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

Unless specifically indicated otherwise, the term "antibody" as used herein encompasses molecules comprising two immunoglobulin heavy chains and two immunoglobulin light chains (sometimes referred to as a "full-length antibody" or "intact antibodies" or "whole antibody" or the like, in all instances referring to an antibody having a structure substantially similar to a native antibody) as well as antigen-binding antibody fragments thereof. An "antigen-binding fragment" or "antigen-binding antibody fragment" refers to a portion of an intact antibody or to a combination of portions derived from an intact antibody or from intact antibodies and binds the antigen(s) to which the intact antibody or antibodies bind.

An antigen-binding fragment of an antibody includes any naturally occurring, enzymatically obtainable, synthetic, or genetically engineered polypeptide or glycoprotein that specifically binds an antigen to form a complex. Exemplary antibody fragments include, but are not limited to: Fv; fragment antigen-binding ("Fab") fragment; Fab' fragment; Fab' containing a free sulfhydryl group ('Fab'-SH'); $F(ab')_2$ fragment; diabodies; linear antibodies; single-chain antibody molecules (e.g. single-chain variable fragment ("scFv"), nanobody or VHH, or VH or VL domains only); and monospecific or multispecific compounds formed from one or more of antibody fragments such as the foregoing. In some embodiments, the antigen-binding fragments of the bispecific antibodies described herein are scFvs. In preferred embodiments, an antigen-binding fragment comprises a CH1 domain which preferentially pairs with a kappa CL or with a lambda CL.

As with full antibody molecules, antigen-binding fragments may be mono-specific or multispecific (e.g., bispecific, trispecific, tetraspecific, etc). A multispecific antigen-binding fragment of an antibody may comprise at least two different variable domains, wherein each variable domain is capable of specifically binding to a separate antigen or to a different epitope of the same antigen.

Figure 1B:
Figure 1C:
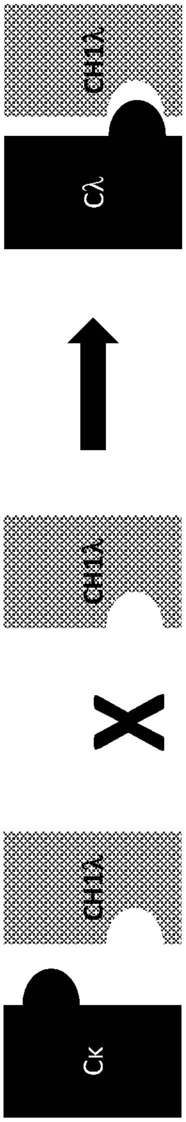

The present disclosure provides CH1 domain variants that preferentially pair with (or bind to) a kappa light chain CL domain or a lambda light chain CL domain. In one embodiment, the CH1 domain variants exhibit no or reduced binding to a kappa-class light chain or a lambda-class light chain and, concurrently, exhibit exclusive or increased preference for binding to a light chain of the other class (lambda or kappa, respectively, in this example). These CH1 domain variants may be used to solve, in whole or in part, heavy and light chain mispairing when generating multispecific, e.g., bispecific, antibodies by promoting proper heavy and light chain pairing. In one embodiment, CH1 domain variants may be optionally used in combination with other variants outside of the CH1 domain to further promote preferential pairing with a kappa light chain CL domain or a lambda light chain CL domain (e.g., VH:VL substitutions such as Q39E/K:Q38K/E (Dillon et al., *MAbs* 2017 9(2): 213-230); or Q39K+R62E:Q38D+D1R or Q39Y+Q105R: Q38R+K42D (Brinkmann et al., *MAbs* 2017 9(2): 182-212). More specifically, bispecific antibodies comprising these CH1 variant domains will form fewer unwanted product-related contaminants, i.e., molecules containing mispaired domains, whose elimination during downstream processing can be challenging. For example, a bispecific antibody comprising (i) the heavy chain and light chain from antibody A (wherein the light chain is a kappa light chain) and (ii) the heavy chain and light chain from antibody B (wherein the light chain is a lambda light chain) may be more efficiently produced, i.e., fewer unwanted product-related contaminants, by engineering the heavy chain CH1 domain of antibody A to a kappa-preferring CH1 domain variant (such as, e.g., 147 Phe and/or 183 Arg, Lys, Tyr) and the heavy chain CH1 domain of antibody B to a lambda-preferring CH1 domain variant (such as e.g., 141 Asp). As a result, the heavy chain of antibody A will favor binding to the light chain of antibody A (and disfavor binding to the light chain of antibody B) while the heavy chain of antibody B will favor binding to the light chain of antibody B (and disfavor binding to the light chain of antibody A). See FIGS. 1 and 7, and Table 6.

In some embodiments, the CH1 domain variants reduce mispairing, i.e., formation of non-cognate HC1-LC2 and/or HC2-LC1 pairs, by at least 25%, at least 30%, at least 35%, at least 40%, at least 45%, at least 50%, at least 55%, at least 60%, at least 65%, at least 70%, at least 75%, or at least 80%. In some embodiments, CH1 domain variants containing a substitution at position 141, e.g., 141D, alone or in combination with other substitutions, e.g., 147F+183R, 147F+183K, 147F+183Y, reduce mispairing, i.e., formation of non-cognate HC1-LC2 and/or HC2-LC1 pairs, by at least 25% to at least 80%. In some embodiments, CH1 domain variants containing a substitution at position 141, e.g., 141D, alone or in combination with other substitutions, e.g., 183R, 183K, 183Y, 147F+183R, 147F+183K, 147F+183Y, reduce mispairing, i.e., formation of non-cognate HC1-LC2 and/or HC2-LC1 pairs, by at least 50%. In some embodiments, CH1 domain variants containing a substitution at position 141, e.g., 141D, alone or in combination with other substitutions, e.g., 183R, 183K, 183Y, 147F+183R, 147F+183K, 147F+183Y, reduce mispairing, i.e., formation of non-cognate HC1-LC2 and/or HC2-LC1 pairs, by at least 75%.

In some embodiments, the CH1 domain variants preferentially pair with (bind to) the cognate CL domain (either Cκ or Cλ) or cognate light chain containing the corresponding CL domain (either Cκ or Cλ) resulting in at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% formation of the desired first and second cognate pairs, i.e., HC1-LC1 and/or HC2-LC2. In some embodiments, the CH1 domain variants preferentially pair with (bind to) the cognate CL domain (either Cκ or Cλ) or cognate light chain containing the corresponding CL domain (either Cκ or Cλ) resulting in about 80% to about 99% or, more particularly, at least about 85% to at least about 95% formation of the desired first and second cognate pairs, i.e., HC1-LC1 and/or HC2-LC2. In some embodiments, CH1 domain variants containing a substitution at position 141, e.g., 141D, alone or in combination with other substitutions, e.g., 183R, 183K, 183Y, 147F+183R, 147F+183K, 147F+183Y, provide about 85% to at least about 95% formation of the desired first and second cognate pairs, i.e., HC1-LC1 and/or HC2-LC2.

In some embodiments, the CH1 domain variants provide decreased formation of mispaired heavy chain-light chain heterodimers, i.e., HC1-LC2 and/or HC2-LC1 pairs, to less than 25%, less than 20%, less than 15%, less than 14%, less than 13%, less than 12%, less than 111% less than 10%, less than 9%, less than 8%, less than 7%, less than 6%, less than 5%, less than 4%, less than 3%, less than 2%, or less than 1%. In some embodiments, CH1 domain variants containing a substitution at position 141, e.g., 141D, alone or in combination with other substitutions, e.g., 183R, 183K, 183Y, 147F+183R, 147F+183K, 147F+183Y, provide decreased formation of mispaired heavy chain-light chain heterodimers to less than about 15%, less than about 10%, or less than about 5%.

Several CH1 domain positions were identified as influencing light chain binding preference, i.e., preferentially pairing with a kappa CL domain or a lambda CL domain, including positions 118, 119, 124, 126-134, 136, 138-143, 145, 147-154, 163, 168, 170-172, 175-176, 181, 183-185, 187, 190, 191, 197, 201, 203-206, 208, 210-214, 216, and 218 (EU numbering). Substituting the wild-type amino acid residue at any one or more of these positions in the CH1 domain with a variant (non-wild-type) amino acid residue results in a heavy chain that has preferential pairing for a light chain containing either a kappa CL domain or a lambda CL domain. For example, each of positions 147 and 183 were identified as having pairing preference for a kappa CL domain and position 141, 170, 171, 175, 181, 184, 185, 187, and 218 were identified as having pairing preference for a lambda CL domain.

Substitution of the wild-type amino acid residue (Ala) at CH1 domain position 141 with Thr, Asp, Lys, Glu, Arg, Met, Val, or Gln was shown to increase the heavy chain preference for binding to a light chain containing a lambda CL domain. Substitution of the wild-type amino acid residue (Phe) at CH1 domain position 170 with Glu, Gly, Ser, Asn, or Thr; substitution of the wild-type amino acid residue (Pro) at CH1 domain position 171 with Glu, Gly, Ser, Asn, Asp, or Ala; substitution of the wild-type amino acid residue (Met) at CH1 domain position 175 with Asp or Met; substitution of the wild-type amino acid residue (Ser) at CH1 domain position 181 with Val, Leu, Ala, Lys, or Thr; substitution of the wild-type amino acid residue (Ser) at CH1 domain position 184 with Arg; substitution of the wild-type amino acid residue (Val) at CH1 domain position 185 with Met, Leu, Ser, Arg, Thr; substitution of the wild-type amino acid residue (Thr) at CH1 domain position 187 with Arg, Asp, Glu, Tyr, or Ser; and/or substitution of the wild-type amino acid residue (Lys) at CH1 domain position 218 with Leu, Glu, Asp, Pro, Ala, His, Ser, Gln, Asn, Thr, Ile, Met, Gly, Cys, Lys, or Trp also contributes to increased heavy chain pairing with a light chain containing a lambda CL domain.

Substitution of the wild-type amino acid residue (Lys) at CH1 domain position 147 with Val, Ala, Phe, Ile, Thr, Ser, Tyr, Leu, Arg, Asn, Glu, His, Met, or Gln was shown to increase the heavy chain preference for binding to a light chain containing a kappa CL domain. Substitution of the wild-type amino acid residue (Ser) at CH1 domain position 183 to Arg, Lys, Tyr, Trp, Glu, Phe, Ile, Leu, Asn, or Gln was shown to increase the heavy chain preference for binding to a light chain containing a kappa CL domain (see FIG. 5). The impact of a given variant amino acid residue at a particular position may vary, but all variants show improved preferential pairing with Cκ or Cλ, based on the amino acid position comprising the variant residue. Additionally, given the high degree of similarity in the CH1 regions of IgG1, IgG2, IgG3 and IgG4, it is expected that the CH1 domain variants described herein will display similar preferential pairing properties in each isotype.

Figure 5:
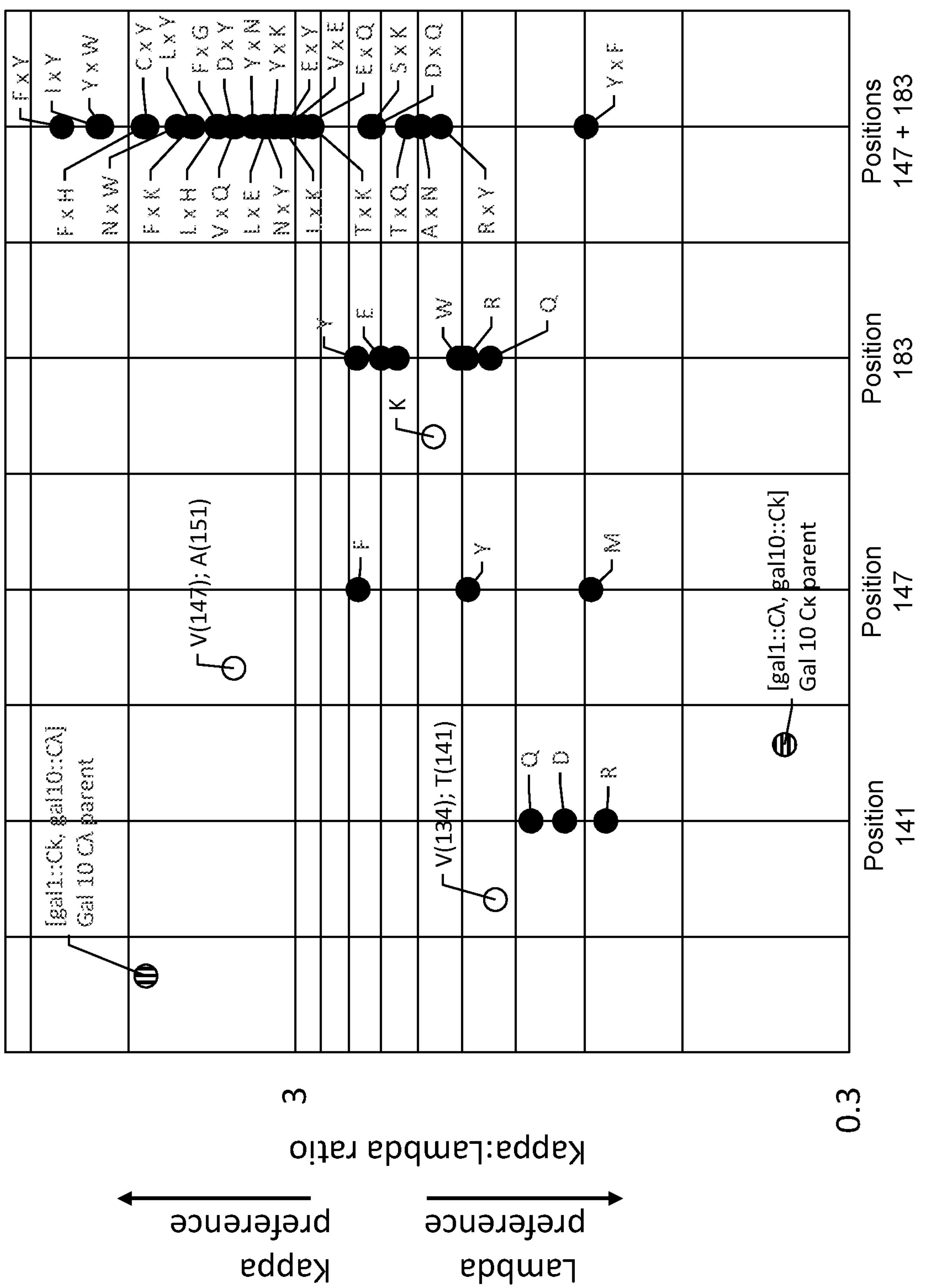
FIG. 5 shows particular amino acid substitutions at positions 141, 147, and/or 183 (EU numbering) in the CH1 domain with lambda CL domain preference (A141T, Q, D, or R) or kappa CL domain preference (K147V, A, F, Y, or M; S183K, Y, E, R, W, Q) as measured by the ratio of anti-kappa MFI to anti-lambda MFI. The amino acid substitutions shown as white dots (V134; T141, V147; A151, and K183) were identified after initial selections from libraries with diversification at multiple positions, and the amino acid substitutions shown as black dots were identified after additional rounds of selection from libraries with diversification targeted to positions 141, 147 and 183. Parental κ:λ ratio (wild-type signal): GAL1 Cκ; GAL10 Cλ: 3.58 and GAL1 Cλ; GAL10 Cκ: 0.3. Parental ratios are averages over experimental replicates. For the CH1 variants with substitutions at both positions 147 and 183, the first amino acid listed is the variant at position 147 and the second amino acid listed is the variant at 183 (e.g., Y×F means a CH1 variant with substitutions K147Y and S183F).
Figure 6A:
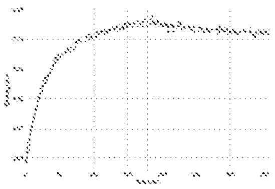
FIG. 6A-E show representative binding data demonstrating that the CH1 domain variant did not alter target binding of the multispecific antibody (BsAb2-BsAb14) as compared to the wild-type CH1 domain (BsAb1 and BsAb15).
Figure 6A:
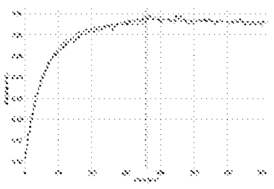
Figure 6A:
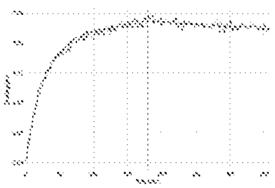
Figure 6A:
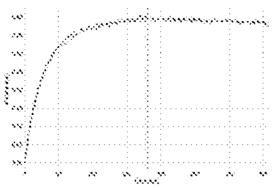
Figure 6A:
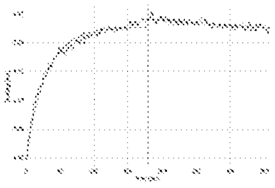
Figure 6A:
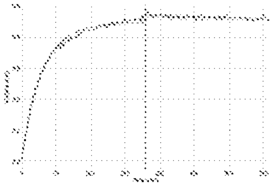
Figure 6B:
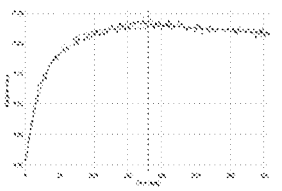
Figure 6B:
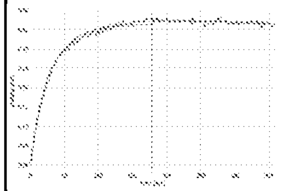
Figure 6B:
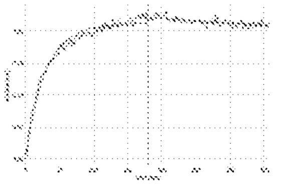
Figure 6B:
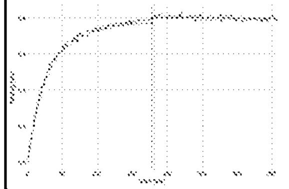
Figure 6B:
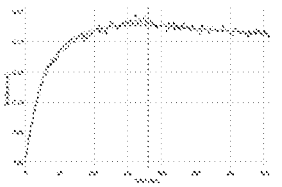
Figure 6B:
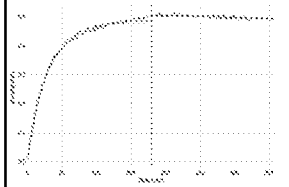
Figure 6C:
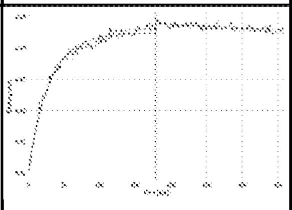
Figure 6C:
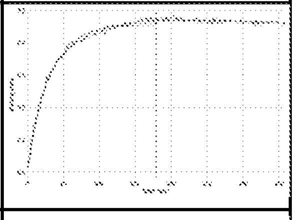
Figure 6C:
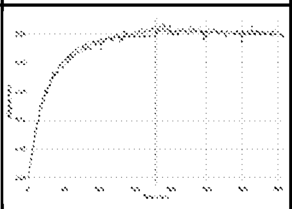
Figure 6C:
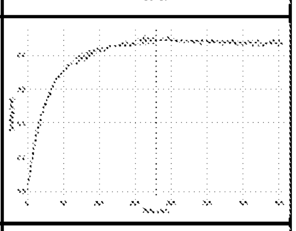
Figure 6C:
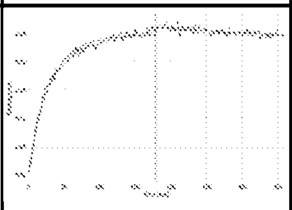
Figure 6C:
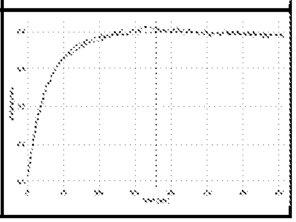
Figure 6D:
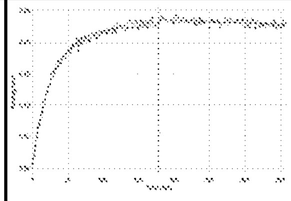
Figure 6D:
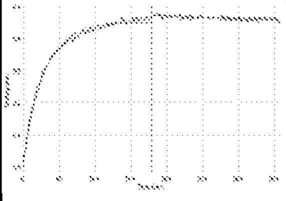
Figure 6D:
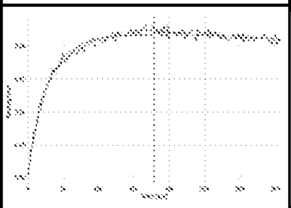
Figure 6D:
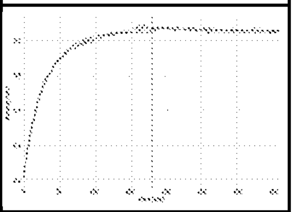
Figure 6D:
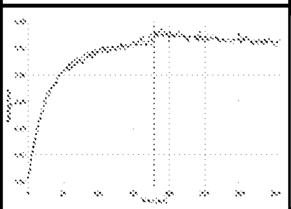
Figure 6D:
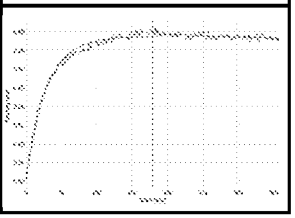
Figure 6E:
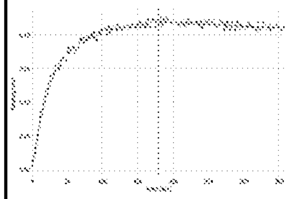
Figure 6E:
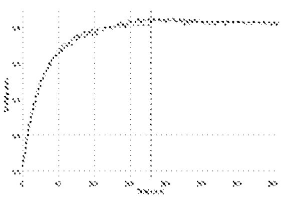
Figure 6E:
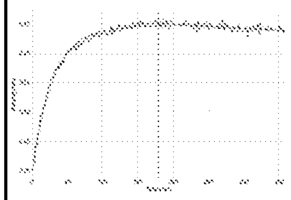
Figure 6E:
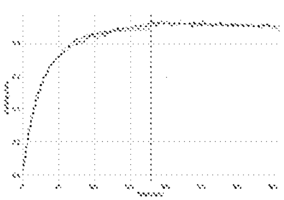
Figure 6E:
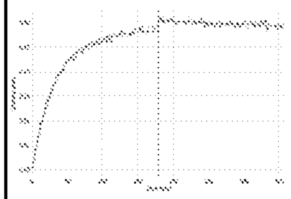
Figure 6E:
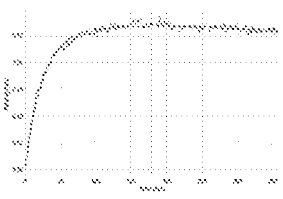

An initial round of selection identified Thr at position 141 as promoting preferential pairing with Cλ as compared to the wild-type CH1 domain sequence (Ala at position 141), but additional rounds of selection identified Asp, Arg, and Gln as providing increased preferential pairing as compared to Thr (see FIG. 5). Additional screening strategy identified Lys and Glu as also providing increased lambda preference (see Example 5, FIGS. 10-14). Glu at position 170; Glu at position 171; Met at position 175; Lys at position 181; Arg at position 184; Arg at position 185; Arg at position 187; and/or Pro, Ala, or Glu at position 218 were also found to increase lambda preference (see Examples 5-7). Furthermore, particular substitution combinations that Applicant shows to increase lambda preference include, but not limited to: Asp at position 141 and Lys at position 181; Asp at position 141, Lys at position 181, and Ala at position 218; Asp at position 141, Lys at position 181, and Pro at position 218; Glu at position 141, Glu at position 170, Val at position 181, and Arg at position 187; Glu at position 141, Asp at position 171 and Arg at position 185; Glu at position 141, Glu at position 171 and Arg at position 185; Glu at position 141, Gly at position 171, Arg at position 185, and Arg at position 187; Glu at position 141, Arg at position 185, and Arg at position 187; Glu at position 141, Ser at position 171, and Lys at position 181; Glu at position 141, Gly at position 170, Met at position 175, Val at position 181, Arg at position 184, and Arg at position 187. In additional screening efforts identified: "Asp at position 141, Glu at position 171, and Arg at position 185" and "Asp at position 141, Glu at position 170, and Arg at position 187" as particularly lambda-preferring CH1 domain substitution combinations (see FIGS. 20, 23, 30, and 31).

Similarly, an initial round of selection identified Val or Ala at position 147 and Lys at position 183 as promoting preferential pairing with Cκ as compared to the wildtype CH1 domain sequence, but additional rounds of selection identified Phe, Ile, Thr, Tyr, Leu, Arg, Asn, Glu, His, Met, or Gln at position 147 and/or Arg, Tyr, Trp, Glu, Phe, or Gln at position 183 as providing increased preferential pairing as compared to 147Val or Ala or 183Lys, respectively. These CH1 domain variants, alone or in combination with other amino acid substitutions, may improve preferential pairing of a heavy chain containing such CH1 domain variant with a light chain containing Cκ or Cλ.

Provided herein are variant CH1 domains that comprise an amino acid substitution at one or more of the following positions and, thus, said CH1 domain variants display preferential pairing for either Cκ or Cλ (or a light chain comprising such domains): 118, 119, 124, 126-134, 136, 138-143, 145, 147-154, 163, 168, 170-172, 175-176, 181, 183-185, 187, 190, 191, 197, 201, 203-206, 208, 210-214, 216, 218, according to EU numbering. As demonstrated herein, different amino acid residue substitutions at one or more of these positions can result in a CH1 domain that preferentially pairs with either Cκ or Cλ (see Table 3 and Table 4). In some embodiments, an amino acid substitution at position 147 (EU numbering) is not a cysteine. In some embodiments, an amino acid substitution at position 183 (EU numbering) is not a cysteine or a threonine. In some embodiments, an amino acid substitution at position 147 (EU numbering) is not a cysteine and an amino acid substitution at position 183 (EU numbering) is not a cysteine or a threonine.

In some embodiments, the CH1 domain variant comprises an amino acid substitution at one or more of the following positions to drive preferential pairing of the CH1 domain variant (or a heavy chain comprising such domain) for Cκ (or a light chain comprising such domain): 118, 124, 126-129, 131-132, 134, 136, 139, 143, 145, 147-151, 153-154, 170, 172, 175-176, 181, 183, 185, 190-191, 197, 201, 203-206, 210, 212-214, and 218 (EU numbering). In some embodiments, the amino acid substitution is one or more of the following: position 118 is substituted with G; position 124 is substituted with H, R, E, L, or V; position 126 is substituted with A, T, or L; position 127 is substituted with V or L; position 128 is substituted with H; position 129 is substituted with P; position 131 is substituted with A; position 132 is substituted with P; position 134 is substituted with G; position 136 is substituted with E; position 139 is substituted with I; position 143 is substituted with V or S; position 145 is substituted with F, I, N, or T; position 147 is substituted with F, I, L, R, T, S, M, V, E, H, Y, or Q; position 148 is substituted with I, Q, Y, or G; position 149 is substituted with C, S, or H; position 150 is substituted with L or S; position 151 is substituted with A or L; position 153 is substituted with S; position 154 is substituted with M or G; position 170 is substituted with G or L; position 172 is substituted with V; position 175 is substituted with G, L, E, A; position 176 is substituted with P; position 181 is substituted with Y, Q, or G; position 183 is substituted with I, W, F, E, Y, L, K, Q, N, or R; position 185 is substituted with W; position 190 is substituted with P; position 191 is substituted with I; position 197 is substituted with A; position 201 is substituted with S; position 203 is substituted with S; position 204 is substituted with Y; position 205 is substituted with Q; position 206 is substituted with S; position 210 is substituted with R; position 212 is substituted with G; position 213 is substituted with E or R; position 214 is substituted with R; and position 218 is substituted with Q. In some embodiments, the CH1 domain variant comprises an amino acid substitution at positions 147 and 183 to drive preferential pairing with (binding to) a kappa light chain. In some embodiments, the amino acid substituted at position 147 is selected from the group consisting of F, I, L, R, T, S, M, V, E, H, Y, and Q, and wherein the amino acid substituted at position 183 is selected from the group consisting of I, W, F, E, Y, L, K, Q, N, and R. In a particular embodiment, the CH1 domain variant comprises R or K or Y at position 183 alone or in combination with F at position 147. Non-limiting examples of kappa-preferring CH1 domain variants may comprise the amino acid sequence of SEQ ID NOS: 137, 138, 139, 60, 41, or 136.

In some embodiments, the CH1 domain variant comprises an amino acid substitution at one or more of the following positions to drive preferential pairing of the CH1 domain variant (or a heavy chain comprising such domain) for Cλ (or a light chain comprising such domain): 119, 124, 126-127, 130-131, 133-134, 138-142, 152, 163, 170-171, 175, 181, 183-185, 187, 197, 203, 208, 210-214, 216, and 218 (EU numbering). In some embodiments, the amino acid substitution is one or more of the following: position 119 is substituted with R; position 124 is substituted with V; position 126 is substituted with V; position 127 is substituted with G; position 130 is substituted with H or S; position 131 is substituted with Q, T, N, R, V, or D; position 133 is substituted with D, T, L, E, S, or P; position 134 is substituted with A, H, I, P, V, N, or L; position 138 is substituted with R; position 139 is substituted with A; position 140 is substituted with I, V, D, Y, K, S, W, R, L or P; position 141 is substituted with D, T, R, E, K, Q, V, or M, preferably D, E, or K; position 142 is substituted with M; position 152 is substituted with G; position 163 is substituted with M; position 168 is substituted with F, I, or V; position 170 is substituted with N, G, E, S, or T, preferably E or G; position 171 is substituted with N, E, G, S, A, D, preferably D, E, G, or S; position 175 is substituted with D or M, preferably M; position 181 is substituted with V, L, A, K, or T, preferably K or V; position 183 is substituted with L or V; position 184 is substituted with R; position 185 is substituted with M, L, S, R, or T, preferably R; position 187 is substituted with R, D, E, Y, or S; position 197 is substituted with S; position 203 is substituted with D; position 208 is substituted with I; position 210 is substituted with T; position 211 is substituted with A; position 212 is substituted with N; position 213 is substituted with E; position 214 is substituted with R; position 216 is substituted with G; and position 218 is substituted with P, A, L, E, D, H, S, Q, N, T, I, M, G, C, K, or W, preferably P or A. In some embodiments, the CH1 domain comprises an amino acid substitution at residue 141 to drive preferential pairing to a lambda light chain. In some embodiments, the amino acid substituted at residue 141 is selected from the group consisting of T, R, E, K, V, D, and M. In a particular embodiment, the CH1 domain variant comprises Asp or Glu at position 141. In some embodiments, the amino acid substitution at position 141 may be combined with one or more substitutions within CH1, for example, Lys at position 181 or Lys at position 181 and Ala or Pro at position 218. Asp or Glu at position 141 may be combined with one or more substitutions at positions 170, 171, 175, 181, 184, 185, and/or 187, such as Glu or Gly at position 170, Asp, Glu, Gly, or Ser at position 171, met at position 175, Val or Lys at position 181, Arg at position 184, Arg at position 185, and/or Arg at position 187. Non-limiting examples of lambda-preferring CH1 domain variants may comprise the amino acid sequence of SEQ ID NOS: 140, 141, 142, 143, 144, 145, 146, 147, 148, 149, 155, 157, 159, 162, 163, 164, 165, 178, 179, 180, 181, 182, 183, 184, 185, 186, 187, 188, or 189.

In a particular embodiment, the CH1 domain variant comprises a combination of 141D, 181K, and 218P, a combination of 141D, 171E, and 185R, or a combination of 141D, 170E, and 187R. In a further embodiment, the CH1 domain variant comprises the amino acid sequence of SEQ ID NO: 188, 186, or 143.

The present disclosure also contemplates polypeptides, e.g., antibodies, comprising CH1 domain variants. Such polypeptides may be multispecific antibodies comprising a first heavy chain containing a first CH1 domain variant and a second heavy chain containing a second CH1 domain variant. The first heavy chain and the second heavy chain may bind to different epitopes. In some embodiments, an antibody comprises a first heavy chain comprising a first CH1 domain. In some embodiments, an antibody further comprises a second heavy chain comprising a second CH1 domain that comprises a different amino acid sequence than the first heavy chain CH1 domain.

In some embodiments, the first CH1 domain variant may preferentially pair with (or bind to) Cκ and the second CH1 domain variant may preferentially bind to Cλ. In this case, the first light chain comprises a Cκ domain and the second light chain comprises a Cλ domain. In some embodiments, the first light chain is a kappa light chain (Cκ and Vκ) or a chimeric light chain (Cκ and Vλ) and the second light chain is a lambda light chain (Cλ and Vλ) or a chimeric light chain (Cλ and Vκ).

In some embodiments, the first CH1 domain variant may preferentially pair with (bind to) Cλ and the second CH1 domain may preferentially pair with (bind to) Cκ. In this case, the first light chain comprises a Cλ domain and the second light chain comprises a Cκ domain. In some embodiments, the first light chain is a lambda light chain (Cλ and Vλ) or a chimeric light chain (Cλ and Vκ) and the second light chain is a kappa light chain (Cκ and Vκ) or a chimeric light chain (Cκ and Vλ).

The first and second light chains may (or may not) comprise an amino acid substitution that drives preferential pairing to the CH1 domain. In some embodiments, the CL domain of the light chain is not modified to alter binding to the heavy chain, e.g., the CH1 domain. In some embodiments, the first light chain contains a wild-type CL domain, e.g., a wild-type Cκ domain or a wild-type Cλ domain. In some embodiments, the second light chain contains a wild-type CL domain, e.g., a wild-type Cκ domain or a wild-type Cλ domain. A wild-type kappa light chain or Cκ domain may be encoded by IGKC. A wild-type lambda light chain or Cλ domain may be encoded by IGLC1, IGLC2, IGLC3, IGLC6, or IGLC7.

In some embodiments, an antibody is a multispecific antibody. In some embodiments, an antibody is a bispecific antibody. Such multispecific and bispecific antibodies may comprise any format containing a CH1 domain, such as but not limited to the structures depicted in FIGS. 24-29. See also, e.g., Brinkmann and Kontermann, *MAbs* 9(2):182-212 (2017) at Table 2, hereby incorporated by reference in its entirety.

A multispecific antibody may comprise one or more of the CH1 domain variants having an amino acid sequence as listed in Table 3, 4, 7, 9, 12, or 13. In some embodiments, an antibody comprises a first heavy chain containing a first CH1 domain variant and a first light chain, which first heavy chain and first light chain form a first cognate pair. A first CH1 domain variant may comprise an amino acid substitution at one or more of the following positions: 118, 119, 124, 126-134, 136, 138-143, 145, 147-154, 163, 168, 170-172, 175-176, 181, 183-185, 187, 190, 191, 197, 201, 203-206, 208, 210-214, 216, 218, according to EU numbering. Such first CH1 domain variant preferentially binds to the first light chain. The CL domain of the first light chain may or may not be modified to alter binding to the first heavy chain.

In some embodiments, an antibody further comprises a second heavy chain containing a second CH1 domain variant and a second light chain, which second heavy chain and second light chain form a second cognate pair. A second CH1 domain variant may comprise an amino acid substitution at one or more of the following positions: 118, 119, 124, 126-134, 136, 138-143, 145, 147-154, 163, 168, 170-172, 175-176, 181, 183-185, 187, 190, 191, 197, 201, 203-206, 208, 210-214, 216, 218, according to EU numbering. Such second CH1 domain variant preferentially binds to the second light chain. The CL domain of the second light chain may or may not be modified to alter binding to the second heavy chain.

In certain embodiments of a multispecific antibody or antibody fragment, the antibody or antibody fragment may comprise a kappa-preferring CH1 domain variant and a lambda-preferring CH1 domain variant. In some instances, the kappa-preferring CH1 domain variant may be a kappa-preferring CH1 domain variant as disclosed herein and the lambda-preferring CH1 domain may be a lambda-preferring CH1 domain that may or may not be described herein. In some instances, the lambda-preferring CH1 domain variant may be a lambda-preferring CH1 domain variant as disclosed herein and the kappa-preferring CH1 domain may be a kappa-preferring CH1 domain that may or may not be described herein. In certain instances, both the kappa-preferring CH1 domain variant and the lambda-preferring CH1 domain variant are the variants as disclosed herein.

Any of the CH1 domain variants disclosed herein may be used to provide pairing preference for the kappa CL domain or for the lambda CL domain, and the CL domains may be wild type or non-wild type. Furthermore, any of the CH1 domain variants disclosed herein may be used to provide kappa/lambda pairing preference in an antibody or antibody fragment structure, with or without introducing a further amino acid alteration to the rest of the antibody structure, e.g., CH2, CH3, VH, VL, or CL domain. For example, the CH1 domain variants disclosed herein may be used with a VH substitution that may further enhance light chain pairing preference (e.g., VH:VL substitutions such as Q39E/K: Q38K/E (Dillon et al., MAbs 2017 9(2): 213-230); or Q39K+R62E:Q38D+D1R or Q39Y+Q105R: Q38R+K42D (Brinkmann et al., MAbs 2017 9(2): 182-212).

Without wishing to affect the scope of the invention, it is highlighted that the CH1 domain variants provided herein provide kappa/lambda pairing preference in the context of a wild-type light chain (or a polypeptide comprising a wild type CL domain) without requiring another modification in CH2, CH3, or variable domains, although such non-CH1 modifications may optionally be used in combination with the novel CH1 domain variants discovered by Inventors herein. This is particularly unexpected considering many reported failures in the field in producing antibodies, particularly multispecific antibodies, wherein modifying only the CH1 domain provides for meaningful kappa or lambda preference.

In some embodiments, an antibody is part of a pharmaceutical composition. Such composition may contain multiple polypeptides, e.g., antibodies, comprising CH1 domain variants described herein.

Also contemplated by the present disclosure are methods for obtaining such CH1 domain variants. Variant CH1 domains described herein may be identified by rational design (in silico) or randomly, e.g., using ePCR or other mutagenic techniques known in the art. In one embodiment, a rational design approach is employed to design variant CH1 domains. For such an approach, a set of structures, e.g., experimentally-derived protein structures, e.g., Fab crystal structures, may be assembled and analyzed to identify solvent-exposed positions involved in contacts across the CH1-CL domain interface (also referred to as CH1-CL domain interface positions). The set may be curated by selecting structures having certain properties, e.g., high percentage identity to reference (wild-type) CH1, Cκ, and Cλ. In some embodiments, positions are described or defined as contacting another residue (or being "in contact") if a pair of side-chain atoms are within a cutoff distance of 5 Å. "CH1 interface residues" may be defined as residues in the CH1 domain that contact a residue in the Cκ domain or Cλ domain. The terms "residue" and "position" may be used interchangeably in this context. It is also of Inventor's unexpected discovery that an amino acid substitution at a CH1 position in the CH1-VH interface (e.g., CH1 position 151) alters light chain isotype preference. Therefore, in some embodiments, CH1 positions contacting a residue of VH (e.g., a pair of side-chain atoms are within a cutoff distance of 5 Å) may be also selected for the rational CH1 domain variant identification.

Selection of which amino acid positions to vary, whether alone or in combination (e.g., singlets, doublets, triplets, etc.), may depend on a variety of different parameters, e.g., consistent role of the position in forming an interface between CH1 and CL or between CH1 and VH in different structures, accessibility of the position(s) in the overall structure, relationship of the position to positions that influence antigen binding or the potential for a residue to impact formation of the CH1:CL or CH1:VH interface in an allosteric fashion without directly participating in intermolecular contacts across said interface. In some embodiments, amino acid residues in the CH1 domain are selected for variation if: 1) the residue is at an interface with the light chain constant domain in at least 10% of the structures in the Cκ set and has a fractional solvent accessible surface area (SASA) greater than 10% in at least 90% of structures in the Cκ set (see Example 1), OR 2) the residue is at an interface with the light chain constant domain in at least 10% of the structures in the Cλ set and has a fractional SASA greater than 10% in at least 90% of structures in the Cλ set, OR 3) the residue at an interface with the VH in at least 10% of a representative set of the $C_\kappa$ and/or $C_\lambda$ set and has a fractional solvent accessible surface area greater than 10% in at least 90% of a representative set of the CG and/or Ca set.

Furthermore, for each of the specific amino acid substitution in the CH1 domain that are provided herein to confer kappa- or lambda-preference, the amino acid included as a result of substitution may be further substituted via a conservative amino acid substitution to obtain another CH1 domain variant that provide equivalent kappa- or lambda-preference. Alternatively, for each CH1 domain variant, one or more amino acid positions that were not affected in the CH1 domain variant relative to the wild-type sequence may be altered via a conservative substitution to obtain another CH1 domain variant that provide equivalent kappa- or lambda-preference.

"Conservative amino acid substitutions" are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a β-branched side-chain substituted for another amino acid with a β-branched side-chain (e.g., Ile, Thr, and Val), an amino acid with an aromatic side-chain substituted for another amino acid with an aromatic side chain (e.g., His, Phe, Trp, and Tyr), etc.

Next, a library may be generated in which CH1 domain residues are varied. One or more CH1 domain residues may be varied in a library. In some embodiments, about one to six CH1 domain residues are varied in the library. The amino acid diversity at individual residue positions may be generated via a degenerate codon, e.g., NNK, to allow for representation of at least all 20 naturally-occurring amino acids at a given CH1 domain position. The selected CH1 domain positions may be varied individually to generate point substitutions (also referred to as singlets), or a subset of positional combinations may be varied in combination, e.g., to generate double and triple substitutions (also referred to as doublets and triplets). In some embodiments, variant combinations are generated that include CH1 domain positions that are near neighbors in 3D space, e.g., positions 147×[124, 126, 145, 148, 175 and 181].

In some embodiments, a method of making a CH1 domain variant library comprises: a) providing a set of structures containing one or more kappa constant (Cκ) domains, one or more lambda constant (Cλ) domains, and one or more CH1 domain; b) selecting for substitution one or more solvent-exposed CH1 domain positions in contact with one or more Cκ domain positions and/or one or more Cλ domain positions; c) substituting the one or more CH1 domain positions identified in step b) with any amino acid other than the parental amino acid; and d) synthesizing polypeptides that encode the CH1 variant domains of step c) to assemble a CH1 variant domain library.

In some embodiments, the one or more Cκ domains, one or more Cλ domains, and one or more CH1 domains are wild-type. In some embodiments, the one or more Cκ domains, one or more Cλ domains, and one or more CH1 domains are human (including all allelic functional variants). In some embodiments, the Cκ amino acid sequence in step a) is encoded by IGKC. In some embodiments, the Cλ amino acid sequence in step a) is encoded by IGLC1, IGLC2, IGLC3, IGLC6, or IGLC7. In a particular embodiment, the Cλ amino acid sequence in step a) is encoded by IGLC2. In some embodiments, the resultant CH1 domain library is designed to require interaction across the CH1-CL interface or the CH1-VH interface.

In some embodiments, the one or more CH1 amino acid residues selected for substitution is (i) at an interface with the light chain constant domain in at least 10% of a representative set of CH1:Cκ structures and has a fractional solvent accessible surface area greater than 10% in at least 90% of a representative set of CH1:Cκ structures, (ii) is at an interface with the light chain constant domain in at least 10% of a representative set of CH1:Cλ structures and has a fractional solvent accessible surface area greater than 10% in at least 90% of a representative set of CH1:Cλ structures, or (iii) is at an interface with the VH in at least 10% of a representative set of $C_\kappa$ and/or $C_\lambda$ structures and has a fractional solvent accessible surface area greater than 10% in at least 90% of a representative set of $C_\kappa$ and/or $C_\lambda$ structures.

In some embodiments, the library is generated by variegating one or more CH1 positions that are disclosed herein as altering light chain isotype preference (e.g., positions 141, 147, 151, 170, 171, 181, 183, 185, 187, or 218, or any combination thereof), and optionally one or more additional CH1 positions of interest. In certain embodiments, the library may be generated by combining a predetermined substitution at one or more CH1 positions that are disclosed herein as altering light chain isotype preference (e.g., positions 141, 147, 151, 170, 171, 181, 183, 185, 187, or 218, or any combination thereof) with one or more additional CH1 positions of interest variegated. In particular examples, the predetermined substitution may comprise A141D, A141E, K147F, P151A, P151L, F170E, P171E, S181K, S183R, V185R, T187R, or K218P, or any combination thereof.

In some embodiments, the library is screened to identify CH1 domain variants displaying preferential binding to a kappa light chain or a lambda light chain. Such screening may begin by expressing the library in a suitable host cell, e.g., a eukaryotic cell, e.g., a yeast cell, e.g., *Saccharomyces cerevisiae*. After expressing the CH1 variant domains included in the library in the host cell, the library of variants may be screened to identify those variants with desirable binding properties, e.g., via FACS or MACS.

In some embodiments, a method of identifying a CH1 domain variant with preferential Cκ or Cλ domain binding comprises: a) providing a set of structures containing one or more kappa constant (Cκ) domains, one or more lambda constant (Cλ) domains, and one or more CH1 domain; b) selecting for substitution one or more solvent-exposed CH1 domain positions in contact with one or more Cκ domain positions and/or one or more Cλ domain positions; c) substituting the one or more CH1 domain positions identified in step b) with any amino acid other than the parental amino acid; d) synthesizing polypeptides that encode the CH1 variant domains of step c) to assemble a CH1 variant domain library; and e) screening the library of d) to identify a CH1 domain variant with preferential Cκ or Cλ domain binding.

In some embodiments, the one or more Cκ domains, one or more Cλ domains, and one or more CH1 domains are wild-type. In some embodiments, the one or more Cκ domains, one or more Cλ domains, and one or more CH1 domains are human (including all allelic functional variants). In some embodiments, the Cκ amino acid sequence in step a) is encoded by IGKC. In some embodiments, the Cλ amino acid sequence in step a) is encoded by IGLC1, IGLC2, IGLC3, IGLC6, or IGLC7. In a particular embodiment, the Cλ amino acid sequence in step a) is encoded by IGLC2. In some embodiments, the resultant CH1 domain library is designed to require interaction across the CH1-CL interface or in the CH1-VH interface.

In some embodiments, the one or more CH1 amino acid residues selected for substitution is (i) at an interface with the light chain constant domain in at least 10% of a representative set of CH1:Cκ structures and has a fractional solvent accessible surface area greater than 10% in at least 90% of a representative set of CH1:Cκ structures, (ii) is at an interface with the light chain constant domain in at least 10% of a representative set of CH1:Cλ structures and has a fractional solvent accessible surface area greater than 10% in at least 90% of a representative set of CH1:Cλ structures, or (iii) is at an interface with the VH in at least 10% of a representative set of CH1:$C_\kappa$ and/or CH1:$C_\lambda$ structures and has a fractional solvent accessible surface area greater than 10% in at least 90% of a representative set of CH1:$C_\kappa$ and/or CH1:$C_\lambda$ structures.

The methods described herein may further comprise validating that the one or more substituted CH1 amino acid residues drives preferential pairing of the heavy chain for a kappa CL domain (or a light chain comprising a kappa CL domain) versus a lambda CL domain (or a light chain comprising a lambda CL domain), or vice versa. A variety of methods can be used to assess preferential light chain pairing, including but not limited to fluorescence-activated cell sorting (FACS), LC-MS, AlphaLISA, and SDS-PAGE. In some embodiments, the one or more CH1 domain positions selected for substitution in step c) occur at the interface with a light chain with a predetermined frequency, e.g., in any given set of wild-type antibody structures the selected CH1 domain positions contact the CL domain in at least 10% of structures. In some embodiments, the one or more CH1 domain positions selected for substitution in step c) has a fractional solvent accessible surface area greater than about 10% in at least about 90% or more of the structures in any given Cκ or Cλ set. In some embodiments, the one or more CH1 domain positions selected for substitution in step c) occur at the interface with a VH region with a predetermined frequency, e.g., in any given set of wild-type antibody structures the selected CH1 domain positions contact the VH in at least 10% of structures.

By employing the methods described herein for identifying CH1 domain variants, the following CH1 domain positions were selected for substitution: 114, 116, 118, 119, 121-124, 124-143, 147-154, 160, 162-165, 167, 168, 170-172, 174, 175, 176, 178, 180, 181, 183-185, 187, 190, 191, 197, 201, 203-208, 210-214, 216, and/or 128 (according to EU numbering). Substituting any one or a combination of these CH1 domain positions may result in a CH1 domain having preferential pairing for a particular CL domain. As a result, a heavy chain comprising such a CH1 domain variant and light chain comprising the particular CL domain are more likely to form a cognate pair, i.e., there is preferential pairing between the heavy chain and light chain that form a cognate pair driven, at least in part, by the one or more CH1 domain substitutions.

In one embodiment, a CH1 domain variant preferentially pairs with Cκ, consequently driving preferential pairing for a light chain containing a Cκ domain and a heavy chain containing the CH1 domain variant. In another embodiment, a CH1 domain variant preferentially pairs with Cλ domain, consequently driving preferential pairing for a light chain containing a Cλ domain and a heavy chain containing the CH1 domain variant. Certain exemplary CH1 domain substitutions were identified as promoting preferential heavy chain pairing with a kappa light chain, e.g., 147F and/or 183R, 183K, or 183Y, while other CH1 domain substitutions were identified as promoting preferential heavy chain pairing with a lambda light chain, e.g., 141D, 141E, 141K, 170E, 170G, 171E, 171D, 171G, 171S, 175M, 181K, 181B, 184R, 185R, 187R, 218A, or 218P. Accordingly, bispecific antibodies comprising such CH1 domain variants can be generated with improved fidelity in heavy chain-light chain pairing. In some embodiments, a bispecific antibody contains a first heavy chain comprising a CH1λ (such as 141D, 141E or 141K, in combination with 170E, 170G, 171E, 171D, 171G, 171S, or 175M, and/or 181K, 181B, 184R, 185R, 187R, 218A, and/or 218P) and a second heavy chain comprising a CH1κ (such as 147F and/or 183R, 183K, or 183Y), each of which preferentially pairs to its cognate light chain. In some embodiments, a bispecific antibody contains a first heavy chain comprising a CH1κ (such as 147F and/or 183R, 183K, or 183Y) and a second heavy chain comprising a CH1λ (such as 141D, 141E or 141K, in combination with 170E, 170G, 171E, 171D, 171G, 171S, or 175M, and/or 181K, 181B, 184R, 185R, 187R, 218A, and/or 218P), for example "141D, 171E, and 185R" or "141D, 170E, and 187R", each of which preferentially pairs to its cognate light chain.

Polypeptides that encode CH1 variant domains obtained by employing the methods described herein may be recombinantly expressed in a host cell, e.g., a eukaryotic cell. In some embodiments, CH1 variant domains are expressed in yeast. In some embodiments, a yeast strain is *Saccharomyces cerevisiae*. In some embodiments, a yeast strain co-expresses one or more wild-type kappa light chains and one or more wild-type lambda light chains.

Examples are provided below to illustrate the present invention. These examples are not meant to constrain the present invention to any particular application or theory of operation.

EXAMPLES

Example 1: In Silico Selection of CH1 Domain Positions for Diversification in a Library A set of Fab crystal structures was assembled from the Protein Data Bank (PDB), and used for a structure-guided approach to identify CH1-CL interface residues for diversification.

An initial set of 2,367 Fab crystal structures was narrowed by selecting structures with a high percentage identity to reference (wild-type) CH1, Cκ and Cλ sequences (shown below). The reference sequence for the CH1 alignment spans CH1 proper (EU residues 118-215) plus a portion of the IgG1 hinge (EU residues 216-229). The Cκ and Cλ reference sequences span EU residue numbers 108-214 and 107A-215, respectively.

```
CH1 (plus upper-to-middle hinge) Reference:
                                        (SEQ ID NO: 1)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPC.

Cκ Reference:
                                        (SEQ ID NO: 2)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.

Cλ Reference:
                                        (SEQ ID NO: 3)
GQPKAAPSVTLFPPSSEELQANKATLVCLISDFYPGAVTVAWKADSSPVK

AGVETTTPSKQSNNKYAASSYLSLTPEQWKSHRSYSCQVTHEGSTVEKTV

APTECS.
```

Residues were defined as being "in contact" if a pair of side-chain atoms were within a cutoff distance of 5 Å. CH1 interface residues were defined as those residues that contacted one or more Cκ or Cλ residues in individual structures.

Solvent Accessible Surface Area (SASA) of individual heavy and light chain residues was computed in the "free state", i.e. without being paired, respectively, with the light and heavy chains. The fractional SASA was defined as the ratio of the residue SASA to that of a model isolated Gly-X-Gly tripeptide incorporating the same amino acid (i.e. X) as the residue. Solvent exposed residues were defined as those with fractional SASA greater than 10%.

Narrowing the initial set of crystal structures by high percentage identity resulted in the identification of a set of 183 CH1:Cκ structures (the "Cκ set") and 43 CH1:Cλ structures (the "Cλ set"). After accounting for gaps in the alignment due to amino acids missing in the structures, all entries in the Cκ set were 100% identical to the reference CH1 and Cκ sequences while the entries in the Cλ set were >99% identical to the reference sequences.

A structure-based sequence alignment between Cκ and Cλ is shown below. CH1 forms a stable interface with both Cκ and Cλ despite the low sequence identity between the latter domains. Conservative and semi-conservative substitutions, according to BLOSUM62 scores, are depicted using "|"and":" respectively. The sequence identity between the domains is 38.3% (41 identities over 107 Cκ residues).

```
Cκ: -RTVAAPSVFIFPPSDEQLKSGTASVVCLLNNFYPREAKVQWKVDNALQSGNSQESVT
        AAPSV |FPPS:E|L::: A::VCL|::FYP  : V WK:D::  ::: | ::
Cλ: GQPKAAPSVTLFPPSSEELQANKATLVCLISDFYPGAVTVAWKADSSPVKAGVETTTP

Cκ: EQDSKDSTYSLSSTLTLSKADYEKHKVYACEVTHQGLSSPVTKSFNRGEC-  (SEQ ID NO: 2)
    :::S: : Y: SS L:L:  :|::H| Y:C|VTH|G  S|V K:    EC
Cλ: SKQSN-NKYAASSYLSLTPEQWKSHRSYSCQVTHEG--STVEKTVAPTECS  (SEQ ID NO: 3)
```

The underlined amino acids represent the Cκ and Cλ residues that are in contact with the CH1 domain. This determination is based on a consensus over the Fab structures in the Cκ and Cλ-sets. There are 25 Cκ interface residues and 26 Cλ interface residues. A 2×2 matrix was constructed focusing on positions that are at the interface in either Cκ or Cλ (N=28), and depending on (1) whether the residue at a given position contacts CH1, and (2) whether the amino acid at the position is identical between Cκ and Cλ (see Table 1).

TABLE 1

Cκ and Cλ amino acid positions at CH1:CL interface

| Contact position for both | Amino acid identical between Cκ and Cλ | |
|---|---|---|
| Cκ and Cλ | Yes | No |
| Yes | 9 | 14 |
| No | 2 | 3 |

Table 1 highlights that there are a set of 14 Cκ and Cλ positions that are structurally conserved, i.e. identical EU residue numbering, but with different amino acid identities, that contact the CH1 domain. Table 2 lists the 14 amino acid positions (EU numbering) and shows the amino acid present in the kappa and lambda light chains. Such differences in the identity of the Cκ and Cλ interface residues may be exploited to generate mutant CH1 domains that bind specifically to only Cκ or Cλ, but not both.

TABLE 2

Structurally conserved CH1-contacting positions with non-identical amino acid residues for Cκ and Cλ

| Position (EU numbering) | Cκ | Cλ |
|---|---|---|
| 116 | F | T |
| 122 | D | S |
| 124 | Q | E |
| 127 | S | A |
| 129 | T | K |
| 131 | S | T |
| 137 | N | S |
| 138 | N | D |
| 160 | Q | E |
| 162 | S | T |
| 167 | D | Q |
| 174 | S | A |
| 178 | T | Y |
| 180 | T | S |

As an initial threshold for selection for variation in the library, individual CH1 domain positions needed to meet the following criteria: 1) the position is at the interface with the light chain constant domain in at least 10% of the structures in the Cκ set and the residue at that position has a fractional SASA greater than 10% in at least 90% of the structures in the Cκ set, or 2) the position is at the interface with the light chain constant domain in at least 10% of the structures in the Cλ set and the residue at that position has a fractional SASA greater than 10% in at least 90% of the structures in the Cλ set, or 3) the position is at the interface with the VH region in at least 10% of the structures in the CH1:Cκ set (Cκ set) or CH1:Cλ set (Cλ set) and the residue at that position has a fractional SASA greater than 10% in at least 90% of the structures in the Cκ and/or Cλ set. The interface definition takes into account CH1 residue contacts with any CL domain residue, i.e. including but not restricted to the set of fourteen CL domain residues listed in Table 2 or CH1 residue contacts with any VH residue.

Based on this threshold criteria, a set of thirty CH1 amino acid positions was identified for potential inclusion (after excluding Cys220 from consideration). From this larger set, a group of 25 CH1 positions were selected to be varied in the library. Amino acid diversity at each position was generated via a degenerate NNK codon representing all 20 natural amino acids (Stemmer et al., *Proc Natl Acad Sci USA* 1994 Oct. 25; 91(22): 10747-51). Amino acid substitutions were individually made at each of the 25 CH1 positions, and a subset of the single substitutions were selectively combined, e.g., to generate double and triple mutants. The final library design consisted of 89 CH1 oligonucleotides representing 25 singlets (NNK codon diversification at a single CH1 position), 48 doublet mutants (NNK codon diversification at two CH1 positions), and 16 triplet mutants (NNK codon diversification at three CH1 positions).

Example 2: CH1 Domain Variant Libraries in Yeast Co-Expressing Cκ and Cλ Light Chains Libraries of human CH1 domain variants were built and expressed in an engineered yeast strain co-expressing wild-type human IgG Cκ and Cλ light chains (at different expression levels to allow for subsequent selection of Cλ-preferential CH1 substitutions and Cκ-preferential CH1 substitutions).

Bidirectional expression plasmids (pAD7064 and pAD4800) were constructed, each of which contained *Saccharomyces cerevisiae* Gal1/Gal10 promoter region flanked by wild-type human IgG light chain kappa and lambda constant domains and *S. cerevisiae* URA3 gene (selection marker). Plasmids pAD7064 and pAD4800 differed in the orientation of the kappa and lambda constant domains relative to the Gal1/10 promoter region. Unique restriction enzyme sites (PME-I and SFI-I) were placed upstream of the kappa and lambda constant domains in each plasmid. pAD7064 and pAD4800 were individually digested with PME-I and SFI-I and then transformed into an engineered yeast strain along with PCR-amplified DNA insert (ADI-26140 light chain region; Gal1/10 promoter region; and differentially encoded ("degenerate") ADI-26140 light chain variable region (IDT gblock) with 5' and 3' ends to guide assembly via homologous recombination to the plasmid). Transformed yeast were plated onto solid agar plates lacking URA3+, grown at 30° C. for 48 hours, before clones were picked and DNA was extracted and purified. After sequencing, two dual-light chain DNA constructs were identified;

(1) Gal10::ADI-26140-VL-Cκ Gal1::ADI-26140-VL-Cλ (human Cλ under control of the dominant promoter, allowing for subsequent selection of Cκ preferential CH1 substitutions); and (2) Gal10::ADI-26140-VL-Cλ Gal1::ADI-26140-VL-Cκ (human Cκ under control of the dominant promoter, allowing for subsequent selection of Cλ preferential CH1 substitutions). ADI-26140 is an anti-hen egg lysozyme (HEL) IgG.

For heavy chain expression, a DNA vector (pAD4466) was constructed containing a Gal1 promoter, an SFI-I restriction site, the CH2-CH3 domains of the human IgG heavy-chain (IgG1 (N297A)), and TRP1 (selectable marker).

In parallel, two independent pools of CH1 domain variant DNA fragments were generated for insertion into pAD4466. The first pool was generated using an in silico design approach as described in Example 1. The second pool was generated via error-prone PCR (ePCR). Briefly, mutagenic nucleotide analogs dPTP (0.01 mM) and 8-oxo-DGTP (0.01 mM) were included in the PCR reaction at a dilution of (a) 1:100 and 1:100 respectively, or (b) 1:100 and 1:10 respectively.

pAD4466 was digested with SFI-I and introduced into the yeast strain expressing the Cκ and Cλ along with PCR-amplified DNA encoding the ADI-26140 HC variable region, and the CH1 domain variant DNA from rational design efforts or ePCR. Each DNA fragment possessed appropriate DNA sequences at the 5' and 3' ends to guide assembly (via homologous recombination) with the digested plasmid or PCR fragment (ADI-26140 heavy-chain variable region or CH1 protein domain).

Assembly of individual libraries was performed via native *Saccharomyces cerevisiae* homologous recombination processes. A dilution of the transformed cells for each library was plated on media lacking uracil and tryptophan to quantify the number of members of each library. Each library numbered greater than 107 members. The remaining portion of transformed cells was cultured in liquid media lacking uracil and tryptophan in order to select for the presence of each (HC and dual-LC) plasmid.

Figure 2A:
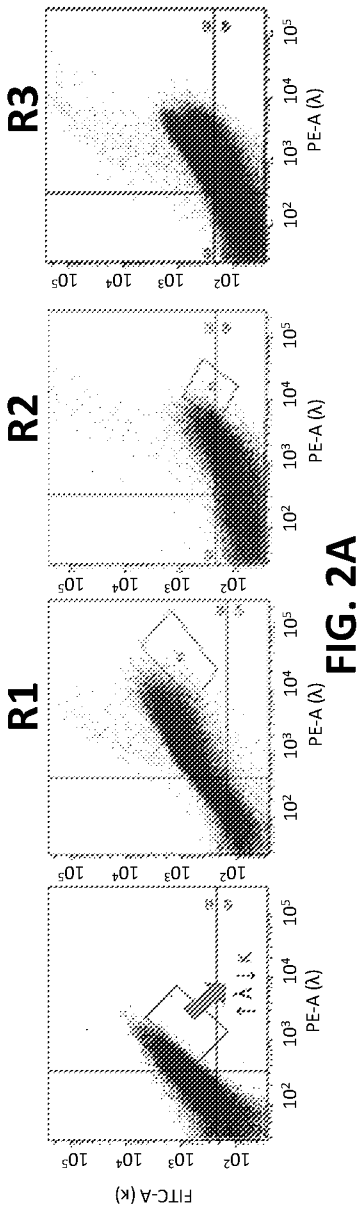
FIGS. 2A and 2B show exemplary FACS plots over multiple rounds of selections to identify CH1 domain variants with lambda CL domain preference (FIG. 2A) or kappa CL domain preference (FIG. 2B). R1=first round of selection, R2=second round of selection, R3=third round of selection. The x-axis shows lambda light chains labeled with PE, and the y-axis shows kappa light chains labeled with FITC.
Figure 2B:
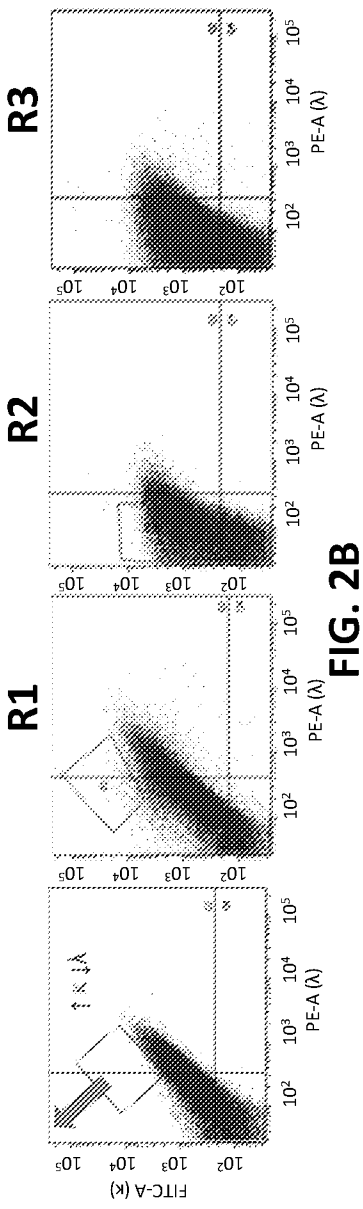

Example 3: Identification of CH1 Domain Positions Influencing Light Chain Binding Libraries were propagated as described previously (see, e.g., WO2009036379; WO2010105256; WO2012009568; Xu et al., *Protein Eng Des Sel.* 2013 October; 26(10):663-70). Briefly, following induction and presentation of IgGs, yeast cells (~10ˆ7-10ˆ8) were stained 15 minutes at 4° C. with goat anti-human F(ab')2 kappa-FITC diluted 1:100 (Southern Biotech, Birmingham, Alabama, Cat #2062-02) and goat anti-human $F(ab')_2$ lambda-PE diluted 1:100 (Southern Biotech, Birmingham, Alabama, Cat #2072-09) in PBSF. After washing twice with ice-cold wash buffer, cell pellets were resuspended in 0.4 mL PBSF and transferred to strainer-capped sort tubes. Sorting was performed using a FACS ARIA sorter (BD Biosciences) and sort gates were determined in order to either (1) increase lambda light chain with commensurate loss of kappa light chain (FIG. 2A), or (2) increase kappa light chain with commensurate loss of lambda light chain (FIG. 2B). Following three rounds of selection, yeast were plated on media lacking uracil and tryptophan to generate single isolates for sequence identification.

Figure 3:
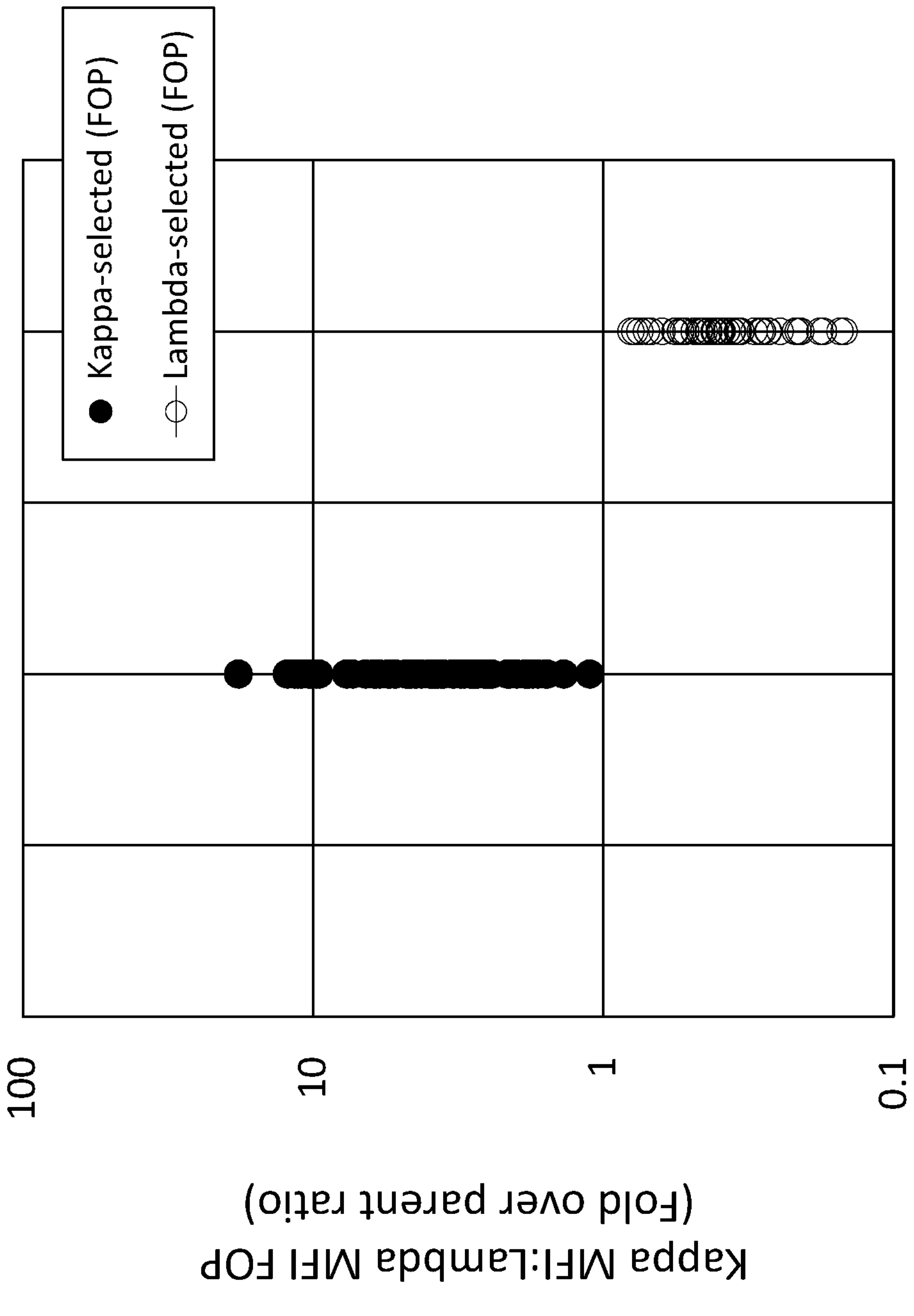
FIG. 3 shows individual unique clones expressing a CH1 domain variant with lambda CL domain preference or kappa CL domain preference. Clones were scored for the ratio of anti-kappa median fluorescence intensity (MFI) to anti-lambda MFI (kappa:lambda ratio). The kappa:lambda ratio for any individual clone was compared to a matched strain with a wild-type CH1 sequence ("parent"). FOP means fold-over-parent.

Individual clones representing unique sequences were cultured in 96-well plates. Following induction and presentation of IgGs, ~$2\times10^6$ yeast cells were stained for 15 min at 4° C. with goat anti-human F(ab')2 kappa-FITC diluted 1:100 (Southern Biotech, Birmingham, Alabama, Cat #2062-02) and goat anti-human $F(ab')_2$ lambda-PE diluted 1:100 (Southern Biotech, Birmingham, Alabama, Cat #2072-09) in PBSF. After washing twice with ice-cold wash buffer, the cell pellets were resuspended in 0.1 mL wash buffer and assessed on a BD FACS Canto instrument affixed with a 96-well plate handler. Individual unique clones were scored for the ratio of anti-kappa median fluorescence intensity (MFI) to anti-lambda MFI (kappa:lambda ratio) (FIG. 3) and then compared to a matched strain with a wild-type CH1 sequence ("parent") to calculate FOP.

The following CH1 domain positions (EU numbering) were identified as influencing light chain binding preference, i.e., preferential binding for either kappa CL domain (or a light chain containing a kappa CL domain) or lambda CL domain (or a light chain containing a lambda CL domain): 118, 119, 124, 126-134, 136, 139-141, 143, 145, 147-154, 163, 168, 170-172, 175-176, 181, 183, 185, 187, 190, 191, 197, 201, 203-206, 208, 210-214, 216, and 218. Table 3 provides a listing of CH1 sequences identified from selections that are preferential for kappa light chains. The bolded amino acid residues in the sequence column indicate the substituted positions, i.e., amino acid substitutions that differ from parent (SEQ ID NO: 1). Table 4 provides a listing of CH1 sequences identified from selections that are preferential for lambda light chains. The bolded amino acid residues in the sequence column indicate the substituted positions.

TABLE 3

CH1 domain sequences that preferentially bind Cκ

| SEQ ID NO: | Clone | Amino Acid Substitutions | Sequence |
|---|---|---|---|
| 4 | SAD9611_P01_B08 | A118G; K147F | **G**STKGPSVFPLAPSSKSTSGGTAALGCLV<br>**F**DYFPEPVTVSWNSGALTSGVHTFPAVLQ<br>SSGLYSLSSVVTVPSSSLGTQTYICNVNH<br>KPSNTKVDKKVEPK |
| 5 | SAD9611_P01_D09 | S124H; K147I | ASTKGP**H**VFPLAPSSKSTSGGTAALGCLV<br>**I**DYFPEPVTVSWNSGALTSGVHTFPAVLQ<br>SSGLYSLSSVVTVPSSSLGTQTYICNVNH<br>KPSNTKVDKKVEPK |

TABLE 3-continued

CH1 domain sequences that preferentially bind Cκ

| SEQ ID NO: | Clone | Amino Acid Substitutions | Sequence |
|---|---|---|---|
| 6 | SAD9611_P01_H09 | S124R; K147L | ASTKGP**R**VFPLAPSSKSTSGGTAALGCLV<br>**L**DYFPEPVTVSWNSGALTSGVHTFPAVLQ<br>SSGLYSLSSVVTVPSSSLGTQTYICNVNH<br>KPSNTKVDKKVEPK |
| 7 | SAD9611_P01_B09 | F126A; S183I | ASTKGPSV**A**PLAPSSKSTSGGTAALGCLV<br>KDYFPEPVTVSWNSGALTSGVHTFPAVLQ<br>SSGLYSL**I**SVVTVPSSSLGTQTYICNVNH<br>KPSNTKVDKKVEPK |
| 8 | SAD9611_P01_E08 | P127V; K213E | ASTKGPSVF**V**LAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVD**E**KVEPK |
| 9 | SAD9611_P01_H07 | L128H; S183W | ASTKGPSVFP**H**APSSKSTSGGTAALGCLV<br>KDYFPEPVTVSWNSGALTSGVHTFPAVLQ<br>SSGLYSL**W**SVVTVPSSSLGTQTYICNVNH<br>KPSNTKVDKKVEPK |
| 10 | SAD9611_P01_F08 | L145F; K147I | ASTKGPSVFPLAPSSKSTSGGTAALGC**F**V<br>**I**DYFPEPVTVSWNSGALTSGVHTFPAVLQ<br>SSGLYSLSSVVTVPSSSLGTQTYICNVNH<br>KPSNTKVDKKVEPK |
| 11 | SAD9611_P01_D07 | L145I; K147T | ASTKGPSVFPLAPSSKSTSGGTAALGC**I**V<br>**T**DYFPEPVTVSWNSGALTSGVHTFPAVLQ<br>SSGLY**Q**LSSVVTVPSSSLGTQTYICNVNH<br>KPSNTKVDKKVEPK |
| 12 | SAD9611_P01_C07 | K147L | ASTKGPSVFPLAPSSKSTSGGTAALGCLV<br>**L**DYFPEPVTVSWNSGALTSGVHTFPAVLQ<br>SSGLYSLSSVVTVPSSSLGTQTYICNVNH<br>KPSNTKVDKKVEPK |
| 13 | SAD9611_P01_E09 | K147S | ASTKGPSVFPLAPSSKSTSGGTAALGCLV<br>**S**DYFPEPVTVSWNSGALTSGVHTFPAVLQ<br>SSGLYSLSSVVTVPSSSLGTQTYICNVNH<br>KPSNTKVDKKVEPK |
| 14 | SAD9611_P01_F09 | K147L; S181Y | ASTKGPSVFPLAPSSKSTSGGTAALGCLV<br>**L**DYFPEPVTVSWNSGALTSGVHTFPAVLQ<br>SSGLY**Y**LSSVVTVPSSSLGTQTYICNVNH<br>KPSNTKVDKKVEPK |
| 15 | SAD9611_P01_A07 | K147M; S181Q | ASTKGPSVFPLAPSSKSTSGGTAALGCLV<br>**M**DYFPEPVTVSWNSGALTSGVHTFPAVLQ<br>SSGLY**Q**LSSVVTVPSSSLGTQTYICNVNH<br>KPSNTKVDKKVEPK |
| 16 | SAD9611_P01_C09 | K147V; Q175G | ASTKGPSVFPLAPSSKSTSGGTAALGCLV<br>**V**DYFPEPVTVSWNSGALTSGVHTFPAVL**G**<br>SSGLYSLSSVVTVPSSSLGTQTYICNVNH<br>KPSNTKVDKKVEPK |
| 17 | SAD9611_P01_B07 | K147E; D148I | ASTKGPSVFPLAPSSKSTSGGTAALGCLV<br>**EI**YFPEPVTVSWNSGALTSGVHTFPAVL**G**<br>SSGLYSLSSVVTVPSSSLGTQTYICNVNH<br>KPSNTKVDKKVEPK |
| 18 | SAD9611_P01_G09 | F170G; S183F | ASTKGPSVFPLAPSSKSTSGGTAALGCLV<br>KDYFPEPVTVSWNSGALTSGVHT**G**PAVLQ<br>SSGLYSL**F**SVVTVPSSSLGTQTYICNVNH<br>KPSNTKVDKKVEPK |
| 19 | SAD9611_P01_C08 | S183E | ASTKGPSVFPLAPSSKSTSGGTAALGCLV<br>KDYFPEPVTVSWNSGALTSGVHTFPAVLQ<br>SSGLYSL**E**SVVTVPSSSLGTQTYICNVNH<br>KPSNTKVDKKVEPK |
| 20 | SAD9611_P01_G08 | S183Y; S191I | ASTKGPSVFPLAPSSKSTSGGTAALGCLV<br>KDYFPEPVTVSWNSGALTSGVHTFPAVLQ |

TABLE 3-continued

| SEQ ID NO: | Clone | Amino Acid Substitutions | Sequence |
|---|---|---|---|
| CH1 domain sequences that preferentially bind Cκ | | | |
| | | | SSGLYSL**Y**SVVTVPS**I**SLGTQTYICNVNH<br>KPSNTKVDKKVEPK |
| 21 | SAD9611_P01_G07 | V185W | ASTKGPSVFPLAPSSKSTSGGTAALGCLV<br>KDYFPEPVTVSWNSGALTSGVHTFPAVLQ<br>SSGLYSLSS**W**VTVPSSSLGTQTYICNVNH<br>KPSNTKVDKKVEPK |
| 22 | SAD9613_P02_D10 | S124E; K147V | ASTKGP**E**VFPLAPSSKSTSGGTAALGCLV<br>**V**DYFPEPVTVSWNSGALTSGVHTFPAVLQ<br>SSGLYSLSSVVTVPSSSLGTQTYICNVNH<br>KPSNTKVDKKVEPK |
| 23 | SAD9613_P02_D12 | S124L; K147F | ASTKGP**L**VFPLAPSSKSTSGGTAALGCLV<br>**F**DYFPEPVTVSWNSGALTSGVHTFPAVLQ<br>SSGLYSLSSVVTVPSSSLGTQTYICNVNH<br>KPSNTKVDKKVEPK |
| 24 | SAD9613_P02_B10 | S124V; K147Y | ASTKGP**V**VFPLAPSSKSTSGGTAALGCLV<br>**Y**DYFPEPVTVSWNSGALTSGVHTFPAVLQ<br>SSGLYSLSSVVTVPSSSLGTQTYICNVNH<br>KPSNTKVDKKVEPK |
| 25 | SAD9613_P02_A11 | F126T | ASTKGPSV**T**PLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPK |
| 26 | SAD9613_P02_E12 | P127L; S136E | ASTKGPSVF**L**LAPSSKST**E**GGTAAL**S**CLV<br>KDYFPEPVTVSWNSGALTSGVHTFPAVLQ<br>SSGLYSLSSVVTVPSSSLGTQTYICNVNH<br>KPSNTKVDKKVEPK |
| 27 | SAD9613_P02_F10 | A129P; S183E | ASTKGPSVFPL**P**PSSKSTSGGTAALGCLV<br>KDYFPEPVTVSWNSGALTSGVHTFPAVLQ<br>SSGLYSL**E**SVVTVPSSSLGTQTYICNVNH<br>KPSNTKVDKKVEPK |
| 28 | SAD9613_P02_A10 | S131A; Q175L | ASTKGPSVFPLAP**A**SKSTSGGTAALGCLV<br>KDYFPEPVTVSWNSGALTSGVHTFPAVL**L**<br>SSGLYSLSSVVTVPSSSLGTQTYICNVNH<br>KPSNTKVDKKVEPK |
| 29 | SAD9613_P02_C12 | L1451; S183Y | ASTKGPSVFPLAPSSKSTSGGTAALGC**I**V<br>KDYFPEPVTVSWNSGALTSGVHTFPAVLQ<br>SSGLYSL**Y**SVVTVPSSSLGTQTYICNVNH<br>KPSNTKVDKKVEPK |
| 30 | SAD9613_P02_H10 | L145N; S183L | ASTKGPSVFPLAPSSKSTSGGTAALGC**N**V<br>KDYFPEPVTVSWNSGALTSGVHTFPAVLQ<br>SSGLYSL**L**SVVTVPSSSLGTQTYICNVNH<br>KPSNTKVDKKVEPK |
| 31 | SAD9613_P02_G11 | L145T; S183F | ASTKGPSVFPLAPSSKSTSGGTAALGC**T**V<br>KDYFPEPVTVSWNSGALTSGVHTFPAVLQ<br>SSGLYSL**F**SVVTVPSSSLGTQTYICNVNH<br>KPSNTKVDKKVEPK |
| 32 | SAD9613_P02_D11 | K147V | ASTKGPSVFPLAPSSKSTSGGTAALGCLV<br>**V**DYFPEPVTVSWNSGALTSGVHTFPAVLQ<br>SSGLYSLSSVVTVPSSSLGTQTYICNVNH<br>KPSNTKVDKKVEPK |
| 33 | SAD9613_P02_E10 | K147E; Q175E | ASTKGPSVFPLAPSSKSTSGGTAALGCLV<br>**E**DYFPEPVTVSWNSGALTSGVHTFPAVL**E**<br>SSGLYSLSSVVTVPSSSLGTQTYICNVNH<br>KPSNTKVDKKVEPK |
| 34 | SAD9613_P02_B12 | K147L; Q175G | ASTKGPSVFPLAPSSKSTSGGTAALGCLV<br>**L**DYFPEPVTVSWNSGALTSGVHTFPAVL**G**<br>SSGLYSLSSVVTVPSSSLGTQTYICNVNH<br>KPSNTKVDKKVEPK |

TABLE 3-continued

CH1 domain sequences that preferentially bind Cκ

| SEQ ID NO: | Clone | Amino Acid Substitutions | Sequence |
|---|---|---|---|
| 35 | SAD9613_P02_F11 | K147Q; Q175E | ASTKGPSVFPLAPSSKSTSGGTAALGCLV<br>**Q**DYFPEPVTVSWNSGALTSGVHTFPAVL**E**<br>SSGLYSLSSVVTVPSSSLGTQTYICNVNH<br>KPSNTKVDKKVEPK |
| 36 | SAD9613 P02_G10 | K147V; P151A | ASTKGPSVFPLAPSSKSTSGGTAALGCLV<br>**V**DYF**A**EPVTVSWNSGALTSGVHTFPAVLQ<br>SSGLYSLSSVVTVPSSSLGTQTYICNVNH<br>KPSNTKVDKKVEPK |
| 37 | SAD9613_P02_A12 | K147Y; S181G | ASTKGPSVFPLAPSSKSTSGGTAALGCLV<br>**Y**DYFPEPVTVSWNSGALTSGVHTFPAVLQ<br>SSGLY**G**LSSVVTVPSSSLGTQTYICNVNH<br>KPSNTKVDKKVEPK |
| 38 | SAD9613_P02_F12 | K147M; D148Q | ASTKGPSVFPLAPSSKSTSGGTAALGCLV<br>**MQ**YFPEPVTVSWNSGALTSGVHTFPAVL**G**<br>SSGLYSLSSVVTVPSSSLGTQTYICNVNH<br>KPSNTKVDKKVEPK |
| 39 | SAD9613_P02_G12 | K147Y; Q175A | ASTKGPSVFPLAPSSKSTSGGTAALGCLV<br>**Y**DYFPEPVTVSWNSGALTSGVHTFPAVL**A**<br>SSGLYSLSSVVTVPYSSLGTQTYICNVNH<br>KPSNTKVDKKVEPK |
| 40 | SAD9613_P02_B11 | K147Y; D148Y | ASTKGPSVFPLAPSSKSTSGGTAALGCLV<br>**YY**YFPEPVTVSWNSGALTSGVHTFPAVL**A**<br>SSGLYSLSSVVTVPSSSLGTQTYICNVNH<br>KPSNTKVDKKVEPK |
| 41 | SAD9613_P02_H11 | S183K | ASTKGPSVFPLAPSSKSTSGGTAALGCLV<br>KDYFPEPVTVSWNSGALTSGVHTFPAVLQ<br>SSGLYSL**K**SVVTVPSSSLGTQTYICNVNH<br>KPSNTKVDKKVEPK |
| 42 | SAD9613_P02_C10 | S183Q | ASTKGPSVFPLAPSSKSTSGGTAALGCLV<br>KDYFPEPVTVSWNSGALTSGVHTFPAVLQ<br>SSGLYSL**Q**SVVTVPSSSLGTQTYICNVNH<br>KPSNTKVDKKVEPK |
| 43 | SAD9613_P02_E11 | S183Q; K210R | ASTKGPSVFPLAPSSKSTSGGTAALGCLV<br>KDYFPEPVTVSWNSGALTSGVHTFPAVLQ<br>SSGLYSL**Q**SVVTVPSSSLGTQTYICNVNH<br>KPSNT**R**VDKKVEPK |
| 44 | SAD9610_P01_C03 | T1391; F150L | ASTKGPSVFPLAPSSKSTSGG**I**AALGCLV<br>KDY**L**PEPVTVSWNSGALTSGVHTFPAVLQ<br>SSGLYSLSSVVTVPSSSLGTQTYICNVNH<br>KPSNTKVDKKVEPK |
| 45 | SAD9610_P01_G03 | G143V | ASTKGPSVFPLAPSSKSTSGGTAAL**V**CLV<br>KDYFPEPVTVSWNSGALTSGVHTFPAVLQ<br>SSGLYSLSSVVTVPSSSLGTQTYICNVNH<br>KPSNTKVDKKVEPK |
| 46 | SAD9610_P01 F03 | K147E | ASTKGPSVFPLAPSSKSTSGGTAALGCLV<br>**E**DYFPEPVTVSWNSGALTSGVHTFPAVLQ<br>SSGLYSLSSVVTVPSSSLGTQTYICNVNH<br>KPSNTKVDKKVEPK |
| 47 | SAD9610_P01_H01 | K147E; T197A | ASTKGPSVFPLAPSSKSTSGGTAALGCLV<br>**E**DYFPEPVTVSWNSGALTSGVHTFPAVLQ<br>SSGLYSLSSVVTVPSSSLGTQ**A**YICNVNH<br>KPSNTKVDKKVEPK |
| 48 | SAD9610_P01_C01 | K147E; P206S | ASTKGPSVFPLAPSSKSTSGGTAALGCLV<br>**E**DYFPEPVTVSWNSGALTSGVHTFPAVLQ<br>SSGLYSLSSVVTVPSSSLGTQTYICNVNH<br>K**S**SNTKVDKKVEPK |
| 49 | SAD9610_P01_A01 | K147E; K205Q | ASTKGPSVFPLAPSSKSTSGGTAALGCLV<br>**E**DYFPEPVTVSWNSGALTSGVHTFPAVLQ |

TABLE 3-continued

CH1 domain sequences that preferentially bind Cκ

| SEQ ID NO: | Clone | Amino Acid Substitutions | Sequence |
|---|---|---|---|
| | | | SSGLYSLSSVVTVPSSSLGTQTYICNVNH<br>**Q**PSNTKVDKKVEPK |
| 50 | SAD9610_P01_D02 | Y149C | ASTKGPSVFPLAPSSKSTSGGTAALGCLV<br>KD**C**FPEPVTVSWNSGALTSGVHTFPAVLQ<br>SSGLYSLSSVVTVPSSSLGTQTYICNVNH<br>KPSNTKVDKKVEPK |
| 51 | SAD9610_P01_H03 | Y149S | ASTKGPSVFPLAPSSKSTSGGTAALGCLV<br>KD**S**FPEPVTVSWNSGALTSGVHTFPAVLQ<br>SSGLYSLSSVVTVPSSSLGTQTYICNVNH<br>KPSNTKVDKKVEPK |
| 52 | SAD9610_P01 B03 | Y149C; K218Q | ASTKGPSVFPLAPSSKSTSGGTAALGCLV<br>KD**C**FPEPVTVSWNSGALTSGVHTFPAVLQ<br>SSGLYSLSSVVTVPSSSLGTQTYICNVNH<br>KPSNTKVDKKVEP**Q** |
| 53 | SAD9610_P01_H02 | Y149H; K214R | ASTKGPSVFPLAPSSKSTSGGTAALGCLV<br>KD**H**FPEPVTVSWNSGALTSGVHTFPAVLQ<br>SSGLYSLSSVVTVPSSSLGTQTYICNVNH<br>KPSNTKVDK**R**VEPK |
| 54 | SAD9610_P01_E02 | Y149H; F150L | ASTKGPSVFPLAPSSKSTSGGTAALGCLV<br>KD**HL**PEPVTVSWNSGALTSGVHTFPAVLQ<br>SSGLYSLSSVVTVPSSSLGTQTYICNVNH<br>KPSNTKVDKKVEPK |
| 55 | SAD9610_P01_B02 | F150L; V154M | ASTKGPSVFPLAPSSKSTSGGTAALGCLV<br>KDY**L**PEP**M**TVSWNSGALTSGVHTFPAVLQ<br>SSGLYSLSSVVTVPSSSLGTQTYICNVNH<br>KPSNTKVDKKVEPK |
| 56 | SAD9610_P01_A03 | F150L; S190P | ASTKGPSVFPLAPSSKSTSGGTAALGCLV<br>KDY**L**PEPVTVSWNSGALTSGVHTFPAVLQ<br>SSGLYSLSSVVTVP**P**SSLGTQTYICNVNH<br>KPSNTKVDKKVEPK |
| 57 | SAD9610_P01_E03 | F150S; D212G | ASTKGPSVFPLAPSSKSTSGGTAALGCLV<br>KDY**S**PEPVTVSWNSGALTSGVHTFPAVLQ<br>SSGLYSLSSVVTVPSSSLGTQTYICNVNH<br>KPSNTKV**G**KKVEPK |
| 58 | SAD9610_P01_D01 | V154G | ASTKGPSVFPLAPSSKSTSGGTAALGCLV<br>KDYFPEP**G**TVSWNSGALTSGVHTFPAVLQ<br>SSGLYSLSSVVTVPSSSLGTQTYICNVNH<br>KPSNTKVDKKVEPK |
| 59 | SAD9610_P01_C02 | S183N | ASTKGPSVFPLAPSSKSTSGGTAALGCLV<br>KDYFPEPVTVSWNSGALTSGVHTFPAVLQ<br>SSGLYSL**N**SVVTVPSSSLGTQTYICNVNH<br>KPSNTKVDKKVEPK |
| 60 | SAD9610_P01_B01 | S183R | ASTKGPSVFPLAPSSKSTSGGTAALGCLV<br>KDYFPEPVTVSWNSGALTSGVHTFPAVLQ<br>SSGLYSL**R**SVVTVPSSSLGTQTYICNVNH<br>KPSNTKVDKKVEPK |
| 61 | SAD9610_P01_G01 | N203S; H204Y | ASTKGPSVFPLAPSSKSTSGGTAALGCLV<br>KDYFPEPVTVSWNSGALTSGVHTFPAVLQ<br>SSGLYSLSSVVTVPSSSLGTQTYICNV**SY**<br>KPSNT**R**VDKKVEPK |
| 62 | SAD9612_P02_E05 | F126L | ASTKGPSV**L**PLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPK |
| 63 | SAD9612_P02_C04 | F126L; S134G | ASTKGPSV**L**PLAPSSK**G**TSGGTAALGCLV<br>KDYFPEPVTVSWNSGALTSGVHTFPAVLQ<br>SSGLYSLSSVVTVPSSSLGTQTYICNVNH<br>KPSNTKVD**E**KVEPK |

TABLE 3-continued

| CH1 domain sequences that preferentially bind Cκ | | | |
|---|---|---|---|
| SEQ ID NO: | Clone | Amino Acid Substitutions | Sequence |
| 64 | SAD9612_P02_B06 | S131A; Y149C | ASTKGPSVFPLAP**A**SKSTSGGTAALGCLV KD**C**FPEPVTVSWNSGALTSGVHTFPAVLQ SSGLYSLSSVVTVPSSSLGTQTYICNVNH KPSNTKVDKKVEPK |
| 65 | SAD9612_P02_F05 | S132P; G143S | ASTKGPSVFPLAPS**P**KSTSGGTAAL**S**CLV KDYFPEPVTVSWNSGALTSGVHTFPAVLQ SSGLYSLSSVVTVPSSSLGTQTYICNVNH KPSNTKVDKKVEPK |
| 66 | SAD9612_P02_D05 | K147E; A172V | ASTKGPSVFPLAPSSKSTSGGTAALGCLV **E**DYFPEPVTVSWNSGALTSGVHTFP**V**VLQ SSGLYSLSSVVTVPSSSLGTQTYICNVNH KPSNTKVDKKVEPK |
| 67 | SAD9612_P02_C06 | D148G | ASTKGPSVFPLAPSSKSTSGGTAALGCLV K**G**YFPEPVTVSWNSGALTSGVHTFPAVLQ SSGLYSLSSVVTVPSSSLGTQTYICNVNH KPSNTKVDKKVEPK |
| 68 | SAD9612_P02_C05 | F150L | ASTKGPSVFPLAPSSKSTSGGTAALGCLV KDY**L**PEPVTVSWNSGALTSGVHTFPAVLQ SSGLYSLSSVVTVPSSSLGTQTYICNVNH KPSNTKVDKKVEPK |
| 69 | SAD9612_P02_H06 | F150L; K213R | ASTKGPSVFPLAPSSKSTSGGTAALGCLV KDY**L**PEPVTVSWNSGALTSGVHTFPAVLQ SSGLYSLSSVVTVPSSSLGTQTYICNVNH KPSNTKVD**R**KVEPK |
| 70 | SAD9612_P02_A06 | P151L; N201S | ASTKGPSVFPLAPSSKSTSGGTAALGCLV KDYF**L**EPVTVSWNSGALTSGVHTFPAVLQ SSGLYSLSSVVTVPSSSLGTQTYIC**S**VNH KPSNTKVDKKVEPK |
| 71 | SAD9612_P02_F06 | P153S | ASTKGPSVFPLAPSSKSTSGGTAALGCLV KDYFPE**S**VTVSWNSGALTSGVHTFPAVLQ SSGLYSLSSVVTVPSSSLGTQTYICNVNH KPSNTKVDKKVEPK |
| 72 | SAD9612_P02_E04 | F170L | ASTKGPSVFPLAPSSKSTSGGTAALGCLV KDYFPEPVTVSWNSGALTSGVHT**L**PAVLQ SSGLYSLSSVVTVPSSSLGTQTYICNVNH KPSNTKVDKKVEPK |
| 73 | SAD9612_P02_B05 | S176P | ASTKGPSVFPLAPSSKSTSGGTAALGCLV KDYFPEPVTVSWNSGALTSGVHTFPAVLQ **P**SGLYSLSSVVTVPSSSLGTQTYICNVNH KPSNTKVDKKVEPK |

TABLE 4

| CH1 domain sequences that preferentially bind Cλ | | | |
|---|---|---|---|
| SEQ ID NO: | Clone | Amino Acid Substitutions | Sequence |
| 74 | SAD9611_P02_F12 | S124V; F126V; A141D; T197S; N208I | ASTKGP**V**V**V**PLAPSSKSTSGGTA**D**LGCLVKDYFPEP VTVSWNSGALTSGVHTFPAVLQSSGLYSLSSVVTVP SSSLGTQ**S**YICNVNHKPS**I**TKVDKKVEPK |
| 75 | SAD9611_P02_D12 | P127G; A141T | ASTKGPSVF**G**LAPSSKSTSGGTA**T**LGCLVKDYFPEP VTVSWNSGALTSGVHTFPAVLQSSGLYSLSSVVTVP SSSLGTQTYICNVNHKPSNTKVDKKVEPK |
| 76 | SAD9611_P02_D11 | P130H; A141R | ASTKGPSVFPLA**H**SSKSTSGGTA**R**LGCLVKDYFPEP VTVSWNSGALTSGVHTFPAVLQSSGLYSLSSVVTVP SSSLGTQTYICNVNHKPSNTKVDKKVEPK |

TABLE 4-continued

CH1 domain sequences that preferentially bind Cλ

| SEQ ID NO: | Clone | Amino Acid Substitutions | Sequence |
|---|---|---|---|
| 77 | SAD9611_P02_C12 | S131Q; A141E | ASTKGPSVFPLAP**Q**SKSTSGGTA**E**LGCLVKDYFPEP VTVSWNSGALTSGVHTFPAVLQSSGLYSLSSVVTVP SSSLGTQTYICNVNHKPSNTKVDKKVEPK |
| 78 | SAD9611_P02_H12 | S131T; A141R | ASTKGPSVFPLAP**T**SKSTSGGTA**R**LGCLVKDYFPEP VTVSWNSGALTSGVHTFPAVLQSSGLYSLSSVVTVP SSSLGTQTYICNVNHKPSNTKVDKKVEPK |
| 79 | SAD9611_P02_C10 | S131N; A141T; H168F; F170N | ASTKGPSVFPLAP**N**SKSTSGGTA**T**LGCLVKDYFPEP VTVSWNSGALTSGV**F**T**N**PAVLQSSGLYSLSSVVTVP SSSLGTQTYICNVNHKPSNTKVDKKVEPK |
| 80 | SAD9611_P02_A11 | K133D; A141E | ASTKGPSVFPLAPSS**D**STSGGTA**E**LGCLVKDYFPEP VTVSWNSGALTSGVHTFPAVLQSSGLYSLSSVVTVP SSSLGTQTYICNVNHKPSNTKVDKKVEPK |
| 81 | SAD9611_P02_A10 | K133T; A141T; K218P | ASTKGPSVFPLAPSS**T**STSGGTA**T**LGCLVKDYFPEP VTVSWNSGALTSGVHTFPAVLQSSGLYSLSSVVTVP SSSLGTQTYICNVNHKPSNTKVDKKVEP**P** |
| 82 | SAD9611_P02_B11 | S134A; A141K | ASTKGPSVFPLAPSSK**A**TSGGTA**K**LGCLVKDYFPEP VTVSWNSGALTSGVHTFPAVLQSSGLYSLSSVVTVP SSSLGTQTYICNVNHKPSNTKVDKKVEPK |
| 83 | SAD9611_P02_G12 | S134H; A141R | ASTKGPSVFPLAPSSK**H**TSGGTA**R**LGCLVKDYFPEP VTVSWNSGALTSGVHTFPAVLQSSGLYSLSSVVTVP SSSLGTQTYICNVNHKPSNTKVDKKVEPK |
| 84 | SAD9611_P02_F11 | S134I; A141R | ASTKGPSVFPLAPSSK**I**TSGGTA**R**LGCLVKDYFPEP VTVSWNSGALTSGVHTFPAVLQSSGLYSLSSVVTVP SSSLGTQTYICNVNHKPSNTKVDKKVEPK |
| 85 | SAD9611_P02_E10 | S134P; A141R | ASTKGPSVFPLAPSSK**P**TSGGTA**R**LGCLVKDYFPEP VTVSWNSGALTSGVHTFPAVLQSSGLYSLSSVVTVP SSSLGTQTYICNVNHKPSNTKVDKKVEPK |
| 86 | SAD9611_P02_A12 | S134V; A141T | ASTKGPSVFPLAPSSK**V**TSGGTA**T**LGCLVKDYFPEP VTVSWNSGALTSGVHTFPAVLQSSGLYSLSSVVTVP SSSLGTQTYICNVNHKPSNTKVDKKVEPK |
| 87 | SAD9611_P02_B10 | S134V; A141T | ASTKGPSVFPLAPSSK**V**TSGGTA**T**LGCLVKDYFPEP VTVSWNSGALTSGVHTFPAVLQSSGLYSLSSVVTVP SSSLGTQTYICNVNHKPSNTKVDKKVEPK |
| 88 | SAD9611_P02_C11 | A141E | ASTKGPSVFPLAPSSKSTSGGTA**E**LGCLVKDYFPEP VTVSWNSGALTSGVHTFPAVLQSSGLYSLSSVVTVP SSSLGTQTYICNVNHKPSNTKVDKKVEPK |
| 89 | SAD9611_P02_H10 | A141R; V185M | ASTKGPSVFPLAPSSKSTSGGTA**R**LGCLVKDYFPEP VTVSWNSGALTSGVHTFPAVLQSSGLYSLSS**M**VTVP SSSLGTQTYICNVNHKPSNTKVDKKVEPK |
| 90 | SAD9611_P02_B12 | A141T; T187R | ASTKGPSVFPLAPSSKSTSGGTA**T**LGCLVKDYFPEP VTVSWNSGALTSGVHTFPAVLQSSGLYSLSSVV**R**VP SSSLGTQTYICNVNHKPSNTKVDKKVEPK |
| 91 | SAD9611_P02_G10 | A141R; V185L; T187D | ASTKGPSVFPLAPSSKSTSGGTA**R**LGCLVKDYFPEP VTVSWNSGALTSGVHTFPAVLQSSGLYSLSS**L**V**D**VP SSSLGTQTYICNVNHKPSNTKVDKKVEPK |
| 92 | SAD9611 P02_E11 | A141T; V185S; T187E | ASTKGPSVFPLAPSSKSTSGGTA**T**LGCLVKDYFPEP VTVSWNSGALTSGVHTFPAVLQSSGLYSLSS**S**V**E**VP SSSLGTQTYICNVNHKPSNTKVDKKVEPK |
| 93 | SAD9611_P02_D10 | A141V; V185S; T187Y | ASTKGPSVFPLAPSSKSTSGGTA**V**LGCLVKDYFPEP VTVSWNSGALTSGVHTFPAVLQSSGLYSLSS**S**V**Y**VP SSSLGTQTYICNVNHKPSNTKVDKKVEPK |
| 94 | SAD9613_P01_F07 | S119R; A141K | A**R**TKGPSVFPLAPSSKSTSGGTA**K**LGCLVKDYFPEP VTVSWNSGALTSGVHTFPAVLQSSGLYSLSSVVTVP SSSLGTQTYICNVNHKPSNTKVDKKVEPK |

TABLE 4-continued

CH1 domain sequences that preferentially bind Cλ

| SEQ ID NO: | Clone | Amino Acid Substitutions | Sequence |
|---|---|---|---|
| 95 | SAD9613_P01_B07 | P130S; A141T; V185T; T187S | ASTKGPSVFPLA**S**SSKSTSGGTA**T**LGCLVKDYFPEP VTVSWNSGALTSGVHTFPAVLQSSGLYSLSS**T**V**S**VP SSSLGTQTYICNVNHKPSNTKVDKKVEPK |
| 96 | SAD9613_P01_A09 | S131N; A141D | ASTKGPSVFPLAP**N**SKSTSGGTA**D**LGCLVKDYFPEP VTVSWNSGALTSGVHTFPAVLQSSGLYSLSSVVTVP SSSLGTQTYICNVNHKPSNTKVDKKVEPK |
| 97 | SAD9613_P01_G08 | S131R; A141M | ASTKGPSVFPLAP**R**SKSTSGGTA**M**LGCLVKDYFPEP VTVSWNSGALTSGVHTFPAVLQSSGLYSLSSVVTVP SSSLGTQTYICNVNHKPSNTKVDKKVEPK |
| 98 | SAD9613_P01_G07 | S131T; A141E | ASTKGPSVFPLAP**T**SKSTSGGTA**E**LGCLVKDYFPEP VTVSWNSGALTSGVHTFPAVLQSSGLYSLSSVVTVP SSSLGTQTYICNVNHKPSNTKVDKKVEPK |
| 99 | SAD9613_P01_B09 | S131D; K133L; S134N | ASTKGPSVFPLAP**D**S**LN**TSGGTAALGCLVKDYFPEP VTVSWNSGALTSGVHTFPAVLQSSGLYSLSSVVTVP SSSLGTQTYICNVNHKPSNTKVDKKVEPK |
| 100 | SAD9613_P01_E07 | S131D; A141R; Q175D; S181V | ASTKGPSVFPLAP**D**SKSTSGGTA**R**LGCLVKDYFPEP VTVSWNSGALTSGVHTFPAVL**D**SSGLY**V**LSSVVTVP SSSLGTQTYICNVNHKPSNTKVDKKVEPK |
| 101 | SAD9613_P01_A08 | K133E; A141R | ASTKGPSVFPLAPSS**E**STSGGTA**R**LGCLVKDYFPEP VTVSWNSGALTSGVHTFPAVLQSSGLYSLSSVVTVP SSSLGTQTYICNVNHKPSNTKVDKKVEPK |
| 102 | SAD9613_P01_H09 | K133P; T139A; A141K | ASTKGPSVFPLAPSS**P**STSGG**A**A**K**LGCLVKDYFPEP VTVSWNSGALTSGVHTFPAVLQSSGLYSLSSVVTVP SSSLGTQTYICNVNHKPSNTKVDKKVEPK |
| 103 | SAD9613_P01_D07 | S134L; A141E | ASTKGPSVFPLAPSSK**L**TSGGTA**E**LGCLVKDYFPEP VTVSWNSGALTSGVHTFPAVLQSSGLYSLSSVVTVP SSSLGTQTYICNVNHKPSNTKVDKKVEPK |
| 104 | SAD9613_P01_A07 | S134N; A141T | ASTKGPSVFPLAPSSK**N**TSGGTA**T**LGCLVKDYFPEP VTVSWNSGALTSGVHTFPAVLQSSGLYSLSSVVTVP SSSLGTQTYICNVNHKPSNTKVDKKVEPK |
| 105 | SAD9613_P01_H08 | S134P; A141K | ASTKGPSVFPLAPSSK**P**TSGGTA**K**LGCLVKDYFPEP VTVSWNSGALTSGVHTFPAVLQSSGLYSLSSVVTVP SSSLGTQTYICNVNHKPSNTKVDKKVEPK |
| 106 | SAD9613_P01_F08 | S134V; A141E | ASTKGPSVFPLAPSSK**V**TSGGTA**E**LGCLVKDYFPEP VTVSWNSGALTSGVHTFPAVLQSSGLYSLSSVVTVP SSSLGTQTYICNVNHKPSNTKVDKKVEPK |
| 107 | SAD9613_P01_D08 | A141K | ASTKGPSVFPLAPSSKSTSGGTA**K**LGCLVKDYFPEP VTVSWNSGALTSGVHTFPAVLQSSGLYSLSSVVTVP SSSLGTQTYICNVNHKPSNTKVDKKVEPK |
| 108 | SAD9613_P01_E09 | A141K; V185T; T187E | ASTKGPSVFPLAPSSKSTSGGTA**K**LGCLVKDYFPEP VTVSWNSGALTSGVHTFPAVLQSSGLYSLSS**T**V**E**VP SSSLGTQTYICNVNHKPSNTKVDKKVEPK |
| 109 | SAD9613_P01_C09 | H168V; F170T; P171N | ASTKGPSVFPLAPSSKSTSGGTAALGCLVKDYFPEP VTVSWNSGALTSGV**V**T**TN**AVLQSSGLYSLSSVVTVP SSSLGTQTYICNVNHKPSNTKVDKKVEPK |
| 110 | SAD9613_P01_H07 | S183L | ASTKGPSVFPLAPSSKSTSGGTAALGCLVKDYFPEP VTVSWNSGALTSGVHTFPAVLQSSGLYSL**L**SVVTVP SSSLGTQTYICNVNHKPSNTKVDKKVEPK |
| 111 | SAD9610_P02_F04 | A140V | ASTKGPSVFPLAPSSKSTSGGT**V**ALGCLVKDYFPEP VTVSWNSGALTSGVHTFPAVLQSSGLYSLSSVVTVP SSSLGTQTYICNVNHKPSNTKVDKKVEPK |
| 112 | SAD9610_P02_B04 | A141T | ASTKGPSVFPLAPSSKSTSGGTA**T**LGCLVKDYFPEP VTVSWNSGALTSGVHTFPAVLQSSGLYSLSSVVTVP SSSLGTQTYICNVNHKPSNTKVDKKVEPK |

TABLE 4-continued

CH1 domain sequences that preferentially bind Cλ

| SEQ ID NO: | Clone | Amino Acid Substitutions | Sequence |
|---|---|---|---|
| 113 | SAD9610 P02_G06 | A141T; N203D | ASTKGPSVFPLAPSSKSTSGGTA**T**LGCLVKDYFPEP<br>VTVSWNSGALTSGVHTFPAVLQSSGLYSLSSVVTVP<br>SSSLGTQTYICNV**D**HKPSNTKVDKKVEPK |
| 114 | SAD9610_P02_G04 | A141T; V211A | ASTKGPSVFPLAPSSKSTSGGTA**T**LGCLVKDYFPEP<br>VTVSWNSGALTSGVHTFPAVLQSSGLYSLSSVVTVP<br>SSSLGTQTYICNVNHKPSNTK**A**DKKVEPK |
| 115 | SAD9610_P02_C06 | A141T; E216G | ASTKGPSVFPLAPSSKSTSGGTA**T**LGCLVKDYFPEP<br>VTVSWNSGALTSGVHTFPAVLQSSGLYSLSSVVTVP<br>SSSLGTQTYICNVNHKPSNTKVDKKV**G**PK |
| 116 | SAD9610 P02_G05 | A141T; L163M | ASTKGPSVFPLAPSSKSTSGGTA**T**LGCLVKDYFPEP<br>VTVSWNSGA**M**TSGVHTFPAVLQSSGLYSLSSVVTVP<br>SSSLGTQTYICNVNHKPSNTKVDKKVEPK |
| 117 | SAD9610_P02_C04 | A141V; D212N | ASTKGPSVFPLAPSSKSTSGGTA**V**LGCLVKDYFPEP<br>VTVSWNSGALTSGVHTFPAVLQSSGLYSLSSVVTVP<br>SSSLGTQTYICNVNHKPSNTKV**N**KKVEPK |
| 118 | SAD9610_P02_E05 | S181T | ASTKGPSVFPLAPSSKSTSGGTAALGCLVKDYFPEP<br>VTVSWNSGALTSGVHTFPAVLQSSGLY**T**LSSVVTVP<br>SSSLGTQTYICNVNHKPSNTKVDKKVEPK |
| 119 | SAD9612 P01_A01 | A140P; A141T | ASTKGPSVFPLAPSSKSTSGGT**PT**LGCLVKDYFPEP<br>VTVSWNSGALTSGVHTFPAVLQSSGLYSLSSVVTVP<br>SSSLGTQTYICNVNHKPSNTKVDKKVEPK |
| 120 | SAD9612_P01_G01 | A140V; E216G | ASTKGPSVFPLAPSSKSTSGGT**V**ALGCLVKDYFPEP<br>VTVSWNSGALTSGVHTFPAVLQSSGLYSLSSVVTVP<br>SSSLGTQTYICNVNHKPSNTKVDKKV**G**PK |
| 121 | SAD9612_P01_H02 | A141T; K213E | ASTKGPSVFPLAPSSKSTSGGTA**T**LGCLVKDYFPEP<br>VTVSWNSGALTSGVHTFPAVLQSSGLYSLSSVVTVP<br>SSSLGTQTYICNVNHKPSNTKVD**E**KVEPK |
| 122 | SAD9612_P01_D03 | A141T; K214R | ASTKGPSVFPLAPSSKSTSGGTA**T**LGCLVKDYFPEP<br>VTVSWNSGALTSGVHTFPAVLQSSGLYSLSSVVTVP<br>SSSLGTQTYICNVNHKPSNTKVDK**R**VEPK |
| 123 | SAD9612_P01_E01 | A141T; E152G | ASTKGPSVFPLAPSSKSTSGGTA**T**LGCLVKDYFP**G**P<br>VTVSWNSGALTSGVHTFPAVLQSSGLYSLSSVVTVP<br>SSSLGTQTYICNVNHKPSNTKVDKKVEPK |
| 124 | SAD9612_P01_H03 | A141V; E152G | ASTKGPSVFPLAPSSKSTSGGTA**V**LGCLVKDYFP**G**P<br>VTVSWNSGALTSGVHTFPAVLQSSGLYSLSSVVTVP<br>SSSLGTQTYICNVNHKPSNTKVDKKVEPK |
| 125 | SAD9612__P01_F02 | E152G | ASTKGPSVFPLAPSSKSTSGGTAALGCLVKDYFP**G**P<br>VTVSWNSGALTSGVHTFPAVLQSSGLYSLSSVVTVP<br>SSSLGTQTYICNVNHKPSNTKVDKKVEPK |
| 126 | SAD9612 P01_A02 | S183V; V185T | ASTKGPSVFPLAPSSKSTSGGTAALGCLVKDYFPEP<br>VTVSWNSGALTSGVHTFPAVLQSSGLYSL**V**S**T**VTVP<br>SSSLGTQTYICNVNHKPSNTKVDKKVEPK |
| 127 | SAD9612_P01_C01 | K210T | ASTKGPSVFPLAPSSKSTSGGTAALGCLVKDYFPEP<br>VTVSWNSGALTSGVHTFPAVLQSSGLYSLSSVVTVP<br>SSSLGTQTYICNVNHKPSNT**T**VDKKVEPK |
| 128 | SAD10791_P01_F07 | A140Y; A141D | ASTKGPSVFPLAPSSKSTSGGT**YD**LGCLVKDYFPEP<br>VTVSWNSGALTSGVHTFPAVLQSSGLYSLSSVVTVP<br>SSSLGTQTYICNVNHKPSNTKVDKKVEPK |
| 129 | SAD10791_P01_C07 | A140K; A141D | ASTKGPSVFPLAPSSKSTSGGT**KD**LGCLVKDYFPEP<br>VTVSWNSGALTSDVHTFPAVLQSSGLYSLSSVVTVP<br>SSSLGTQTYICNVNHKPSNTKVDKKVEPK |
| 130 | SAD10791_P01_A07 | A140S; A141D | ASTKGPSVFPLAPSSKSTSGGT**SD**LGCLVKDYFPEP<br>VTVSWNSGALTSGVHTFSAVLQSSGLYSLSSVVTVP<br>SSSLGTQTYICNVNHKPSNTKVDKKVEPK |

TABLE 4-continued

CH1 domain sequences that preferentially bind Cλ

| SEQ ID NO: | Clone | Amino Acid Substitutions | Sequence |
|---|---|---|---|
| 131 | SAD10791 P02_G08 | A140W; A141D | ASTKGPSVFPLAPSSKSTSGGT**WD**LGCLVKDYFPEPVTVSWNSGALTSGVHTFPAVLQSSGLYSLSSVVTVPSSSLGTQTYICNVNHKPSNTKVDKKVEPK |
| 132 | SAD10791_P02_D08 | A140R; A141D; K218N; S219Δ | ASTKGPSVFPLAPSSKTSGGT**RD**LGCLVKDYFPEPVTVSWNSGALTSGVHTFPAVLQSSGLYSLSSVVTVPSSSLGTQTYICNVNHKPSNTKVDKKVEPN |
| 133 | SAD10791_P02_F07 | A140L; A141D | ASTKGPSVFPLAPSSKSTSGGT**LD**LGCLVKDYFPEPVTVSWNSGALTSGVHTFPAVLQSSGLYSLSSVVTVPSSSLGTQTYICNVNHKPSNTKVDKKVEPK |
| 134 | | A140I; A141D | ASTKGPSVFPLAPSSKSTSGGT**ID**LGCLVKDYFPEPVTVSWNSGALTSGVHTFPAVLQSSGLYSLSSVVTVPSSSLGTQTYICNVNHKPSNTKVDKKVEPK |
| 135 | | A140V; A141D | ASTKGPSVFPLAPSSKSTSGGT**VD**LGCLVKDYFPEPVTVSWNSGALTSGVHTFPAVLQSSGLYSLSSVVTVPSSSLGTQTYICNVNHKPSNTKVDKKVEPK |

Δrepresents amino acid deletion.

It was unexpectedly found that some CH1 amino acid substitutions located at the VH:CH1 interface, rather than the CH1:Light chain interface, gave rise to a kappa binding preference in the 3-chain system. In particular, the mutation sets K147V+P151A and P151L+N201S (SEQ ID NOS: 36 and 70, Table 3) returned kappa FOP values of 18.1 and 10.4 respectively. While position CH1:147 is at the CH1:LC interface, CH1:201 is not (it is completely solvent-exposed and not part of any interdomain interface); thus, the appearance of P151 substitutions in both these high FOP clones suggests a potential role for this position in determining kappa over lambda preference. Without wishing to be bound by theory, such distal mutations are thought to impact HC:LC pairing for the reasons discussed below and so it may be possible to exploit mutations at the VH:CH1 interface for preferential kappa over lambda pairing.

First, P151 is part of the so-called "ball-and-socket joint" between the VH and the CH1 domains (Lesk A. M. et al., *Nature.* 1988 Sep. 8; 335(6186):188-90; Landolfi N. F. et al., *J Immunol.* 2001 Feb. 1; 166(3):1748-54). This joint has been hypothesized to modulate intradomain flexibility via its impact on the "elbow-angle" (Stanfield R. L. et al., *J Mol Biol.* 2006 Apr. 14; 357(5):1566-74) between the antibody variable and constant domains. Substitutions in the ball-and-socket joint can have a functional consequence, as in the case of an anti-IFN-gamma monoclonal antibody with reduced neutralization activity due to a single amino acid substitution in this region (Landolfi N. F. et al., *J Immunol.* 2001 Feb. 1; 166(3):1748-54). This effect has been attributed to altered flexibility and an allosteric mechanism, rather than by direct changes at the antigen binding interface. Second, it is also known that Fabs with lambda constant domains have a greater range of elbow angles, relative to Fabs with kappa domains (Stanfield R. L. et al., *J Mol Biol.* 2006 Apr. 14; 357(5):1566-74. doi: 10.1016/j.jmb.2006.01.023. Epub 2006 Jan. 25.). This hyperflexibility has been attributed to a single residue insertion in the so-called switch region between the VL and CL domains. Third, further analysis of Fab crystal structures (Adimab unpublished data) reveals differences, between kappa and lambda Fabs, of the atomic packing in the region of the ball-and-socket joint. Thus, modulation of Fab flexibility by the ball-and-socket joint, together with inherent difference between Fabs with kappa and lambda light chains suggest a novel mechanism for deriving differential kappa vs lambda preference via mutations at the VH:CH1 interface.

Figure 4:
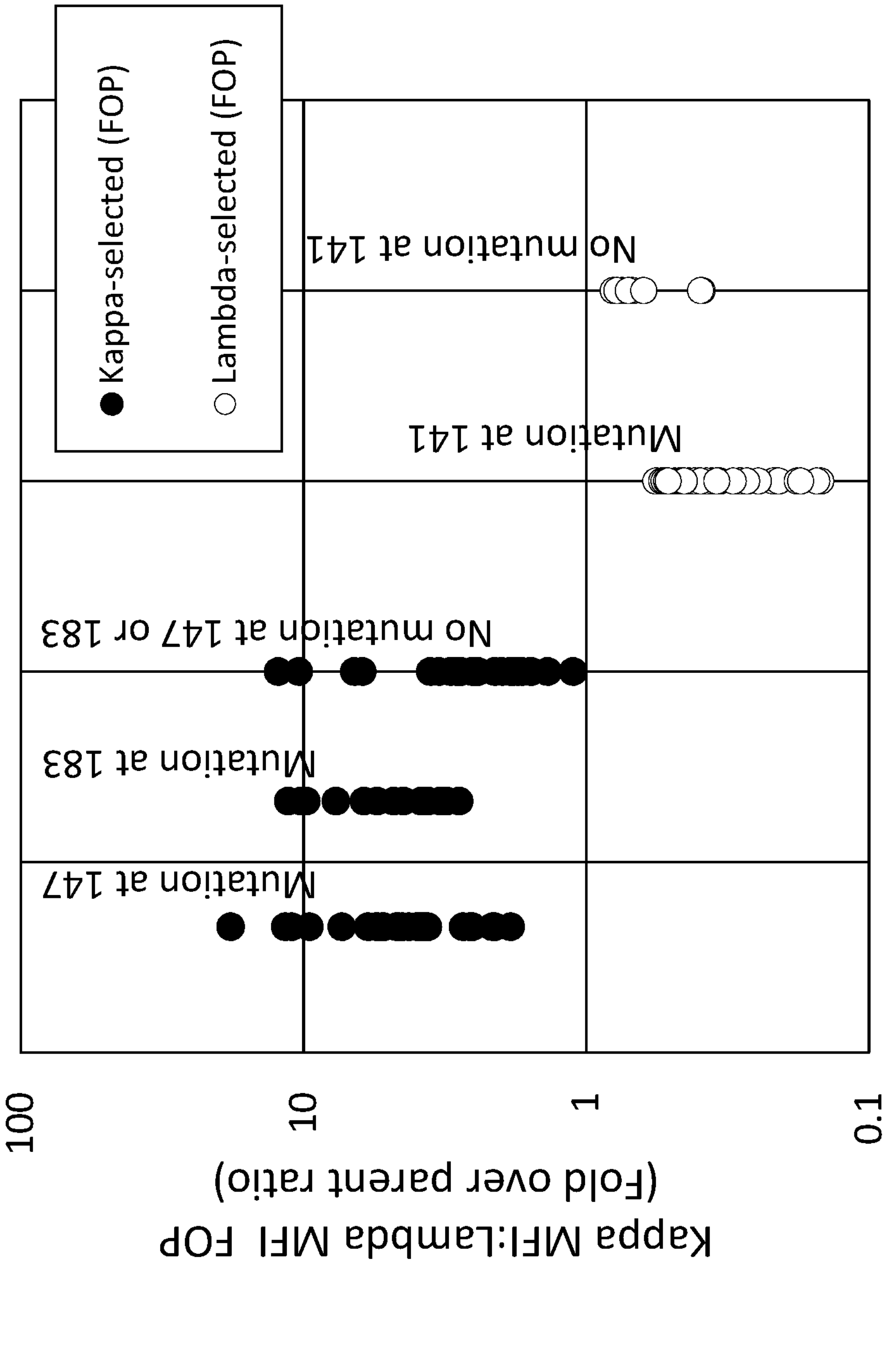
FIG. 4 shows individual unique clones expressing a CH1 domain variant with an amino acid substitution at position 141, 147, or 183 (EU numbering). Clones were scored for the ratio of anti-kappa MFI to anti-lambda MFI and compared to parent to determine FOP. CH1 positions 147 and 183 were identified as two positions providing kappa CL domain preference. CH1 position 141 was identified as a position providing lambda CL domain preference.

Example 4: Identification and Characterization of CH1 Domain Variants with Kappa-Preferential or Lambda Preferential Light Chain Pairing Clones derived from selections for increased Cκ and Cλ preference were selected for further characterization based on the MFI ratio between kappa and lambda (see FIG. 4). A pool of DNA singly mutated at each position of interest (141, 147, or 183) to each of the 20 amino acids (NNK) was isolated and amplified. Using the appropriate light chain base strain, these single position targeting libraries were constructed in a manner as previously described. Four libraries were constructed with variation present at position 141, 147, 183, or 147+183 respectively of the CH1 domain. Selection for kappa- or lambda-preference was conducted as described above. Outputs were sequenced as previously described, and FACS-based quantification of kappa or lambda preference versus the appropriate parent was performed to determine the amino acid substitutions that provided light-chain kappa- or lambda-preferential pairing.

Several CH1 domain variants with amino acid residue substitutions at each of positions 141, 147, and 183 were identified as having pairing preference to either a kappa CL domain (or a light chain containing a kappa CL domain) or a lambda CL domain (or a light chain containing a lambda CL domain). A substitution at CH1 domain position 141 with D, R, or Q (as compared to wild-type A) increases preferential pairing with a lambda CL domain (or a light chain containing a lambda CL domain) (i.e., decreased kappa:lambda MFI ratio) (see FIG. 5). A substitution at CH1 domain position 147 with F, I, T, Y, L, R, N, E, H, M, or Q (as compared to wild-type K) increases preferential pairing with a kappa CL domain (or a light chain comprising a kappa CL domain) (i.e., increased kappa:lambda MFI ratio) (see FIG. 5). A substitution at CH1 domain position 183 to R, K, Y, W, E, F, or Q (as compared to wild-type S) increases preferential pairing with a kappa CL domain (or a light chain containing a kappa CL domain) (i.e., increased kappa: lambda MFI ratio) (see FIG. 5). Table 5 shows the number of observed CH1 domain variants having specific amino acid substitutions that drive pairing preference.

TABLE 5

| Observed amino acid substitutions in CH1 domain variants with light chain preference | | |
|---|---|---|
| Amino Acid Substitution | Observed Count | Light Chain Preference |
| A141D | 35 | Lambda |
| A141R | 7 | Lambda |
| A141Q | 5 | Lambda |
| K147F | 24 | Kappa |
| K147I | 5 | Kappa |
| K147T | 3 | Kappa |
| K147Y | 3 | Kappa |
| K147L | 2 | Kappa |
| K147R | 2 | Kappa |
| K147N | 2 | Kappa |
| K147E | 1 | Kappa |
| K147H | 1 | Kappa |
| K147M | 1 | Kappa |
| K147Q | 1 | Kappa |
| S183R | 19 | Kappa |
| S183K | 11 | Kappa |
| S183Y | 5 | Kappa |
| S183W | 3 | Kappa |
| S183E | 2 | Kappa |
| S183F | 1 | Kappa |
| S183Q | 1 | Kappa |

Next, the impact of the identified CH1 domain variants on control standard bispecific antibody (2 heavy chain×2 light chain) in an IgG-like format (2 Fab regions attached N-terminally to a dimeric Fc molecule) was assessed. VH-CH1 sequences derived from two approved clinical therapeutic antibodies, ustekinumab and panitumumab, were used. 'Knob' (S354C; T366W) and 'hole' (Y349C; T366S; L368A; Y407V) mutations were introduced to promote desired heterodimeric pairing of the heavy chains. DNA plasmids were confirmed via Sanger sequencing prior to transfection into HEK293 cells via standard protocols.

Transfected HEK cells were cultured in CD optiCHO media (Invitrogen), and on day 6 post transfection the supernatants were collected and subjected to Protein A-based affinity purification. Purified IgGs were treated with GingisKHAN® (Genovis AB) to enzymatically cleave the Fab region from the Fc portion.

Figure 7:
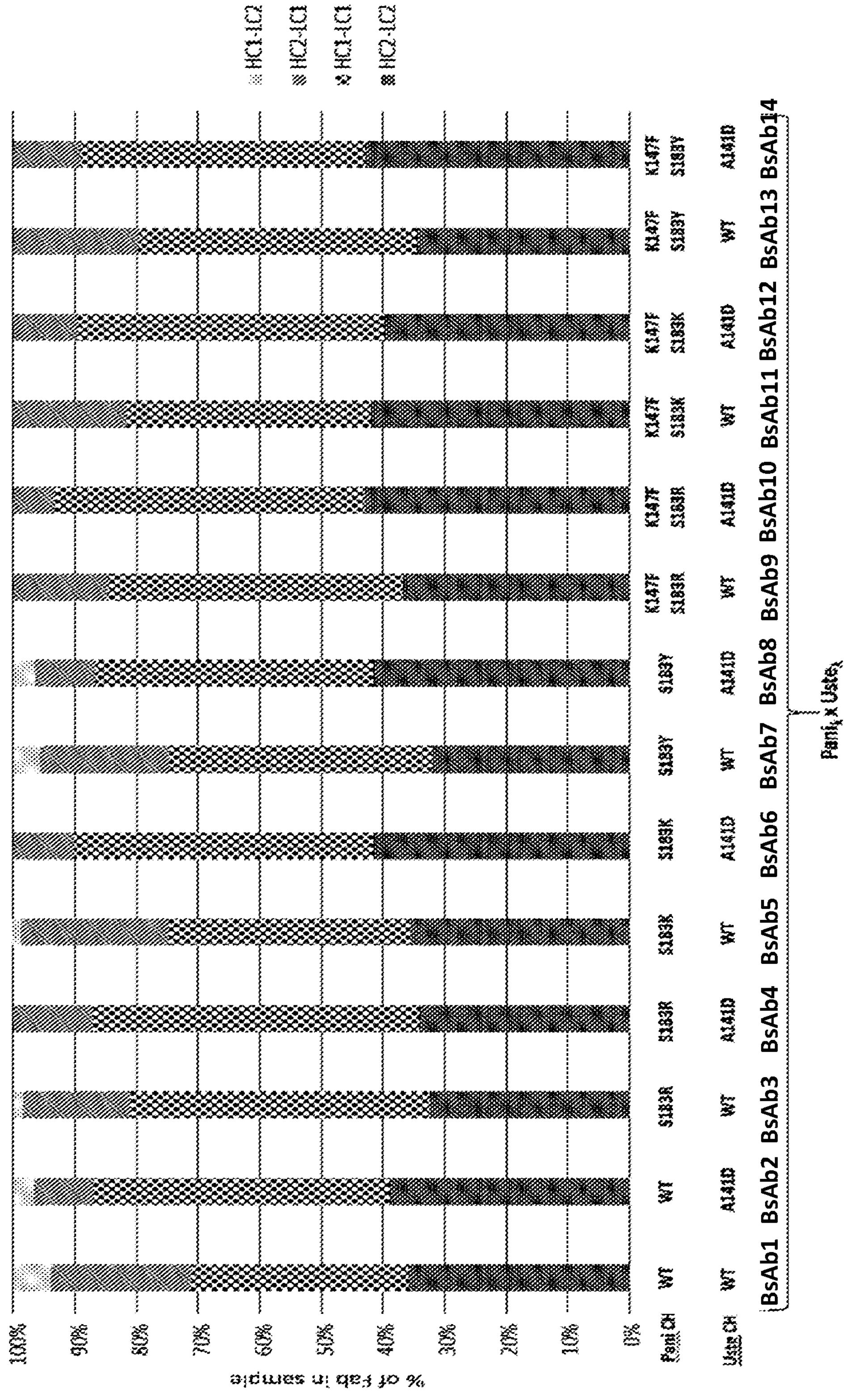
FIG. 7 shows an increase in correct heavy chain-light chain pairing (HC1-LC1 or HC2-LC2), and a concurrent decrease in heavy chain-light chain mispairing (HC1-LC2 and HC2-LC1), in bispecific antibodies containing a CH1 domain variant (BsAb2-BsAb14) as compared to a bispecific antibody containing a wild-type CH1 domain (BsAb1).

LCMS was performed for purified Fabs to confirm the sequence of each IgG component (2 heavy chain×2 light chain) and to determine the relative percentage of each component (see FIG. 7). Briefly, purified IgGs were digested with GingisKHAN to enzymatically cleave the Fab region from the Fc portion. Fab samples were injected onto an Agilent 1100 series HPLC with an Applied Biosystems POROS® R2 10 μm column (2.1×30 mm, 0.1 mL) maintained at 65° C. After injection, samples were eluted from the column using a 0.21 minute gradient of 2-95% acetonitrile at a flow rate of 2 mL/min (mobile phase A: 0.1% formic acid in $H_2O$; mobile phase B: 0.1% formic acid in acetonitrile). Using a divert valve, 150 μL/min of the total flow was loaded into a Bruker maXis 4G mass spectrometer. The mass spectrometer was run in positive ion mode with m/z range of 700 to 2500. The remaining source parameters were set as follows: the capillary was set at 5500 V, the nebulizer at 4.0 Bar, dry gas at 4.0 L/min, and dry temp at 200° C. Acquired MS spectra was analyzed using Bruker Compass Data Analysis Version 4.1. Detection of intact Fab species was confirmed based on mass measurement as compared to the theoretical sequence. Relative quantitation for each species was calculated based on the intensities of each species' peaks compared with the sum of all of the peak intensities.

When both heavy chains are wild-type, incorrect pairing occurs about 30% of the time; however, when the heavy chains comprise a CH1 variant domain as described herein, there is a significant improvement in correct pairing of the heavy chains and light chains (see FIG. 7 and Table 6). Pani light chain is wild-type. Uste light chain is a lambda fusion. HC1 is pani; LC1 is pani kappa; HC2 is uste; LC2 is uste lambda For example, when a first heavy chain (HC1) contains K147F and S183R/K/Y and a second heavy chain contains A141D (BsAbs 10, 12, and 14, respectively), mispairing is alleviated by at least half, i.e., occurring only 6.8, 10.5, or 110% of the time. Indeed, a single substitution at position 141 (141D) results in a 50% reduction of mispairing, i.e., 6.1% vs. 3.1% HC1-LC2 and 22.8% vs. 9.9% HC2-LC1 (BsAb2). Based thereon, applicant provides exemplary CH1 domain sequences that have kappa or lambda light chain/CL domain preference in Table 7.

TABLE 6

| Percent heavy chain-light chain product formation | | | | | | | |
|---|---|---|---|---|---|---|---|
| | HC1 | | HC2 | HC1-LC1 | HC1-LC2 | HC2-LC1 | HC2-LC2 |
| BsAb1 | Pani wt | X | Uste wt | 35.3% | 6.1% | 22.8% | 35.8% |
| BsAb2 | Pani wt | X | Uste A141D | 47.9% | 3.1% | 9.9% | 39.0% |
| BsAb3 | Pani S183R | X | Uste wt | 48.5% | 1.5% | 17.5% | 32.5% |
| BsAb4 | Pani S183R | X | Uste A141D | 53.0% | 0.0% | 12.9% | 34.0% |
| BsAb5 | Pani S183K | X | Uste wt | 39.1% | 1.5% | 23.9% | 35.6% |
| BsAb6 | Pani S183K | X | Uste A141D | 48.5% | 0.0% | 9.9% | 41.6% |
| BsAb7 | Pani S183Y | X | Uste wt | 42.5% | 4.5% | 21.0% | 32.0% |
| BsAb8 | Pani S183Y | X | Uste A141D | 45.1% | 3.5% | 9.9% | 41.5% |
| BsAb9 | Pani K147F S183R | X | Uste wt | 47.7% | 0.0% | 15.4% | 36.9% |
| BsAb10 | Pani K147F S183R | X | Uste A141D | 50.1% | 0.0% | 6.8% | 43.1% |
| BsAb11 | Pani K147F S183K | X | Uste wt | 39.7% | 0.0% | 18.4% | 41.9% |
| BsAb12 | Pani K147F S183K | X | Uste A141D | 49.7% | 0.0% | 10.5% | 39.8% |

TABLE 6-continued

| Percent heavy chain-light chain product formation | | | | | | | |
|---|---|---|---|---|---|---|---|
| | HC1 | | HC2 | HC1-LC1 | HC1-LC2 | HC2-LC1 | HC2-LC2 |
| BsAb13 | Pani K147F S183Y | X | Uste wt | 45.0% | 0.0% | 20.4% | 34.6% |
| BsAb14 | Pani K147F S183Y | X | Uste A141D | 46.2% | 0.0% | 11.0% | 42.8% |

TABLE 7

CH1 domains with kappa or lambda chain preference

| SEQ ID NO: | Amino acid substitutions | Sequence | CL domain preference |
|---|---|---|---|
| 60 | S183R | ASTKGPSVFPLAPSSKSTSGGTAALGCLVKDYFPEPV TVSWNSGALTSGVHTFPAVLQSSGLYSL**R**SVVTVPSS SLGTQTYICNVNHKPSNTKVDKKVEPK | kappa |
| 41 | S183K | ASTKGPSVFPLAPSSKSTSGGTAALGCLVKDYFPEPV TVSWNSGALTSGVHTFPAVLQSSGLYSL**K**SVVTVPSS SLGTQTYICNVNHKPSNTKVDKKVEPK | kappa |
| 136 | S183Y | ASTKGPSVFPLAPSSKSTSGGTAALGCLVKDYFPEPV TVSWNSGALTSGVHTFPAVLQSSGLYSL**Y**SVVTVPSS SLGTQTYICNVNHKPSNTKVDKKVEPK | kappa |
| 137 | K147F; S183R | ASTKGPSVFPLAPSSKSTSGGTAALGCLV**F**DYFPEPV TVSWNSGALTSGVHTFPAVLQSSGLYSL**R**SVVTVPSS SLGTQTYICNVNHKPSNTKVDKKVEPK | kappa |
| 138 | K147F; S183K | ASTKGPSVFPLAPSSKSTSGGTAALGCLV**F**DYFPEPV TVSWNSGALTSGVHTFPAVLQSSGLYSL**K**SVVTVPSS SLGTQTYICNVNHKPSNTKVDKKVEPK | kappa |
| 139 | K147F S183Y | ASTKGPSVFPLAPSSKSTSGGTAALGCLV**F**DYFPEPV TVSWNSGALTSGVHTFPAVLQSSGLYSL**Y**SVVTVPSS SLGTQTYICNVNHKPSNTKVDKKVEPK | kappa |
| 140 | A141D | ASTKGPSVFPLAPSSKSTSGGTA**D**LGCLVKDYFPEPV TVSWNSGALTSGVHTFPAVLQSSGLYSLSSVVTVPSS SLGTQTYICNVNHKPSNTKVDKKVEPK | lambda |

Expression and quality of the purified antibodies was assessed by size exclusion chromatography (SEC). Briefly, an Agilent 1 100 HPLC was employed to monitor the column chromatography (TSKgel Super SW3000 column). The column was pre-conditioned with highly glycosylated and aggregated IgG in order to minimize potential for antibody-column interactions and equilibrated with wash buffer (200 mM Sodium Phosphate, 250 mM Sodium Chloride pH 6.8) prior to use. Approximately 2-5 μg of protein sample was injected onto column and flow rate adjusted to 0.400 mL/min. Protein migration was monitored at wavelength 280 nm. Total assay time was approximately 11 minutes. Data was analyzed using ChemStation software. The SEC profiles confirmed that the CH1 domain substitutions had no effect on variant profiles compared to wild-type (data not shown).

The binding affinities and kinetics for the purified bispecific antibodies' binding to human IL-12B (Uste) and human EGFR (Pani) were measured to confirm that the CH1 variant domain did not impact target binding (see FIG. 6A-6E). Using an Octet® QKe instrument (ForteBio) with 100 nM of antigen, bispecific IgG samples were captured on anti-hIgG Fc sensor tip and binding kinetics to IL12B or EGFR was measured (on rate: 180 s and off rate: 180 s). The BLI analysis was performed at 29° C. using 1× kinetics buffer (ForteBio) as assay buffer. Anti-human IgG Fc capture (AHC) biosensors (ForteBio) were first presoaked in assay buffer for over five minutes. Bispecific IgG samples (5 μg/mL) was captured on the sensor for 300 seconds. Sensors were then dipped in assay buffer for 120 seconds to establish a baseline before measuring binding to IL12B or EGFR protein (100 nM concentration). Dissociation of IL12B or EGFR was measured by moving the sensors into assay buffer for 180 seconds. Agitation at all steps was 1000 rpm. Kinetic parameters were generated with Octet® Data Analysis Software Version 8.2.0.7 using reference subtraction, dissociation based inter-step correction, 1-to-1 binding model, and global fit (Rmax unlinked by sensor). The association rate constant (ka), dissociation rate constant (kd) and equilibrium constant ($K_D$) values were individually assigned for each measurement.

Example 5: 141×181×218 Library Builds and Selections

Additional CH1 amino acid substitutions that provide preferential pairing with lambda CL domain were also identified. Based on previous selection data as well as structural analysis, a set of three CH1 positions (141, 181, and 218) were selected for additional variegation. The amino acid diversity at position 141 was generated via the degenerate codon RMW representing six naturally occurring amino acids (D, T, A, E, K, and N). The amino acid diversity at positions 181 and 218 was generated via the degenerate codon NNK representing all 20 naturally occurring amino acids. The library design included all possible combinations of amino acids at these three positions with diversity of 2,400. Using the light chain strain with lambda light chain under the GAL10 promoter (GAL1::ADI-26140 VL-Ck× GAL10::ADI-26140 VL-Cl), this library was constructed in a manner as previously described. Selection for lambda-preference was conducted via staining with anti-human kappa-FITC and anti-human lambda-PE antibodies, followed by multiple rounds of cell sorting, as previously described. Outputs (96 clones) were sequenced as previously described, and FACS-based quantification of lambda-preference versus the parent strain were quantified. Wild-type ("WT") and the previously identified lead clone, A141D, were included in the analysis. Based on these data, the amino acid combinations which provided for the greatest improvement in light-chain lambda preferential pairing over parent and A141D were identified.

Figure 8:
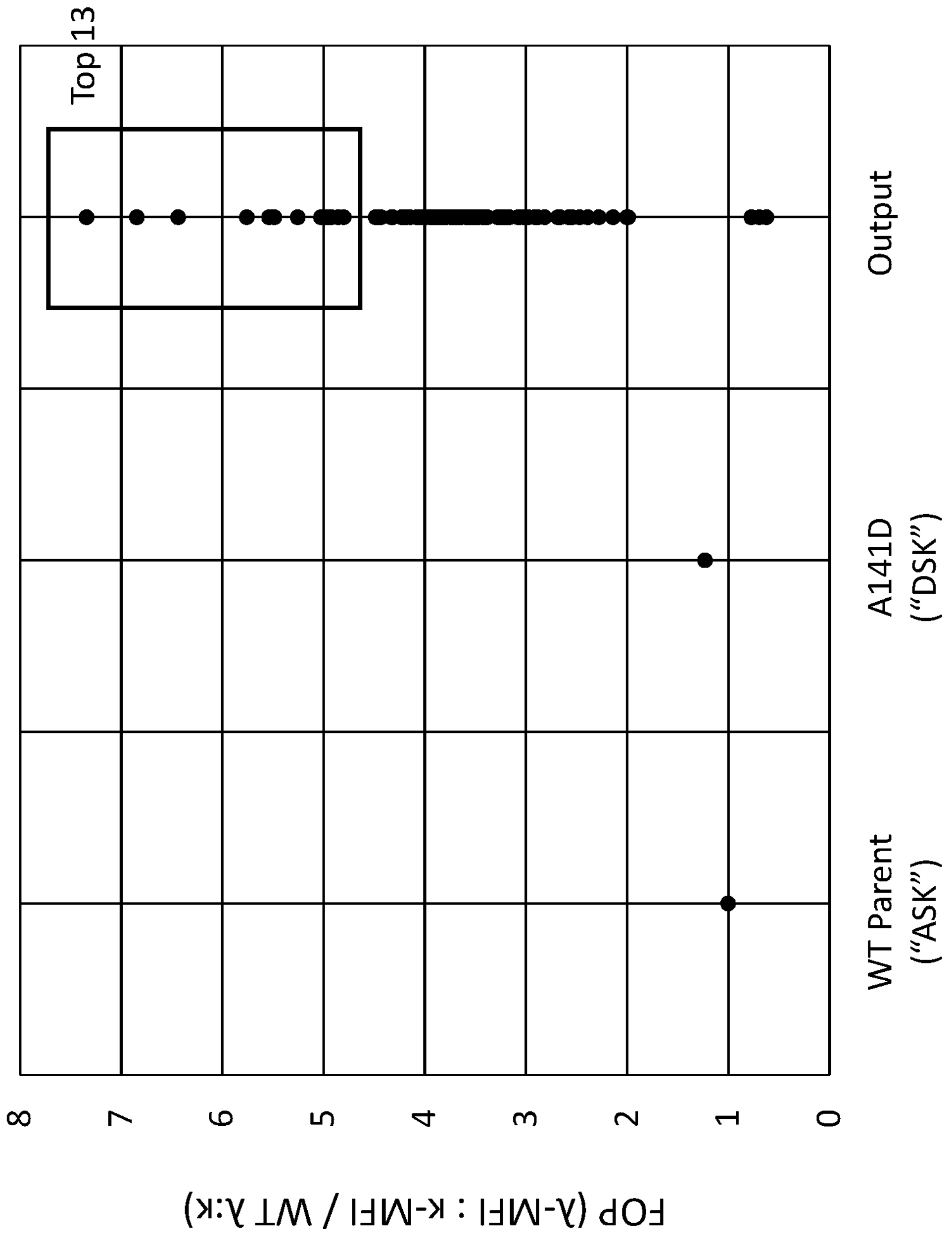
FIG. 8 shows lambda preference FOP values for a WT clone, an A141D clone, and individual clones having different amino acid substitutions at positions 141, 181, and 218 of CH1 domain obtained from the 141×181×218 library selection output in Example 5. 13 data points marked in the rectangle correspond to clones with highest FOP values, and the amino acid residues at CH1 positions 141, 181, and 218 and the FOP value for each clone are provided in Table 8.

FIG. 8 shows that the majority of the output clones have higher preference in pairing with the lambda chain, as determined by the FOP value. Table 8 provides the CH1 domain substitutions and FOP values of lambda:kappa MFI ratio for the top 13 clones marked in FIG. 8.

TABLE 8

Top 13 FOP values from the output clones

| Amino acid residues at position 141, 181, and 218 | FOP |
|---|---|
| EIL | 7.34 |
| KKE | 6.84 |
| EKP | 6.44 |
| KLD | 5.76 |
| KKP | 5.54 |
| KKA | 5.49 |
| KKE | 5.25 |
| KKP | 5.03 |
| KKH | 4.99 |
| EKD | 4.98 |
| KKP | 4.96 |

Figure 9:
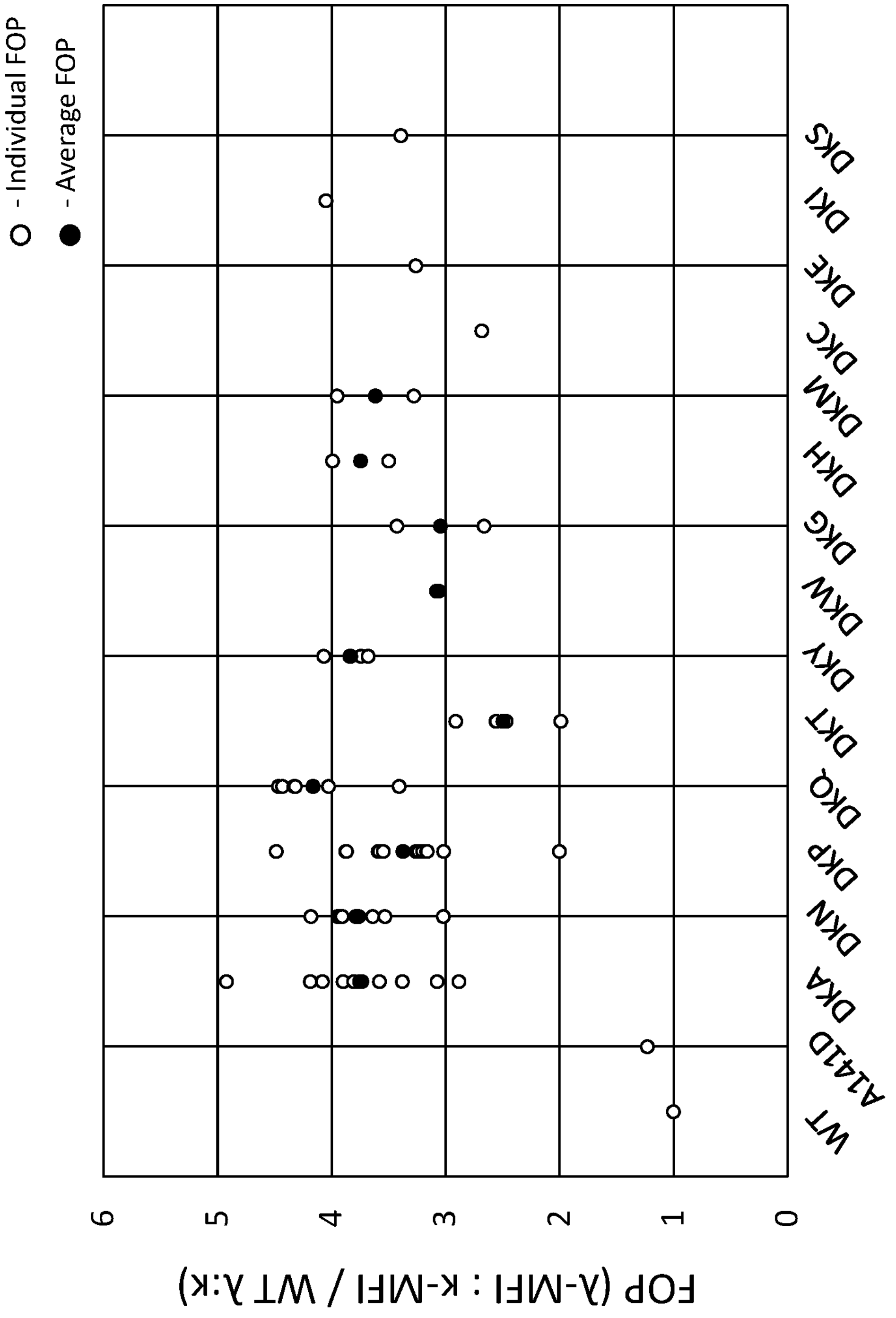
FIG. 9 shows lambda preference FOP values for a WT clone, an A141D clone, and individual clones having D at position 141, K at position 181, and various amino acids at position 218 of CH1 domain in the 141×181×218 library selection output in Example 5. Open data points represent the FOP of individual clones having the same CH1 sequence and filled data points represent average FOP values.
Figure 10:
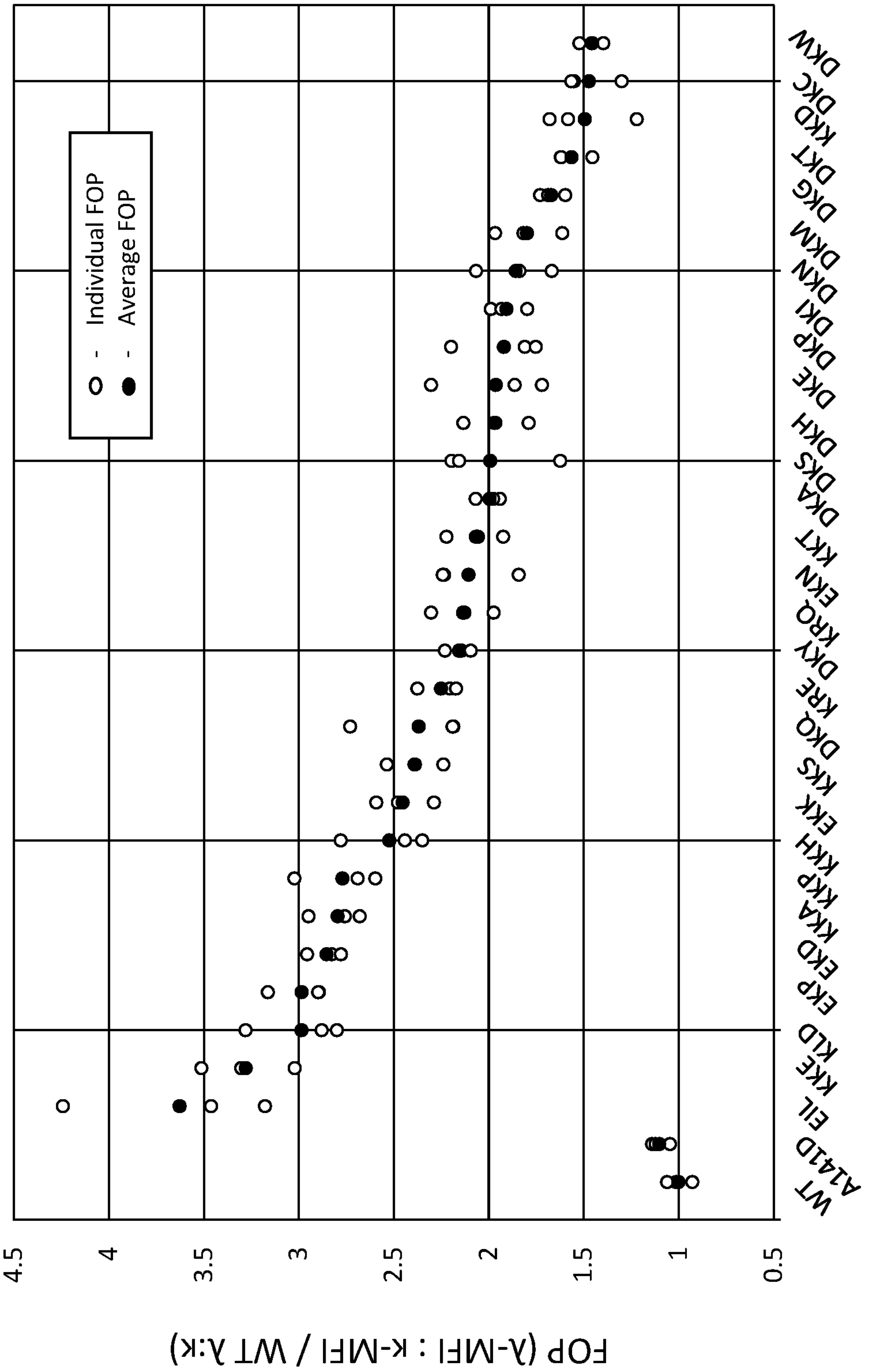
FIG. 10 shows lambda preference FOP values measured with re-cloned clones and WT and A141D clones, which confirms maintained lambda preference.

Analysis showed that a substitution at position 141 to D, K, or E paired with a substitution at position 181 to K and a substitution at position 218 to L, E, D, P, A, H, S, Q, N, T, I, M, G, C, or W were frequent among the output clones and increase lambda light chain preference over A141D (increased lambda:kappa MFI ratio). FIG. 9 shows individual and average FOP values measured in clones having D at position 141, K at position 181, and various amino acid at position 218 of CH. The lead CH1 sequences were cloned back into the LC stain (this process is subsequently employed in all assays) and clones and the lambda preference was confirmed by calculating the FOP values in triplicates (FIG. 10).

Additional analysis generated 9 unique candidate CH1 sequences for mammalian IgG production (see Table 9).

TABLE 9

CH1 domains with kappa or lambda chain preference

| SEQ ID NO: | Amino acid substitutions | Sequence | Also referred to herein as: |
|---|---|---|---|
| 141 | A141D; S181K | ASTKGPSVFPLAPSSKSTSGGTA**D**LGCLVKDYFP EPVTVSWNSGALTSGVHTFPAVLQSSGLY**K**LSSV VTVPSSSLGTQTYICNVNHKPSNTKVDKKVEPK | "DKK"; "DxKxWT"; or "D_K_WT" |
| 142 | A141D; S181K; K218A | ASTKGPSVFPLAPSSKSTSGGTA**D**LGCLVKDYFP EPVTVSWNSGALTSGVHTFPAVLQSSGLY**K**LSSV VTVPSSSLGTQTYICNVNHKPSNTKVDKKVEP**A** | "DKA"; "DxKxA" or "D_K_A" |
| 143 | A141D; S181K; K218P | ASTKGPSVFPLAPSSKSTSGGTA**D**LGCLVKDYFP EPVTVSWNSGALTSGVHTFPAVLQSSGLY**K**LSSV VTVPSSSLGTQTYICNVNHKPSNTKVDKKVEP**P** | "DKP"; "DxKxP"; or "D_K_P" |
| 144 | A141E | ASTKGPSVFPLAPSSKSTSGGTA**E**LGCLVKDYFP EPVTVSWNSGALTSGVHTFPAVLQSSGLYSLSSV VTVPSSSLGTQTYICNVNHKPSNTKVDKKVEPK | "ESK"; "ExWTxWT" or "E_WT_WT" |
| 145 | A141E; S181K | ASTKGPSVFPLAPSSKSTSGGTA**E**LGCLVKDYFP EPVTVSWNSGALTSGVHTFPAVLQSSGLY**K**LSSV VTVPSSSLGTQTYICNVNHKPSNTKVDKKVEPK | "EKK"; "ExKxWT" or "E_K_WT" |
| 146 | A141K | ASTKGPSVFPLAPSSKSTSGGTA**K**LGCLVKDYFP EPVTVSWNSGALTSGVHTFPAVLQSSGLYSLSSV VTVPSSSLGTQTYICNVNHKPSNTKVDKKVEPK | "KSK"; "KxWTxWT" or "K_WT_WT" |
| 147 | A141K; S181K; | ASTKGPSVFPLAPSSKSTSGGTA**K**LGCLVKDYFP EPVTVSWNSGALTSGVHTFPAVLQSSGLY**K**LSSV VTVPSSSLGTQTYICNVNHKPSNTKVDKKVEPK | "KKK"; "KxKxWT" or "K_K_WT" |
| 148 | A141K; S181K; K218E | ASTKGPSVFPLAPSSKSTSGGTA**K**LGCLVKDYFP EPVTVSWNSGALTSGVHTFPAVLQSSGLY**K**LSSV VTVPSSSLGTQTYICNVNHKPSNTKVDKKVEP**E** | "KKE"; "KxKxE" or "K_K_E" |

TABLE 9-continued

| CH1 domains with kappa or lambda chain preference | | | |
|---|---|---|---|
| SEQ ID NO: | Amino acid substitutions | Sequence | Also referred to herein as: |
| 149 | A141K; S181K; K218P | ASTKGPSVFPLAPSSKSTSGGTAKLGCLVKDYFP EPVTVSWNSGALTSGVHTFPAVLQSSGLYKLSSV VTVPSSSLGTQTYICNVNHKPSNTKVDKKVEPP | "KKP"; "KxKxP" or "K_K_P" |

The 9 candidate CH1 sequences, along with WT (i.e., "ASK") and A141D (i.e., "DSK"), were cloned into mammalian expression vectors via standard methods. To determine lambda preference, plasmids representing the desired heavy chain, lambda light chain, and kappa light chain were transfected into HEK293 cells at a 2:1:1 plasmid ratio. Transfected HEK cells were cultured and IgGs were purified using previously described protocols. Without wishing to be bound by theory, expressing approximately equal amounts of the total heavy chain and total light chain polypeptides (HC:kappa LC:lambdaLC="2:1:1" here results in total HC:total LC=1:1) (i.e. no excess HC and no excess LC) appeared to have allowed Inventors to avoid various biases, leading to visualization of true kappa or lambda preference of CH1 domain variants.

Figure 11:
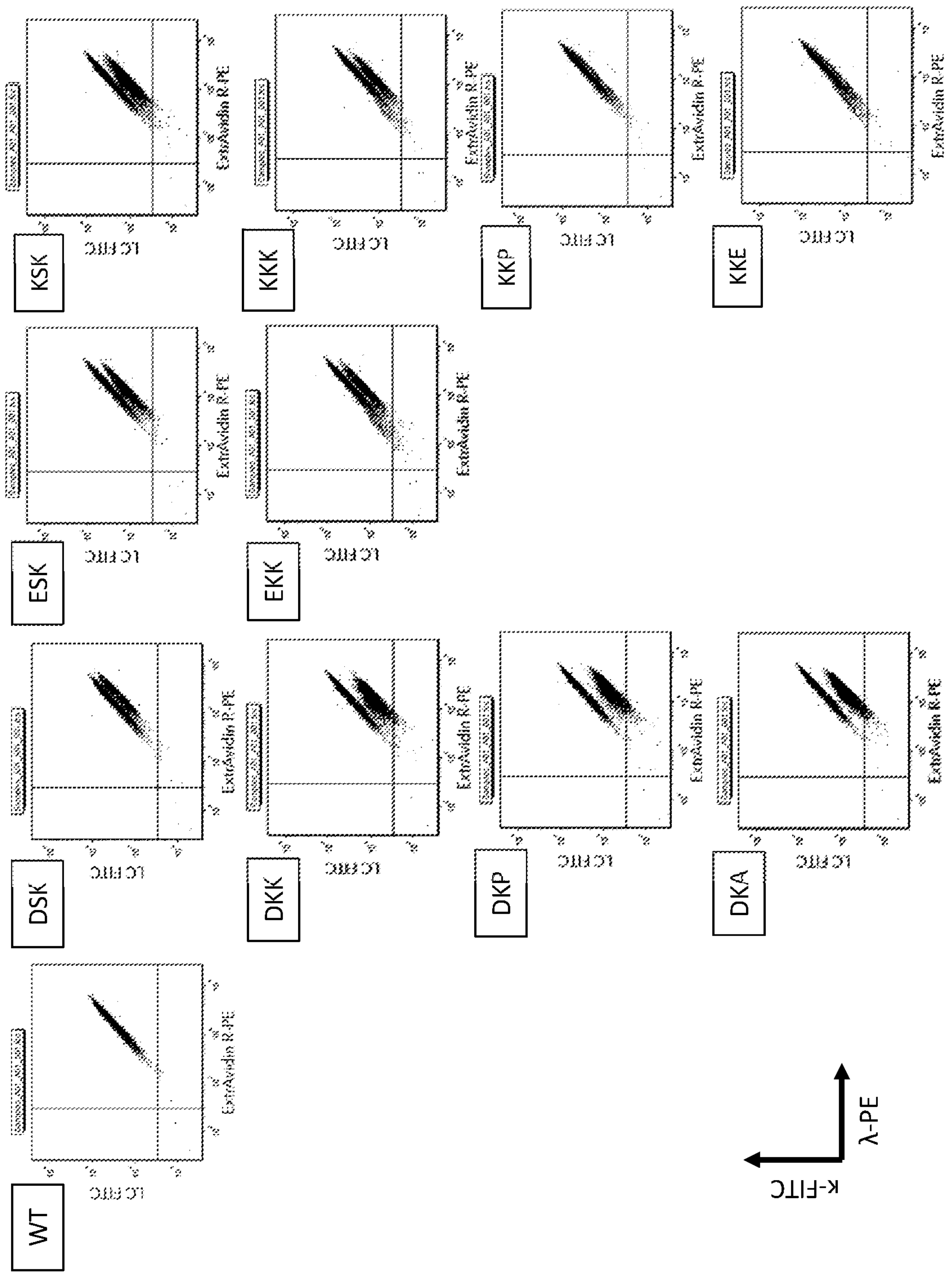
FIG. 11 shows exemplary scatterplots of HEK293 produced IgGs having CH1 of one of the nine 141×181×218 leads selected in Example 5 and of WT and A14D, stained for kappa CL and lambda CL. Scatter plots of individual clones are overlaid with the WT plot. The x-axis shows lambda light chains labeled with PE, and the y-axis shows kappa light chains labeled with FITC.
Figure 12:
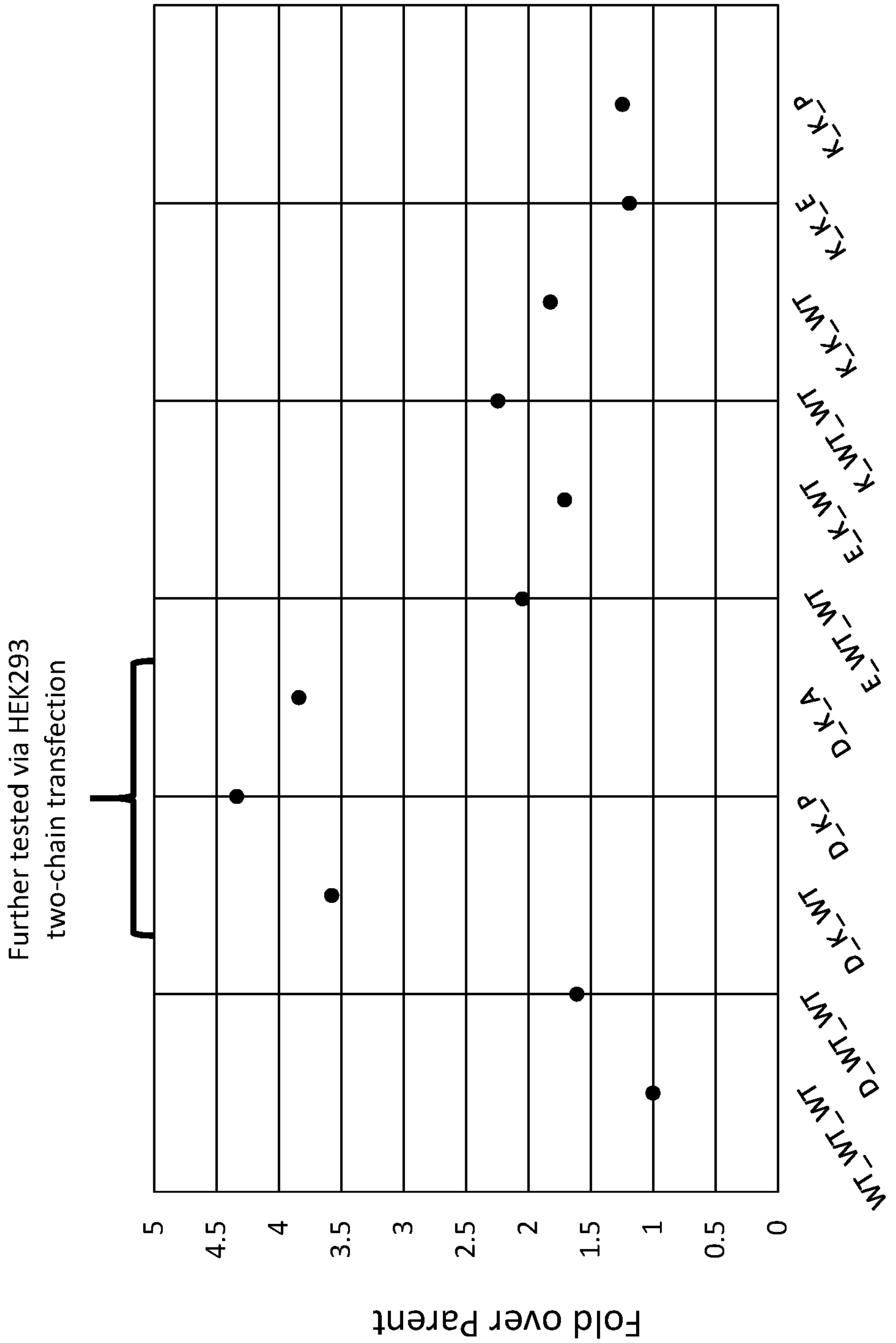
FIG. 12 shows lambda preference FOP values for nine leads from Example 5, along with WT and A141D. The three CH1 variants with highest FOP values (D_K_WT, D_K_P, and D_K_A) were selected for subsequent two-chain (kappa or lambda) transfection in HEK293.
Figure 13:
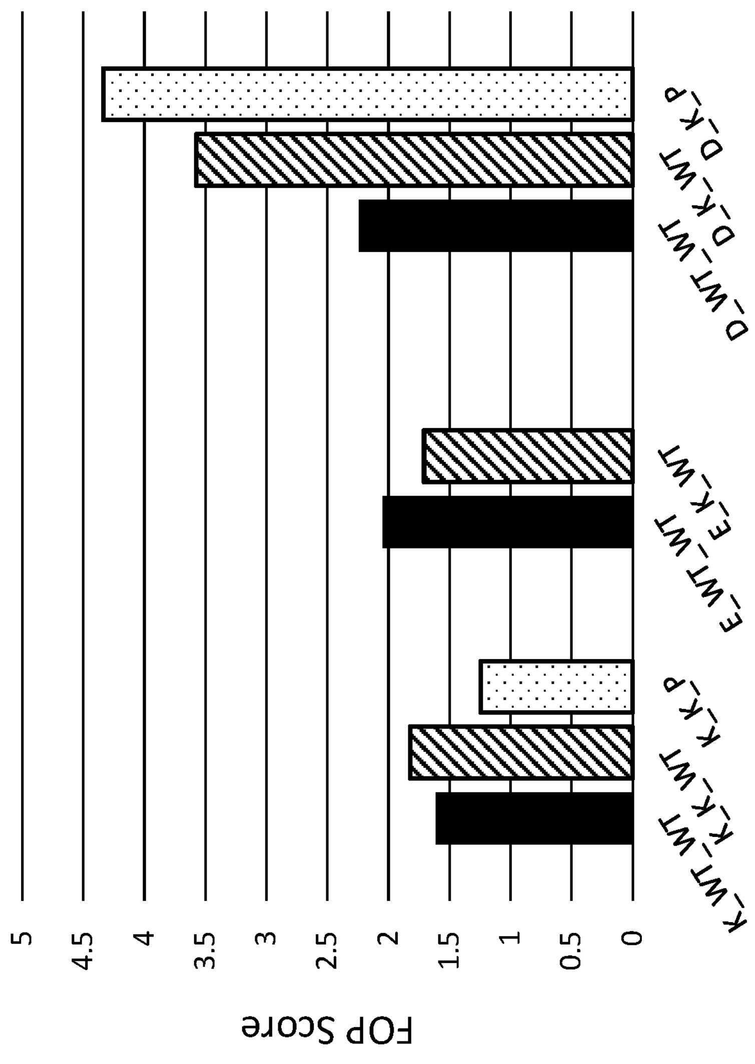
FIG. 13 compares lambda preference FOP values among CH1 variants having the same amino acid at position 141. When position 141 is D, an additional amino acid substitution at position 181 or at positions 181 and 218 further increases the FOP value.

FACS-based quantification of lambda-preference was carried out for the mammalian produced IgG. FIG. 11 provides FACS plots and FIG. 12 and Table 10 provide the FOP values (lambda:kappa MFI) for the 9 CH1 variants and for WT and A141D (i.e., "DSK"). FIG. 13 shows that when CH1 has D at position 141, additional substitutions at position 181 or at positions 181 and 218 further improve lambda preference (based on the lambda:kappa MFI ratio).

TABLE 10

FOP values for the 9 CH1 variants

| CH1 substitutions (at 141, 181, and 218) | FOP |
|---|---|
| D_K_P | 4.33 |
| D_K_A | 3.83 |
| D_K_WT | 3.57 |
| K_WT_WT | 2.24 |
| E_WT_WT | 2.04 |
| K_K_WT | 1.82 |
| E_K_WT | 1.70 |
| D_WT_WT | 1.61 |
| K_K_P | 1.24 |
| K_K_E | 1.18 |
| WT_WT_WT | 1.00 |

Figure 14:
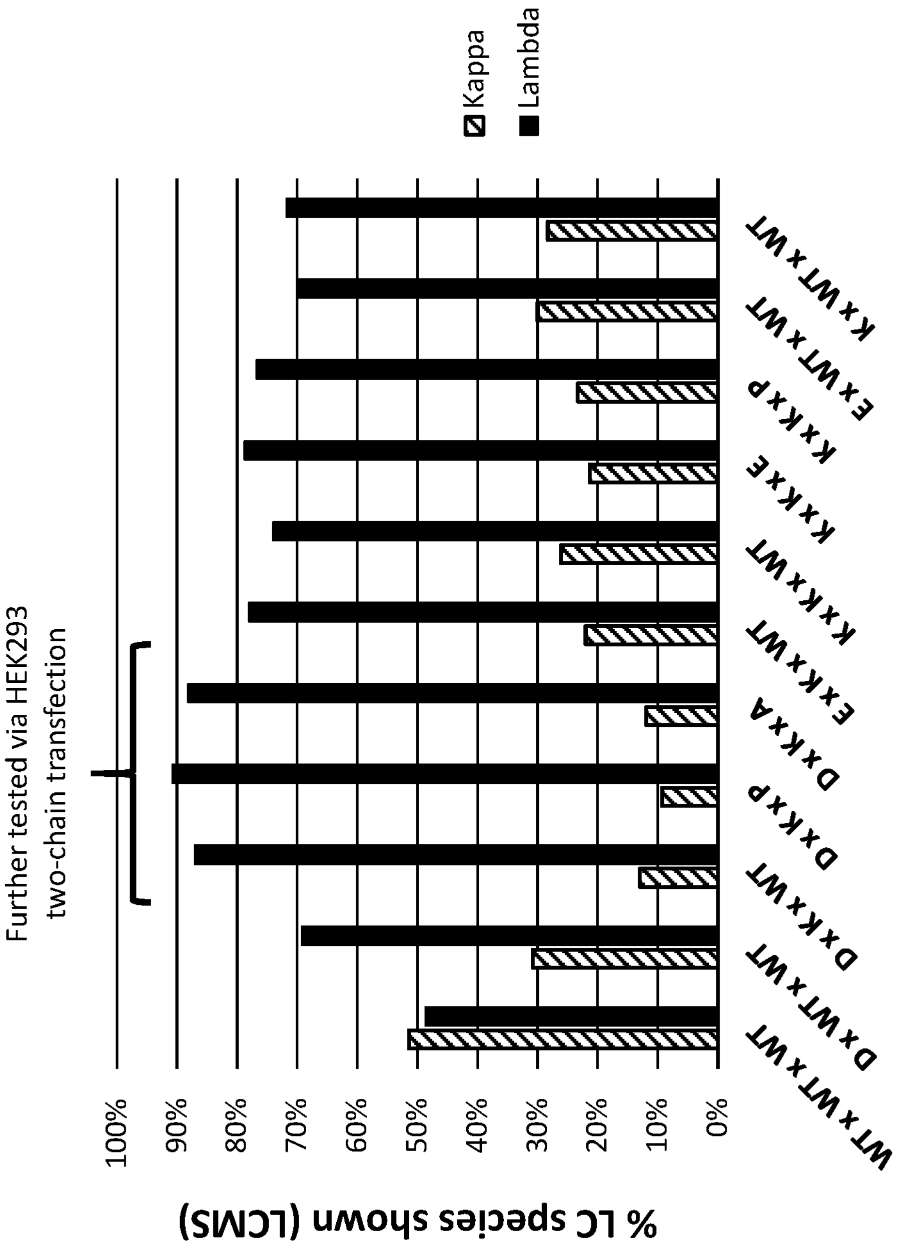
FIG. 14 shows % light chain species (comparing kappa and lambda) of nine lead full-length IgGs produced in HEK293, as measured by liquid chromatography-mass spectrometry ("LCMS"). The three CH1 variants with highest FOP values (D_K_WT, D_K_P, and D_K_A) were selected for subsequent transfection in HEK293.

Additionally, LCMS data of reduced full-length IgGs were used to determine the relative amount of lambda light chain and kappa light chain in the purified IgG sample. FIG. 14 compares % species paired with a kappa light chain (LC) and % species paired with a lambda light chain.

Analysis of these data yielded three CH1 sequences (SEQ ID NOS: 143, 142, and 141, having DKP, DKA, and DKK substitutions, respectively) with improved lambda preference over the parent and previously identified lead, A141D.

Figure 15:
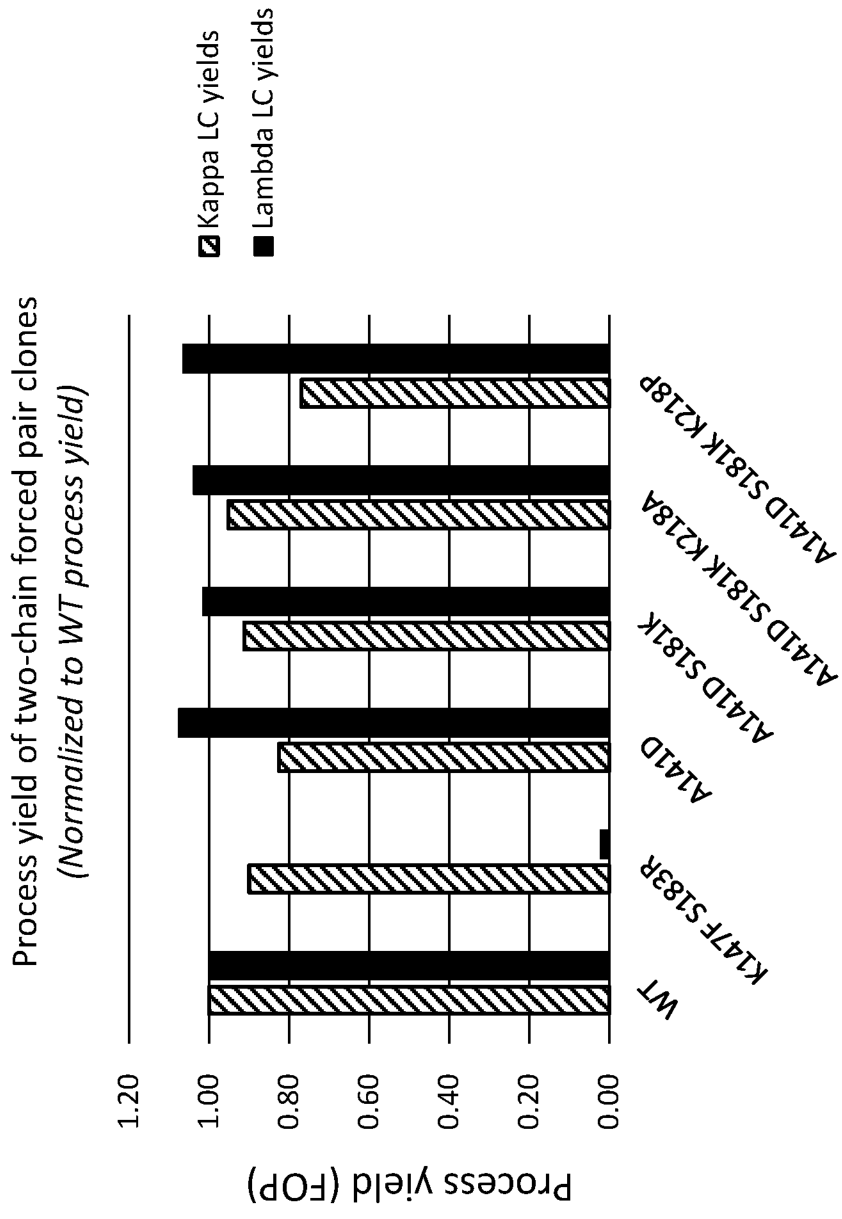
FIG. 15 shows exemplary process yields of the three leads (D_K_WT, D_K_P, and D_K_A) and A141D relative to the yield of WT, shown as fold-over-parent ("FOP") values.
Figure 16:
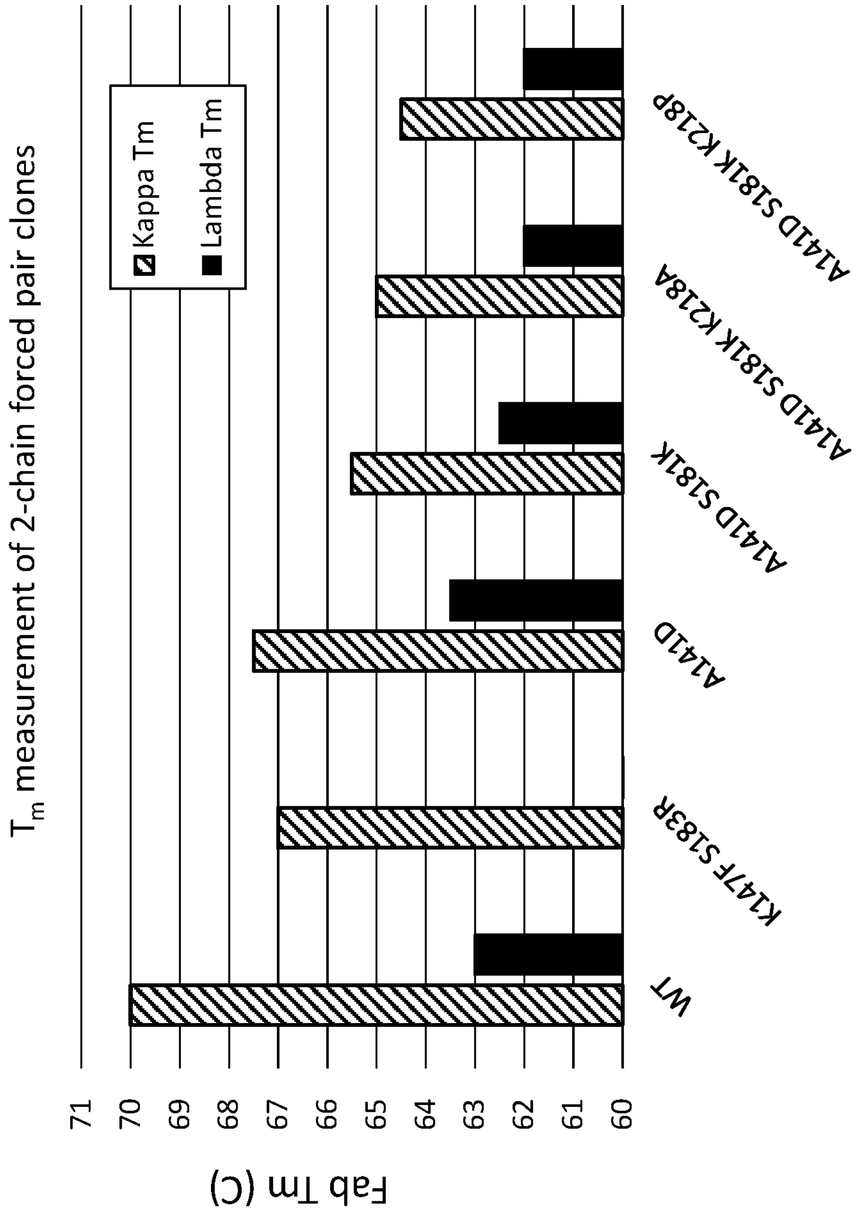
FIG. 16 shows Tm (° C.) of kappa-paired Fabs and lambda-paired Fabs having one of the three lead CH1 variants (D_K_WT, D_K_P, and D_K_A) or A141D or WT.
Figure 17:
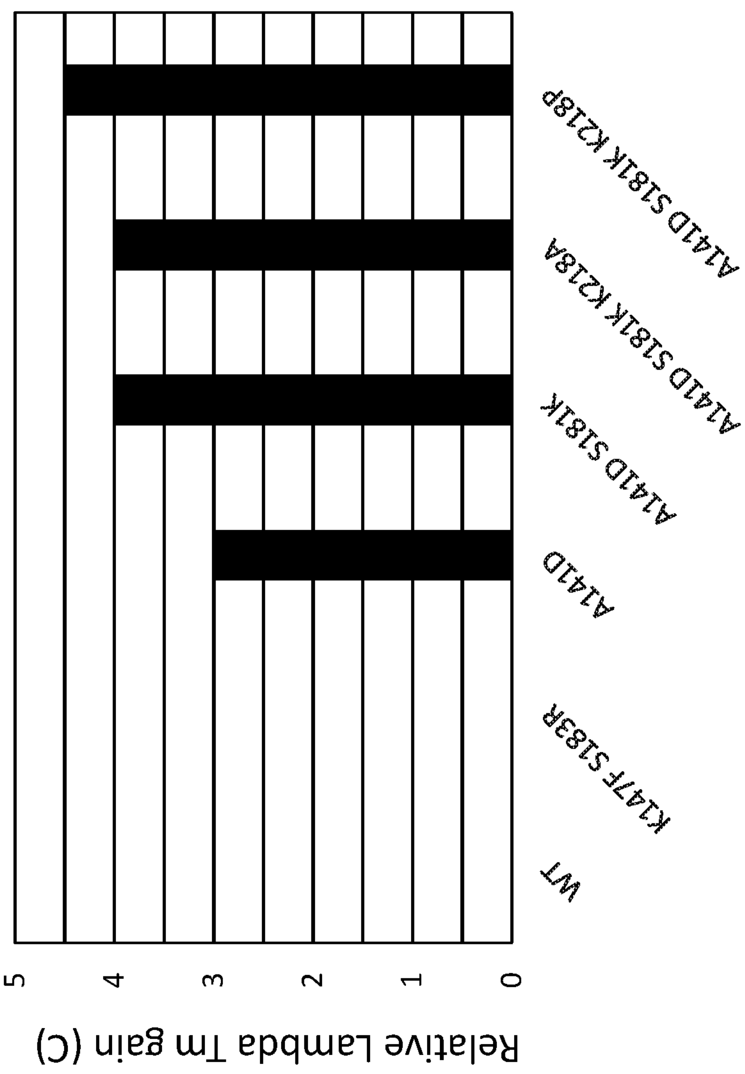
FIG. 17 shows relative lambda Tm (° C.), as defined as: [Tm change in lambda-paired variant Fab relative to lambda-paired WT Fab ("Δlambda Tm")]−[Tm change in kappa-paired variant Fab relative to kappa-paired WT Fab ("Δkappa Tm")].

To determine if these CH1 sequences pair with kappa light-chain, the candidate CH1 heavy chain plasmids were transfected into HE293 cells with either 1.) kappa light-chain or 2.) lambda light-chain. K147F S183R as a CH1 with kappa preference, WT, A141D were also included as controls. Transfected HEK cells were cultured and purified via standard methods. Linked heavy-chain and light-chain Fabs were generated from the purified IgG using previously described methods. Process Yield was determined using standard methods and normalized to the WT process yield to calculate the "FOP" process yield. Based on the process yield FOP, A141D, A141D S181K, A141D S181K K218A, and A141D S181K K218P all still bound to kappa LC when only kappa LC (but not lambda LC) was present, but more binding occurred with lambda LC than with kappa LC (FIG. 15). Fab Tm of the kappa- and lambda-Fabs was measured by Differential Scanning Fluorometry using the BioRad CFX96 RT PCR (FIG. 16). For each CH1 variant, lambda-paired Fab's relative gain in Tm ("relative lambda Tm gain" or "net lambda Tm gain"), as defined as: [Tm change in lambda-paired variant Fab relative to lambda-paired WT Fab ("Δlambda Tm")]−[Tm change in kappa-paired variant Fab relative to kappa-paired WT Fab ("Δkappa Tm")], was calculated (FIG. 17). As shown in FIG. 17, relative lambda Tm gain increased with an additional substitution(s) at S181 or at S181 and K218. Without wishing to be bound by theory, based on FIGS. 16 and 17, destabilization of kappa LC pairing seems to have contributed to the relative lambda Tm gain and increase in pairing with lambda CL.

Example 6: 141×ALL Library Builds and Selections

Additional libraries were constructed to sample additional residues in the CH1 for driving lambda preferential binding when paired with a substitution at position 141. Six new libraries (LAD11522-LAD11527) were designed to have a maximum of three substitutions across three regions (DOR1, DOR2, and DOR3) of the CH1 (Table 11). Together, the six libraries represent every possible substitution set that includes two substitutions within three domains of interest paired with position 141. In all libraries, the amino acid diversity at position 141 was generated via the degenerate codon RMW and the amino acid diversity at the other two variegated positions was generated via the degenerate codon NNK. The libraries were constructed using previously described methods. Selection for lambda-preference was conducted as previously described.

TABLE 11

| Library design and build | | | | | | | | | | | |
|---|---|---|---|---|---|---|---|---|---|---|---|
| | DOR1 Pool | | | DOR2 Pool | | | DOR3 Pool | | | Total | |
| Library LAD# | Code | # of Diversified positions | Diversity | Code | # of Diversified positions | Diversity | Code | # of Diversified positions | Diversity | Total # od Diversified positions | Total diversity |
| 11522 | B | 1 | 8 | E | 0 | 1 | J | 2 | 6144 | 3 | 4.92E+04 |
| 11523 | B | 1 | 8 | F | 1 | 320 | I | 1 | 128 | 3 | 3.28E+05 |
| 11524 | B | 1 | 8 | G | 2 | 46080 | H | 0 | 1 | 3 | 3.69E+05 |
| 11525 | C | 2 | 3840 | E | 0 | 1 | I | 1 | 128 | 3 | 4.92E+05 |
| 11526 | C | 2 | 3840 | F | 1 | 320 | H | 0 | 1 | 3 | 1.23E+06 |
| 11527 | D | 3 | 860160 | E | 0 | 1 | H | 0 | 1 | 3 | 8.60E+05 |

Starting after the second round of FACS selections, the selection output CH1 diversity was isolated and re-cloned into the appropriate two-chain light chain strain to recover diminished kappa light chain expression in the library. The CH1 diversity was isolated using PCR amplification with the appropriate primers and standard DNA purification. This pool of DNA fragments was then electroporated with ADI-26140 heavy-chain variable region and digested plasmid into the appropriate two-chain light chain strain.

Figure 18:
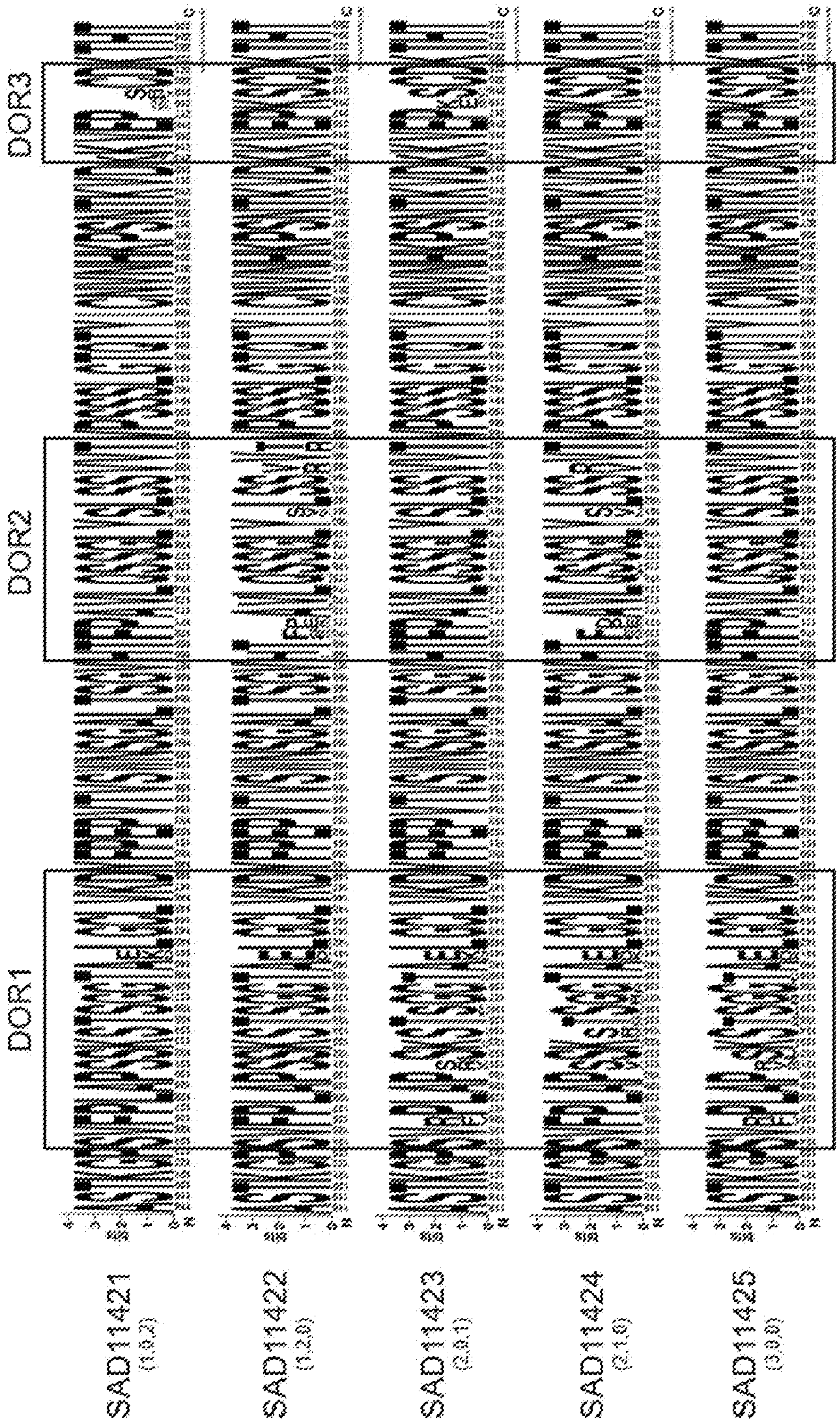
FIG. 18 provides the sequencing results from re-cloning output in Example 6, visualizing frequent amino acid substitutions observed among the output clones.

Outputs were sequenced as previously described (FIG. 18), and FACS-based quantification of lambda-preference versus the parent strain were quantified. The previously identified lead clone, AT4TD S181K K218P, was included in the analysis. Based on these data, the amino acid combinations with the greatest improvement in light-chain lambda preferential pairing over parent were determined.

Figure 19:
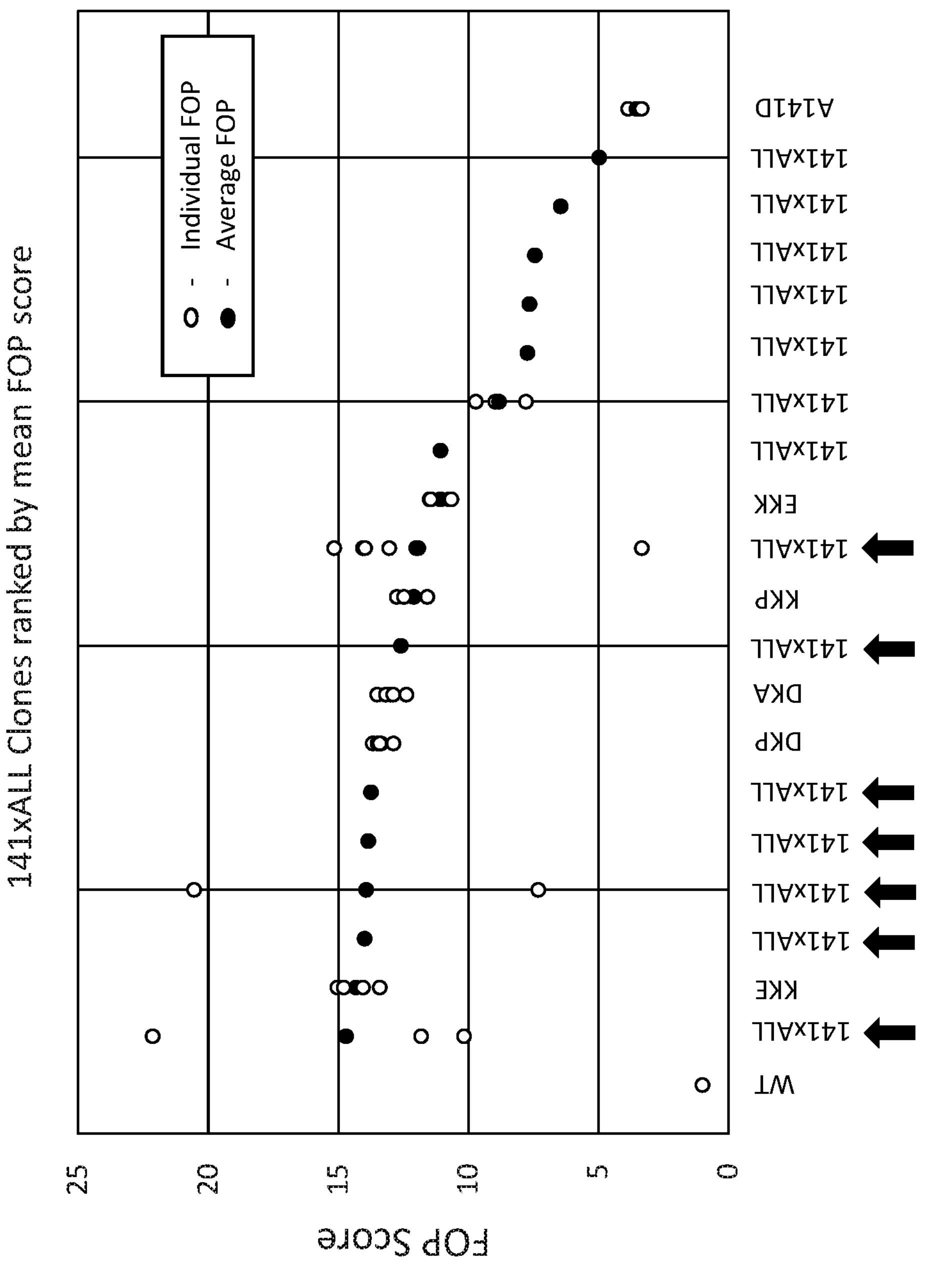
FIG. 19 shows lambda preference FOP values (lambda MFI:kappa MFI) for leads from re-cloning output in Example 6, as well as some of the 141×181×218 leads (DKP, DKA, KKE, KKP, and EKK) from Example 5, expressed as an IgG in yeast. At least seven leads, marked with an arrow, have a FOP value equivalent to or higher than the value of the tested 141×181×218 leads.
Figure 20:
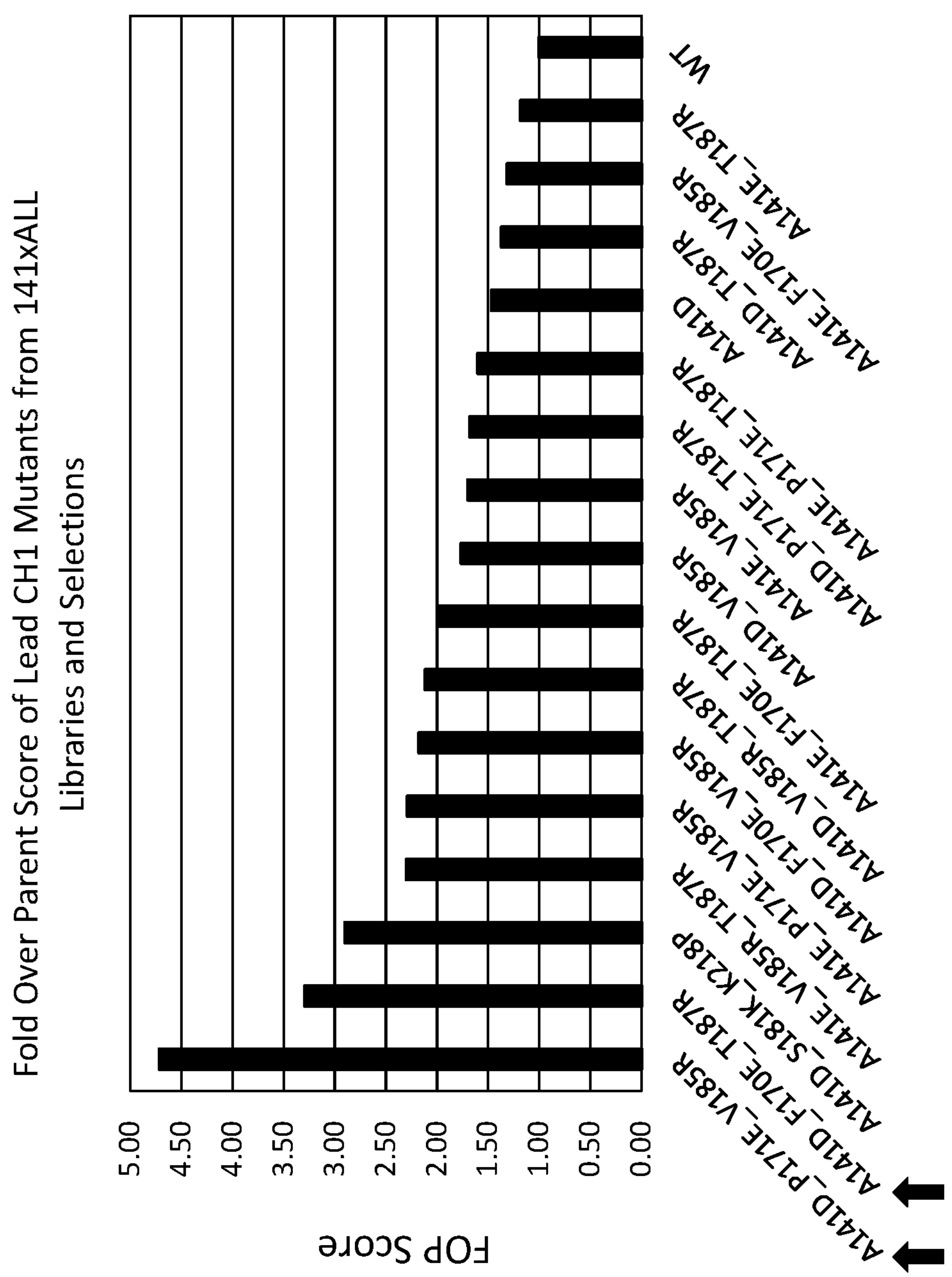
FIG. 20 shows lambda preference FOP values for 14 leads from Example 7, as well as DKP identified in Example 5, A141D, and wild type. Two leads, "A414D_P17TE_V185R" and "A14TD_F170E_T187R" marked with an arrow showed higher FOP values than DKP. All 14 leads showed higher FOP value than the wild-type.

Top 46 clones, containing 28 unique CH1 sequences (Table 12) were expressed as an IgG in yeast. The new CH1 sequences, along with WT, AT4TD (or "DSK"), and some of the leads from the 141×181×218 series (DKP, DKA, KKE, KKP, and EKK) in Example 5, were compared for the FOP value determined by flow cytometry (lambda MFI:kappa MFI) (FIG. 19). At least seven having the CH1 sequence of SEQ ID NOS: 155, 157, 159, 162, 163, 164, or 165, corresponding to the data points marked with an arrow in FIG. 19, showed FOP values equivalent to or higher than the value of the tested 141×181×218 leads.

TABLE 12

| 28 unique CH1 sequences from 141 x ALL series with lambda preference | | |
|---|---|---|
| SEQ ID NO: | Amino acid substitutions | CH1 Sequence |
| 150 | P127G; G138R; A141T; F170G; S176R; S181L | ASTKGPSVFGLAPSSKSTSGRTATLGCLVKDYFPEPVTVSWNSGALTSGVH TGPAVLQRSGLYLLSSVVTVPSSSLGTQTYICNVNHKPSNTKVDKKVEPK |
| 151 | S131R; A141E; S181K | ASTKGPSVFPLAPRSKSTSGGTAELGCLVKDYFPEPVTVSWNSGALTSGVH TFPAVLQSSGLYKLSSVVTVPSSSLGTQTYICNVNHKPSNTKVDKKVEPK |
| 152 | S134R; A141E; P171D; S181V; V185R | ASTKGPSVFPLAPSSKRTSGGTAELGCLVKDYFPEPVTVSWNSGALTSGVH TFDAVLQSSGLYVLSSRVTVPSSSLGTQTYICNVNHKPSNTKVDKKVEPK |
| 153 | A141D; H1681; F170G; T187R | ASTKGPSVFPLAPSSKSTSGGTADLGCLVKDYFPEPVTVSWNSGALTSGVI TGPAVLQSSGLYSLSSVVRVPSSSLGTQTYICNVNHKPSNTKVDKKVEPK |
| 154 | A141E; F170E; S181L; T187R | ASTKGPSVFPLAPSSKSTSGGTAELGCLVKDYFPEPVTVSWNSGALTSGVH TEPAVLQSSGLYLLSSVVRVPSSSLGTQTYICNVNHKPSNTKVDKKVEPK |
| 155 | A141E; F170E; S181V; T187R | ASTKGPSVFPLAPSSKSTSGGTAELGCLVKDYFPEPVTVSWNSGALTSGVH TEPAVLQSSGLYVLSSVVRVPSSSLGTQTYICNVNHKPSNTKVDKKVEPK |
| 156 | A141E; P171D; V185R; K218F | ASTKGPSVFPLAPSSKSTSGGTAELGCLVKDYFPEPVTVSWNSGALTSGVH TFDAVLQSSGLYSLSSRVTVPSSSLGTQTYICNVNHKPSNTKVDKKVEPF |
| 157 | A141E; P171D; V185R | ASTKGPSVFPLAPSSKSTSGGTAELGCLVKDYFPEPVTVSWNSGALTSGVH TFDAVLQSSGLYSLSSRVTVPSSSLGTQTYICNVNHKPSNTKVDKKVEPK |
| 158 | A141E; P171E; S181A | ASTKGPSVFPLAPSSKSTSGGTAELGCLVKDYFPEPVTVSWNSGALTSGVH TFEAVLQSSGLYALSSVVTVPSSSLGTQTYICNVNHKPSNTKVDKKVEPK |
| 159 | A141E; P171E; V185R | ASTKGPSVFPLAPSSKSTSGGTAELGCLVKDYFPEPVTVSWNSGALTSGVH TFEAVLQSSGLYSLSSRVTVPSSSLGTQTYICNVNHKPSNTKVDKKVEPK |
| 160 | A141E; P171E; S181T; V185R | ASTKGPSVFPLAPSSKSTSGGTAELGCLVKDYFPEPVTVSWNSGALTSGVH TFEAVLQSSGLYTLSSRVTVPSSSLGTQTYICNVNHKPSNTKVDKKVEPK |

TABLE 12-continued 28 unique CH1 sequences from 141 x ALL series with lambda preference

| SEQ ID NO: | Amino acid substitutions | CH1 Sequence |
|---|---|---|
| 161 | A141E; P171E; S181V | ASTKGPSVFPLAPSSKSTSGGTA**E**LGCLVKDYFPEPVTVSWNSGALTSGVH TF**E**AVLQSSGLY**V**LSSVVTVPSSSLGTQTYICNVNHKPSNTKVDKKVEPK |
| 162 | A141E; P171G; V185R; T187R | ASTKGPSVFPLAPSSKSTSGGTA**E**LGCLVKDYFPEPVTVSWNSGALTSGVH TF**G**AVLQSSGLYSLSS**R**V**R**VPSSSLGTQTYICNVNHKPSNTKVDKKVEPK |
| 163 | A141E; V185R; T187R | ASTKGPSVFPLAPSSKSTSGGTA**E**LGCLVKDYFPEPVTVSWNSGALTSGVH TFPAVLQSSGLYSLSS**R**V**R**VPSSSLGTQTYICNVNHKPSNTKVDKKVEPK |
| 164 | A141E; P171S; S181K | ASTKGPSVFPLAPSSKSTSGGTA**E**LGCLVKDYFPEPVTVSWNSGALTSGVH TFSAVLQSSGLY**K**LSSVVTVPSSSLGTQTYICNVNHKPSNTKVDKKVEPK |
| 165 | A141E; F170G; Q175M; S181V; S184R; T187R | ASTKGPSVFPLAPSSKSTSGGTA**E**LGCLVKDYFPEPVTVSWNSGALTSGVH T**G**PAVL**M**SSGLY**V**LS**R**VV**R**VPSSSLGTQTYICNVNHKPSNTKVDKKVEPK |
| 166 | A141E; F170R; V173H; S181V | ASTKGPSVFPLAPSSKSTSGGTA**E**LGCLVKDYFPEPVTVSWNSGALTSGVH T**R**PA**H**LQSSGLY**V**LSSVVTVPSSSLGTQTYICNVNHKPSNTKVDKKVEPK |
| 167 | A141E; F170S; P171A; S181V | ASTKGPSVFPLAPSSKSTSGGTA**E**LGCLVKDYFPEPVTVSWNSGALTSGVH T**SA**AVLQSSGLY**V**LSSVVTVPSSSLGTQTYICNVNHKPSNTKVDKKVEPK |
| 168 | A141E; L142M; F170S; P171A; S181V | ASTKGPSVFPLAPSSKSTSGGTA**EM**GCLVKDYFPEPVTVSWNSGALTSGVH T**SA**AVLQSSGLY**V**LSSVVTVPSSSLGTQTYICNVNHKPSNTKVDKKVEPK |
| 169 | A141K; S181K; V185E | ASTKGPSVFPLAPSSKSTSGGTA**K**LGCLVKDYFPEPVTVSWNSGALTSGVH TFPAVLQSSGLY**K**LSS**E**VTVPSSSLGTQTYICNVNHKPSNTKVDKKVEPK |
| 170 | A141K; S181K; K218D | ASTKGPSVFPLAPSSKSTSGGTA**K**LGCLVKDYFPEPVTVSWNSGALTSGVH TFPAVLQSSGLY**K**LSSVVTVPSSSLGTQTYICNVNHKPSNTKVDKKVEP**D** |
| 171 | A141T; F170V; P171A; S181V | ASTKGPSVFPLAPSSKSTSGGTA**T**LGCLVKDYFPEPVTVSWNSGALTSGVH T**VA**AVLQSSGLY**V**LSSVVTVPSSSLGTQTYICNVNHKPSNTKVDKKVEPK |
| 172 | G137R; A141E; P171E; S181V | ASTKGPSVFPLAPSSKSTS**R**GTA**E**LGCLVKDYFPEPVTVSWNSGALTSGVH TF**E**AVLQSSGLY**V**LSSVVTVPSSSLGTQTYICNVNHKPSNTKVDKKVEPK |
| 173 | F126R; S131V; T139V; A141E; K218E | ASTKGPSV**R**PLAP**V**SKSTSGG**V**A**E**LGCLVKDYFPEPVTVSWNSGALTSGVH TFPAVLQSSGLYSLSSVVTVPSSSLGTQTYICNVNHKPSNTKVDKKVEP**E** |
| 174 | F126V; S131V; S136P; A141D | ASTKGPSV**V**PLAP**V**SKST**P**GGTA**D**LGCLVKDYFPEPVTVSWNSGALTSGVH TFPAVLQSSGLYSLSSVVTVPSSSLGTQTYICNVNHKPSNTKVDKKVEPK |
| 175 | F126V; S131V; S136P; G137R; A141D | ASTKGPSV**V**PLAP**V**SKST**PR**GTA**D**LGCLVKDYFPEPVTVSWNSGALTSGVH TFPAVLQSSGLYSLSSVVTVPSSSLGTQTYICNVNHKPSNTKVDKKVEPK |
| 176 | F126V; S131V; A141D; K218S | ASTKGPSV**V**PLAP**V**SKSTSGGTA**D**LGCLVKDYFPEPVTVSWNSGALTSGVH TFPAVLQSSGLYSLSSVVTVPSSSLGTQTYICNVNHKPSNTKVDKKVEPS**S** |
| 177 | F126V; S131V; K133S; A141K; K218A | ASTKGPSV**V**PLAP**V**S**S**STSGGTA**K**LGCLVKDYFPEPVTVSWNSGALTSGVH TFPAVLQSSGLYSLSSVVTVPSSSLGTQTYICNVNHKPSNTKVDKKVEP**A** |

Example 7: Constructs and Screening of 141×(170/171)×(185/187) Series

Analysis of the results in Example 6 yielded four new positions/residues of interest including F170, P171, V185, and T187. Based on the amino acids frequently observed at positions 170, 171, 185, and 187, along with 141 which produced high FOP values in the previous studies (e.g., E and D frequent at position 141; E frequent at position 170 or 171 in 141×ALL outputs; and R frequent at positions 185 and/or 187 when position 141 is substituted and independently with position 171), 14 unique CH1 domain variants having maximum of three amino acid substitutions per CH1 domain (Table 13) were rationally designed as candidates for lead lambda-preferential substitution sets. The 14 leads in Table 13 includes "A141E; V185R; T187R" (SEQ ID NO: 163) and "A141E; P171E; V185R (SEQ ID NO: 159)", which were tested in Example 6.

TABLE 13

New CH1 sequences from the 141 x (170/171) x (185 x 187) series

| SEQ ID NO: | Amino acid substi- tutions | Also referred to herein as: | CH1 Sequence |
|---|---|---|---|
| 178 | A141E;<br>V185R | A141E_V185R | ASTKGPSVFPLAPSSKSTSGGTA**E**LGCLVKDYFPEPVTVSWN<br>SGALTSGVHTFPAVLQSSGLYSLSS**R**VTVPSSSLGTQTYICN<br>VNHKPSNTKVDKKVEPK |
| 179 | A141E;<br>T187R | A141E_T187R | ASTKGPSVFPLAPSSKSTSGGTA**E**LGCLVKDYFPEPVTVSWN<br>SGALTSGVHTFPAVLQSSGLYSLSSVV**R**VPSSSLGTQTYICN<br>VNHKPSNTKVDKKVEPK |
| 163 | A141E;<br>V185R;<br>T187R | A141E_V185R_T187R | ASTKGPSVFPLAPSSKSTSGGTA**E**LGCLVKDYFPEPVTVSWN<br>SGALTSGVHTFPAVLQSSGLYSLSS**R**V**R**VPSSSLGTQTYICN<br>VNHKPSNTKVDKKVEPK |
| 180 | A141E;<br>F170E;<br>V185R | A141E_F170E_V185R | ASTKGPSVFPLAPSSKSTSGGTA**E**LGCLVKDYFPEPVTVSWN<br>SGALTSGVHT**E**PAVLQSSGLYSLSS**R**VTVPSSSLGTQTYICN<br>VNHKPSNTKVDKKVEPK |
| 181 | A141E;<br>F170E;<br>T187R | A141E_F170E_T187R | ASTKGPSVFPLAPSSKSTSGGTA**E**LGCLVKDYFPEPVTVSWN<br>SGALTSGVHT**E**PAVLQSSGLYSLSSVV**R**VPSSSLGTQTYICN<br>VNHKPSNTKVDKKVEPK |
| 182 | A141D;<br>V185R | A141D_V185R | ASTKGPSVFPLAPSSKSTSGGTA**D**LGCLVKDYFPEPVTVSWN<br>SGALTSGVHTFPAVLQSSGLYSLSS**R**VTVPSSSLGTQTYICN<br>VNHKPSNTKVDKKVEPK |
| 183 | A141D;<br>T187R | A141D_T187R | ASTKGPSVFPLAPSSKSTSGGTA**D**LGCLVKDYFPEPVTVSWN<br>SGALTSGVHTFPAVLQSSGLYSLSSVV**R**VPSSSLGTQTYICN<br>VNHKPSNTKVDKKVEPK |
| 184 | A141D;<br>V185R;<br>T187R | A141D_V185R_T187R | ASTKGPSVFPLAPSSKSTSGGTA**D**LGCLVKDYFPEPVTVSWN<br>SGALTSGVHTFPAVLQSSGLYSLSS**R**V**R**VPSSSLGTQTYICN<br>VNHKPSNTKVDKKVEPK |
| 185 | A141D;<br>F170E;<br>V185R | A141D_F170E_V185R | ASTKGPSVFPLAPSSKSTSGGTA**D**LGCLVKDYFPEPVTVSWN<br>SGALTSGVHT**E**PAVLQSSGLYSLSS**R**VTVPSSSLGTQTYICN<br>VNHKPSNTKVDKKVEPK |
| 186 | A141D;<br>F170E;<br>T187R | A141D_F170E_T187R | ASTKGPSVFPLAPSSKSTSGGTA**D**LGCLVKDYFPEPVTVSWN<br>SGALTSGVHT**E**PAVLQSSGLYSLSSVV**R**VPSSSLGTQTYICN<br>VNHKPSNTKVDKKVEPK |
| 159 | A141E;<br>P171E;<br>V185R | A141E_P171E_V185R | ASTKGPSVFPLAPSSKSTSGGTA**E**LGCLVKDYFPEPVTVSWN<br>SGALTSGVHTF**E**AVLQSSGLYSLSS**R**VTVPSSSLGTQTYICN<br>VNHKPSNTKVDKKVEPK |
| 187 | A141E;<br>P171E;<br>T187R | A141E_P171E_T187R | ASTKGPSVFPLAPSSKSTSGGTA**E**LGCLVKDYFPEPVTVSWN<br>SGALTSGVHTF**E**AVLQSSGLYSLSSVV**R**VPSSSLGTQTYICN<br>VNHKPSNTKVDKKVEPK |
| 188 | A141D;<br>P171E;<br>V185R | A141D_P171E_V185R | ASTKGPSVFPLAPSSKSTSGGTA**D**LGCLVKDYFPEPVTVSWN<br>SGALTSGVHTF**E**AVLQSSGLYSLSS**R**VTVPSSSLGTQTYICN<br>VNHKPSNTKVDKKVEPK |
| 189 | A141D;<br>P171E;<br>T187R | A141D_P171E_T187R | ASTKGPSVFPLAPSSKSTSGGTA**D**LGCLVKDYFPEPVTVSWN<br>SGALTSGVHTF**E**AVLQSSGLYSLSSVV**R**VPSSSLGTQTYICN<br>VNHKPSNTKVDKKVEPK |

Heavy chains containing one of the 14 CH1 domain variant sequences were cloned into mammalian (HEK) cells co-expressing kappa and lambda light chains (with the ratio of heavy chain (HC):lambda light chain (LC):kappa LC=2:1:1, i.e., the ratio of HC:LC is always 1:1) as described above. Wild type (ADI-26140 heavy chain), the "A141D" variant, and the "A141D_S181K_K218P" variant were also included as controls. Lambda preference was determined using identical assays as described above.

Figure 21:
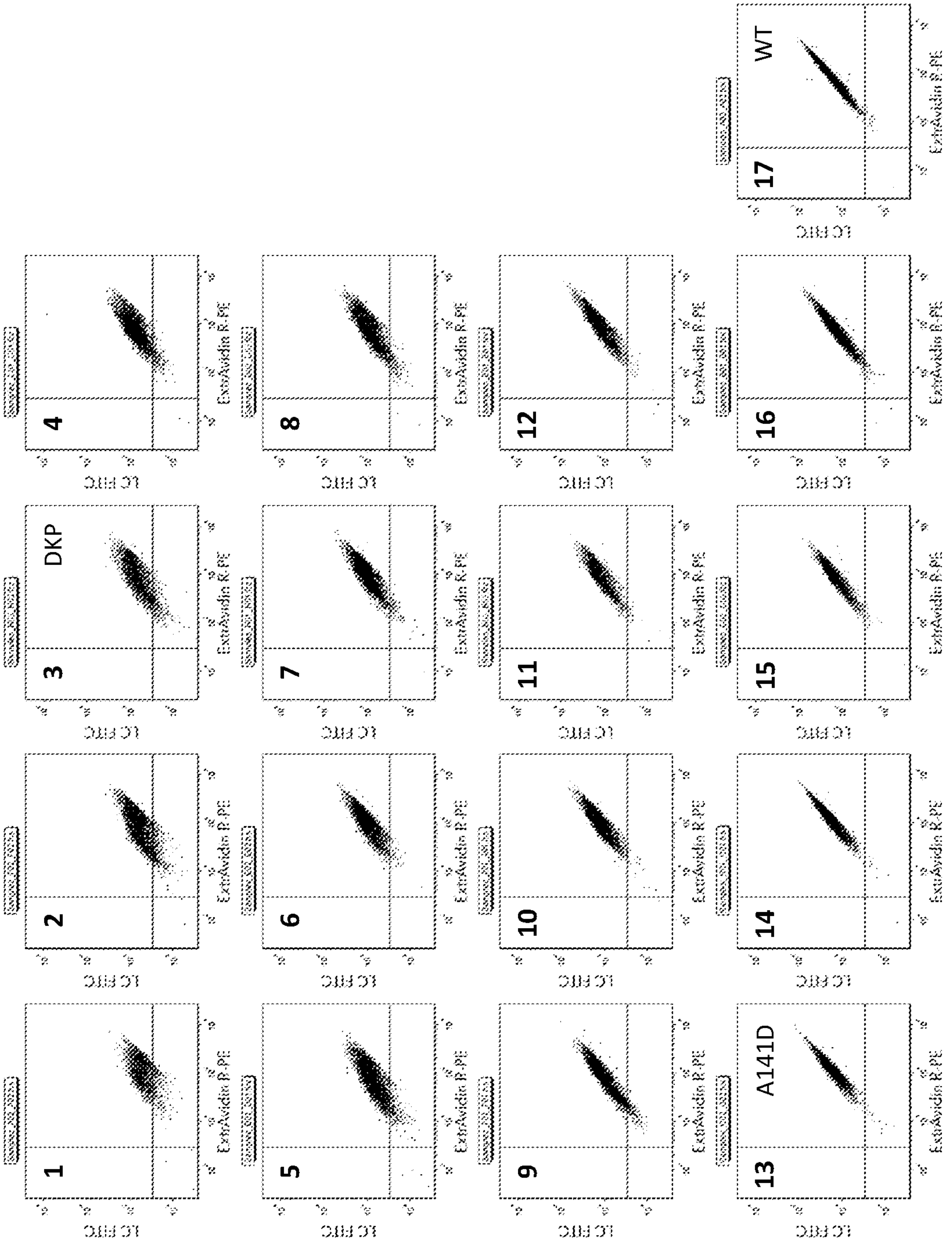
FIG. 21 shows exemplary FACS plots comparing lambda preference for 14 CH1 domain variants in Example 7 and three controls (DKP identified in Example 5, A141D, and wild-type). The x-axis shows lambda light chains labeled with PE, and the y-axis shows kappa light chains labeled with FITC. Numbering in each plot is Rank #shown in Table 14. For example, the first two plots numbered "1" and "2" are plots of "A414D_PT7TE_V185R" and "A141D_FT70E_T187R", respectively.
Figure 22:
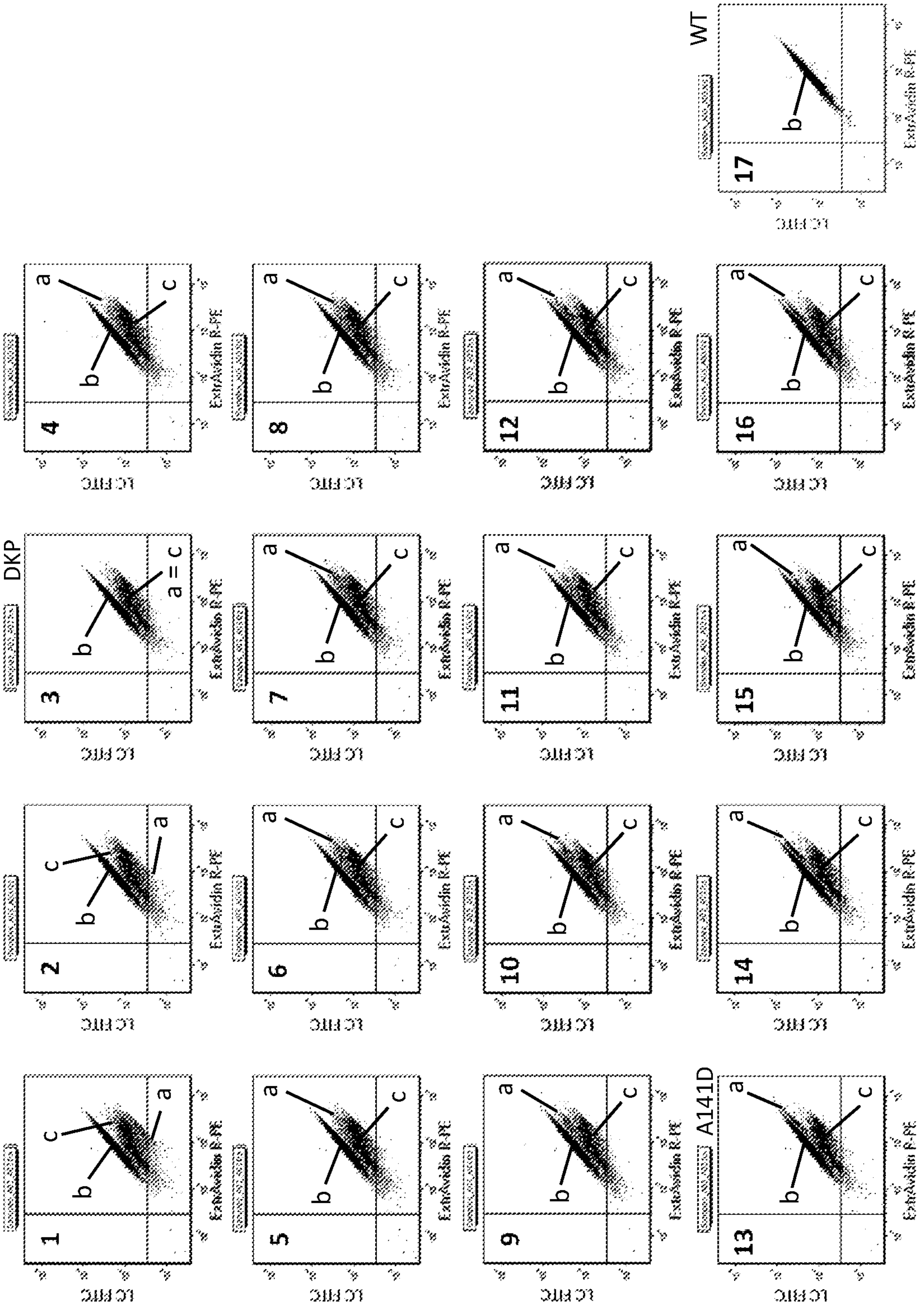
FIG. 22 shows exemplary FACS plot overlays of the individual plot (marked as "a"), wild-type plot (marked as "b), and DKP plot (marked as "c") from FIG. 21.

Lambda MFI-to-kappa MFI ratios were assessed by flow cytometry. FOP values of the 14 leads and individual FACS plots are provided in Table 14 and FIGS. 20-22 (numbering in each plot is Rank #shown in Table 14). Among the 14 leads, "A141D_P171E_V185R" and "A141D_F170E_T187R" showed even higher FOP values than "AT4TD_S181K_K218P", a lead identified in Example 5. Many other variants among the 14 leads also showed higher FOP values compared to "AT4TD" and all 14 leads showed higher FOP values compared to the wild-type.

TABLE 14

FOP values of 14 CH1 variant leads and controls (ranks based on the FOP value)

| | Substitutions in CH1 | FOP value | |
|---|---|---|---|
| 1 | A141D_P171E_V185R | 4.71 | |
| 2 | A141D_F170E_T187R | 3.29 | |
| 3 | A141D_S181K_K218P | 2.90 | Control (Lead from Example 6) |
| 4 | A141E_V185R_T187R | 2.30 | |
| 5 | A141E_P171E_V185R | 2.29 | |
| 6 | A141D_F170E_V185R | 2.18 | |
| 7 | A141D_V185R_T187R | 2.11 | |
| 8 | A141E_F170E_T187R | 2.00 | |
| 9 | A141D_V185R | 1.76 | |
| 10 | A141E_V185R | 1.70 | |
| 11 | A141D_P171E_T187R | 1.68 | |
| 12 | A141E_P171E_T187R | 1.60 | |
| 13 | A141D | 1.47 | Control |
| 14 | A141D_T187R | 1.37 | |
| 15 | A141E_F170E_V185R | 1.31 | |
| 16 | A141E_T187R | 1.18 | |
| 17 | WT | 1.00 | Control |

Figure 23:
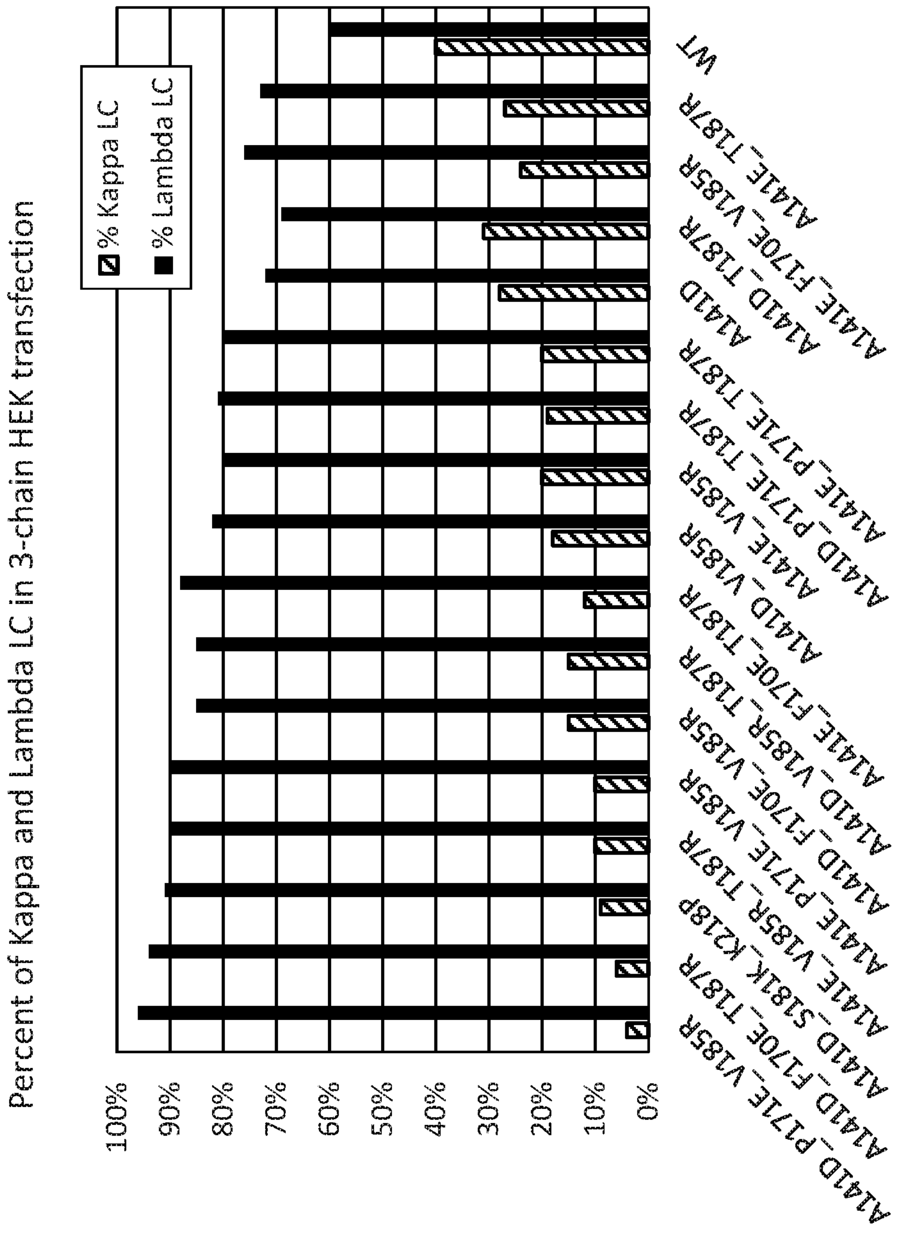
FIG. 23 shows % light chain species (comparing kappa and lambda) of 14 lead and three control full-length IgGs produced in HEK293, as measured by LCMS in Example 7. Three controls are shown with an open arrow. "A414D_P17TE_V185R" and "A14TD_FT70E_T187R"

The amount of kappa and lambda LC per sample was quantified using LCMS (Table 15 and FIG. 23). Similar to the findings from the FACS-based lambda preference assessment "A141D_P171E_V185R" and "A141D_F170E_T187R" showed even higher 00 lambda and even lower 0 kappa chains compared to "A141D_S181K_K218P", a lead identified in Example 6. Many other variants among the 14 leads also showed higher % lambda and lower % kappa compared to "A141D", and all 14 leads showed higher 0 lambda and lower % kappa compared to the wild-type.

TABLE 15

% lambda LC and % kappa LC measured by LCMS (with the FOP values from Table 14)

| Substitutions in CH1 | % Kappa LC | % Lambda LC | Score |
|---|---|---|---|
| A141D_P171E_V185R | 4% | 96% | 4.71 |
| A141D_F170E_T187R | 6% | 94% | 3.29 |
| A141D_S181K_K218P | 9% | 91% | 2.90 |
| A141E_V185R_T187R | 10% | 90% | 2.30 |
| A141E_P171E_V185R | 10% | 90% | 2.29 |
| A141D_F170E_V185R | 15% | 85% | 2.18 |
| A141D_V185R_T187R | 15% | 85% | 2.11 |
| A141E_F170E_T187R | 12% | 88% | 2.00 |
| A141D_V185R | 18% | 82% | 1.76 |
| A141E_V185R | 20% | 80% | 1.70 |
| A141D_P171E_T187R | 19% | 81% | 1.68 |
| A141E_P171E_T187R | 20% | 80% | 1.60 |
| A141D | 28% | 72% | 1.47 |
| A141D_T187R | 31% | 69% | 1.37 |
| A141E_F170E_V185R | 24% | 76% | 1.31 |
| A141E_T187R | 27% | 73% | 1.18 |
| WT | 40% | 60% | 1.00 |

To determine if the two top lambda-preferring CH1 variants ("A141D_P171E_V185R" and "A141D_F170E_T187R") pair with kappa light-chain, the CH1 variant heavy chain plasmids were transfected into HEK293 cells with either 1.) kappa light-chain or 2.) lambda light-chain (with the ration of heavy chain:light chain=1:1). K147F S183R as a CH1 with kappa preference, WT, was also included as controls. Transfected HEK cells were cultured and IgGs were purified via standard methods using a Protein A column. Process Yield (mg/L) was determined using standard methods and normalized to the WT process yield. Based on the normalized process yield, both "A141D_P171E_V185R" and "A141D_F170E_T187R" still bound to kappa LC when only kappa LC (but not lambda LC) was present, but more binding occurred with lambda LC than with kappa LC (FIG. 30).

Process yields of the Fab format were also evaluated. IgGs having CH1 variant heavy chains were produced and purified using the same method. K147F S183R as a CH1 with kappa preference, WT, A141D, and A141D S181K K218P were also included as controls. Linked heavy-chain and light-chain Fabs were generated from the purified IgG via papain enzyme digestion and CH1 column purification using standard methods. Normalized Fab Digest was calculated as % recovery of Fab from IgG digest (amount of Fab recovered/amount of IgG in digest) normalized to parent % recovery for each light chain. Process Yield was determined using standard methods and normalized to the WT process yield. Consistent with the data from FIG. 15, "A141D" and "A141D S181K K218P' had higher process yields with lambda LC over kappa LC, and "K147F S183R" showed extremely high kappa preference (FIG. 31). Both "A141D_P171E_V185R" and "A141D_FT70E_T187R" still bound to kappa CH1 when only kappa CH1 (but not lambda CH1) was present, but markedly higher yield was obtained with lambda LC than with kappa LC (FIG. 31). The addition of "P171E_V185R" or "F170E_T187R" to "A141D" mutation further enhanced the lambda preference of "A141D".

Example 8: Structure Analysis on "A141D" and "K147F S183R" Variants

Methods

Crystallization and Structure Determination of Panitumumab Wildtype CH1-Cλ

Panitumumab wildtype CH1-constant lambda (Cλ) Fab protein at 6.5 mg/ml was centrifuged at 14,000×g at 4° C. for 5 minutes. 305 nL protein was mixed with 150 nL reservoir drop and 50 nL seed solution and equilibrated with 40 ul reservoir solution at 20° C. in MRC 3-well plates. Seed crystals identified from the BCS screen (Molecular Dimensions) were used in microseed matrix-screening (MMS) (D'Arcy, A., Villard, F., and Marsh, M. (2007) "An automated microseed matrix-screening method for protein crystallization" *Acta Crystallogr D Biol Crystallogr* 63, 550-554.) crystallization experiments to obtain crystals grown in 0.1 M phosphate/citrate pH 5.5 and 36% (v/v) PEG Smear Low and transferred to 0.1 M phosphate/citrate pH 5.5, 38% PEG Smear Low, and 4% glycerol, followed by flash-freezing in liquid nitrogen. Diffraction data were collected to 1.09 Å at 100 K at station I03, Diamond Light Source, Didcot, England equipped with an Eiger2 XE 16M detector (DECTRIS). The data set was integrated in autoPROC (Vonrhein, C. et al. (2011) "Data processing and analysis with the autoPROC toolbox" *Acta Cryst. D*67, 293-302.) using XDS (Kabsch W. (2010) "XDS" *Acta. Crystallogr. D Biol. Crystallogr.* 66, 125-132.) and scaled using Aimless (Evans P. R. and Murshudov, G. N. (2013) "How good are my data and what is the resolution" *Acta Crystallogr D Biol. Crystallogr.* 69, 1204-1214.) of the CCP4 software package (Winn M. D. et al. (2011) "Overview of the CCP4 suite and current developments" *Acta Crystallog. D Biol. Crystallogr.* 67, 235-242. 235-242.). Crystals consisted of 2 molecules per asymmetric unit (ASU) in $P12_11$ space group. The structure was solved with the automated molecular replacement system MoRDA (Vagin A. and Lebedev A. (2015) "MoRDa, an automatic molecular replacement pipeline" *Acta Cryst A.* A71, s19.) (incorporating MOLREP (Vagin A., Teplyakov A. (1997) "MOLREP: an automated program for molecular replacement" *J Appl. Cryst.* 30, 1022-1025.) and Refmac5 (Murshudov, G. N., Skubak, P., Lebedev, A. A., Pannu, N. S., Steiner, R. A., Nicholls, R. A., Winn, M. D. Long, F. and Vagin, A. A. (2011) REFMAC5 for the refinement of macromolecular crystal structures, *Acta Crystallogr. D Biol. Crystallogr.* 67, 355-367.)) which selected Protein Data Bank (Berman H. M. et al. (2000) The "Protein Data Bank" Nucleic Acids Research, 28.) entries 5N7W and 5SX4 as initial search models. Automated model building was done using the BUCCANEER software (Cowtan K. (2006) "The Buccaneer software for automated model building. 1. Tracing protein chains" *Acta Crystallographica* D62, 1002-1011.). The model was further improved by manual refinement in Coot (Emsley P., Lohkamp, B., Scott, W. G. and Cowtan K. (2010) "Features and development of Coot" *Acta Crystallogr. D Biol. Crystallogr.* 66, 486-501.) as well as refinement in Refmac5 (Murshudov, G. N., Skubak, P., Lebedev, A. A., Pannu, N. S., Steiner, R. A., Nicholls, R. A., Winn, M. D. Long, F. and Vagin, A. A. (2011) REFMAC5 for the refinement of macromolecular crystal structures, *Acta Crystallogr. D Biol. Crystallogr.* 67, 355-367.) and Buster (Bricogne G, Blanc E, Brandl M, Flensburg C, Keller P, Paciorek W, Roversi P, Sharff A, Smart O, Vonrhein C, Womack T. (2011). BUSTER version 2.11.7. Global Phasing Ltd, Cambridge, United Kingdom.) to a final R and $R_{free}$ of 14.5% and 16.9%, respectively (FIG. 32).

Crystallization and Structure Determination of Panitumumab A141D CH1-Cλ Wildtype CH1-Cκ, and K147F-S183R CH1-Cκ

Panitumumab A141D CH1-Cλ, panitumumab wildtype CH1-constant kappa (Cκ), and panitumumab K147F-S183R CH1-Cκ Fabs were centrifuged at 14,000×g at 4° C. for 5 minutes. For panitumumab A141D CH1-Cλ and K147F-S183R CH1-Cκ, 200 nL of 10.0 mg/ml Fab was mixed with 150 nL reservoir drop and 50 nL seed solution equilibrated with 40 ul reservoir solution. Seed crystals identified from the BCS screen were used in MMS experiments to find optimal crystallization conditions. 0.1 M phosphate/citrate buffer pH 5.5 and 36% (v/v) PEG Smear Low was used for panitumumab A141D CH1-Cλ and 0.1 M sodium acetate pH 4.5 with 30% v/v PEG Smear Low for panitumumab K147F-S183R CH1-Cκ. 150 nL of 19.2 mg/ml wildtype CH1-Cκ was mixed with 150 nL reservoir drop and added to 40 ul reservoir solution and screened using the PACT Suite (Molecular Dimensions). Final crystallization condition consisted of 0.1 M MES pH 6.0 with 20% w/v PEG 6000 and 0.2 M calcium chloride dihydrate. Crystals were transferred to cryo solutions consisting of 0.1 M phosphate/citrate buffer pH 5.5, 38% PEG Smear Low, 4% glycerol; 0.07 M MES, pH 6.0, 21% PEG 6000, 0.2 M $CaCl_2$), 23.5% glycerol; and 0.1 M NaAc pH 4.5, 32.5% PEG Smear Low, 25% glycerol for panitumumab A141D CH1-Cλ, wildtype CH1-Cκ, and K147F-S183R CH1-Cκ, respectively. All crystals were flash-frozen in liquid nitrogen and crystallographic data collected at 100 K at station 103, Diamond Light Source, Didcot, England equipped with an Eiger2 XE 16M detector (DECTRIS) to 1.2-2.6 Å resolution. Data were indexed and integrated in iMOSFLM (Battye, T. G. G., Kontogiannis, L., Johnson, O., Powell, H. R., & Leslie, A. G. (2011). iMOSFLM: a new graphical interface for diffraction-image processing with MOSFLM. *Acta Crystallographica* Section D: Biological *Crystallography,* 67(4), 271-281.) and scaled and merged with AIMLESS (Evans P. R. and Murshudov, G. N. (2013) "How good are my data and what is the resolution" *Acta Crystallogr D Biol. Crystallogr.* 69, 1204-1214.) through the CCP4 suite (Winn M. D. et al. (2011) "Overview of the CCP4 suite and current developments" *Acta Crystallog. D Biol. Crystallogr.* 67, 235-242. 235-242.).

Panitumumab A141D-CH1-Cλ structure was solved by molecular replacement using the crystal structure of wildtype CH1-Cλ as a search model. Several rounds of anisotropic B factor and simple restrained refinement was performed in Refmac5 (Murshudov, G. N., Skubak, P., Lebedev, A. A., Pannu, N. S., Steiner, R. A., Nicholls, R. A., Winn, M. D. Long, F. and Vagin, A. A. (2011) REFMAC5 for the refinement of macromolecular crystal structures, *Acta Crystallogr. D Biol. Crystallogr.* 67, 355-367.), with the application of a blurring factor in the final rounds of refinement. Positional occupancies of A141D CH1-Cλ were assigned based on occupancies of wildtype CH1-Cλ and manually adjusted in Coot (Emsley P., Lohkamp, B., Scott, W. G. and Cowtan K. (2010) "Features and development of Coot" *Acta Crystallogr. D Biol. Crystallogr.* 66, 486-501.) during iterative refinement. The final structure, solved in $P12_11$ with 2 molecules per ASU, had R and $R_{free}$ values of 15.2% and 17.0%, respectively (FIG. 33).

Panitumumab wildtype CH1-Cκ and K147F-S183R-CH1-Cκ structures were solved by molecular replacement with Phaser (McCoy, A. J., Grosse-Kunstleve, R. W., Adams, P. D., Winn, M. D., Storoni, L. C., & Read, R. J. (2007). Phaser crystallographic software. *Journal of Applied Crystallography,* 40(4), 658-674.) using coordinates of the panitumumab Fab fragment in complex with EGFR (PDB code 5SX4) and with the solved wildtype CH1-Cκ structure, respectively, followed by iterative rounds of manual model building using Coot (Emsley P., Lohkamp, B., Scott, W. G. and Cowtan K. (2010) "Features and development of Coot" *Acta Crystallogr. D Biol. Crystallogr.* 66, 486-501.) and automatic refinement in Refmac5 (Murshudov, G. N., Skubak, P., Lebedev, A. A., Pannu, N. S., Steiner, R. A., Nicholls, R. A., Winn, M. D. Long, F. and Vagin, A. A. (2011) REFMAC5 for the refinement of macromolecular crystal structures, *Acta Crystallogr. D Biol. Crystallogr.* 67, 355-367.). Translational non-crystallographic symmetry was observed for the wildtype CH1-Cκ structure, so the structure was solved in a lower space group ($P12_11$) with 6 Fab molecules in the ASU. The structure was refined to final R and $R_{free}$ values of 19.8% and 23.2%, respectively (FIG. 34). The K147F-S183R CH1-Cκ structure was solved in the $P3_1$ space group with 1 molecule per ASU to final R and $R_{free}$ values of 19.8% and 23.3%, respectively (FIG. 35).

Structure Analyses and Interpretation

Lambda LC Preference Mediated by HC-A141D

Without wishing to be bound by theory, enhanced lambda preference of panitumumab A141D CH1-Cλ is potentially mediated by an interchain hydrogen bond formed between the side chain carboxyl group of HC-Asp141 and side chain hydroxyl group of λLC-Thr116 (FIG. 36C), which cannot form with HC-Ala141 in panitumumab wildtype CH1-Cλ (FIG. 36A). The κLC region surrounding HC-Ala141 consist of hydrophobic residues Phe116, Phe118 and Leu135, while the κLC-Phe116 is replaced by the polar residue Thr116 in λLC (FIG. 36B). Thus, a charge introduction via the A141D mutation may lower kappa preference by disrupting CH1-κLC interface hydrophobicity while stabilizing CH1-λLC pairing through hydrogen bonding with λLC-Thr116. Additionally, without wishing to be bound by theory, kappa preference may be further reduced through steric clash of HC-Asp141 with κLC-Phe116, as shown by alignment of panitumumab A141D CH1-Cλ and wildtype CH1-κLC (FIG. 36D).

In the hydrogen bond between HC-Asp141 and λLC-Thr116, the bond is formed between the hydrogen acceptor atom (O) in the side chain of Asp141 and the hydrogen donor atom (H) of the side chain of Thr116. Therefore, another amino acid that has a hydrogen acceptor atom in the side chain may also form a hydrogen bond with Thr116 of λLC, providing lambda preference. Based on the fact that the side chain of glutamate also has a hydrogen acceptor atom (O) and glutamate is similar in size and shape to aspartate, glutamate likely forms a hydrogen bond with Thr116 of λLC while causing steric clash with κLC as shown in FIG. 36D, overall providing lambda preference. In fact, A141E substitution provided strong lambda preference as demonstrated in the Examples above, confirming the structural analyses by Applicant.

Kappa LC Preference Mediated by HC-K147F-S183R

Observed kappa preference of panitumumab K147F-S183R CH1-Cκ may be mediated by two new hydrogen bonds at the CH1 and Cκ interface. In the panitumumab wildtype CH1-Cκ structure, a hydrogen bond network coordinated by HC-Lys147 and HC-Asp148 sequesters HC-Gln175, contributing to a baseline kappa pairing preference (FIG. 37A). One explanation is that substitution of CH1 HC-Lys147 with phenylalanine at this position breaks this network and liberates the HC-Gln175 side chain, which interacts with κLC via hydrogen bonding to the formamide oxygen of κLC-Gln160, thus increasing kappa preference (FIG. 37B). Additionally, without wishing to be bound by theory, the HC-S183R substitution results in an additional hydrogen bond between the guanidinium group of the HC-Arg183 side chain and the hydroxyl group of κLC-Thr178 (FIG. 37B, FIG. 38C). Conversely, without wishing to be bound by theory, hydrogen bonding observed at the HC 183 position between HC-Ser183 and λLC-Tyr178 in panitumumab wildtype CH1-Cλ is abolished by severe steric clashing of HC-Arg183 and λLC-Tyr178 side chains in the modeled pairing of K147F-S183R CH1 and λLC, de-stabilizing lambda pairing in favor of the κLC (FIGS. 38B and 38D).

In the hydrogen bond between HC-Arg183 and κLC-Thr178, the bond is formed between the hydrogen donor atom (H) in the side chain of Arg183 and the hydrogen acceptor atom (O) of the side chain of Thr178. Therefore, another amino acid that has a hydrogen donor atom in the side chain may also form a hydrogen bond with Thr178 of κLC, providing kappa preference. A larger side chain such as that of Arg may help generate steric clash with Tyr178 of λLC, providing additional kappa preference. For example, the side chain of both lysine and tryptophan have a large side chain that contains a hydrogen donor atom (H). Therefore, lysin and tryptophan likely form a hydrogen bond with Thr178 of κLC and likely experience steric clash with λLC as shown in FIG. 38D, overall providing kappa preference. The side chain of threonine can also function as a hydrogen donor via the H atom of —OH. Therefore, Applicant further envisions that an amino acid having a relatively large side chain that can function as a hydrogen acceptor may also form a hydrogen bond with Thr178 of κLC to provide kappa preference. For example, glutamate, glutamine, histidine, or tyrosine, which have a relatively large side chain with a hydrogen acceptor atom, when placed at residue 183 of HC may also provide kappa preference. In fact, most of these newly proposed amino acid substitutions at residue 183 were in fact identified as kappa preferring in Example 3 (see Table 3).

As noted above, substitution of Lys147 with Phe disrupted the hydrogen bond between Lys147 and Gln175, thereby liberating Gln175 for forming a hydrogen bond with Gln160 of κLC and thus contributing to kappa preference. Therefore, substitution of Lys147 with another amino acid whose chide chain does not contain a hydrogen donor or acceptor atom, such as alanine, glycine, isoleucine, leucine, or valine, may also help with kappa preference. In fact, most of these newly proposed amino acid substitutions at residue 147 were in fact identified as kappa preferring in Example 3 (see Table 3).

What is claimed is:

1. A heavy chain constant region 1 (CH1) domain variant polypeptide, comprising amino acid substitutions that increase pairing of the CH1 domain variant polypeptide with a kappa light chain constant region (CL) domain as compared to a lambda CL domain and/or with a kappa light chain polypeptide as compared to a lambda light chain polypeptide, wherein the amino acid substitutions comprise or consist of a substitution to F at position 147 and a substitution to R at position 183, wherein the positions are according to EU numbering.

2. The CH1 domain variant polypeptide of claim 1, which is a variant of a human IgG CH1 domain polypeptide.

3. The CH1 domain variant polypeptide of claim 1, wherein the amino acid substitutions are relative to SEQ ID NO: 1.

4. The CH1 domain variant polypeptide of claim 1, wherein the amino acid substitutions increase pairing with a kappa CL domain as compared to a lambda CL domain and/or with a kappa light chain polypeptide as compared to a lambda light chain polypeptide by:

at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%, optionally as measured by liquid chromatography-mass spectrometry (LCMS); or at least 1.2-fold, at least 1.5-fold, at least 2-fold, by at least 2.5-fold, by at least 3-fold, by at least 3.5-fold, by at least 4-fold, by at least 4.5-fold, by at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, or at least 25-fold, optionally as measured by flow cytometry, optionally by comparing the mean fluorescence intensity (MFI) ration of kappa CL staining to lambda CL staining.

5. An antibody or antibody fragment comprising a first heavy chain polypeptide and a first light chain polypeptide, wherein:

(a) the first heavy chain polypeptide and the first light chain polypeptide form a first cognate pair;

(b) the first heavy chain polypeptide comprises a first CH1 domain variant according to claim 1; and (c) the first light chain polypeptide comprises a kappa CL domain and optionally is a kappa light chain polypeptide, optionally wherein the kappa CL domain is a wild-type kappa CL domain.

6. The antibody or antibody fragment of claim 5, which further comprises a second heavy chain polypeptide and a second light chain polypeptide, wherein:

(a) the second heavy chain polypeptide and the second light chain polypeptide form a second cognate pair; and (b) the second light chain polypeptide comprises a lambda CL domain and optionally is a lambda light chain polypeptide, optionally wherein the lambda CL domain is a wild-type lambda CL domain.

7. The antibody or antibody fragment of claim 6, which is multispecific, optionally bispecific, further optionally wherein the structure of said antibody or antibody fragment is as depicted in any one of FIGS. 24-29.

8. A composition, which comprises an antibody or antibody fragment comprising according to claim 5.

9. A pharmaceutical composition, which comprises an antibody or antibody fragment according to claim 6.

10. A heavy chain constant region 1 (CH1) domain variant polypeptide, which comprises the amino acid sequence of SEQ ID NO: 137.

11. An antibody or antibody fragment, which comprises a first heavy chain polypeptide and a first light chain polypeptide, wherein:

(a) the first heavy chain polypeptide and the first light chain polypeptide form a first cognate pair;

(b) the first heavy chain polypeptide comprises a first CH1 domain variant according to claim 10; and (c) the first light chain polypeptide comprises a kappa CL domain and optionally is a kappa light chain polypeptide, optionally wherein the kappa CL domain is a wild-type kappa CL domain.

12. The antibody or antibody fragment of claim 11, which further comprises a second heavy chain polypeptide and a second light chain polypeptide, wherein:

(a) the second heavy chain polypeptide and the second light chain polypeptide form a second cognate pair; and (b) the second light chain polypeptide comprises a lambda CL domain and optionally is a lambda light chain polypeptide, optionally wherein the lambda CL domain is a wild-type lambda CL domain.

13. A composition, which comprises an antibody or antibody fragment comprising according to claim 11.

14. A pharmaceutical composition, which comprises an antibody or antibody fragment according to claim 12.

* * * * *